(12) United States Patent
Olivera et al.

(10) Patent No.: US 6,762,165 B2
(45) Date of Patent: Jul. 13, 2004

(54) O-SUPERFAMILY CONOTOXIN PEPTIDES

(75) Inventors: Baldomero M. Olivera, Salt Lake City, UT (US); G. Edward Cartier, Salt Lake City, UT (US); Maren Watkins, Salt Lake City, UT (US); David R. Hillyard, Salt Lake City, UT (US); J. Michael McIntosh, Salt Lake City, UT (US); Richard T. Layer, Sandy, UT (US); Robert M. Jones, Salt Lake City, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 24 days.

(21) Appl. No.: 09/749,637

(22) Filed: Dec. 28, 2000

(65) Prior Publication Data

US 2002/0173449 A1 Nov. 21, 2002

Related U.S. Application Data

(60) Provisional application No. 60/243,412, filed on Oct. 27, 2000, provisional application No. 60/219,440, filed on Jul. 20, 2000, provisional application No. 60/214,263, filed on Jun. 26, 2000, and provisional application No. 60/173,754, filed on Dec. 30, 1999.

(51) Int. Cl.[7] .................. C07K 14/435; A61K 38/17
(52) U.S. Cl. .................. 514/12; 514/2; 530/300; 530/324
(58) Field of Search .................. 530/324, 300; 514/12, 2

(56) References Cited

U.S. PATENT DOCUMENTS

| | | | |
|---|---|---|---|
| 5,051,403 A | 9/1991 | Miljanich et al. | 514/12 |
| 5,587,454 A | 12/1996 | Justice et al. | 530/324 |
| 5,591,821 A | 1/1997 | Olivera et al. | 530/324 |
| 5,672,682 A | 9/1997 | Terlau et al. | 530/324 |
| 5,719,264 A | 2/1998 | Shon et al. | 530/324 |
| 5,739,276 A | 4/1998 | Shon et al. | 530/324 |
| 5,859,186 A | 1/1999 | Justice et al. | 530/324 |

FOREIGN PATENT DOCUMENTS

| | | |
|---|---|---|
| WO | WO 00/76532 A1 | 12/2000 |
| WO | WO 01/21648 A1 | 3/2001 |

OTHER PUBLICATIONS

Olivera, B.M. et al. (1985). "Peptide Neurotoxins from Fish–Hunting Cone Snails," *Science* 230:1338–1343.
Hillyard, D.R. et al. (1989). "A Molluscivorous *Conus* Toxin: Conserved Frameworks in Conotoxins," *Biochemistry* 28:358–361.
Olivera, B.M. et al. (1990). "Diversity of *Conus* Neuropeptides," *Science* 249:257–263.
Fainzilber, M. et al. (1991). "Mollusc–Specific Toxins from the Venom of *Conus textile neovicarius*," *Eur. J. Biochem.* 202:589–595.
Fainzilber, M. et al. (1995). "A New Conotoxin Affecting Sodium Current Inactivation Interacts with the ō–Conotoxin Receptor Site," *J. Biol. Chem.* 270:1123–1129.
Nakamura, T. et al. (1996). "Mass Spectrometric–Based Revision of the Structure of a Cysteine–Rich Peptide Toxin with γ–Carboxyglutamic Acid, TxVIIA, from the Sea Snail, *Conus textile*," *Protein Science* 5:524–530.
McIntosh, J. M. et al. (1999). "*Conus* Peptides as Probes for Ion Channels," *Meths. in Enzymol.* 294:605–624.
Jones, R.M. et al. (2000). "*Conus* Peptides—Combinatorial Chemistry at a Cone Snail's Pace," *Curr. Op. Drug Discovery & Devel.* 3:141–154.
Jones, R. M. et al. (2000). Conotoxins—New Vistas for Peptide Therapeutics, *Current Pharmaceut. Design* 6:1249–1285.

*Primary Examiner*—Gabriele Bugaisky
(74) *Attorney, Agent, or Firm*—Rothwell, Figg, Ernst & Manbeck, p.c.

(57) ABSTRACT

The invention relates to relatively short peptides (termed O-Superfamily conotoxins herein), about 20–40 residues in length, which are naturally available in minute amounts in the venom of the cone snails or analogous to the naturally available peptides, and which preferably include two disulfide bonds.

18 Claims, No Drawings

O-SUPERFAMILY CONOTOXIN PEPTIDES

CROSS-REFERENCE TO RELATED APPLICATIONS

The present application is related to U.S. provisional patent applications Serial No. 60/173,754 filed Dec. 30, 1999, Serial No. 60/214,263 filed 26 Jun. 2000, Serial No. 60/219,440 filed 20 Jul. 2000 and Serial No. 60/243,412 filed 27 Oct. 2000.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed O-Superfamily conotoxins herein), about 20–40 residues in length, which are naturally available in minute amounts in the venom of the cone snails or analogous to the naturally available peptides, and which preferably include three disulfide bonds.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Conus is a genus of predatory marine gastropods (snails) which envenomate their prey. Venomous cone snails use a highly developed apparatus to deliver their cocktail of toxic conotoxins into their prey. In fish-eating species such as Conus magus the cone detects the presence of the fish using chemosensors in its siphon. When close enough the cone extends its proboscis and impales the fish with a hollow harpoon-like tooth containing venom. This immobilizes the fish and enables the cone snail to wind it into its mouth via the tooth held at the end of its proboscis. Prey capture is accomplished through a sophisticated arsenal of peptides which target specific ion channel and receptor subtypes. Each Con us species venom appears to contain a unique set of 50–200 peptides. The composition of the venom differs greatly between species and between individual snails within each species, each optimally evolved to paralyze its prey. The active components of the venom are small peptide toxins, typically 10–30 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the ω-conotoxins target the voltage-gated calcium channels (Olivera et al., 1985; Olivera et al., 1990). For example a linkage has been established between α-, αA- & ψ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel. Five δ-conotoxins have been described: GmVIA (U.S. Pat. No. 5,719,264); PVIA (U.S. Pat. No. 5,739,276); TxVIA (Hillyard et al., 1989; Fainzilber et al., 1991); TxVIB (Fainzilber et al., 1991); NgVIA (Fainzilber et al., 1995); and TxIIA (Nakamura et al., 1996).

However, the structure and function of only a small minority of these peptides have been determined to date. For peptides where function has been determined, three classes of targets have been elucidated: voltage-gated ion channels; ligand-gated ion channels, and G-protein-linked receptors.

Conus peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by a specific disulfide bond frameworks combined with hypervariable amino acids within disulfide loops (for a review see McIntosh et al., 1998).

Potassium channels comprise a large and diverse group of proteins that, through maintenance of the cellular membrane potential, are fundamental in normal biological function. These channels are vital in controlling the resting membrane potential in excitable cells and can be broadly sub-divided into three classes: voltage-gated $K^+$ channels, $Ca^{2+}$ activated $K^+$ channels and ATP-sensitive $K^+$ channels. Many disorders are associated with abnormal flow of potassium ions through these channels. The identification of agents which would regulate the flow of potassium ions through each of these channel types would be useful in treating disorders associated with such abnormal flow.

It is desired to identify additional conotoxin peptides having activities of the above conopeptides, as well as conotoxin peptides having additional activities.

SUMMARY OF THE INVENTION

The invention relates to relatively short peptides (termed O-Superfamily conotoxins herein), about 20–40 residues in length, which are naturally available in minute amounts in the venom of the cone snails or analogous to the naturally available peptides, and which preferably include three disulfide bonds. The O-superfamily conotoxins include ω-conotxins, κ-conotoxins, δ-conotoxins, μO-conotoxins and GS conotoxin.

Thus, in one embodiment, the present invention is directed to the conotoxin peptides set forth in Table 2 and the corresponding peptides set forth in Table 1.

In a second embodiment, the present invention is directed to all of the propeptides and nucleic acid sequences encoding the propeptides or peptides set forth in Table 1.

In a third embodiment, the present invention is directed to derivatives or pharmaceutically acceptable salts of the conotoxin peptides disclosed herein. Examples of derivatives include peptides in which the Arg residues may be substituted by Lys, ornithine, homoargine, nor-Lys, N-methyl-Lys, N,N-dimethyl-Lys, N,N,N-trimethyl-Lys or any synthetic basic amino acid; the Lys residues may be substituted by Arg, ornithine, homoargine, nor-Lys, or any synthetic basic amino acid; the Tyr residues may be substituted with $^{125}$I-Tyr, meta-Tyr, ortho-Tyr, nor-Tyr, mono-halo-Tyr, di-halo-Tyr, O-sulpho-Tyr, O-phospho-Tyr, nitro-Tyr or any synthetic hydroxy containing amino acid; the Ser residues may be substituted with Thr or any synthetic hydroxylated amino acid; the Thr residues may be substituted with Ser or any synthetic hydroxylated amino acid; the Phe residues may be substituted with any synthetic aromatic amino acid; the Trp residues may be substituted with Trp (D), neo-Trp, halo-Trp (D or L) or any aromatic synthetic amino acid; and the Asn, Ser, Thr or Hyp residues may be glycosylated. The halogen may be iodo, chloro, fluoro or bromo; preferably iodo for halogen substituted-Tyr and bromo for halogen-substituted Trp. The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The aliphatic amino acids may be substituted by synthetic derivatives bearing non-natural aliphatic branched or linear side chains $C_nH_{2n+2}$ up to and including n=8. The Leu residues may be substituted with Leu (D). The Glu residues may be substituted with Gla. The Gla residues may be substituted with Glu. The Met residues may be substituted with norleucine (Nle). The Cys residues may be in D or L configuration and may optionally be substituted with homocysteine (D or L).

Examples of synthetic aromatic amino acid include, but are not limited to, nitro-Phe, 4-substituted-Phe wherein the substituent is $C_1-C_3$ alkyl, carboxyl, hyrdroxymethyl, sulphomethyl, halo, phenyl, —CHO, —CN, —SO$_3$H and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperidinyl)-Gly, 2-(4-piperidinyl)-Ala, 2-[3-(2S) pyrrolidininyl)-Gly and 2-[3-(2S)pyrrolidininyl)-Ala. These and other synthetic basic amino acids, synthetic hydroxy containing amino acids or synthetic aromatic amino acids are described in Building Block Index, Version 3.0 (1999 Catalog, pages 4–47 for hydroxy containing amino acids and aromatic amino acids and pages 66–87 for basic amino acids, incorporated herein by reference, by and available from RSP Amino Acid Analogues, Inc., Worcester, Mass. The residues containing protecting groups are deprotected using conventional techniques. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference.

Optionally, in the peptides of the present invention, the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N—, S— or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420,797 filed 19 Oct. 1999 and in PCT Application No. PCT/US99/24380 filed 19 Oct. 1999 (PCT Published Application No. WO 00/23092), each incorporated herein by reference. A preferred glycan is Gal(β1→3)GalNAc(α1→).

Optionally, in the peptides of general formula I and the specific peptides described herein, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The present invention is further directed to derivatives of the above peptides and peptide derivatives which are acylic permutations in which the cyclic permutants retain the native bridging pattern of native toxin. See, Craik et al. (2001).

In a fourth embodiment, the present invention is directed to uses of the conotoxin peptides described herein. In one aspect of this embodiment, members of the O-Superfamily conotoxins disclosed herein or a pharmaceutically acceptable salt or solvate thereof are used for regulating the flow of sodium ions through Na$^+$ channels. Disorders which can be treated using these conopeptides include multiple sclerosis, other demyelinating diseases (such as acute dissenmiated encephalomyelitis, optic neuromyelitis, adrenoleukodystrophy, acute transverse myelitis, progressive multifocal leukoencephalopathy), sub-acute sclerosing panencephalomyelitis (SSPE), metachromatic leukodystrophy, Pelizaeus-Merzbacher disease, spinal cord injury, botulinum toxin poisoning, Huntington's chorea, compression and entrapment neurophathies (such as carpal tunnel syndrome, ulnar nerve palsy), cardiovascular disorders (such as cardiac arrhythmias, congestive heart failure), reactive gliosis, hyperglycemia, immunosuppression, cocaine addiction, cancer, cognitive dysfunction, disorders resulting from defects in neurotransmitter release (such as Eaton-Lambert syndrome), and reversal of the actions of curare and other neuromuscular blocking drugs.

In a second apsect of this embodiment, a method of treating disorders associated with voltage gated ion channel disorders in a subject is provided which comprises administering to the subject an effective amount of the pharmaceutical composition comprising a therapeutically effective amount of a member of the O-Superfamily contoxins described herein or a pharmaceutically acceptable salt or solvate thereof. Thus, these peptides can be used to treat neurologic disorders, such as anticonvulsant agents, or as neuroprotective agents, such as for treating stroke, or as cardiovascular agents or for the management of pain. These peptides can further be used to treat spasticity, spinal cord injury or upper motor neuron syndrome.

In a third aspect of this embodiment, a method of reducing/alleviating/decreasing the perception of pain by a subject or for inducing analgesia, particularly local analgesia, in a subject is provided which comprises administering to the subject an effective amount of the pharmaceutical composition comprising a therapeutically effective amount of a member of the O-Superfamily contoxins described herein or a pharmaceutically acceptable salt or solvate thereof.

In a fourth aspect of this embodiment, a method for activating (i.e., opening) ATP-sensitive $K^+$ channels in a subject is provided which comprises administering to the subject an effective amount of the pharmaceutical composition comprising a therapeutically effective amount of a member of the O-Superfamily contoxins described herein or a pharmaceutically acceptable salt or solvate thereof.

In a fifth aspect of this embodiment, a method of treating disorders and conditions associated with proton-gated ion channels in a subject comprising administering to the subject an effective amount of the pharmaceutical composition comprising a therapeutically effective amount of a member of the O-Superfamily conotoxins described herein or a pharmaceutically acceptable salt or solvate thereof.

Another embodiment of the invention contemplates a method of identifying compounds that mimic the therapeutic activity of the instant peptide, comprising the steps of: (a) conducting a biological assay on a test compound to determine the therapeutic activity; and (b) comparing the results obtained from the biological assay of the test compound to the results obtained from the biological assay of the peptide. The peptide is labeled with any conventional label, preferably a radioiodine on an available Tyr. Thus, the invention is also directed to radioiodinated O-Superfamily conotoxins.

DETAILED DESCRIPTION OF THE PREFERRED EMBODIMENT

The invention relates to relatively short peptides (termed O-Superfamily conotoxins herein), about 20–40 residues in length, which are naturally available in minute amounts in the venom of the cone snails or analogous to the naturally available peptides, and which preferably include three disulfide bonds.

The present invention, in another aspect, relates to a pharmaceutical composition comprising an effective amount of an O-Superfamily conotoxin peptide, a mutein thereof, an analog thereof, an active fragment thereof or pharmaceutically acceptable salts.

In one embodiment, such a pharmaceutical composition comprises a member of the O-Superfamily conotoxins described herein which has the capability of delaying inactivation of sodium channels. The activity of δ-conotoxin peptides, members of the O-Superfamily, on sodium channels is described in U.S. Pat. No. 5,739,276, incorporated herein by reference. The treatment of disorders according to this embodiment comprises the step of administering to such a living animal body, including a human, in need thereof a therapeutically effective amount of a pharmaceutical composition of the present invention.

Sodium channels comprise a large and diverse group of proteins that, through maintenance of the cellular membrane potential, are fundamental in normal biological function. The therapeutic applications for compounds that regulate the flow of sodium ions through $Na^+$ channels are far-reaching and include treatments of a wide range of disease and injury states. Disorders which can be treated using these conopeptides include multiple sclerosis, other demyelinating diseases (such as acute dissenmiated encephalomyelitis, optic neuromyelitis, adrenoleukodystrophy, acute transverse myelitis, progressive multifocal leukoencephalopathy), subacute sclerosing panencephalomyelitis (SSPE), metachromatic leukodystrophy, Pelizaeus-Merzbacher disease, spinal cord injury, botulinum toxin poisoning, Huntington's chorea, compression and entrapment neurophathies (such as carpal tunnel syndrome, ulnar nerve palsy), cardiovascular disorders (such as cardiac arrhythmias, congestive heart failure), reactive gliosis, hyperglycemia, immunosuppression, cocaine addiction, cancer, cognitive dysfunction, disorders resulting from defects in neurotransmitter release (such as Eaton-Lambert syndrome), and reversal of the actions of curare and other neuromuscular blocking drugs.

In a second embodiment, such a pharmaceutical composition comprises a member of the O-Superfamily conotoxins described herein which has the channels, particularly calcium channels, and are thus useful for treating a disorder or disease of a living animal body, including a human, which disorder or disease is responsive to the partial or complete blockade of voltage gated ion channels of the central nervous system. The activity of ω-conotoxin peptides, members of the O-Superfamily, on calcium channels is described in U.S. Pat. Nos. 5,587,454; 5,559,095 and 5,824,645, incorporated herein by reference. The treatment according to this embodiment comprises the step of administering to such a living animal body, including a human, in need thereof a therapeutically effective amount of a pharmaceutical composition of the present invention.

Voltage-gated calcium channels are present in neurons, and in cardiac, smooth, and skeletal muscle and other excitable cells, and are known to play a variety of roles in membrane excitability, muscle contraction, and cellular secretion, such as in synaptic transmission (McCleskey). In neuronal cells, voltage-gated calcium channels have been classified by their electrophysiological as well as by their biochemical (binding) properties. Six classes of physiologically distinct calcium channels have been identified to date, namely the T, L, N, P, Q, and R-type channels.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the central nervous system (CNS) is known to cause most of the degenerative changes connected with the above diseases. Compounds which can block the calcium channels of brain cells are therefore useful in the treatment of stroke, anoxia, ischemia, migraine, psychosis, or epilepsy, any other convulsive disorder and in the prevention of the degenerative changes connected with the same.

Compounds blocking the so called L-type calcium channels in the CNS are useful for the treatment of the above disorders by directly blocking the calcium uptake in the CNS. Further, it is well known that the so called N- and P-types of calcium channels, as well as possibly other types of calcium channels, are involved in the regulation of neurotransmitter release. Compounds blocking the N- and/or P-types of calcium channels indirectly and very powerfully prevent calcium overload in the CNS after the hyperactivity periods of the brain as described above by inhibiting the enhanced neurotransmitter release seen after such hyperactivity periods of the CNS, and especially the neurotoxic, enhanced glutamate release after such hyperactivity periods of the CNS. Furthermore, blockers of the N- and/or P-types of calcium channels, as dependent upon the selectivity of the compound in question, inhibit the release of various other neurotransmitters such as aspartate, GABA, glycine, dopamine, serotonin and noradrenaline.

Thus, the pharmaceutical compositions comprising a member of the O-Superfamily conotoxins of the present invention are useful as neuroprotectants, cardiovascular agents, anticonvulsants, analgesics or adjuvants to general anesthetics. A "neurological disorder or disease" is a disorder or disease of the nervous system including, but not limited to, global and focal ischemic and hemorrhagic stroke, head trauma, spinal cord injury, hypoxia-induced nerve cell damage as in cardiac arrest or neonatal distress or epilepsy. In addition, a "neurological disorder or disease" is a disease state and condition in which a neuroprotectant, anticonvulsant, analgesic and/or as an adjunct in general anesthesia may be indicated, useful, recommended or prescribed.

More specifically, the present invention is directed to the use of a member of the O-Superfamily conotoxins for the treatment and alleviation of epilepsy and as a general anticonvulsant agent. The present invention is also directed to the use of these compounds for reducing neurotoxic injury associated with conditions of hypoxia, anoxia or ischemia which typically follows stroke, cerebrovascular accident, brain or spinal cord trauma, myocardial infarct, physical trauma, drowning, suffocation, perinatal asphyxia, or hypoglycemic events. The present invention is further directed to the use of O-superfamily-conotoxin peptides for treating pain, including acute and chronic pain, such migraine, nociceptive and neuropathic pain. These peptides can further be used to treat spasticity, spinal cord injury or upper motor neuron syndrome. Other uses of these compounds are described in U.S. Pat. No. 5,859,186, incorporated herein by reference.

A "neuroprotectant" is a compound capable of preventing the neuronal death associated with a neurological disorder or disease. An "anticonvulsant" is a compound capable of reducing convulsions produced by conditions such as simple partial seizures, complex partial seizures, status epilepticus, and trauma-induced seizures such as occur following head injury, including head surgery. An "analgesic" is a compound capable of relieving pain by altering perception of nociceptive stimuli without producing anesthesia or loss of consciousness. A "muscle relaxant" is a compound that reduces muscular tension. A "adjunct in general anesthesia" is a compound useful in conjunction with anesthetic agents in producing the loss of ability to perceive pain associated with the loss of consciousness.

The invention relates as well to methods useful for treatment of neurological disorders and diseases, including, but not limited to, global and focal ischemic and hemorrhagic stroke, head trauma, spinal cord injury, hypoxia-induced nerve cell damage such as in cardiac arrest or neonatal distress, epilepsy or other convulsive disorders without undesirable side effects.

Thus, in one aspect, the invention provides a method of reducing/alleviating/decreasing the perception of pain by a subject or for inducing analgesia in a subject comprising administering to the subject an effective amount of the pharmaceutical composition comprising a therapeutically effective amount of a member of the O-Superfamily conotoxins of the present invention or a pharmaceutically acceptable salt or solvate thereof. The pain may be acute, persistent, inflammatory or neuropathic pain.

In a second aspect, the invention provides a method of treating stroke, head or spinal cord trauma or injury, anoxia, hypoxia-induced nerve cell damage, ischemia, migraine, psychosis, anxiety, schizophrenia, inflammation, movement disorder, epilepsy, any other convulsive disorder or in the prevention of the degenerative changes connected with the same in a subject comprising administering to the subject an effective amount of the pharmaceutical composition comprising a therapeutically effective amount of a member of the O-Superfamily conotoxins of the present invention or a pharmaceutically acceptable salt or solvate thereof.

In a third embodiment, such a pharmaceutical composition comprises a member of the O-Superfamily conotoxins described herein which is useful These conopeptides have long lasting anesthetic activity and are particularly useful for spinal anesthesia, either administered acutely for postoperative pain or via an intrathecal pump for severe chronic pain situations or for treatment of pain in epithelial tissue. The activity of $\mu$O-conotoxin peptides, members of the O-Superfamily, on sodium channels is described in U.S. patent application Ser. No. 09/590,386 (International Application No. PCT/US00/15779) filed on Jun. 9, 2000, incorporated herein by reference. The treatment according to this embodiment comprises the step of administering to such a living animal body, including a human, in need thereof a therapeutically effective amount of a pharmaceutical composition of the present invention.

More specifically, in one aspect, the pain results from surgical or medical procedures, and a member of the O-Superfamily conotoxins as described herein is administered to the central nervous system (CNS), e.g. to the spine for spinal analgesia. In a second aspect, the pain is in an epithelial tissue region associated with damage or loss of epithelial tissue as a result of, for example, plastic surgery, canker sores, burns, sore throats, genital lesions, upper or lower gastrointestinal bronchoscopy or endoscopy, intubation, dermatologic abrasions or chemical skin peels, and a member of the O-Superfamily conotoxins as described herein is administered to alleviate the associated pain.

In a fourth embodiment, such a pharmaceutical composition comprises a member of the O-Superfamily conotoxins which has the capability of activating (i.e., opening) ATP-sensitive $K^+$ channels, and is thus useful for treating a disorder or disease of a living animal body, including a human, which disorder or disease is responsive to the activation of ATP-sensitive $K^+$ channels. The activity of $\kappa$-conotoxin peptides, members of the O-Superfamily, on sodium channels is described in U.S. patent application Ser. No. 09/666,837 (International Application No. PCT/US00/25827) filed on Sep. 21, 2000, incorporated herein by reference. The treatment according to this embodiment comprises the step of administering to such a living animal body, including a human, in need thereof a therapeutically effective amount of a pharmaceutical composition of the present invention. Thus the invention provides a method for treating cardiac ischemia, neuronal ischemia, ocular ischemia or asthma in a subject comprising administering to the subject an effective amount of the pharmaceutical composition comprising a therapeutically effective amount of a member of the O-Superfamily conotoxins described herein or a pharmaceutically acceptable salt or solvate thereof.

In a fifth embodiment, such a pharmaceutical composition comprises a member of the O-Superfamily conotoxins which has the capability of acting on proton gated ion channels, and ise thus useful for treating a disorder, disease or condition of a living animal body, including a human, which disorder, disease or condition is responsive to the partial or complete blockade of proton-gated ion channels. Since, these members of the O-Superfamily antagonize the proton-gated ion channel, they are useful as analgesics, especially for pain associated with inflammation, hematomas, cardiac or muscle ischemia, or cancer. Thus, in one aspect of the present invention, the peptides and derivatives disclosed herein are useful as analgesics, i.e., for the reduction in the perception of pain or the induction of analgesia. The treatment according to this embodiment comprises the step of administering to such a living animal body, including a human, in need thereof a therapeutically effective amount of a pharmaceutical composition of the present invention.

The conotoxin peptides of the present invention are identified by isolation from Conus venom. Alternatively, the conotoxin peptides of the present invention are identified using recombinant DNA techniques by screening cDNA libraries of various Conus species using conventional techniques, such as the use of reverse-transcriptase polymerase chain reaction (RT-PCR) or the use of degenerate probes. Primers for RT-PCR are based on conserved sequences in the signal sequence and 3' untranslated region of the conotoxin peptides genes isolated using degenerate probes. Clones which hybridize to degenerate probes are analyzed to identify those which meet minimal size requirements, i.e., clones having approximately 300 nucleotides (for a propeptide), as determined using PCR primers which flank the cDNA cloning sites for the specific cDNA library being examined. These minimal-sized clones and the clones produced by RT-PCR are then sequenced. The sequences are then examined for the presence of a peptide having the characteristics noted above for the O-Superfamily conotoxin peptides.

The conotoxin peptides described herein are sufficiently small to be chemically synthesized. General chemical syntheses for preparing the foregoing conotoxin peptides are described hereinafter. Various ones of the conotoxin peptides can also be obtained by isolation and purification from specific Conus species using the technique described in U.S. Pat. Nos. 4,447,356 (Olivera et al., 1984); U.S. Pat. Nos. 5,514,774; 5,719,264; and 5,591,821, as well as in PCT published application WO 98/03189, the disclosures of which are incorporated herein by reference.

Although the conotoxin peptides of the present invention can be obtained by purification from cone snails, because the amounts of conotoxin peptides obtainable from individual snails are very small, the desired substantially pure conotoxin peptides are best practically obtained in commercially valuable amounts by chemical synthesis using solid-phase strategy. For example, the yield from a single cone snail may be about 10 micrograms or less of conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active conotoxin peptides depends of course upon correct determination of the amino acid sequence.

The conotoxin peptides can also be produced by recombinant DNA techniques well known in the art. Such techniques are described by Sambrook et al. (1989). A gene of interest (i.e., a gene that encodes a suitable conotoxin peptide) can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/expression vector combinations may be used to express a gene encoding a conotoxin peptide of interest. Such combinations are well known to a skilled artisan. The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an a-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH-BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HOBt or HOAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetramethyluronium hexafluorophosphate (HBTU) and diethylisopro- pylethylamine (DIEA). The FMOC protecting group is removed by treatment with a 20% solution of piperidine in dimethylformamide (DMF). Resins are subsequently washed with DMF (twice), followed by methanol and NMP.

Muteins, analogs or active fragments, of the foregoing conotoxin peptides are also contemplated here. See, e.g., Hammerland et al, Eur. J. Pharmacol., 226, pp. 239–244 (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50—col. 3, line 8); U.S. Pat. No. 5,534,615 (see particularly col. 19, line 45—col. 22, line 33); and U.S. Pat. No. 5,364,769 (see particularly col. 4, line 55—col. 7, line 26), each herein incorporated by reference.

Pharmaceutical compositions containing a compound of the present invention or its pharmaceutically acceptable salts or solvates as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alohatocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer & Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally. This administration is preferably by a pump.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in a therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Dosage may be adjusted appropriately to achieve desired drug levels, locally or systemically. Typically the active agents of the present invention exhibit their effect at a dosage range from about 0.001 mg/kg to about 250 mg/kg, preferably from about 0.01 mg/kg to about 100 mg/kg of the active ingredient, more preferably from a bout 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

For the treatment of pain, if the route of administration is directly to the CNS, the dosage contemplated is from about 1 ng to about 100 mg per day, preferably from about 100 ng to about 10 mg per day, more preferably from about 1 $\mu$g to about 100 $\mu$g per day. If administered peripherally, the dosage contemplated is somewhat higher, from about 100 ng to about 1000 mg per day, preferably from about 10 $\mu$g to about 100 mg per day, more preferably from about 100 $\mu$g to about 10 mg per day. If the conopeptide is delivered by continuous infusion (e.g., by pump delivery, biodegradable polymer delivery or cell-based delivery), then a lower dosage is contemplated than for bolus delivery.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conotoxin peptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Meth-*

*ods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Isolation of O-Superfamily Conotoxins

Crude venom was extracted from venom ducts (Cruz et al., 1976), and the components were purified as previously described (Cartier et al., 1996). The crude extract from venom ducts was purified by reverse phase liquid chromatography (RPLC) using a Vydac $C_{18}$ semi-preparative column (10×250 mm). Further purification of bioactive peaks was done on a Vydac $C_{18}$ analytical column (4.6×220 mm). The effluents were monitored at 220 nm. Peaks were collected, and aliquots were assayed for activity.

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, peptides δ-GmVIA, δ-PVIA, δ-SVIE, δ-SVIE [D1E], δ-NgVIA, δ-TxVIA and Israel TxVIA were obtained.

Example 2

Synthesis of Conopeptides

The synthesis of conopeptides, either the mature toxins or the precursor peptides, was separately performed using conventional protection chemistry as described by Cartier et al. (1996). Briefly, the linear chains were built on Rink amide resin by Fmoc procedures with 2-(1H-benzotriol-1-yl)-1,1,3,3,-tetramethyluronium tetrafluoroborated coupling using an ABI model 430A peptide sythesizer with amino acid derivatives purchased from Bachem (Torrence Calif.). Orthogonal protection was used on cysteines: two cysteines were protected as the stable Cys(S-acetamidomethyl), while the other two cysteines were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except the Cys(S-acetamidomethyl). The peptides were dissolved in 0.1% TFA and 60% acetonitrile and purified by RPLC on a Vydac $C_{18}$ preparative column (22×250 mm) and eluted at a flow rate of 20 mL/min with a gradient of acetonitrile in 0.1% TFA.

The disulfide bridges in the three conopeptides were formed as described in Cartier et al. (1996). Briefly, the disulfide bridges between one pair of cysteines were formed by air oxidation which was judged to be complete by analytical RPLC. The monocyclic peptides were purified by RPLC on a Vydac $C_{18}$ prepartive column (22×250 mm) and eluted with a gradient of acetonitrile in 0.1% TFA. Removal of S-acetamidomethyl groups and closure of the disulfide bridge between the other pair of cysteines was carried out simultaneously be iodine oxidation. The cyclic peptides were purified by RPLC on a Vydac $C_{18}$ prepartive column (22×250 mm) and eluted with a gradient of acetonitrile in 0.1% TFA.

Example 3

Isolation of DNA Encoding O-Superfamily Conotoxins

DNA coding for conotoxins described herein was isolated and cloned in accordance with conventional techniques using general procedures well known in the art, such as described in Olivera et al. (1996). Alternatively, cDNA libraries was prepared from Conus venom duct using conventional techniques. DNA from single clones was amplified by conventional techniques using primers which correspond approximately to the M13 universal priming site and the M13 reverse universal priming site. Clones having a size of approximately 300–500 nucleotides were sequenced and screened for similarity in sequence to known O-Superfamily conotoxins, including the δ-conotoxins isolated in Example 1. The DNA sequences, encoded propeptide sequences and sequences of the mature toxins are set forth in the attached Table 1. DNA sequences coding for the mature toxin can also be prepared on the basis of the DNA sequences set forth on these pages. An alignment of the conotoxins is set forth in Table 2.

TABLE 1

Sequences of Mature O-Superfamily Conotoxins,
Propeptides and DNA Encoding Propeptides

Name: δ-GmVIA

Species: *gloriamaris*

Isolated: Yes

Cloned: Yes

DNA Sequence:

ATGAAACTGACGTGCATGATGATCGTTGCTGTGCTGTTCTTGACCGCCTGGACATTC (SEQ ID NO:1)

GTCACGGCTGATGACTCCGGAAATGGAATGGAGATTCTTTTTCCGAAGGCGGGTCA

CGAAATGGAGAACCTCGAAGTCTCTAATCGGGTCAAGCCGTGCCGTAAAGAAGGTC

TABLE 1-continued

Sequences of Mature O-Superfamily Conotoxins,
Propeptides and DNA Encoding Propeptides

AACTTTGTGATCCGATATTTCAAAACTGCTGCCGTGGCTGGAATTGCGTTCTTTTCTG

CGTCTGAAACTACCGTGATGTCTTCTCTCCCCTC

Translation:

MKLTCMMIVAVLFLTAWTFVTADDSGNGMEILFPKAGHEMENLEVSNRVKPCRKEGQ (SEQ ID NO:2)

LCDPIFQNCCRGWNCVLFCV

Toxin Sequence:

Val-Lys-Xaa3-Cys-Arg-Lys-Xaa1-Gly-Gln-Leu-Cys-Asp-Xaa3-Ile-Phe-Gln-Asn-Cys-Cys-Arg- (SEQ ID NO:3)

Gly-Xaa4-Asn-Cys-Val-Leu-Phe-Cys-Val-^

Name: δ-GmVIA [F15Y]

Species: gloriamaris

Toxin Sequence:

Val-Lys-Xaa3-Cys-Arg-Lys-Xaa1-Gly-Gln-Leu-Cys-Asp-Xaa3-Ile-Xaa5-Gln-Asn-Cys-Cys- (SEQ ID NO:4)

Arg-Gly-Xaa4-Asn-Cys-Val-Leu-Phe-Cys-Val-^

Name: δ-GmVIA [F27Y]

Species: gloriamaris

Isolated: No

Toxin Sequence:

Val-Lys-Xaa3-Cys-Arg-Lys-Xaa1-Gly-Gln-Leu-Cys-Asp-Xaa3-Ile-Phe-Gln-Asn-Cys-Cys-Arg- (SEQ ID NO:5)

Gly-Xaa4-Asn-Cys-Val-Leu-Xaa5-Cys-Val-^

Name: Omaria9

Species: omaria

Isolated: No

Cloned: Yes

DNA Sequence:

GAAGCTGGTACGCCTGCAGGTACCGGTCCGGAATTCCCGGGTCGACATCATCATCA (SEQ ID NO:6)

TCGATCCATCTGTCCATCCATCCATTCATTCATTCGCTGCCAGACTATAATAAACATT

CAAGTCTCTCTTTCTTTTTGTGTCTGACAGATCGATCAGGATGTGCCGTAGAGAAGC

TCAACTTTGTGATCCGATTTTTCAAAACTGCTGCCATGGCTTGTTTTGCGTTTTGGTC

TGCGTCTAAAACTACCGTGATGTCTTCTCCTCCCCTCTAGTAGTAGTAGGCGGCCGC

TCTAGAGGATCCAAGCTTACGTACGCGTGCATGCGACGTCATAGCTCTTCTATAGTG

TCACCTAAATTCAATTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGGACGCGCCCTGTAGCGGCGCATTAT

Translation:

SIRMCRREAQLCDPIFQNCCHGLFCVLVCV (SEQ ID NO:7)

TABLE 1-continued

Sequences of Mature O-Superfamily Conotoxins,
Propeptides and DNA Encoding Propeptides

Toxin Sequence:

Met-Cys-Arg-Arg-Xaa1-Ala-Gln-Leu-Cys-Asp-Xaa3-Ile-Phe-Gln-Asn-Cys-Cys-His-Gly-Leu- (SEQ ID NO:8)

Phe-Cys-Val-Leu-Val-Cys-Val-^

Name: Tx6.11

Species: *textile*

Isolated: No

Cloned: Yes

DNA Sequence:

GGCATTACCTAAAACATCACCAAGATGAAACTGACGTGCATGATGATCGTTGCTGT (SEQ ID NO:9)

GCTGTTCTTGACCGCCTGGACATTCGTCACGGCTGATGACTCCAGAAATGGAATGGA

GAATCTTTTTCCGAAGGCAGGTCACGAAATGGAGAACCTCGAAGACTCTAAACACA

GGCACCAGGAGAGACCGGACACCGGCGACAAAGAAGAGATGCTGCTACAGAGACA

GGTCAAGCCGTGTCGTAAAGAACATCAACTTTGTGATCTGATTTTTCAAAACTGCTG

CCGTGGCTGGTATTGCGTTGTTCTGTCTTGCACTTGAAAGCTACCTGATGTTCTAC

TCCCATC

Translation:

MKLTCMMIVAVLFLTAWTFVTADDSRNGMENLFPKAGHEMENLEDSKHRHQERPDTG (SEQ ID NO:10)

DKEEMLLQRQVKPCRKEHQLCDLIFQNCCRGWYCVVLSCT

Toxin Sequence:

Xaa2-Val-Lys-Xaa3-Cys-Arg-Lys-Xaa1-His-Gln-Leu-Cys-Asp-Leu-Ile-Phe-Gln-Asn-Cys-Cys- (SEQ ID NO:11)

Arg-Gly-Xaa4-Xaa5-Cys-Val-Val-Leu-Ser-Cys-Thr-^

Name: Om6.6

Species: *omaria*

Isolated: No

Cloned: Yes

DNA Sequence:

ATGAAACTGACGTGCCTGATGATCGTTGCCGTGCTGTCCTTGACCGGCTGGACATTC (SEQ ID NO:12)

GTCACGGCTGATGACTCTGGAAATGGATTGGGGAATCTTTTTTCGAATGCACATCAC

GAAATGAAGAACCCCGAAGCCTCTAAATTGAACAAGAGGTGCGTTCCACACGAGGG

CCCTTGTAATTGGCTTACACAAAACTGCTGCAGTGGTTATAATTGCATCATTTTTTTC

TGCCTATAAAACTACCGTGATGTCTTCTCTTCCCCTC

Translation:

MKLTCLMIVAVLSLTGWTFVTADDSGNGLGNLFSNAHHEMKNPEASKLNKRCVPHEG (SEQ ID NO:13)

PCNWLTQNCCSGYNCIIFFCL

TABLE 1-continued

Sequences of Mature O-Superfamily Conotoxins,
Propeptides and DNA Encoding Propeptides

Toxin Sequence:

Cys-Val-Xaa3-His-Xaa1-Gly-Xaa3-Cys-Asn-Xaa4-Leu-Thr-Gln-Asn-Cys-Cys-Ser-Gly-Xaa5- (SEQ ID NO:14)

Asn-Cys-Ile-Phe-Phe-Cys-Leu-

Name: Da6.2

Species: dalli

Isolated: No

Cloned: Yes

DNA Sequence:

ATGAAACTGACGTGCCTGCTGATCATTGCTGTGCTGTTCTTGACCGCCTGGACATTC (SEQ ID NO:15)

GTCACGGCTGATGACTCCGGAAATGGAATGGAGAATCTTTTTCCGAAGGCACGTCA

CGAAATGGAGAACCTCGAAGACTCTAAACACAGGCACCAGGAGAGACCGGACACG

GGCGACAAAGAAGAGATGCTGCTACAGAGACAGGTCAAGCCGTGTCGTAAAGAAC

ATCAACTTTGTGATCTGATTTTTCAAAACTGCTGCCGTGGCTGGTATTGCTTGCTTCG

TCCTTGCATCTGAAACTACCGTGATGTCTTCTCTCCCATC

Translation:

MKLTCLLIIAVLFLTAWTFVTADDSGNGMENLFPKARHEMENLEDSKHRHQERPDTGD (SEQ ID NO:16)

KEEMLLQRQVKPCRKEHQLCDLIFQNCCRGWYCLLRPCI

Toxin Sequence:

Xaa2-Val-Lys-Xaa3-Cys-Arg-Lys-Xaa1-His-Gln-Leu-Cys-Asp-Leu-Ile-Phe-Gln-Asn-Cys-Cys- (SEQ ID NO:17)

Arg-Gly-Xaa4-Xaa5-Cys-Leu-Leu-Arg-Xaa3-Cys-Ile-

Name: Da6.6

Species: dalli

Isolated: No

Cloned: Yes

DNA Sequence:

ATGAAACTGACGTGTATGCTGATCATTGCTGTGCTGTTCTTGACCGCCTGGACATTC (SEQ ID NO:18)

GTCACGGCTGATGACTCCGGAAATGGAATGGAGAATCTTTTTCCGAAGGCACGTCA

CGAAATGGAGAACCTCGAAGACTCTAAACACAGGCACCAGGAGAGACCGGACACG

GGCGACAAAGAAGAGATGCTGCTACAGAGACGGGTCAAGCCGTGCAGTGAAGAAG

GTCAACTTTGTGATCCACTTTCTCAAAACTGCTGCCGTGGCTGGCATTGCGTTCTTGT

CTCTTGCGTCTGAAACTACCGTGATGTCTTCTCTCCCATC

Translation:

MKLTCMLIIAVLFLTAWTFVTADDSGNGMENLFPKARHEMENLEDSKHRHQERPDTGD (SEQ ID NO:19)

KEEMLLQRRVKPCSEEGQLCDPLSQNCCRGWHCVLVSCV

TABLE 1-continued

Sequences of Mature O-Superfamily Conotoxins,
Propeptides and DNA Encoding Propeptides

Toxin Sequence:

Val-Lys-Xaa3-Cys-Ser-Xaa1-Xaa1-Gly-Gln-Leu-Cys-Asp-Xaa3-Leu-Ser-Gln-Asn-Cys-Cys- (SEQ ID NO:20)

Arg-Gly-Xaa4-His-Cys-Val-Leu-Val-Ser-Cys-Val-^

Name: δ-TxVIA

Species: *textile*

Isolated: Yes

Cloned: Yes

DNA Sequence:

AAACATCGCCAAGATGAAACTGACGTGCATGATGATCGTTGCTGTGCTGTTCTTGAC (SEQ ID NO:21)

CGCCTGGACATTTGCCACGGCTGATGACCCCAGAAATGGATTGGGGAATCTTTTTTC

GAATGCACATCACGAAATGAAGAACCCCGAAGCCTCTAAATTGAACAAGAGGTGGT

GCAAACAAAGCGGTGAAATGTGTAATTTGTTAGACCAAAACTGCTGCGACGGCTAT

TGCATAGTACTTGTCTGCACATAAAACTGCCGTGATGTCTTCTCTTCCCTCTGTGCT

ACCTGGCTTGATCTTTGATTGGCGCGTGTCGTTCACTGGTTATGAACCCCCCCCCC

CCCCCCCCCCCCCCCCTTCCGGCTCTCTGGAGGCCTCGGGGGTTCAACATCCAATAA

AGTGACAG

Translation:

MRLTCMMIVAVLFLTAWTFATADDPRNCLGNLFSNAHHEMKNEASKLNKRWCKQS (SEQ ID NO:22)

GEMCNLLDQNCCDGYCIVLVCT

Toxin Sequence:

Xaa4-Cys-Lys-Gln-Ser-Gly-Xaa1-Met-Cys-Asn-Leu-Leu-Asp-Gln-Asn-Cys-Cys-Asp-Gly- (SEQ ID NO:23)

Xaa5-Cys-Ile-Val-Leu-Val-Cys-Thr-^

Name: δ-TxVIA [M8J]

Species: *textile*

Toxin Sequence:

Xaa4-Cys-Lys-Gln-Ser-Gly-Xaa1-Xaa6-Cys-Asn-Leu-Leu-Asp-Gln-Asn-Cys-Cys-Asp-Gly- (SEQ ID NO:24)

Xaa5-Cys-Ile-Val-Leu-Val-Cys-Thr-^

Name: M6.4

Species: *magus*

Isolated: No

Cloned: Yes

DNA Sequence:

ATGAAACTGACGTGTGTGATGATCGTTGCTGTGCTGTTCTTGACCGCCTGGACATTT (SEQ ID NO:25)

GCCACGGCTGATGACCCCAGAAATGGATTGGGGAATCTTTTTTCGAATGCACATCAC

GAAATGAAGAACCCCGAAGCCTCTAAATTGAACAAGAGGTGGTGCAAACAAAGCG

GTGAAATGTGTAATTTGTTAGACCAAAACTGCTGCGACGGCTATTGCATAGTACTTG

TCTGCACATAAAACTGCCGTGATGTCTTCTCCTCCCCTC

TABLE 1-continued

Sequences of Mature O-Superfamily Conotoxins,
Propeptides and DNA Encoding Propeptides

Translation:

MKLTCVMIVAVLFLTAWTFATADDPRNGLGNLFSNAHHEMKNPEASKLNKRWCKQSG

EMCNLLDQNCCDGYCIVLVCT

Toxin Sequence:

Xaa4-Cys-Lys-Gln-Ser-Gly-Xaa1-Met-Cys-Asn-Leu-Leu-Asp-Gln-Asn-Cys-Cys-Asp-Gly-    (SEQ ID NO:27)

Xaa5-Cys-Ile-Val-Leu-Val-Cys-Thr-^

Name: Israel TxIA

Species: *textile*

Isolated: Yes

Cloned: No

Toxin Sequence:

Xaa4-Cys-Lys-Gln-Ser-Gly-Xaa1-Met-Cys-Asn-Leu-Leu-Asp-Gln-Asn-Cys-Cys-Asp-Gly-    (SEQ ID NO:28)

Xaa5-Cys-Ile-Phe-Val-Cys-Thr-^

Name: Di6.2

Species: *distans*

Isolated: No

Cloned: Yes

DNA Sequence:

ATGAAACTGACGTGCCTGATGATCGTTGCTGTGCTGTTCTTGACCGCCTGGACATTT    (SEQ ID NO:29)

GCCACGGCTGATGACCCCAGAAATGGATTGGGGAATCTTTTTTCGAATGCACATCAC

GAAATGAAGAACCCCGAAGCCTCTAAATTGAACAAGAGGTGGTGCAAACAAAGCG

GTGAAATGTGTAATTTGTTAGACCAAAACTGCTGCGACGGCTATTGCATAGTACTTG

TCTGCACATAAAACTGCCGTGATGTCTTCTCCTCCCCTC

Translation:

MKLTCLMIVAVLFLTAWTFATADDPRNGLGNLFSNAHHEMKNPEASKLNKRWECKQSG    (SEQ ID NO:30)

EMCNLLDQNCCDGYCIVLVCT

Toxin Sequence:

Xaa4-Cys-Lys-Gln-Ser-Gly-Xaa1-Met-Cys-Asn-Leu-Leu-Asp-Gln-Asn-Cys-Cys-Asp-Gly-    (SEQ ID NO:31)

Xaa5-Cys-Ile-Val-Leu-Val-Cys-Thr-^

Name: Af6.9

Species: *ammiralis*

Isolated: No

Cloned: Yes

DNA Sequence:

ATGAAACTGACGTGCGTGATGATCGTTGCTGTGCTGTTCTTGACCGCCTGGACATTT    (SEQ ID NO:32)

GCCACGGCTGATGACCCCAGAAATGGATTGGGGAATCTTTTTTCGAATGCACATCAC

GAAATGAAGAACCCCGAAGCCTCTAAATTGAACAAGAGGTGGTGCAAACAAAGCG

TABLE 1-continued

Sequences of Mature O-Superfamily Conotoxins,
Propeptides and DNA Encoding Propeptides

GTGAAATGTGTAATTTGTTAGACCAAAACTGCTGCGAGGGCTATTGCATAGTACTTG

TCTGCACATAAAACTGCCGTGATGTCTTCTCCTCCCCTC

Translation:

MKLTCVMIVAVLFLTAWTFATADDPRNGLGNLFSNAHHEMKNPEASKLNKRWCKQSG (SEQ ID NO:33)

EMCNLLDQNCCEGYCIVLVCT

Toxin Sequence:

Xaa4-Cys-Lys-Gln-Ser-Gly-Xaa1-Met-Cys-Asn-Leu-Leu-Asp-Gln-Asn-Cys-Cys-Xaa1-Gly- (SEQ ID NO:34)

Xaa5-Cys-Ile-Val-Leu-Val-Cys-Thr-^

Name: Da6.4

Species: *dalli*

Isolated: No

Cloned: Yes

DNA Sequence:

ATGAAACTGACGTGCGTGATGATCGTTGCTGTGCTGTTCTTGACCGCCTGGACATTC (SEQ ID NO:35)

GCCACGGCTGATGACCCCAGAAATGGATTGGAGAATCTTTTTTTGAAGGCACATCA

CGAAATGAACCCCGAAGCCTCTAAGTTGAATGAGAGGTGCCTTGGTGGTGGTGAAG

TTTGTGATATCTTTTTTCCACAATGCTGTGGCTATTGCATTCTTCTTTTCTGCACATAA

AACTACCGTGATGTCTTCTCCTCCCCTC

Translation:

MKLTCVMIVAVLFLTAWTFATADDPRNGLENLFLKAHHPEASKLNERCLGGGEV (SEQ ID NO:36)

CDIFFPQCCGYCILLFCT

Toxin Sequence:

Cys-Leu-Gly-Gly-Gly-Xaa1-Val-Cys-Asp-Ile-Phe-Phe-Xaa3-Gln-Cys-Cys-Gly-Xaa5-Cys-Ile- (SEQ ID NO:37)

Leu-Leu-Phe-Cys-Thr-^

Name: Gm6.5

Species: *gloriamaris*

Isolated: No

Cloned: Yes

DNA Sequence:

GCTTGCACGGTGAATTTGGCTTCACAGTTTTCCACTGTCGTCTTTGGCATCATCTGAA (SEQ ID NO:38)

ACATCGCCAAGATGAAACTGACGTGCATGATGATCGTTGCTGTGCTGTTCTTGACCG

CCTGGACATTTGCCACGGCTGATGACCCCAGAAATGGATTGGGGAATATTTTTTCGA

ATGCACATCACGAAATGAAGAATCCCGAAGCCTCTAAATTGAACAAGAGGTGCCGT

CTAGGGGCTGAAAGTTGTGATGTAATTTCACAAAACTGCTGCCAAGGCACGTGCGT

TTTTTTCTGCTTACCATGATGTCTTCTATTCTCCTCTGTGCTACCTGGCTTGATCTTTC

ATTAGCGCGTGCCTTTCACTGGTTATGAACCCCCTGATCCGACTCTCTGGCAGCCTC

GGGGGTTCAACATCCAAATAAAACGACAGCACAATGACAAA

TABLE 1-continued

Sequences of Mature O-Superfamily Conotoxins, Propeptides and DNA Encoding Propeptides

Translation:

MKLTCMMIVAVLFLTAWTFATADDPRNGLGNIFSNAHHEMKNPEASKLNKRCRLGAE (SEQ ID NO:39)

SCDVISQNCCQGTCVFFCLP

Toxin Sequence:

Cys-Arg-Leu-Gly-Ala-Xaa1-Ser-Cys-Asp-Val-Ile-Ser-Gln-Asn-Cys-Cys-Gln-Gly-Thr-Cys-Val- (SEQ ID NO:40)

Phe-Phe-Cys-Leu-Xaa3-^

Name: Gm6.6

Species: gloriamaris

Isolated: No

Cloned: Yes

DNA Sequence:

GGATCCTTGCACGGTGAATTTGGCTTCACAGTTTTCCACTGTCGTCTTTCGCATCATC (SEQ ID NO:41)

CAAAACATCACCAAGATGAAACTGACGTGCATGATGATCGTTGCTGTGCTGTTCTTG

ACCGCCTGGACATTCGCCACGGCTGATGACCCCAGAAATGGATTGGAGAAACTTTT

TTCGAATACACATCACGAAATGAAGAACCCCGAAGCCTCTAAATTGAACAAGAGGT

GCAAACAAGCTGATGAATCTTGTAATGTATTTTCACTTGACTGCTGCACCGGCTTAT

GCTTGGGATTCTGCGTATCGTGATGTCTTCTACTCCCCTCTGTgCTACCTGGCTTGAT

CTTTGATTGGCGTGTGCCTTTCATTGGTTATGAACCCCCCTGATCCGATTCTTTGGCG

GCCTCGGGGGTTCAACATCCAAATAAAGCGACAGCACAATAAAAAA

Translation:

MKLTCMMIVAVLFLTAWTFATADDPRNGLEKLFSNTHHEMKNPEASKLNKRCKQADE (SEQ ID NO:42)

SCNVFSLDCCTGLCLGFCVS

Toxin Sequence:

Cys-Lys-Gln-Ala-Asp-Xaa1-Ser-Cys-Asn-Val-Phe-Ser-Leu-Asp-Cys-Cys-Thr-Gly-Leu-Cys- (SEQ ID NO:43)

Leu-Gly-Phe-Cys-Val-Ser-^

Name: Gm6.3

Species: gloriamaris

Isolated: No

Cloned: Yes

DNA Sequence:

ATGAAACTGACGTGCATGATGATCGTTGCTGTGCTGTTCTTGACCACCTGGACATTC (SEQ ID NO:44)

GCCACGGCCATCACCAGGAATGGATTGGGGAATCTTTTTCCGAAGAATCATCACGA

AATGAAGAACCCCGAAGCCTCTAAATTGAACAAGAGGTGCGTTCCATACGAGGGCC

CTTGTAATTGGCTTACACAAAACTGCTGCGATGAGCTATGCGTATTTTTCTGCCTAT

AAAACTAGCCTGATGT

TABLE 1-continued

Sequences of Mature O-Superfamily Conotoxins,
Propeptides and DNA Encoding Propeptides

Translation:

MKLTCMMIVAVLFLTTWTFATAITRNGLGNLFPKNHHEMKNPEASKLNKRCVPYEGPC (SEQ ID NO:45)

NWLTQNCCDELCVFFCL

Toxin Sequence:

Cys-Val-Xaa3-Xaa5-Xaa1-Gly-Xaa3-Cys-Asn-Xaa4-Leu-Thr-Gln-Asn-Cys-Cys-Asp-Xaa1- (SEQ ID NO:46)

Leu-Cys-Val-Phe-Phe-Cys-Leu-^

Name: M6.5

Species: *magus*

Isolated: No

Cloned: Yes

DNA Sequence:

ATGAAACTGACGTGCGTGATGATCGTTGCTGTGCTCTTCTTGACCGTCTGGACATTC (SEQ ID NO:47)

GCCACGGCTGATGACTCCGGAAATGGATTGGAGAAACTTTTTTCGAATGCACATCA

CGAAATGAAGAACCCCGAAGCCTCTAAATTGAACAAGAGGTGCAAACAAGCTGAT

GAACCTTGTGATGTATTTTCACTTGAATGCTGCACCGGCATATGTCTTGGATTCTGC

ACGTGGTGATGTCTTCCCTCCCCTC

Translation:

MKLTCVMIVAVLFLTVWTFATADDSGNGLEKLFSNAHHEMKNPEASKLNKRCKQADE (SEQ ID NO:48)

PCDVFSLECCTGICLGFCTW

Toxin Sequence:

Cys-Lys-Gln-Ala-Asp-Xaa1-Xaa3-Cys-Asp-Val-Phe-Ser-Leu-Xaa1-Cys-Cys-Thr-Gly-Ile-Cys- (SEQ ID NO:49)

Leu-Gly-Phe-Cys-Thr-Xaa4-^

Name: Tx6.2

Species: *textile*

Isolated: No

Cloned: Yes

DNA Sequence:

GCCTTGCACGGTGAATTTGGCTTCATAGTTTTCCACTGTCGTCTTTGGCATCATCCAA (SEQ ID NO:50)

AACATCACCAAGATGAAACTGACGTGCATGATGATCGTTGCTGTGCTGTTCTTGACC

GCCTGGACATTCGCCACGGCTGATGACTCCAGCAATGGATTGGAGAATCTTTTTTTG

AAGGCACATCACGAAATGAACCCCGAAGCCTCTAAGTTGAACGAGAGGTGCCTTGA

TGCTGGTGAAGTTTGTGATATTTTTTTTCCAACATGCTGCGGCTATTGCATTCTTCTT

TTCTGCGCATAAAACTACCGTGATGTCTTCTACTCCCCTCTGTGCTACCTGGCTTGAT

CTTTGATTGGCGCGTACCCTTCACTGGTTATGAAACCCCTGATCCAGCTCTCTGGAG

GCCTCGGGGGTTCAACATCCAAATAAAGCGACA

TABLE 1-continued

Sequences of Mature O-Superfamily Conotoxins,
Propeptides and DNA Encoding Propeptides

Translation:

MKLTCMMIVAVLFLTAWTFATADDSSNGLENLFLKAHHEMNPEASKLNERCLDAGEV (SEQ ID NO:51)

CDIFFPTCCGYCILLFCA

Toxin Sequence:

Cys-Leu-Asp-Ala-Gly-Xaa1-Val-Cys-Asp-Ile-Phe-Phe-Xaa3-Thr-Cys-Cys-Gly-Xaa5-Cys-Ile- (SEQ ID NO:52)

Leu-Leu-Phe-Cys-Ala-^

Name: KK-1

Species: *textile*

Toxin Sequence:

Cys-Ile-Xaa1-Gln-Phe-Asp-Xaa3-Cys-Xaa1-Met-Ile-Arg-His-Thr-Cys-Cys-Val-Gly-Val-Cys- (SEQ ID NO:53)

Phe-Leu-Met-Ala-Cys-Ile-^

Name: KK-2

Species: *textile*

Toxin Sequence:

Cys-Ala-Xaa3-Phe-Leu-His-Xaa3-Cys-Thr-Phe-Phe-Phe-Xaa3-Asn-Cys-Cys-Asn-Ser-Xaa5- (SEQ ID NO:54)

Cys-Val-Gln-Phe-Ile-^

Name: Om6.1

Species: *omaria*

Isolated: No

Cloned: Yes

DNA Sequence:

ATGAAACTGACGTGCATGATGATCGTTGCTGTGCTGTTCTTGACCGCCTGGACATTC (SEQ ID NO:55)

GCCACGGCTGATGACCCCAGAAATGGATTGGAGAATTTTTTTTCGAAGACACAACA

CGAAATGAAGAACCCCGAAGCCTCTAAATTGAACAAGAGGTGCCTAGCAGAACATG

AAACTTGTAATATATTTACACAAAACTGCTGCGAAGGCGTGTGCATTTTTATCTGCG

TACAAGCTCCAGAGTGATGTCTTCTCCTCCCCTC

Translation:

MKLTCMMIVAVLFLTAWTFATADDPRNGLENFFSKTQHEMKNPEASKLNKRCLAEHE (SEQ ID NO:56)

TCNIFTQNCCEGVCIFICVQAPE

Toxin Sequence:

Cys-Leu-Ala-Xaa1-His-Xaa1-Thr-Cys-Asn-Ile-Phe-Thr-Gln-Asn-Cys-Cys-Xaa1-Gly-Val-Cys- (SEQ ID NO:57)

Ile-Phe-Ile-Cys-Val-Gln-Ala-Xaa3-Xaa1-^

Name: Om6.3

Species: *omaria*

Isolated: No

Cloned: Yes

TABLE 1-continued

Sequences of Mature O-Superfamily Conotoxins,
Propeptides and DNA Encoding Propeptides

DNA Sequence:

ATGAAACTGACTGTCATGATGATCGTTGCTGTGCTGTTCTTGACCGCCTGGACATTT (SEQ ID NO:58)

GCCACGGCTGAAGACCCCAGACATGGATTGGAGAATCTTTTTTCGAAGGCACATCA

CGAAATGAAGAACCCTGAAGACTCTAAATTGGACAAGAGGTGCATTCCACATTTTG

ACCCTTGTGACCCGATACGCCACACCTGCTGCTTTGGCCTGTGCCTACTAATAGCCT

GCATCTAAAACTGCCGTGATGTCTTCTCTCCCATC

Translation:

MKLTVMMIVAVLFLTAWTFATAEDPRHGLENLFSKAHHEMKNPEDSKLDKRCIPHEDP (SEQ ID NO:59)

CDPIRHTCCFGLCLLIACI

Toxin Sequence:

Cys-Ile-Xaa3-His-Phe-Asp-Xaa3-Cys-Asp-Xaa3-Ile-Arg-His-Thr-Cys-Cys-Phe-Gly-Leu-Cys- (SEQ ID NO:60)

Leu-Leu-Lle-Ala-Cys-Ile-

Name: Om6.4

Species: *omaria*

Isolated: No

Cloned: Yes

DNA Sequence:

ATGAAACTGACGTGCGTGATGACCGTTGCTGTGCTGTTCTTGACCGCCTGGACATTC (SEQ ID NO:61)

GTCACGGCTGAAGACCCCAGAGATGGATTGAAGAATCTTTTATCAAATGCACATAA

CGAAATGAAGAACCCCGAAGCCTCTACATTGAACGAGAGGTGCCTTGGGTTTGGTG

AAGCTTGTCTTATACTTTATTCAGACTGCTGCGGCTATTGCGTTGGTGCTATCTGCCT

ATAAAACTACCGTGATGTCTTCTCCTCCCCTC

Translation:

MKLTCVMTVAVLFLTAWTFVTAEDPRDGLKNLLSNAHNEMKNPEASTLNERCLGFGE (SEQ ID NO:62)

ACLILYSDCCGYCVGAICL

Toxin Sequence:

Cys-Leu-Gly-Phe-Gly-Xaa1-Ala-Cys-Leu-Ile-Leu-Xaa5-Ser-Asp-Cys-Cys-Gly-Xaa5-Cys-Val- (SEQ ID NO:63)

Gly-Ala-Ile-Cys-Leu-

Name: Au6.1

Species: *aulicus*

Isolated: No

Cloned: Yes

DNA Sequence:

ATGAAACTGACGTGTGTGATGATCGTTGCTGTGCTGTTCTTGACCGCCTGGACATTC (SEQ ID NO:64)

GCCACGGCTGATGACCCCAGAAATGGATTGGAGAATCTTTTTTCGAAGACACAACA

CAAAATGAAGAACCCCGAAGCCTCTAAATTGAACAAGAGGTGCAAAGCAGAAAAT

GAACTTTGTAATATATTTATACAAAACTGCTGCGACGGGACGTGCCTTCTTATCTGC

ATACAAAATCCACAGTGATGTCTTCTCTCCTACCCTC

TABLE 1-continued

Sequences of Mature O-Superfamily Conotoxins,
Propeptides and DNA Encoding Propeptides

Translation:

MKLTCVMIVAVLFLTAWTFATADDPRNGLENLFSKTQHKMKNPEASKLNKRCKAENE (SEQ ID NO:65)

LCNIFIQNCCDGTCLLICIQNPQ

Toxin Sequence:

Cys-Lys-Ala-Xaa1-Asn-Xaa1-Leu-Cys-Asn-Ile-Phe-Ile-Gln-Asn-Cys-Cys-Asp-Gly-Thr-Cys- (SEQ ID NO:66)

Leu-Leu-Ile-Cys-Ile-Cln-Asn-Xaa3-Gln-

Name: Au6.2

Species: *aulicus*

Isolated: No

Cloned: Yes

DNA Sequence:

ATGAAACTGACGTGCGTGATGATCGTTGCTGTGCTGTTCTTGACCGCCTGGACATTT (SEQ ID NO:67)

GCCACGGCTGATGACCCCAGAAATGGATTGGATAATCGTTTTTCGAAGGCACGTCA

CGAAATGAATAACCGCAGAGCCTCTAAATTGAACAAGAGGTGCCTTGAGTTTGGTG

AACTTTGTAATTTTTTTTTCCCAACCTGCTGCGGCTATTGCGTTCTTCTTGTCTGCCTA

TAAACTACCGTGATGTCTTCTCTTCCCCTC

Translation:

MKLTCVMIVAVLFLTAWTFATADDPRNGLDNRFSKARHEMNNRRASKLNKRCLEFGE (SEQ ID NO:68)

LCNFFFPTCCGYCVLLVCL

Toxin Sequence:

Cys-Leu-Xaa1-Phe-Gly-Xaa1-Leu-Cys-Asn-Phe-Phe-Phe-Xaa3-Thr-Cys-Cys-Gly-Xaa5-Cys- (SEQ ID NO:69)

Val-Leu-Leu-Val-Cys-Leu-

Name: Da6.5

Species: *dalli*

Isolated: No

Cloned: Yes

DNA Sequence:

ATGAAACTGACGTGTGTGATGATCGTTGCTGTGCTGTTCTTGACCGCCTGGACATTT (SEQ ID NO:70)

GTCATGGCTGATGACTCCGGAAATGGATTGGAAAATCTGTTTTCGAAGGCACATCA

CGAAATGAAGAACCCTGAAGCCTCTAAATTGAACAAGAGGTGCGCTCAAAGCAGTG

AATTATGTGATGCGCTGGACTCAGACTGCTGCAGTGGTGTTTGCATGGTATTTTTCT

GCCTATAAAACTGCCGTGATGTCTTCTCTATCCCCTC

Translation:

MKLTCVMIVAVLFLTAWTFVMADDSGNGLENLFSKAHHEMKNPEASKLNKRCAQSSE (SEQ ID NO:71)

LCDALDSDCCSGVCMVFFCL

TABLE 1-continued

Sequences of Mature O-Superfamily Conotoxins, Propeptides and DNA Encoding Propeptides

Toxin Sequence:

Cys-Ala-Gln-Ser-Ser-Xaa1-Leu-Cys-Asp-Ala-Leu-Asp-Ser-Asp-Cys-Cys-Ser-Gly-Val-Cys-Met-Val-Phe-Phe-Cys-Leu- (SEQ ID NO:72)

Name: Di6.4

Species: *distans*

Isolated: No

Cloned: Yes

DNA Sequence:

ATGAAACTGACGTGCGTGATGACCGTTGCTGTGCTGTTCTTGACCGCCTGGACATTC (SEQ ID NO:73)
GTCACGGCTGAAGACCCCAGAGATGGATTGAGGAATCTTTTATCGAATGCACGTCA
TGAAATGAAGAACCCCGAAGCCTCTAAATTGAACGAGAGGTGCCTTGGGTTTGGTG
AAGCTTGTCTTATGCTTTATTCAGACTGCTGCAGCTATTGCGTTGGTGCTGTCTGCCT
ATAAAACTACCGTGATGTCTTCTACTCCCATC

Translation:

MKLTCVMTVAVLFLTAWTFVTAEDPRDGLRNLLSNARHEMKNPEASKLNERCLGFGE (SEQ ID NO:74)
ACLMLYSDCCSYCVGAVCL

Toxin Sequence:

Cys-Leu-Gly-Phe-Gly-Xaa1-Ala-Cys-Leu-Met-Leu-Xaa5-Ser-Asp-Cys-Cys-Ser-Xaa5-Cys-Val-Gly-Ala-Val-Cys-Leu- (SEQ ID NO:75)

Name: Pn6.2

Species: *pennaceus*

Isolated: No

Cloned: Yes

DNA Sequence:

ATGAAACTGACGTGCCTGATGACCGTTGCTGTGCTGTTCTTGACCGCCTGGACATTT (SEQ ID NO:76)
GCCACGGCTGAAGACCCCAGAAATGGATTGGAGAATCTTTTTTCGAAGGCACATCA
CGAAATGAAGAACCCTGAAGACTCTAAATTGGACAAGAGGTGCGTTAAATATCTTG
ACCCTTGTGACATGTTACGCCACACCTGCTGCTTTGGCCTGTGCGTACTAATAGCCT
GCATCTAAAACTGCCGTGATGTCTTCTACTCCCATC

Translation:

MKLTCLMTVAVLFLTAWTFATAEDPRNGLENLFSKAHHEMKNPEDSKLDKRCVKYLD (SEQ ID NO:77)
PCDMLRHTCCFGLCVLIACI

Toxin Sequence:

Cys-Val-Lys-Xaa5-Leu-Asp-Xaa3-Cys-Asp-Met-Leu-Arg-His-Thr-Cys-Cys-Phe-Gly-Leu-Cys-Val-Leu-Ile-Ala-Cys-Ile- (SEQ ID NO:78)

Name: Pn6.3

Species: *pennaceus*

TABLE 1-continued

Sequences of Mature O-Superfamily Conotoxins,
Propeptides and DNA Encoding Propeptides

Isolated: No

Cloned: Yes

DNA Sequence:

ATGAAACTGACGTGTGTGATGATCGTTGCTGTGCTGTTCTTGACCGCCTGGACATTT (SEQ ID NO:79)

GCCACGGCTGATGACCCCAGAAATGGATTGGGGAATCTTTTTTCGAATGCACATCAC

GAAATGAAGAACCCCGAAGCTTCTAAATTGAACGAGAGGTGCCTTGGGTTTGGTGA

AGTTTGCAATTTCTTTTTTCCAAACTGCTGCAGCTATTGCGTTGCTCTTGTCTGCCTA

TAAAACTACCGTGATGTCTTCTATTCCCCTC

Translation:

MKLTCVMIVAVLFLTAWTFATADDPRNGLGNLFSNAHHEMKNPEASKLNERCLGFGE (SEQ ID NO:80)

VCKFFFPNCCSYCVALVCL

Toxin Sequence:

Cys-Leu-Gly-Phe-Gly-Xaa1-Val-Cys-Asn-Phe-Phe-Phe-Xaa3-Asn-Cys-Cys-Ser-Xaa5-Cys-Val- (SEQ ID NO:81)

Ala-Leu-Val-Cys-Leu-^

Name: Pn6.4

Species: *pennaceus*

Isolated: No

Cloned: Yes

DNA Sequence:

ATGAAACTGACGTGCGTGATGCTCGTTGCTGTGCTGTTCTTGACCGCCTGGACATTC (SEQ ID NO:82)

GCCACGGCTGATGACTCCAGCAATGGACTGGAGAATCTTTTTTCGAAGGCACATCA

CGAAATGAAGAACCCCGAAGCCTCTAAATTGAACAAGAGGTGCATTCCACAATTTG

ATCCTTGTGACATGGTACGTCACACTTGCTGCAAAGGGTTGTGCGTACTAATAGCCT

GCTCTAAAACTGCGTGATGTCTTCATCTCCCCTC

Translation:

MKLTCVMLVAVLFLTAWTFATADDSSNGLENLFSKAHHEMKNPEASKLNKRCIPQFDP (SEQ ID NO:83)

CDMVRHTCCKGLCVLIACSKTA

Toxin Sequence:

Cys-Ile-Xaa3-Gln-Phe-Asp-Xaa3-Cys-Asp-Met-Val-Arg-His-Thr-Cys-Cys-Lys-Gly-Leu-Cys- (SEQ ID NO:84)

Val-Leu-Ile-Ala-Cys-Ser-Lys-Thr-Ala-^

Name: Pn6.7

Species: *pennaceus*

Isolated: No

Cloned: Yes

DNA Sequence:

ATGAAACTGACGTGCTTGATGATCGTTGCTGTGCTGTTCTTGACCGCCTGGACATTC (SEQ ID NO:85)

GCCACGGCTGATGACCCCAGAAATGGATTGGAGAATTTTTTTTCGAAGACACAACA

CGAAATGAAGAACCCCGAAGCCTCTAAATTGAACAAGAGGTGCAAAGCAGAAAGT

TABLE 1-continued

Sequences of Mature O-Superfamily Conotoxins,
Propeptides and DNA Encoding Propeptides

GAAGCTTGTAATATAATTACACAAAACTGCTGCGACGGCAAGTGCCTTTTTTTCTGC

ATACAAATTCCAGAGTGATGTCTTCTCCTCCCATC

Translation:

MKLTCLMIVAVLFLTAWTFATADDPRNGLENFFSKTQHEMKNPEASKLNKRCKAESEA  (SEQ ID NO:86)

CNIITQNCCDGKCLFFCIQIPE

Toxin Sequence:

Cys-Lys-Ala-Xaa1-Ser-Xaa1-Ala-Cys-Asn-Ile-Ile-Thr-Gln-Asn-Cys-Cys-Asp-Gly-Lys-Cys-

Leu-Phe-Phe-Cys-Ile-Gln-Ile-Xaa3-Xaa1-^

Name: Omaria3

Species: omaria

Isolated: No

Cloned: Yes

DNA Sequence:

GGTCGACATCATCATCATCATCGATCCATCTGTCCATCCATCCATTCATTCATTCGCT  (SEQ ID NO:88)

GCCAGACTGTCATAAATATTCGAGTCTCTCCTTCTGTTTGTATCTGACAGATTGAAC

AAGAGGTGCATTGACGGTGGTGAAATTTGTGATATTTTTTTTCCAAACTGCTGCAGT

GGGTGGTGCATTATTCTCGTCTGCGCATGAAACTACCGTGATGTCTTCTACTCCCTC

TAGTAGTAGTAGGCGGCCGCTCTAGAGGATCCAAGCTTACGTACGCGTGCATGCGA

CGTCATAGCTCTTCTATAGTGTCACCTAAATTCAATTCACTGGCCGTCGTTTTACAAC

GTCGTGACTGGGAAAACCCTGGCGTTACCCAACTTAATCGCCTTGCAGCACATCCCC

CTTTCGCCAGCTGGCGTAATAGCGAAGAGGCCCGCACCGATCGCCCTTCCAACAGT

TTGCGCAGCCTGAATGGCGAATGGGACGCGCCCTGTAGCGGCGCATTAAGCGCGGC

GGGTGTGGTGGGTaCGCGCAGCGTGACCGGTACACTTGCCAGCGCCCTAGCGCCCGC

TCCTTTTGCTTTCTTCCCTTCCTTTCTCGCCACCGTTCgCCCGGGGTTTTCCCGTCaAG

CTC

Translation:

LNKRCIDGGEICDIFFPNCCSGWCIILVCA  (SEQ ID NO:89)

Toxin Sequence:

Cys-Ile-Asp-Gly-Gly-Xaa1-Ile-Cys-Asp-Ile-Phe-Phe-Xaa3-Asn-Cys-Cys-Ser-Gly-Xaa4-Cys-  (SEQ ID NO:90)

Ile-Ile-Leu-ValCys-Ala-^

Name: Omaria1

Species: omaria

Isolated: No

Cloned: Yes

DNA Sequence:

GGTCGACATCATCATCATCGATCCATCTGTCCATCCATCCATTCATTCATTCGCTGCC  (SEQ ID NO:91)

AGACTGTCATAAATATTCGAGTCTCTCCTTCTGTTTGTATCTGACAGATTGAACAAG

AGGTGCCTTGACGGTGGTGAAATTTGTGGTATTTTGTTTCCAAGCTGCTGCAGTGGG

TABLE 1-continued

Sequences of Mature O-Superfamily Conotoxins,
Propeptides and DNA Encoding Propeptides

TGGTGCATTGTTCTCGTCTGCGCATGAAACTACCGTGATGTCTTCTACTCCCCTCTAG

TAGTAGTAGGCGGCCGCTCTAGAGGATCCAAGCTTACGTACGCGTGCATGCGACGT

CATAGCTCTTCTATAGTGTCACCTAAATTCAATTCACTGGCCGTCGTTTTACAACGTC

GTGACTGGGAAAACCCTGGCGTTACCCAACTTAATCGCCTTGCAGCACATCCCCCTT

TCGCCAGCTGGCGTAATAGCGAAGAGGCCCGCACCGATCGCCCTTCCCAACAAGTT

GCGCAGCCTGAATGGCGAATGGGACGCGCCCTGTAGCGGCGCATTAAGCGCGGCGG

GTGTGGTGGTTACGCGCACCGTGACCGCTACACTTGCCAGCGCCCTAGCCGCCCGCT

CCTTTCGCTTTCTTCCCTTcCTTTCTCGCACGTTCGGCCGGCTTTCCCCGTCAAGCTCT

AAATCGGGGCTTCCCTTTTA

Translation:

LNKRCLDGGEICGILFPSCCSGWCIVLVCA (SEQ ID NO:92)

Toxin Sequence:

Cys-Leu-Asp-Gly-Gly-Xaa1-Ile-Cys-Gly-Ile-Leu-Phe-Xaa3-Ser-Cys-Cys-Ser-Gly-Xaa4-Cys- (SEQ ID NO:93)

Ile-Val-Leu-ValCycs-Ala-

Name: Marm7

Species: *marmoreus*

Isolated: No

Cloned: Yes

DNA Sequence:

GGTCGACATCATCATCATCGATCCATCTGTCCATCCATCCATCCATTCATTCGCTGCC (SEQ ID NO:94)

AGACTGTAATAAATATTCGAGTCTCTCTTTCTGTTTGTATCTGACAGATTGAACAAG

AGGTGCCTTGAGTTTGGTGAAGTTTGTAATTTTTTTTTCCCAACCTGCTGCGGCTATT

GCGTTCTTCTTGTCTGCCTATAAAACTACCGTGATGTCTTCTACTCCCCTCTAGTAGT

AGTAGGCGGCCGCTCTAGAGGATCCAAGCTTACGTACGCGTGCATGCGACGTCATA

GCTCTTCTATAGTGTCACCTAAATTCAATTCACTGGCCGTCGTTTTACAACGTCGTGA

CTGGGAAAACCCTGGCGTTACCCAACTTAATCGCCTTGCAGCACATCCCCCTTTCGC

CAGCTGGCGTAATAGCGAAGAGGCCCGCACCGATCGCCCTTCCCAACAGTTGCGCA

GCCTGAATGGCGAATGGGACGCGCCCTGTAGCGGCGCATTAAGCGCGGCGGGTGTG

GTGGTTACGCGCAGCGTGACCGCTACACTTGCAGCGCCCTAGCGCCCGCTCCTTTCG

CTTTCTTCCCTTCCTTTCTCGCCACGTTCGCCGGCTTTCCCCGTCAA

Translation:

LNKRCLEFGEVCNFFFPTCCGYCVLLVCL (SEQ ID NO:95)

TABLE 1-continued

Sequences of Mature O-Superfamily Conotoxins,
Propeptides and DNA Encoding Propeptides

Toxin Sequence:

Cys-Leu-Xaa1-Phe-Gly-Xaa1-Val-Cys-Asn-Phe-Phe-Phe-Xaa3-Thr-Cys-Cys-Gly-Xaa5-Cys-    (SEQ ID NO:96)

Val-Leu-Leu-Val-Cys-Leu-^

Name: Marm12

Species: marmoreus

Isolated: No

Cloned: Yes

DNA Sequence:

GAAAGCTGGTACGCCTGCAGGTACCGGTCCGGAATTCCCGGGTCGACATCATCATC    (SEQ ID NO:97)

ATCATCGATCCATCTGTCCATCCATCCATTCATTCATTCGCTGCCAGACTGTAATAA

ATATTCGAGTTTCTCCTTCTGTTTGTATCTGACAGGTTGAACAAGAGGTGCCAAGAG

TTCGGTGAAGTTTGTAATTTTTTTTCCCAGACTGCTGCGGCTATTGCGTTCTTTTAC

TCTGCATATAAAACTACCGTGATGTCTTCTCTTCCCATCTAGTAGTAGTAGTAGTAG

TAGGCGGCCGCTCTAGAGGATCCAAGCTTACGTACGCGTGCATGCGACGTCATAGC

TCTTCTATAGTGTCACCTAAATTCAATTCACTGGCCGTCGTTTTACAACCGTCGTGAC

TGGGAAAACCCTGGCGTTCCCAACTTAATTCGCCTTGCAGCACAT

Translation:

LNKRCQEFGEVCNFFFPDCCGYCVLLLCI    (SEQ ID NO:98)

Toxin Sequence:

Cys-Gln-Xaa1-Phe-Gly-Xaa1-Val-Cys-Asn-Phe-Phe-Phe-Xaa3-Asp-Cys-Cys-Gly-Xaa5-Cys-    (SEQ ID NO:99)

Val-Leu-Leu-Leu-Cys-Ile-^

Name: Omaria7

Species: omaria

Isolated: No

Cloned: Yes

DNA Sequence:

TTTTGAAGCNGGTACGCCTGCAGGTACCGGTCCGGAATTCCCGGGTCGACATCATCA    (SEQ ID NO:100)

TCATCATCGATCCATCTGTCCATCCATCCATTCATTCATTCGCTACCAGACTGTAATA

AATATTCGGGTCTCTCTTTCTGTTTGTATCTGACAGATTGGACAAGAGGTGCATTCC

ACATTTTGACCCTTGTGACCCGATACGCCACACCTGCTGCTTTGGCCTGTGCCTACT

AATAGCCTGCATCTAAAACTGCCGTGATGTCTTCTCCTCCCCTCTAGTAGTAGTAGG

CGGCCGCTCTAGAGGATCCAAGCTTACGTACGCGTGCATGCGACGTCATAGCTCTTC

TATAGTGTCACCTAAATTCAATTCACTGGCCGTCGTTTTACAACGTCGTGACTGGGA

AAACCCTGGCGTTACCCAACTTAATCGCCTTGCAGCACATCCCCCTTTCGCCAGCTG

GCGTAATAGCGAAGAGGCCCGCACCGATCGCCCTTCCCAACAGTTGCGCAGCCTGA

ATGGCGAATGGACGCGCCCTGTAGCGGCGCT

TABLE 1-continued

Sequences of Mature O-Superfamily Conotoxins, Propeptides and DNA Encoding Propeptides

Translation:

LDKRCIPHFDPCDPIRHTCCFGLCLLIACI (SEQ ID NO:101)

Toxin Sequence:

Cys-Ile-Xaa3-His-Phe-Asp-Xaa3-Cys-Asp-Xaa3-Ile-Arg-His-Thr-Cys-Cys-Phe-Gly-Leu-Cys- (SEQ ID NO:102)

Leu-Leu-Ile-Ala-Cys-Ile-^

Name: Omaria11

Species: *omaria*

Isolated: No

Cloned: Yes

DNA Sequence:

GGTACGCCTGCAGGTACCGGTCCGGAATTCCCGGGTCGACATCATCATCATCGATCC (SEQ ID NO:103)

ATCTGTCCATCCATCCATTCTTTCATTTGCTGCCAGACTGTAATAAATATTCGAGTCT

CTCTTTCTGTTTGTATCTGACAGATTGAACAAGAGGTGCCTTGAGTTTGGTGAAGTT

TGTAATTTTTTTTTCCCAACCTGCTGCGGCTATTGCGTTCTTCTTGTCTGCCTATAAA

ACTACCGTGATGTCTTCTCTTCCCCTCTAGTAGTAGTAGGCGGCCGCTCTAGAGGAT

CCAAGCTTACGTACGCGTGCATGCGACGTCATAGCTCTTCTATAGTGTCACCTAAAT

TCAATTCACTGGCCGTCGTTTTACAACGTCGTGACTGGGAAAACCCTGGCGTTACCC

AACTTAATCGCCTTGCAGCACATCCCCCTTTCGCCAGCTGGCGTAATAGCGAAGAGG

CCCGCACCGATCGCCCTTCCCAACAGTTGCGCAGCCTGAATGGCGAATGGGACGCG

CCCTGTAGCGGCGCATTAAG

Translation:

LNKRCLEFGEVCNFFFPTCCGYCVLLVCL (SEQ ID NO:104)

Toxin Sequence:

Cys-Leu-Xaa1-Phe-Gly-Xaa1-Val-Cys-Asn-Phe-Phe-Phe-Xaa3-Thr-Cys-Cys-Gly-Xaa5-Cys- (SEQ ID NO:105)

Val-Leu-Leu-Val-Cys-Leu-^

Name: O6.5

Species: *obseurus*

Isolated: No

Cloned: Yes

DNA Sequence:

cgatccatctgtccatccatccattcgttcgttcgctgccaaactgtaataaataaccgagtctctctgtttgtatctgacagATC (SEQ ID NO:106)

GAAAAAGCAATGCCGTCAAAATGGTGAAGTGTGTGATGCGAATTTGGCACACTGCTGCAGT

GGCCCGTGTTTTCTCTTCTGTCTAAACCAGCCGTGATGTCTTCTACTCCCCTC

Translation:

VSDRSKKQCRQNGEVCDANLAHCCSGPCFLFCLNQP (SEQ ID NO:107)

TABLE 1-continued

Sequences of Mature O-Superfamily Conotoxins,
Propeptides and DNA Encoding Propeptides

Toxin Sequence:

Ser-Lys-Lys-Gln-Cys-Arg-Gln-Asn-Gly-Xaa1-Val-Cys-Asp-Ala-Asn-Leu-Ala-His-Cys-Cys- (SEQ ID NO:108)

Ser-Gly-Xaa3-Cys-Phe-Leu-Phe-Cys-Leu-Asn-Gln-Xaa3-^

Name: Af6.8

Species: *ammiralis*

Isolated: No

Cloned: Yes

DNA Sequence:

ATGAAACTGACGTGCGTGATGATCATTGCTGTGCTGTTCTTGACCGCCTGGACATTT (SEQ ID NO:109)

GCCACGGCTGATGACTCCGGAAATGGATTGGAAAATCTTTTTTCGAAGGCACATCA

CGAAATGAAGAACCCCAAAGCCTCTAAATTGAACAAGAGGTGCACTCAAAGCGGTG

AACTTTGTGATGTGATAGACCCAGACTGCTGCAATAATTTTTGCATTATATTTTTCTG

CATATAAAACTGCCGTGATGTCTTCTACTCCCCTC

Translation:

MKLTCVMIIAVLFLTAWTFATADDSGNGLENLFSKAHHEMKNPKASKLNKRCTQSGEL (SEQ ID NO:110)

CDVIDPDCCNNFCIIFFCI

Toxin Sequence:

Cys-Thr-Gln-Ser-Gly-Xaa1-Leu-Cys-Asp-Val-Ile-Asp-Xaa3-Asp-Cys-Cys-Asn-Asn-Phe-Cys- (SEQ ID NO:111)

Ile-Ile-Phe-Phe-Cys-Ile-^

Name: KK-2A

Species: *textile*

Isolated: No

Cloned: Yes

DNA Sequence:

GGCATTACCTAAAACATCACCAAAATGAAACTGACGTGCATGATGATCGTTGCTGT (SEQ ID NO:112)

GCTGTTCTTGACCGCCTGGACATTCGCCACGGCTGATGACTCCGGAAATGGATTGGA

GAAACTTTTTTCGAATGCACATCACGAAATGAAGAACCCCGAAGCCTCTAATTTGA

ACAAGAGGTGCGCTCCTTTTCTTCACCTTTGTACCTTTTTCTTCCCAAACTGCTGCAA

CGGCTATTGCGTTCAATTTATCTGCCTATAAAACTACTGTGATGTCTTCTATTCCCCTC

Translation:

MKLTCMMIVAVLFLTAWTFATADDSGNGLEKLFSNAHHEMKNPEASNLNKRCAYFLH (SEQ ID NO:113)

LCTFFFPNCCNGYCVQFICL

TABLE 1-continued

Sequences of Mature O-Superfamily Conotoxins,
Propeptides and DNA Encoding Propeptides

Toxin Sequence:

Cys-Ala-Xaa3-Phe-Leu-His-Leu-Cys-Thr-Phe-Phe-Phe-Xaa3-Asn-Cys-Cys-Asn-Gly-Xaa5-Cys- (SEQ ID NO:114)

Val-Gln-Phe-Ile-Cys-Leu-^

Name: KKM1

Species: marmoreus

Isolated: No

Cloned: Yes

DNA Sequence:

GGATCCTAGCACAGTGAATTTGGCTTCACAGTTTTCCACTGTCGTCTTTGGCATCATC (SEQ ID NO:115)

CAAAACATCACCAAGATGAAACTGACGTGCATGATGATCGTTGCTGTGCTGTTCTTG

ACCGCCTGGACATTTGCCACGGCTGATGACCCCAGANATGGATTGGAGAATCTTTTT

TCGAAGGCACATCACGAAATGAAGAACCCCAAAGACTCTAAATTGAACAAGAGGT

GCCTTGACGCTGGTGAAATGTGTGATCTTTTTAATTCAAAATGCTGCAGTGGGTGGT

GCATTATTCTCTTCTGCGCATAAAACTACCGTGATGTCTTCTACTCCCCTCTGTGCTA

CCTGGCTTGATCTTTGATTGGCGCGTGCCCTTCACTGGTTATGAACCCCCCTGATCC

GACTCTCTGGCGGCCTCGGGGGTTCAACATCCAAATAAAGCCGACACGATACTGAC

GTAGAAAAAAAAAAAAAAAAAAAAAAAAAA

Translation:

MKLTCMMIVAVLFLTAWTFATADDPRNGLENLFSKAHHEMKNPKDSKLKRCLDAGE (SEQ ID NO:116)

MCDLFNSKCCSGWCIILFCA

Toxin Sequence:

Cys-Leu-Asp-Ala-Gly-Xaa1-Met-Cys-Asp-Leu-Phe-Asn-Ser-Lys-Cys-Cys-Ser-Gly-Xaa4-Cys- (SEQ ID NO:117)

Ile-Ile-Leu-Phe-Cys-Ala-^

Name: KKM4

Species: marmoreus

Isolated: No

Cloned: Yes

DNA Sequence:

GCCGAAAACATCACCAAGATGAAACTGACGAGCATGATGATCGTTGCTGTGCTGTT (SEQ ID NO:118)

CTTGACCGCCTGGACATTCGTCACGGCTGACGACTCCGGAAATGGATTGGAGAATC

TTTTTTCGAAGGCACATCACGAGATGAAGAACCCCAAAGACTCTAAATTGAACAAG

AGGTGCCTTGACGGTGGTGAAATTTGTGGTATTTTGTTTCCAAGCTGCTGCAGTGGG

TGGTGCATTGTTCTCGTCTGCGCATGAAACTACCGTGATGTCTTCTACTCCCCTCTGT

GCTACCTGGCTTGATCTTTGATTGGCGCGTGCCCTTCACTGGTTATGAACCCCCCTG

ATCCGACTCTCTGGCGGCCTCGGGGGTTCAACATCCAAATAAAGCGACACGACAAT

GACAAAAAAAAAAAAAAAAAAAAAAAAAA

TABLE 1-continued

Sequences of Mature O-Superfamily Conotoxins,
Propeptides and DNA Encoding Propeptides

Translation:

MKLTSMMIVAVLFLTAWTFVTADDSGNGLENLFSKAHHEMKNPKDSKLNKRCLDGGE  (SEQ ID NO:119)

ICGILFPSCCSGWCIVLVCA

Toxin Sequence:

Cys-Leu-Asp-Gly-Gly-Xaa1-Ile-Cys-Gly-Ile-Leu-Phe-Xaa3-Ser-Cys-Cys-Ser-Gly-Xaa4-Cys-  (SEQ ID NO:120)

Ile-Val-Leu-Val-Cys-Ala-^

Name: KKM5

Species: *marmoreus*

Isolated: No

Cloned: Yes

DNA Sequence:

GCTAGCACAGTGAATTTGGCTTCACAGTTTTCCACTGTCGTCTTTGGCATCATCCAA  (SEQ ID NO:121)

AACATCACCAAGATGAAACTGACGTGCATGATGATCGAAGCAGAGCTGTTCTTGAC

CGCCTGGACATTTGCCACGGCTGATGACCCCAGAAATGGATTGGAGAATCTTTTTTC

GAAGGCACATCACGAAATGAAGAACCCCGAAGCCTCTAAATTGAACAAGAGGTGC

CCTAACACTGGTGAATTATGTGATGTGGTTGAACAAAACTGCTGCTATACCTATTGC

TTTATTGTAGTCTGCCCTATATAACTACCGTGATGTCTTCTACTCCCCTCTGTGCTGC

CTGGCTTGATCTTTGATTGGCGCGTGCCCTTCACTGGTTATGAACCCCCCTGATCCG

ACTCTCTTGCGGCCTCAGGGGTTCAACATCCAAATAAAGCGACACGAAAATGAAAA

AAAAAAAAAAAAAAAAAA

Translation:

MKLTCMMIEAELFLTAWTFATADDPRNGLENLFSKAHHEMKNPEASKLNKRCPNTGEL  (SEQ ID NO:122)

CDVVEQNCCYTYCFIVVCPI

Toxin Sequence:

Cys-Xaa3-Asn-Thr-Gly-Xaa1-Leu-Cys-Asp-Val-Val-Xaa1-Gln-Asn-Cys-Cys-Xaa5-Thr-Xaa5-  (SEQ ID NO:123)

Cys-Phe-Ile-Val-Val-Cys-Xaa3-Ile-^

Name: KKM6

Species: *marmoreus*

Isolated: No

Cloned: Yes

DNA Sequence:

TTGCACGGTGAATTTCGCTTATATTTTTCTACTGTCGTCTTTGGCATCATCCAAAACA  (SEQ ID NO:124)

TCACCAAGATGAAACTGACGTGCATGATGATCGTTGCTGTGCTGTTCTTGACCGCCT

GGACATTCGTCACGGCTGTGCCTCACTCCAGCGATGTATTGGAGAATCTTTATCTGA

AGGCACTTCACGAAACGGAAAACCACGAAGCCTCTAAATTGAACGTGAGAGACGA

CGAGTGCGAACCTCCTGGAGATTTTTGTGGCTTTTTTAAAATTGGGCCGCCTTGCTG

CAGTGGCTGGTGCTTCCTCTGGTGCGCCTAAAACTGCCGTGATGTCTTCTATTCCCCT

CTGTGCTACCTGGCTTGATCTTTGATTGGCGCGTGCCCTTCAGTGGTTATGAACCCCC

TABLE 1-continued

Sequences of Mature O-Superfamily Conotoxins,
Propeptides and DNA Encoding Propeptides

CTGATCCGACTCTCTGGGGGCCTCGGGGGTTCAACATCCAAATAAAGCTGACAACA

CAATAAAAAAAAAA

Translation:

MKLTCMMIVAVLFLTAWTFVTAVPHSSDVLENLYLKALHETENHEASKLNVRDDECEP (SEQ ID NO:125)

PGDFCGFFKIGPPCCSGWCFLWCA

Toxin Sequence:

Asp-Asp-Xaa1-Cys-Xaa1-Xaa3-Xaa3-Gly-Asp-Phe-Cys-Gly-Phe-Phe-Lys-Ile-Gly-Xaa3-Xaa3- (SEQ ID NO:126)

Cys-Cys-Ser-Gly-Xaa4-Cys-Phe-Leu-Xaa4-Cys-Ala-^

Name: *C. striatus* S2

Species: *striatus*

Isolated: No

Cloned: Yes

DNA Sequence:

ATGAAACTGACGTGTGTGATGATCGTTGCTGTGCTGTTCTTGACCGCCTGGACATTC (SEQ ID NO:127)

GTCACGGCTGTGCCTCACTCCAGCGATGCATTGGAGAATCTTTATCTGAAGGCACTT

CACGAAACGGAAAACCACGAAGCCTCTAAATTGAACGTGAGAGACGACGAGTGCG

AACCTCCTGGAGATTTTTGTGGCTTTTTTAAAATTGGGCCGCCTTGCTGCAGTGGCT

GGTGCTTCCTCTGGTGCGCATAAAACTGCCGTGATGTCTTCTCCTCCCCTC

Translation:

MKLTCVMIVAVLFLTAWTFVTAVPHSSDALENLYLKALHETENHEASKLNVRDDDCEP (SEQ ID NO:128)

PGDFCGFFKIGPPCCSGWCFLWCA

Toxin Sequence:

Asp-Asp-Xaa1-Cys-Xaa1-Xaa3-Xaa3-Gly-Asp-Phe-Cys-Gly-Phe-Phe-Lys-Ile-Gly-Xaa3-Xaa3- (SEQ ID NO:129)

Cys-Cys-Ser-Gly-Xaa4-Cys-Phe-Leu-Xaa4-Cys-Ala-^

Name: Om6.5

Species: *omaria*

Isolated: No

Cloned: Yes

DNA Sequence:

ATGAAACTGACGTGCGTGATGATCGTTGCTGTGCTGTTCTTGACCGCCTGGACATTC (SEQ ID NO:130)

GTCACGGCTGTGCCTCACTCCAGCAATGCATTGGAAAATCTTTATCTGAAGGCACGT

CACGAAATGGAAAACCCCGAAGCCTCTAAATTGAACACGAGAGACGACGATTGCG

AACCTCCTGGAAATTTTTGTGGCATGATAAAAATTGGGCCGCCTTGCTGCAGTGGCT

GGTGCTTTTTCGCCTGCGCCTAAAACTGCCGTGATGTCTTCTCCTCCCCTC

TABLE 1-continued

Sequences of Mature O-Superfamily Conotoxins,
Propeptides and DNA Encoding Propeptides

Translation:

MKLTCVMIVAVLFLTAWTFVTAVPHSSNALENLYLKARHEMENPEASKLNTRDDDCEP (SEQ ID NO:131)

PGNFCGMIKIGPPCCSGWCFFACA

Toxin Sequence:

Asp-Asp-Asp-Cys-Xaa1-Xaa3-Xaa3-Gly-Asn-Phe-Cys-Gly-Met-Ile-Lys-Ile-Gly-Xaa3-Xaa3- (SEQ ID NO:132)

Cys-Cys-Ser-Gly-Xaa4-Cys-Phe-Phe-Ala-Cys-Ala-^

Name: Au6.3

Species: *aulicus*

Isolated: No

Cloned: Yes

DNA Sequence:

ATGAAACTGACGTGCCTGATGATAGTTGCTGTGCTGTTCTTGACCGCCTGGACATTC (SEQ ID NO:133)

GTCACGGCTGTGCCTCACTCCAGCAATGCATTGGAGAATCTTTATCTGAAGGCACGT

CACGAAATGGAAAACCCCGAAGCCTCTAAATTGAACACGAGAGACTACGATTGCGA

ACCTCCTGGAAATTTTTGTGGCATGATAAAAATTGGGCCGCCTTGCTGCAGTGGCTG

GTGCTTTTTCGCCTGCGCCTAAAACTGCCGTGATGTCTTCTCCTCCCCTC

Translation:

MKLTCLMIVAVLFLTAWTFVTAVPHSSNALENLYLKARHEMENPEASKLNTRDYDCEP (SEQ ID NO:134)

PGNFCGMIKIGPPCCSGWCFFACA

Toxin Sequence:

Asp-Xaa5-Asp-Cys-Xaa1-Xaa3-Xaa3-Gly-Asn-Phe-Cys-Gly-Met-Ile-Lys-Ile-Gly-Xaa3-Xaa3- (SEQ ID NO:135)

Cys-Cys-Ser-Gly-Xaa4-Cys-Phe-Phe-Ala-Cys-Ala-^

Name: Marm9

Species: *marmoreus*

Isolated: No

Cloned: Yes

DNA Sequence:

GGTCGACATCATCATCATCATCGATCCATCTGTCCATCCATCTATTCATTCATTCGTG (SEQ ID NO:136)

GCCAAACTGTAATAAATAATGCAAGTCTCTCTTTCTGTTTGTATCTGACAGATTGAA

CACGAGAGACGACGATTGCGAACCTCCTGGAAATTTTTGTGGCATGATAAAAATTG

GGCCGCCTTGCTGCAGTGGCTGGTGCTTTTTCGCCTGCGCCTAAAACTGCCGTGATG

TCTTCTCTTCCCCTCTAGTAGTAGTAGGCGGCCGCTCTAGAGGATCCAAGCTTACGT

ACGCGTGCATGCGACGTCATAGCTCTTCTATAGTGTCACCTAAATTCAATTCACTGG

CCGTCGTTTTACAACGTCGTGACTGGGAAAACCCTGGCGTTACCCAACTTAATCGCC

TTGCAGCACATCCCCCTTTCGCCAGCTGGCGTAATAGCGAAGAGGCCCGCACCGAT

CGCCCTTCCCAACAGTTGCGCAGCCTGAATGGCGAATGGGACGCGCCCTGTAGCGG

CGCATTAAGCGCGGCGGGTGTGGTGGTTACGCCGCAGCCGTGACCCGCTACACTTG

TABLE 1-continued

Sequences of Mature O-Superfamily Conotoxins,
Propeptides and DNA Encoding Propeptides

CCAGCGCCCTAGCGCCCGCTCCTTTCGCTTTCTTCCTTCCTTTCTCGCCACGTTCGCC

GGCTTTTCCCGTCAAGCTCTAAATCGGGGGCTCCTTTAGGGTCCGATTTAAGTGCTT

TAC

Translation:

LNTRDDDCEPPGNFCGMIKIGPPCCSGWCFFACA (SEQ ID NO:137)

Toxin Sequence:

Asp-Asp-Asp-Cys-Xaa1-Xaa3-Xaa3-Gly-Asn-Phe-Cys-Gly-Met-Ile-Lys-Ile-Gly-Xaa3-Xaa3- (SEQ ID NO:138)

Cys-Cys-Ser-Gly-Xaa4-Cys-Phe-Phe-Ala-Cys-Ala-

Name: Rg6.4

Species: *regius*

Isolated: No

Cloned: Yes

DNA Sequence:

TTGAACCAGAGAGACTGCCTTAGTAAAAACGCTTTCTGTGCCTGGCCGATACTTGGA (SEQ ID NO:139)

CCACTGTGCTGCAGTGGCTGGTGCTTATACGTCTGCATGTAAAACTGCCGTGATGTC

TTCTATCCCCTC

Translation:

LNQRDCLSKNAFCAWPILGPLCCSGWCLYVCM (SEQ ID NO:140)

Toxin Sequence:

Asp-Cys-Leu-Ser-Lys-Asn-Ala-Phe-Cys-Ala-Xaa4-Xaa3-Ile-Leu-Gly-Xaa3-Leu-Cys-Cys-Ser- (SEQ ID NO:141)

Gly-Xaa4-Cys-Leu-Xaa5-Val-Cys-Met-

Name: R6.5

Species: *radiatus*

Isolated: No

Cloned: Yes

DNA Sequence:

ATTGAACAAGAAAGGTGATGACTGCCTTGCTGTTAAAAAAAATTGTGGCTTTCCAA (SEQ ID NO:142)

AACTTGGAGGGCCATGCTGCAGTGGCTTGTGCTTTTTCGTCTGCGCCTAAAACTGCC

GTGATGTCTTCTCCTCCCCT

Translation:

LNKKGDDCLAVKKNCGFPKLGGPCCSGLCFFVCA (SEQ ID NO:143)

Toxin Sequence:

Gly-Asp-Asp-Cys-Leu-Ala-Val-Lys-Lys-Asn-Cys-Gly-Phe-Xaa3-Lys-Leu-Gly-Gly-Xaa3-Cys- (SEQ ID NO:144)

Cys-Ser-Gly-Leu-Cys-Phe-Phe-Val-Cys-Ala-

Name: Rg6.2

Species: *regius*

Isolated: No

Cloned: Yes

TABLE 1-continued

Sequences of Mature O-Superfamily Conotoxins,
Propeptides and DNA Encoding Propeptides

DNA Sequence:

TTGAATCAGAGCGACTGCCTTCCTAGAGACACATTCTGTGCCTTGCCGCAACTTGGA (SEQ ID NO:145)

CTACTGTGCTGCAGTGGCCGGTGCTTACTCTTCTGCGTGTAAAACTGCCGTGATGTC

TTCTCCTCCCCTC

Translation:

LNQSDCLPRDTFCALPQLGLLCCSGRCLLFCV (SEQ ID NO:146)

Toxin Sequence:

Asp-Cys-Leu-Xaa3-Arg-Asp-Thr-Phe-Cys-Ala-Leu-Xaa3-Gln-Leu-Gly-Leu-Leu-Cys-Cys-Ser- (SEQ ID NO:147)

Gly-Arg-Cys-Leu-Leu-Phe-Cys-Val-^

Name: A6.5

Species: *aurisiacus*

Isolated: No

Cloned: Yes

DNA Sequence:

ATGAAACTGACGTGCGTGATGACCGTTGCTGTGCTGTTCTTGACCGCCTGGACATTC (SEQ ID NO:148)

GTCACGGCTGATGACTCCAGAAATGGACTGAAGAATCTTTTTCCGAAGGCACGTCA

TGAAATGAAGAACCCCGAAGCCTCTAAATTGAACAAGAGAGATGGGTGCTCTAATG

CTGGTGCATTTTGTGGCATCCATCCAGGACTCTGCTGCAGCGAGATTTGCATTGTTT

GGTGCACATGAGTCGTATTCTGCTGGTACATTTTGTGGCTTCAACGGAGGACTCTGC

TGCAGCAACCTTTGCTTATTTTTCGTGTGCTTAACATATTCGTGATGTCTTCTACTCC

CATC

Translation:

MKLTCVMTVAVLFLTAWTFVTADDSRNGLKNLFPKARHEMKNPEASKLNKRDGCSNA (SEQ ID NO:149)

GAFCGIHPGLCCSEICIVWCT

Toxin Sequence:

Asp-Gly-Cys-Ser-Asn-Ala-Gly-Ala-Phe-Cys-Gly-Ile-His-Xaa3-Gly-Leu-Cys-Cys-Ser-Xaa1-Ile- (SEQ ID NO:150)

Cys-Ile-Val-Xaa4-Cys-Thr-^

Name: 6-P VIA

Species: *purpurascens*

Isolated: Yes

Cloned: Yes

DNA Sequence:

ATGAAACTGACGTGCGTGATGATCGTTGCTGTGCTGTTCTTGACTGCCTGGACATTC (SEQ ID NO:151)

GTCACGGCTGATGACTCCAAAAATGGACTGGAGAATCATTTTTGGAAGGCACGTGA

CGAAATGAAGAACCGCGAAGCCTCTAAATTGGACAAAAAGGAAGCCTGCTATGCGC

CTGGTACTTTTTGTGGCATAAAGCCCGGGCTATGCTGCAGTGAGTTTTGTCTCCCGG

GCGTCTGCTTCGGTGGTTAACTGCCGTGATGTCTTCTACTCCCCTCTGTGCTACCTGG

CTTGATCTTTGATCGGCGTGTGCCCTTCACTGGTTATGAACCCACTGATCTTACCTCT

TABLE 1-continued

Sequences of Mature O-Superfamily Conotoxins,
Propeptides and DNA Encoding Propeptides

CTTGAAGGACCTCTGGGGTCCAGCATCCAAATAAGCGACATCCCAATGAAAAAAAA

AAAAAAAAAAAAAA

Translation:

MKLTCVMIVAVLFLTAWTFVTADDSKNGLENHFWKARDEMKNREASKLDKKEACYA (SEQ ID NO:152)

PGTFCGIKPGLCCSEFCLPGVCFGG

Toxin Sequence:

Xaa1-Ala-Cys-Xaa5-Ala-Xaa3-Gly-Thr-Phe-Cys-Gly-Ile-Lys-Xaa3-Gly-Leu-Cys-Cys-Ser- (SEQ ID NO:153)

Xaa1-Phe-Cys-Leu-Xaa3-Gly-Val-Cys-Phe-Gly-#

Name: δ-PVIA-OH

Species: *purpurascens*

Isolated: Yes

Toxin Sequence:

Xaa1-Ala-Cys-Xaa5-Ala-Xaa3-Gly-Thr-Phe-Cys-Gly-Ile-Lys-Xaa3-Gly-Leu-Cys-Cys-Ser- (SEQ ID NO:153)

Xaa1-Phe-Cys-Leu-Xaa3-Gly-Val-Cys-Phe-Gly-^

Name: δ-PVIA[F9A]

Species: *purpurascens*

Toxin Sequence:

Xaa1-Ala-Cys-Xaa5-Ala-Xaa3-Gly-Thr-Ala-Cys-Gly-Ile-Lys-Xaa3-Gly-Leu-Cys-Cys-Ser- (SEQ ID NO:154)

Xaa1-Phe-Cys-Leu-Xaa3-Gly-Val-Cys-Phe-Gly-^

Name: δ-PVIA[I12A]

Species: *purpurascens*

Isolated:

Toxin Sequence:

Xaa1-Ala-Cys-Xaa5-Ala-Xaa3-Gly-Thr-Phe-Cys-Gly-Ala-Lys-Xaa3-Gly-Leu-Cys-Cys-Ser- (SEQ ID NO:155)

Xaa1-Phe-Cys-Leu-Xaa3-Gly-Val-Cys-Phe-Gly-^

Name: δ-PVIA[T8A]

Species: *purpurascens*

Toxin Sequence:

Xaa1-Ala-Cys-Xaa5-Ala-Xaa3-Gly-Ala-Phe-Cys-Gly-Ile-Lys-Xaa3-Gly-Leu-Cys-Cys-Ser- (SEQ ID NO:156)

Xaa1-Phe-Cys-Leu-Xaa3-Gly-Val-Cys-Phe-Gly-^

Name: M6.3

Species: *magus*

Isolated: No

Cloned: Yes

DNA Sequence:

ATGAAACTGACGTGCGTGATGATCGTTGCTGTGCTGTTCTTGACCACGTGGACATTC (SEQ ID NO:157)

GTCACGGCTGATGACTCCAGATATGGATTGAAGAATCTTTTTCCGAAGGCACGTCAT

GAAATGAAGAACCCTGAAGCCTCTAAATTGAACAAGAGAGATGGGTGCTATAATGC

TABLE 1-continued

Sequences of Mature O-Superfamily Conotoxins, Propeptides and DNA Encoding Propeptides

TGGTACATTTTGTGGCATCCGTCCAGGACTCTGCTGCAGCGAGTTTTGCTTTTTATGG

TGCATAACATTTGTTGATTCTGGCTAACAGTGTGCGTTGGTTAGTGTCTTCTCCTCCC

CTC

Translation:

MKLTCVMIVAVLFLTTWTFVTADDSRYGLKNLFPKARHEMKNPEASKLNKRDGCYNA (SEQ ID NO:158)

GTFCGIRPGLCCSEFCFLWCITFVDSG

Toxin Sequence:

Asp-Gly-Cys-Xaa5-Asn-Ala-Gly-Thr-Phe-Cys-Gly-Ile-Arg-Xaa3-Gly-Leu-Cys-Cys-Ser-Xaa1- (SEQ ID NO:159)

Phe-Cys-Phe-Leu-Xaa4-Cys-Ile-Thr-Phe-Val-Asp-Ser-#

Name: M6.6

Species: *magus*

Isolated: No

Cloned: Yes

DNA Sequence:

ATGAAACTGACGTGCGTGATGATCGTTGCTGTGCTGTTCTTGACCACCTGGACATTC (SEQ ID NO:160)

GTCACGGCTGATGACTCCAGATATGGATTGAAGAATCTTTTTCCGAAGGCACGTCAT

GAAATGAAGAACCCTGAAGCCTCTAAATTGAACAAGAGAGATGAATGCTATCCTCC

TGGTACATTTTGTGGCATCAAACCAGGACTTTGCTGCAGCGCGATATGCTTATCGTT

TGTCTGCATATCATTTGATTTTTGATTGATGTCTTCTCCTCCCCTC

Translation:

MKLTCVMIVAVLFLTTWTFVTADDSRYGLKNLFPKARHEMKNPEASKLNKRDECYPP (SEQ ID NO:161)

GTFCGIKPGLCCSAICLSFVCISFDF

Toxin Sequence:

Asp-Xaa1-Cys-Xaa5-Xaa3-Xaa3-Gly-Thr-Phe-Cys-Gly-Ile-Lys-Xaa3-Gly-Leu-Cys-Cys-Ser- (SEQ ID NO:162)

Ala-Ile-Cys-Leu-Ser-Phe-Val-Cys-Ile-Ser-Phe-Asp-Phe-^

Name: M6.7

Species: *magus*

Isolated: No

Cloned: Yes

DNA Sequence:

ATGAAACTGACGTGCGTGATGATCGTTGCTGTACTGTTCTTGACCGCCTGGACATTC (SEQ ID NO:163)

GTCACGGCTGATGACTCCAGATATGGACTGAAGGATCTGTTTCCGAAGGAACGTCA

TGAAATGAAGAACCCCGAAGCCTCTAAATTGAACCAGAGAGAAGCCTGCTATAATG

CTGGTTCATTTTGTGGCATCCATCCAGGACTCTGCTGCAGCGAGTTTTGCATTCTTTG

GTGCATAACATTTGTTGATTCTGGCTAACTGTGTGCGTTGGTTGATGTCTTCTCCTCC

CATC

TABLE 1-continued

Sequences of Mature O-Superfamily Conotoxins,
Propeptides and DNA Encoding Propeptides

Translation:

MKLTCVMIVAVLFLTAWTFVTADDSRYGLKDLFPKERHEMKNPEASKLNQREACYNA (SEQ ID NO:164)

GSFCGIHPGLCCSEFCILWCITFVDSG

Toxin Sequence:

Xaa1-Ala-Cys-Xaa5-Asn-Ala-Gly-Ser-Phe-Cys-Gly-Ile-His-Xaa3-Gly-Leu-Cys-Cys-Ser-Xaa1- (SEQ ID NO:165)

Phe-Cys-Ile-Leu-Xaa4-Cys-Ile-Thr-Phe-Val-Asp-Ser-#

Name: M6.8

Species: *magus*

Isolated: No

Cloned: Yes

DNA Sequence:

ATGAAACTGACGTGCATGATGATCGTTGCTGTACTGTTCTTGACCGCCTGGACATTC (SEQ ID NO:166)

GTCACGGCTGATGACTCCAGATATGGACTGAAGGATCTGTTTCCGAAGGAACGTCA

TGAAATGAAGAACCCCGAAGCCTCTAAATTGAACCAGAGAGAAGCCTGCTATAATG

CTGGTACATTTTGTGGCATCAAACCAGGACTTTGCTGCAGCGCGATATGCTTATCGT

TTGTCTGCATATCATTTGATTTTTGATTGATGTCTTCTCCTCCCCTC

Translation:

MKLTCMMIVAVLFLTAWTFVTADDSRYGLKDLFPKERHEMKNPEASKLNQREACYNA (SEQ ID NO:167)

GTFCGIKPGLCCSAICLSFVCISFDF

Toxin Sequence:

Xaa1-Ala-Cys-Xaa5-Asn-Ala-Gly-Thr-Phe-Cys-Gly-Ile-Lys-Xaa3-Gly-Leu-Cys-Cys-Ser-Ala (SEQ ID NO:168)

Ile-Cys-Leu-Ser-Phe-Val-Cys-Ile-Ser-Phe-Asp-Phe-

Name: E6.4

Species: *ermineus*

Isolated: No

Cloned: Yes

DNA Sequence:

ATGAAACTGACGTGCGTGATGATCGTTGCTGTGCTGTTCTTGACTGCCTGGACATTC (SEQ ID NO:169)

GTCACGGCTGATGACTCCAAAAATGGACTGGAGAATCATTTTTGGAAGGCACGTGA

CGAAATGAAGAACCGCGAAGCCTCTAAATTGGACAAAAAGGAAGCCTGCTATCCGC

CTGGTACTTTTTGTGGCATAAAGCCCGGGCTATGCTGCAGTGAGTTGTGTTTACCGG

CCGTCTGCGTCGGTGGTTAACTGCCGTGATGTCTTCTCCTCCCCTC

Translation:

MKLTCVMIVAVLFLTAWTFVTADDSKNGLENHFWKARDEMKNREASKLDKKEACYP (SEQ ID NO:170)

PGTFCGIKPGLCCSELCLPAVCVGG

TABLE 1-continued

Sequences of Mature O-Superfamily Conotoxins,
Propeptides and DNA Encoding Propeptides

Toxin Sequence:

Xaa1-Ala-Cys-Xaa5-Xaa3-Xaa3-Gly-Thr-Phe-Cys-Gly-Ile-Lys-Xaa3-Gly-Leu-Cys-Cys-Ser- (SEQ ID NO:171)

Xaa1-Leu-Cys-Leu-Xaa3-Ala-Val-Cys-Val-Gly-#

Name: P6.4

Speciet: *purpurascens*

Isolated: No

Cloned: Yes

DNA Sequence:

ATGAAACTGACGTGCATGATGATCGTTGCTGTGCTGTTCTTGACTGCCTGGACATTC (SEQ ID NO:172)

GTCACGGCTGATGACTCCAAAAATGGACTGGAGAATCATTTTTGGAAGGCACGTGA

CGAAATGAAGAACCGCGAAGCCTCTAAATTGGACAAAAAGGAAGCCTGCTATCCGC

CTGGTACTTTTTGTGGCATAAAGCCCGGGCTATGCTGCAGTGAGTTGTGTTTACCGG

CCGTCTGCGTCGGTGGTTAACTGCCGTGATGTCTTCTCCTCCCCTC

Translation:

MKLTCMMIVAVLFLTAWTFVTADDSKNGLENHFWKARDEMKNREASKLDKKEACYP (SEQ ID NO:173)

PGTFCGIKPGLCCSELCLPAVCVGG

Toxin Sequence:

Xaa1-Ala-Cys-Xaa5-Xaa3-Xaa3-Gly-Thr-Phe-Cys-Gly-Ile-Lys-Xaa3-Gly-Leu-Cys-Cys-Ser- (SEQ ID NO:174)

Xaa1-Leu-Cys-Leu-Xaa3-Ala-Val-Cys-Val-Gly-#

Name: δ-SVIE[D1E]

Species: *striatus*

Isolated: Yes

Cloned: Yes

DNA Sequence:

ATGAAACTGACGTGCGTGATGATCGTTGCTGTGCTGTTCTTGACCACTTGGACATTC (SEQ ID NO:175)

GTCACGGCTGATGACTCCAGATATGGATTGAAGAATCTTTTTCCGAAGGCACGTCAT

GAAATGAAGAACCCCGAAGCCTCTAAATTGAACAAGAGAGAAGGGTGCTCTAGTG

GTGGTACATTTTGTGGCATCCATCCAGGACTCTGCTGCAGCGAGTTTTGCTTTCTTTG

GTGCATAACATTTATTGATTGATGTCTTCTCCTCCCCTC

Translation:

MKLTCVMIVAVLFLTTWTFVTADDSRYGLKNLFPKARHEMKNPEASKLNKREGCSSG (SEQ ID NO:176)

GTFCGIHPGLCCSEFCFLWCITFID

TABLE 1-continued

Sequences of Mature O-Superfamily Conotoxins,
Propeptides and DNA Encoding Propeptides

Toxin Sequence:

Xaa1-Gly-Cys-Ser-Ser-Gly-Gly-Thr-Phe-Cys-Gly-Ile-His-Xaa3-Gly-Leu-Cys-Cys-Ser-Xaa1- (SEQ ID NO:177)

Phe-Cys-Phe-Leu-Xaa4-Cys-Ile-Thr-Phe-Ile-Asp-^

Name: δ-SVIE

Species: *striatus*

Isolated: Yes

Cloned: Yes

DNA Sequence:

ATGAAACTGACGTGCGTGATGATCGTTGCTGTGCTGTTCTTGACCACTTGGACATTC (SEQ ID NO:178)

GTCACGGCTGATGACTCCAGATATGGATTGAAGAATCTTTTTCCGAAGGCACGTCAT

GAAATGAAGAACCCCGAAGCCTCTAAATTGAACAAGAGAGATGGGTGCTCTAGTGG

TGGTACATTTTGTGGCATCCATCCAGGACTCTGCTGCAGCGAGTTTTGCTTTCTTTGG

TGCATAACATTTATTGATTGATGTCTTCTCCTCCCCTC

Translation:

MKLTCVMIVAVLFLTTWTFVTADDSRYGLKNLFPKARHEMKNPEASKLNKRDGCSSG (SEQ ID NO:179)

GTFCGIHPGLCCSEFCFLWCITFID

Toxin Sequence:

Asp-Gly-Cys-Ser-Ser-Gly-Gly-Thr-Phe-Cys-Gly-Ile-His-Xaa3-Gly-Leu-Cys-Cys-Ser-Xaa1- (SEQ ID NO:180)

Phe-Cys-Phe-Leu-Xaa4-Cys-Ile-Thr-Phe-Ile-Asp-^

Name: δ-NgVIA

Species: *striolatus*

Isolated: Yes

Toxin Sequence:

Ser-Lys-Cys-Phe-Ser-Xaa3-Gly-Thr-Phe-Cys-Gly-Ile-Lys-Xaa3-Gly-Leu-Cys-Cys-Ser-Val- (SEQ ID NO:181)

Arg-Cys-Phe-Ser-Leu-Phe-Cys-Ile-Ser-Phe-Xaa1-^

Name: C6.2

Species: *catus*

Isolated: No

Cloned: Yes

DNA Sequence:

ATGAAACTGACGTGCATGATGATCGTTGCTGTGCTGTTCTTGACCGCCTGGACATTC (SEQ ID NO:182)

GTCACGGCTGATGACTCCAGAAATGGACTGAAGAATCTTTTTCCGAAGGCACGTCA

TGAAATGAAGAACCCCGAAGCCTCTAAATTGAACAAGAGATATGGGTGCTCTAATG

CTGGTGCATTTTGTGGCATCCATCCAGGACTCTGCTGCAGCGAGCTTTGCCTGGTTT

GGTGCACATGAGTGCTATTCTTCTGGTACATTTTGTGGCTTCAACGGAGGACTCTGC

TGCAGCAACCTTTGCTTATTTTCGTGTGCTTAACATTTCGTGATGTCTTCTCTATTCC

CCTC

TABLE 1-continued

Sequences of Mature O-Superfamily Conotoxins,
Propeptides and DNA Encoding Propeptides

Translation:

MKLTCMMIVAVLFLTAWTFVTADDSRNGLKNLFPKARHEMKNPEASKLNKRYGCSNA  (SEQ ID NO:183)

GAFCGIHPGLCCSELCLVWCT

Toxin Sequence:

Xaa5-Gly-Cys-Ser-Asn-Ala-Gly-Ala-Phe-Cys-Gly-Ile-His-Xaa3-Gly-Leu-Cys-Cys-Ser-Xaa1-  (SEQ ID NO:184)

Leu-Cys-Leu-Val-Xaa4-Cys-Thr-

Name: C6.3

Species: catus

Isolated: No

Cloned: Yes

DNA Sequence:

ATGAAACTGACGTGTATGATGATCGTTGCTGTGCTGTTCTTGACCGCCTGGACATTC  (SEQ ID NO:185)

GTCACGGCTGATGACTCCAGATATGGACTGAAGAATCTTTTTCCGAAGGCACGTCAT

GAAATGAAGAACCCCGAAGCCTCTAAATTGAACAAGAGATATGGGTGCTCTAATGC

TGGTGCATTTTGTGGCATCCATCCAGGACTCTGCTGCAGCGAGCTTTGCCTGGGTTG

GTGCACATGAGTGCTATTCTACTGGTACATTTTGTGGCTTCAACGGAGGACTCTGCT

GCAGCAACCTTTGCTTATTTTCGTGTGCTTAACATTTCGTGATGTCTTCTCTATTCCC

CTC

Translation:

MKLTCMMIVAVLFLTAWTFVTADDSRYGLKLNLFPKARHEMKNPEASKLNKRYGCSNA  (SEQ ID NO:186)

GAFCGIHPGLCCSELCLGWCT

Toxin Sequence:

Xaa5-Gly-Cys-Ser-Asn-Ala-Gly-Ala-Phe-Cys-Gly-Ile-His-Xaa3-Gly-Leu-Cys-Cys-Ser-Xaa1-  (SEQ ID NO:187)

Leu-Cys-Leu-Gly-Xaa4-Cys-Thr-

Name: Di6.3

Species: distans

Isolated: No

Cloned: Yes

DNA Sequence:

ATGAAACTGACGTGTCTGATGATCGTTGCTGTGCTGTTCTTGACCGCCTGGACATTC  (SEQ ID NO:188)

GTCACGGCTGATGACTCCAGAAATGGATTGGAGAATCTCTCTCCGAAGGCACCTCA

CGAAATGAAGAACCCCGAAGCCTCTAAATCGAACAAGAGATATGAGTGCTATCTAC

TGGTACATTTTGTGGCATCAACGGAGGACTCTGCTGCAGCAACCTTTGCTTATTTTT

CGTGTGCTTAACATTTCGTGATGTCTTCTCCTCCCATC

Translation:

MKLTCLMIVAVLFLTAWTFVTADDSRNGLENLSPKAPHEMKNPEASKSNKRYECYLLV  (SEQ ID NO:189)

HFCGINGGLCCSNLCLFFVCLTFS

TABLE 1-continued

Sequences of Mature O-Superfamily Conotoxins,
Propeptides and DNA Encoding Propeptides

Toxin Sequence:

Xaa5-Xaa1-Cys-Xaa5-Leu-Leu-Val-His-Phe-Cys-Gly-Ile-Asn-Gly-Gly-Leu-Cys-Cys-Ser-Asn- (SEQ ID NO:190)

Leu-Cys-Leu-Phe-Phe-Val-Cys-Leu-Thr-Phe-Ser-^

Name: Rg6.1

Species: *regius*

Isolated: No

Cloned: Yes

DNA Sequence:

TTGAGCAAGAGAGACTGCCTTCCTGACTACACGATTTGTGCCTTCAATATGGGTCTG (SEQ ID NO:191)

TGCTGCAGCGACAAGTGCATGCTCGTCTGCCTGCCGTGATGTCTTCTCCTCCCCTC

Translation:

LSKRDCLPDYTICAFNMGLCCSDKCMLVCLP (SEQ ID NO:192)

Toxin Sequence:

Asp-Cys-Leu-Xaa3-Asp-Xaa5-Thr-Ile-Cys-Ala-Phe-Asn-Met-Gly-Leu-Cys-Cys-Ser-Asp-Lys- (SEQ ID NO:193)

Cys-Met-Leu-Val-Cys-Leu-Xaa3-^

Name: Rg6.3

Species: *regius*

Isolated: No

Cloned: Yes

DNA Sequence:

TTGAACAAGAGAATCATCTGCTTTCCTGACTACATGTTTTGTGGCGTCKAATGTGTTTC (SEQ ID NO:194)

TGTGCTGCAGTGGCAACTGCCTTCTCATCTGCGTGCCGTGATGTCTTCTACTCCCCTC

Translation:

LNKRIICEPDYMFCGVNVFLCCSGNCLLICVP (SEQ ID NO:195)

Toxin Sequence:

Ile-Ile-Cys-Phe-Xaa3-Asp-Xaa5-Met-Phe-Cys-Gly-Val-Asn-Val-Phe-Leu-Cys-Cys-Ser-Gly- (SEQ ID NO:196)

Asn-Cys-Leu-Leu-Ile-Cys-Val-Xaa3-^

Name: Gm6.2

Species: *gloriamaris*

Isolated: No

Cloned: Yes

DNA Sequence:

ATGAAACTGACGTGCATGATGATCGTTGCTGTGCTGTTCTTGACCGCCTGGACATTC (SEQ ID NO:197)

GTCACGGCTGTGCCTCACTCCAGCAATGCGTTGGAGAATCTTTATCTGAAGGCACAT

CATGAAATGAACAACCCCGAAGACTCTGAATTGAACAAGAGGTGCTATGATGGTGG

GACAGGTTGTGACTCTGGAAACCAATGCTGCAGTGGCTGGTGCATTTTCGCCTGCCT

CTAAAACTGTCGTGATGTCTTCTCCTCCCCTC

TABLE 1-continued

Sequences of Mature O-Superfamily Conotoxins,
Propeptides and DNA Encoding Propeptides

Translation:

MKLTCMMIVAVLFLTAWTFVTAVPHSSNALENLYLKAHHEMNNPEDSELNKRCYDGG (SEQ ID NO:198)

TGCDSGNQCCSGWCIFACL

Toxin Sequence:

Cys-Xaa5-Asp-Gly-Gly-Thr-Gly-Cys-Asp-Ser-Gly-Asn-Gln-Cys-Cys-Ser-Gly-Xaa4-Cys-Ile- (SEQ ID NO:199)

Phe-Ala-Cys-Leu-^

Name: Da6.1

Species: *dalli*

Isolated: No

Cloned: Yes

DNA Sequence:

ATGAAACTGACGTGCATTATGATCGTTGCTGTGCTGTTCTTGACCGCCTGGACATTC (SEQ ID NO:200)

GTCACGGCTGTGCCTCACTCCAGCAATGCGTTGGAGAATCTTTATCTGAAGGCACAT

CATGAAATGAACAACCCCGAGGACTCTGAATTGAACAAGAGGTGCTATGATGGTGG

GACAGGTTGTGACTCTGGAAACCAATGCTGCAGTGGCTGGTGCATTTTCGTCTGCCT

CTAAAACTGCCGTGATGTCTTCTCTCCCATC

Translation:

MKLTCIMIVAVLFLTAWTFVTAVPHSSNALENLYLKAHHEMNNPEDSELNKRCYDGGT (SEQ ID NO:201)

GCDSGNQCCSGWCIFVCL

Toxin Sequence:

Cys-Xaa5-Asp-Gly-Gly-Thr-Gly-Cys-Asp-Ser-Gly-Asn-Gln-Cys-Cys-Ser-Gly-Xaa4-Cys-Ile- (SEQ ID NO:202)

Phe-Val-Cys-Leu-^

Name: Pn6.6

Species: *pennaceus*

Isolated: No

Cloned: Yes

DNA Sequence:

ATGAAACTGACGTGCGTGATGATCGTTGCTGTGCTGTTCTTGACCGCCTGGACAGTC (SEQ ID NO:203)

GTCACGGCTGTGCCTCACTCCAACAAGCGGTTGGCGAATCTTTATCTGAAGGCACGT

CACGAAATGAAAAACCCCGAAGCCTCTAATGTGGACAAGAGGTGCTTTGAGAGTTG

GGTAGCTTGTGAGTCTCCAAAACGATGCTGCAGTCACGTGTGCCTTTTCGTCTGCAC

CTGAAACTGCCGTGATGTCTTCTCCTCCCCTC

Translation:

MKLTCVMIVAVLFLTAWTVVTAVPHSNKRLANLYLKARHEMKNPEASNVDKRCFESW (SEQ ID NO:204)

VACESPKRCCSHVCLFVCT

TABLE 1-continued

Sequences of Mature O-Superfamily Conotoxins,
Propeptides and DNA Encoding Propeptides

Toxin Sequence:

Cys-Phe-Xaa1-Ser-Xaa4-Val-Ala-Cys-Xaa1-Ser-Xaa3-Lys-Arg-Cys-Cys-Ser-His-Val-Cys-Leu- (SEQ ID NO:205)

Phe-Val-Cys-Thr-^

Name: Di6.5

Species: *distans*

Isolated: No

Cloned: Yes

DNA Sequence:

ATGAAACTGACGTGTATGTTGATCATCGCTGTGCTGTTCCTGACGGCCTGTCAACTC (SEQ ID NO:206)

TCTACAAATGCGAGTTACGCCAGAAGTAAGCAGAAGCATCGTGTTCTGAGGTCGAC

TGACAAAAACTCCAAGTTGACCCAGCGTTGCAATGAAGCTCAAGAACATTGCACTC

AAAATCCTGACTGCTGCAGTGAGTCTTGCAATAAGTTTGTCGGCAGATGCTTGTCAG

ACTGATCTGATGTCTTCTCCTCCCATC

Translation:

MKLTCMLIIAVLFLTACQLSTNASYARSKQKHRVLRSTDKNSKLTQRCNEAQEHCTQN (SEQ ID NO:207)

PDCCSESCNKFVGRCLSD

Toxin Sequence:

Cys-Asn-Xaa1-Ala-Gln-Xaa1-His-Cys-Thr-Gln-Asn-Xaa3-Asp-Cys-Cys-Ser-Xaa1-Ser-Cys- (SEQ ID NO:208)

Asn-Lys-Phe-Val-Gly-Arg-Cys-Leu-Ser-Asp-^

Name: Af6.10

Species: *ammiralis*

Isolated: No

Cloned: Yes

DNA Sequence:

ATGAAACTGACGTGCCTGATGATCGTTGCTGTGCTGTTCTTGACCGCCTGGACATTC (SEQ ID NO:209)

GTCACGGCTGTGCCTGACTCCAGCAATGCGTTGGAGAATCTTTATCTGAAGGCACAT

CATGAAATGAACAACCCCGAAGACTCTGAATTGAACAAGAGGTGCTATGATGGTGG

GACAAGTTGTAACACTGGAAACCAATGCTGCAGTGGCTGGTGCATTTTCCTCTGCCT

CTAAAACTGCCGTGATGTCTTCTCTTCCCCTC

Translation:

MKLTCLMIVAVLFLTAWTFVTAVPDSSNALENLYLKAHHEMNNPEDSELNKRCYDGG (SEQ ID NO:210)

TSCNTGNQCCSGWCIFLCL

TABLE 1-continued

Sequences of Mature O-Superfamily Conotoxins,
Propeptides and DNA Encoding Propeptides

Toxin Sequence:

Cys-Xaa5-Asp-Gly-Gly-Thr-Ser-Cys-Asn-Thr-Gly-Asn-Gln-Cys-Cys-Ser-Gly-Xaa4-Cys-Ile-  (SEQ ID NO:211)

Phe-Leu-Cys-Leu-^

Name: Tx6.10

Species: *textile*

Isolated: No

Cloned: Yes

DNA Sequence:

GGCATTACCTAAAACATCACCAAGATGAAACTGACGTGCATGATGATCGTTGCTGT  (SEQ ID NO:212)

GCTGTTCTTGACCGCCTGGACATTCGTCACGGCTGCGCCTCACTCCAGCAATGCGTT

GGAGAATCTTTATCTGAAGGCACATCATGAAATGAACAACCCCGAAGCCTCTGAAT

TGAACAAGAGGTGCTATGATAGTGGGACAAGTTGTAACACTGGAAACCAATGCTGC

AGTGGCTGGTGCATTTTCGTCTCTTGCCTCTAAAACTACCGTGATGTCTTCTCCTCCC

CTC

Translation:

MKLTCMMIVAVLFLTAWTFVTAAPHSSNALELYLKAHHEMNNPEASELNKRCYDSG  (SEQ ID NO:213)

TSCNTGNQCCSGWCIFVSCL

Toxin Sequence:

Cys-Xaa5-Asp-Ser-Gly-Thr-Cys-Asn-Thr-Gly-Asn-Cyc-Cys-Ser-Gly-Xaa4-Cys-Ile-  (SEQ ID NO:214)

Phe-Val-Ser-Cys-Leu-^

Name: Gm6.4

Species: *gloriamaris*

Isolated: No

Cloned: Yes

DNA Sequence:

ATGAAAACTGACGTGCATGATGATCGTTGCTGTGCTGTTCCTGACAGCCTGGACGCTA  (SEQ ID NO:215)

GTCATGGCTGATGACTCCAACAATGGACTGGCGAATCTTTTTTCGAAATCACGTGAC

GAAATGGAGGACCCCGAAGCTTCTAAATTGGAGAAAAGGGATTGCCAAGCACTATG

GGATTATTGTCCAGTACCGCTCTTGTCATCGGGTGATTGCTGCTATGGCTTAATCTGT

GGCCCTTTCGTCTGCATTGGATGGTGATGTCTTCTACTCCCATC

Translation:

MKLTCMMIVAVLFLTAWTLVMADDSNNGLANLFSKSRDEMEDPEASKLEKRDCQAL

WDYCPVPLLSSGDCCYGLICGPFVCIGW

Toxin Sequence:

Asp-Cys-Gln-Ala-Leu-Xaa4-Asp-Xaa5-Cys-Xaa3-Val-Xaa3-Leu-Leu-Ser-Ser-Gly-Asp-Cys-  (SEQ ID NO:217)

Cys-Xaa5-Gly-Leu-Ile-Cys-Gly-Xaa3-Phe-Val-Cys-Ile-Gly-Xaa4-^

Name: Om6.2

Species: *omaria*

TABLE 1-continued

Sequences of Mature O-Superfamily Conotoxins,
Propeptides and DNA Encoding Propeptides

Isolated: No

Cloned: Yes

DNA Sequence:

ATGAAACTGACGTGCCTGATGATCGTTGCTGTGCTGTTCTTGACCGCCTGGACATTC (SEQ ID NO:218)

GTCATGGCTGATGACTCCAACAATGGACTGGCAAATCTTTTCTCGAAATCACGTGAC

GAAATGGAGGATACCGATCCTTCTAAATTGGAGAACAGAAAAACTTGCCAAAGAAG

GTGGGATTTTTGTCCAGGATCGCTCGTTGGAGTGATAACTTGCTGCGGTGGCTTAAT

CTGTTTTCTGTTCTTCTGCGTTTGATAGTGATGCTCTTCTCCTCCCCT

Translation:

MKLTCLMIVAVLFLTAWTFVMADDSNNGLANLFSKSRDEMEDTDPSKLENRKTCQRR (SEQ ID NO:219)

WDFCPGSLVGVITCCGGLICFLFFCV

Toxin Sequence:

Lys-Thr-Cys-Gln-Arg-Arg-Xaa4-Asp-Phe-Cys-Xaa3-Gly-Ser-Leu-Val-Gly-Val-Ile-Thr-Cys- (SEQ ID NO:220)

Cys-Gly-Gly-Leu-Ile-Cys-Phe-Leu-Phe-Phe-Cys-Val-^

Name: Da6.3

Species: *dalli*

Isolated: No

Cloned: Yes

DNA Sequence:

ATGAAACTGACGTGTGTGATGATCGTTGCTGTGCTGTTCCTGACAGCCTGGACGCTA (SEQ ID NO:221)

GTCATGGCTGATGACTCCAACAATGGACTGGCGAATCTTTTTTCGAAATTACGTGAC

GAAATGGAGGACCCCGAAGGTTCTAAATTGGAGAAAAAGGATTGCCAAGAAAAAT

GGGATTATTGTCCAGTACCGTTCTTGGGATCGAGGTATTGCTGCGATGGCTTTATCT

GTCCATCTTTCTTCTGCGCTTGATAGTGATGTCTTCTCTATTCCCCTC

Translation:

MKLTCVMIVAVLFLTAWTLVMADDSNNGLANLFSKLRDEMEDPEGSKLEKKDCQEK (SEQ ID NO:222)

WDYCPVPFLGSRYCCDGFICPSFFCA

Toxin Sequence:

Asp-Cys-Gln-Xaa1-Lys-Xaa4-Asp-Xaa5-Cys-Xaa3-Val-Xaa3-Phe-Leu-Gly-Ser-Arg-Xaa5-Cys- (SEQ ID NO:223)

Cys-Asp-Gly-Phe-Ile-Cys-Xaa3-Ser-Phe-Phe-Cys-Ala-^

Name: Da6.7

Species: *dalli*

Isolated: No

Cloned: Yes

DNA Sequence:

ATGAAACTGACGTGCGTGATGATCGTTGCTGTGTTGTTCCTGACAGCCTGGACGCTA (SEQ ID NO:224)

GTCATGGCTGATGACTCCAACAATGGACTGGCGAATCATTTTTGGKAATCACGTGAC

GAAATGGAGGACCCTGAAGCTTCTAAATTGGAGAAAAGGGATTGCCAAGGCGAAT

TABLE 1-continued

Sequences of Mature O-Superfamily Conotoxins,
Propeptides and DNA Encoding Propeptides

GGAGTTTTGTATAGTACCGGTCCTTGGATTTGTGTATTGCTGCCCCTGGCTTATCTGT

GGCCCTTTCGTCTGCGTTGATATCTGATGTCTTCTATCCCCTC

Translation:

MKLTCVMIVAVLFLTAWTLVMADDSNNGLANHFWKSRDEMEDPEASKLEKRDCQGE (SEQ ID NO:225)

WEFCIVPVLGFVYCCPWLICGPFVCVDI

Toxin Sequence:

Asp-Cys-Gln-Gly-Xaa1-Xaa4-Xaa1-Phe-Cys-Ile-Val-Xaa3-Val-Leu-Gly-Phe-Val-Xaa5-Cys- (SEQ ID NO:226)

Cyd-Xaa3-Xaa4-Leu-Ile-Cys-Gly-Xaa3-Phe-Val-Cys-Val-Asp-Ile-^

Name: Pn6.5

Species: *pennaceus*

Isolated: No

Cloned: Yes

DNA Sequence:

ATGAAACTGACGTGCCTGATGATCATTGCTGTGCTGTTCTTGACCGCCTGGACATTC (SEQ ID NO:227)

GTCATGGCTGATGACCCCAGAGATGAACCGGAGGCACGTGACGAAATGAACCCCGC

AGCCTCTAAATTGAACGAGAGAGGCTGCCTTGAAGTTGATTATTTTTGCGGCATACC

GTTTGTGAACAACGGGCTATGCTGCAGTGGCAATTGTGTTTTTGTCTGCACACCCCA

AGGGAAGTAAAACTGCTGTGATGTCTTCTCTTCCCATC

Translation:

MKLTCLMIIAVLFLTAWTFVMADDPRDEPEARDEMNPAASKLNERGCLEVDYFCGIPF (SEQ ID NO:228)

VNNGLCCSGNCVFVCTPQGK

Toxin Sequence:

Gly-Cys-Leu-Xaa1-Val-Asp-Xaa5-Phe-Cys-Gly-Ile-Xaa3-Phe-Val-Asn-Asn-Gly-Leu-Cys-Cys- (SEQ ID NO:229)

Ser-Gly-Asn-Cys-Val-Phe-Val-Cys-Thr-Xaa3-Gln-#

Name: Marm6

Species: *marmoreus*

Isolated: No

Cloned: Yes

DNA Sequence:

GGTCGACATCATCATCATCGATCCATCTGTCCATCCATCTGTCCATCCATCCATTCAT (SEQ ID NO:230)

TCATTCACTGCCAAACTGTCATAAATATTTGAGTCTCTCTTTCTGTTTTTATCTGACA

GATTGAACGAGAGAGACTGCCTTAATGTTGATTATTTTTGCGGCATACCGTTTGTGA

ACAACGGGCTATGCTGCAGTGGCAATTGTGTTTTTGTCTGCACACCCCAAGGGAAGT

AAAACTGCCGTGATGTCTTCTCTTCCCCTCTAGTAGTAGTAGGCGGCCGCTCTAGAG

GATCCAAGCTTACGTACGCGTGCATGCGACGTCATAGCTCTTCTATAGTGTCACCTA

AATTCAATTCACTGGCCGTCCGTTTTACAACGTCGTGACTGGGAAAACCCTGGCGTT

ACCCAACTTAATCGCCTTGCAGCACAT

TABLE 1-continued

Sequences of Mature O-Superfamily Conotoxins,
Propeptides and DNA Encoding Propeptides

Translation:

NERDCLNVDYFCGIPFVNNGLCCSGNCVFVCTPQGK (SEQ ID NO:231)

Toxin Sequence:

Cys-Leu-Asn-Val-Asp-Xaa5-Phe-Cys-Gly-Ile-Xaa3-Phe-Val-Asn-Asn-Gly-Leu-Cys-Cys-Ser- (SEQ ID NO:232)

Gly-Asn-Cys-Val-Phe-Val-Cys-Thr-Xaa3-Gln-#

Name: Marm15

Species: *marmoreus*

Isolated: No

Cloned: Yes

DNA Sequence:

TCGACATCATCATCATCGATCCATCTGTCCATCCATCCATTCATTCATTCGCTGCCAA (SEQ ID NO:233)

ACTGTCATAAATATTTGAGTCTCTCTTTCTGTTTTTATCTGACAGATTGGACAAGAGA

GAGTGCCTGGAAGCTGATTATTATTGCGTCTTACCGTTTGTGGGCAAcGGGATGTGC

TGCAGTGGCATTTGTGTTTTTGTCTGCATAGCCC

Translation:

LDKRECLEADYYCVLPFVGNGMCCSGICVFVCIAQRFKTV (SEQ ID NO:234)

Toxin Sequence:

Xaa1-Cys-Leu-Xaa1-Ala-Asp-Xaa5-Xaa5-Cys-Val-Leu-Xaa3-Phe-Val-Gly-Asn-Gly-Met-Cys- (SEQ ID NO:235)

Cys-Ser-Gly-Ile-Cys-Val-Phe-Val-Cys-Ile-Ala-Gln-Arg-Phe-Lys-Thr-Val-^

Name: Marm10

Species: *marmoreus*

Isolated: No

Cloned: Yes

DNA Sequence:

GTACCGGTCCGGAATTCCCGGGTCGACATCATCATCATCGATCCATCTGTCCATCCA (SEQ ID NO:236)

TCCATCCATTCATTCATTCGCTGCCAAACTGTCATAAACATTTGAGTCTCTCTTTCTG

TTTTTATCTGACAGATTGAACGAGAGAGACTGCCTTGAACCTGATTATGTTTGCGGC

ATACCGTTTGTGTTCAACGGGCTATGCTGCAGTGGAATTTGTGTTTTTATCTGCATAG

CCCAAAAGTATTAAAACGCCGTGATGTCTTCTATTCCCATCTAGTAGTAGTAGGCGG

CCGCTCTAGAGGATCCAAGCTTACGTACGCGTGCATGCGACGTCATAGCTCTTCTAT

AGTGTCACCTAAATTCAATTCACTGGCCGTCGTTTTACAACGTCGTGACTGGGAAAA

CCCTGGCGTTACCCAACTTAATCGCCTTGCAGCACATCCCCCTTTCGCCAGCTGGCG

TAATAGCCGAAGAGGCCCGCACCGATCGCCCTTCCCAACAGTTGCGCAGCCTGAAT

GGCGAATGGGG

TABLE 1-continued

Sequences of Mature O-Superfamily Conotoxins,
Propeptides and DNA Encoding Propeptides

Translation:

LNERDCLEPDYVCGIPFVFNGLCCSGICVFICIAQKY (SEQ ID NO:237)

Toxin Sequence:

Asp-Cys-Leu-Xaa1-Xaa3-Asp-Xaa5-Val-Cys-Gly-Ile-Xaa3-Phe-Val-Phe-Asn-Gly-Leu-Cys- (SEQ ID NO:238)

Cys-Ser-Gly-Ile-Cys-Val-Phe-Ile-Cys-Ile-Ala-Gln-Lys-Xaa5-^

Name: Marm14

Species: *marmoreus*

Isolated: No

Cloned: Yes

DNA Sequence:

GGTACGCCTGCAGGTACCGGTCCGGAATTCCCGGGTCGACATCATCATCATCGA (SEQ ID NO:239)

TCCATCTGTCCATCCATCTATTCATTCATTCGCTGTCAAACTGTAATACATATTAGAA

TCTCTCTTTCTGTTTGTATCTGACAGATTGGAGAAAAGGGCGTGCAGCAAAAAATGG

GAATATTGTATAGTACCGATCCTTGGATTCGTATATTGCTGCCCTGGCTTAATCTGTG

GTCCTTTCGTCTGCGTTTGATAGTGATGTCTTCTCCTCCCATCTAGTAGTAGTAGGCG

GCCGCTCTAGAGGATCCAAGCTTACGTACGCGTGCATGCGACGTCATAGCTCTTCTA

TAGTGTCACCTAAATTCAATTCACTGGCCGTCGTTTTACAACGTCGTGACTGGGAAA

ACCCTGGCGTTACCCAACTTAATCGCCTTGCAGCACATCCCCCTTTCGCCAGCTGGC

GTAATAAGCGAAGAGGCCCGCACCGATCGCCCTTCCCAACAGTTGCGCAGCCTGAA

TGGCGAAATGGGACGCGCCCTG

Translation:

LEKRACSKKWEYCIVPILGFVYCCPGLICGPFVCV (SEQ ID NO:240)

Toxin Sequence:

Ala-Cys-Ser-Lys-Lys-Xaa4-Xaa1-Xaa5-Cys-Ile-Val-Xaa3-Ile-Leu-Gly-Phe-Val-Xaa5-Cys-Cys- (SEQ ID NO:241)

Xaa3-Gly-Leu-Ile-Cys-Gly-Xaa3-Phe-Val-Cys-Val-^

Name: Omaria14

Species: *omaria*

Isolated: No

Cloned: Yes

DNA Sequence:

AAAGCCGGTACGCCTGCAGGTACCGGTCCGGAATTCCCGGGTCGACATCATCATCA (SEQ ID NO:242)

TCATCGATCCATCTGTCCATCCATCCATTCATTCATTCACTGCCACTGTCATAAAT

ATTTGAGTCTCTCTTTCTGTTTTTATCTGACAGATTGAACGAGAGAGACTGCCTTAAT

GTTGATTATTTTTGTGGCATACCGTTTGTGAACAACGGGCTATGCTGCAGTGGCAAT

TGTGTTTTTTGTCTGCACACCCCAAGGGAAGTAAAACTGCCGTGATGTCTTCTCTTCC

TABLE 1-continued

Sequences of Mature O-Superfamily Conotoxins,
Propeptides and DNA Encoding Propeptides

CCTCTAGTAGTAGTAGGCGGCCGCTCTAGAGGATCCAAGCTTACGTACGCGTGCAT

GCGACGTCATAGCTCTTCTATAGTGTCACCTAAATTCAATTCACTGGCCGTCGTTTTA

CAACGTCGTGACTGGGAAAACCCTGGCGTTACCCAACTTAATCGCCTTGCAGCACAT

CCCCCTTTCGCCAGCTGGCGTAATAGCGAAGAGCCCGCACCGATCGCCCTTCCCA

ACAGTTGCGCAGCCTGAATGGCGAATGGGACGCGCCCT

Translation:

LNERDCLNVDYFCGIPFVNNGLCCSGNCVFCLHTPREVKLP (SEQ ID NO:243)

Toxin Sequence:

Asp-Cys-Leu-Asn-Val-Asp-Xaa5-Phe-Cys-Gly-Ile-Xaa3-Phe-Val-Asn-Asn-Gly-Leu-Cys-Cys- (SEQ ID NO:244)

Ser-Gly-Asn-Cys-Val-Phe-Cys-Leu-His-Thr-Xaa3-Arg-Xaa1-Val-Lys-Leu-Xaa3-^

Name: O6.4

Species: *obscurus*

Isolated: No

Cloned: Yes

DNA Sequence:

cgatccatctgtccatccatccattcattcattcattgccaaactgtaacaaatattcaagtctctctttctgtttgtgtctgaca (SEQ ID NO:245)

gATCGAAACGGTGCCTTGTTTACGGTACACCTTGTGACTGGCTGACCATTGCGGGTATGGAGTGC

TGCAGTAAAAAGTGCTTTATGATGTGCTGGTAAAACTGCCGTGATGTCTTCTACTCC

CCTC

Translation:

RSKRCLVYGTPCDWLTIAGMECCSKKCFMMCW (SEQ ID NO:246)

Toxin Sequence:

Cys-Leu-Val-Xaa5-Gly-Thr-Xaa3-Cys-Asp-Xaa4-Leu-Thr-Ile-Ala-Gly-Met-Xaa1-Cys-Cys-Ser- (SEQ ID NO:247)

Lys-Lys-Cys-Phe-Met-Met-Cys-Xaa4-^

Name: R6.4

Species: *radiatus*

Isolated: No

Cloned: Yes

DNA Sequence:

ATTGAACCAGAGAGACTGCCATGAAGTTGGTGAATTTTGTGGCTTACCGTTAATAAA (SEQ ID NO:248)

GAACGGGCTATGCTGCAGTCAGATTTGTTTAGGTGTCTGCGCAAAGTGTTTTAAAA

CTGCCGTGATGTCTTCTACTCCCAT

TABLE 1-continued

Sequences of Mature O-Superfamily Conotoxins,
Propeptides and DNA Encoding Propeptides

Translation:

LNQRDCHEVGEFCGLPLIKNGLCCSQICLGVCAKVF (SEQ ID NO:249)

Toxin Sequence:

Asp-Cys-His-Xaa1-Val-Gly-Xaa1-Phe-Cys-Gly-Leu-Xaa3-Leu-Ile-Lys-Asn-Gly-Leu-Cys-Cys- (SEQ ID NO:250)

Ser-Gln-Ile-Cys-Leu-Gly-Val-Cys-Ala-Lys-Val-Phe-^

Name: R6.6

Species: *radiatus*

Isolated: No

Cloned: Yes

DNA Sequence:

ATTAGACAAGAAAGAGTGCACTGCCAATGGTGAATTTTGTGGCATATCGGTCTTTGG (SEQ ID NO:251)

AAGCTACCTATGCTGCAGTGGCCGGTGTGTATTCGTCTGCATCTAGTTGAACTGCCG

TGATGTCTTCTACTCCCCT

Translation:

LDKKECTANGEFCGISVFGSYLCCSGRCVFVCI (SEQ ID NO:252)

Toxin Sequence:

Xaa1-Cys-Thr-Ala-Asn-Gly-Xaa1-Phe-Cys-Gly-Ile-Ser-Val-Phe-Gly-Ser-Xaa5-Leu-Cys-Cys- (SEQ ID NO:253)

Ser-Gly-Arg-Cys-Val-Phe-Val-Cys-Ile-^

Name: R6.7

Species: *radiatus*

Isolated: No

Cloned: Yes

DNA Sequence:

ATTGGACAAGAAAGAGTGCACTACCAATGGTGAATTTTGTGGCATATCGGTCTTTGC (SEQ ID NO:254)

AAGCTTCCTATGCTGCAGTGGCCTGTGTGTATTCGTCTGCATCTAGCTGAACTGCCG

TGATGTCTTCTCTTCCCCT

Translation:

LDKKECTTNGEFCGISVFASFLCCSGLCVFVCI (SEQ ID NO:255)

Toxin Sequence:

Xaa1-Cys-Thr-Thr-Asn-Gly-Xaa1-Phe-Cys-Gly-Ile-Ser-Val-Phe-Ala-Ser-Phe-Leu-Cys-Cys- (SEQ ID NO:256)

Ser-Gly-Leu-Cys-Val-Phe-Val-Cycs-Ile-^

Name: R6.8

Species: *radiatus*

Isolated: No

Cloned: Yes

TABLE 1-continued

Sequences of Mature O-Superfamily Conotoxins,
Propeptides and DNA Encoding Propeptides

DNA Sequence:

ATTGGACAAGAGAAAATGCTTTCCCAAAAATCATTTTTGTGGCTTTGTGGTGATGCT (SEQ ID NO:257)

GAACTACCTATGCTGCAGTGGCCGGTGTATATTCGTCTGCGTCTAGTTGAACTGCCG

TGATGTCTTCTACTCCCAT

Translation:

LDKRKCFPKNHFCGFVVMLNYLCCSGRCIFVCV (SEQ ID NO:258)

Toxin Sequence:

Lys-Cys-Phe-Xaa3-Lys-Asn-His-Phe-Cys-Gly-Phe-Val-Val-Met-Leu-Asn-Xaa5-Leu-Cys-Cys- (SEQ ID NO:259)

Ser-Gly-Arg-Cys-Ile-Phe-Val-Cys-Val-^

Name: Rg6.5

Species: *regius*

Isolated: No

Cloned: Yes

DNA Sequence:

TTGAACAAGAGAAGCTGCCTTCCTCTAGACTGGTTTTGTGGCTTCAATATAATTGGA (SEQ ID NO:260)

GCGTTTCTGTGCTGTAGTGGCTACTGCCTTGTCGTCTGCATGTAAAACTGCCGTGAT

GTCTTCTCCTCCCCTC

Translation:

LNKRSCLPLDWFCGFNIIGAFLCCSGYCLVVCM (SEQ ID NO:261)

Toxin Sequence:

Ser-Cys-Leu-Xaa3-Leu-Asp-Xaa4-Phe-Cys-Gly-Phe-Asn-Ile-Ile-Gly-Ala-Phe-Leu-Cys-Cys- (SEQ ID NO:262)

Ser-Gly-Xaa5-Cys-Leu-Val-Val-Cys-Met-^

Name: De6.2

Species: *delessertii*

Isolated: No

Cloned: Yes

DNA Sequence:

ATGAAACTGACGTGTCTGCTGATCGTTGCTGTGCTGGTCTTGGCAGCCTGTCAGTTC

ATCGTAGCTGGCGACTCGAGTGATGGCCAGGAGAATCCTGCTCTGAGGTCACCTAG

CGATTCCTCTGGGAAAATGTCATCAATGAAGCGCTTCCAGACACGGCTGATGGTGG

GGCAATCTGCATCGAAAAGACCAAGCAAGAGGGACTGCATCCCCGGCGGCGAAAA

TTGTGATGTATTCCGACCATACCGGTGCTGCAGTGGATATTGCATACTACTCCTTTG

CGCATGATAAAGCTGCCTTGATGTCTTCTCCTCCCCTC (SEQ ID NO:263)

TABLE 1-continued

Sequences of Mature O-Superfamily Conotoxins,
Propeptides and DNA Encoding Propeptides

Translation:

MKLTCLLIVAVLVLAACQIVAGDSSDGQENPALRSPSDSSGKMSSMKRFQTRLMVGQ (SEQ ID NO:264)

SASKRPSKRDCJPGGENCDVFRPYRCCSGYCILLLCA

Toxin Sequence:

Asp-Cys-Ile-Xaa3-Gly-Gly-Xaa1-Asn-Cys-Asp-Val-Phe-Arg-Xaa3-Xaa5-Arg-Cys-Cys-Ser- (SEQ ID NO:265)

Gly-Xaa5-Cys-Ile-Leu-Leu-Leu-Cys-Ala-^

Name: Striat21

Species: *striatus*

Isolated: No

Cloned: Yes

DNA Sequence:

GCTGGTTCGCCTGCAGGTACCGGTCCGGAATTCCCGGGTCGACATCATCATCATCGA (SEQ ID NO:266)

TCCATCTGTCCATCCATCTATTCATTCATTCATTCGCTGCCAAACTGTATTAAATATT

CAAGTCTCTCTTTCTGTTTGTGTCTAACAGATTGAGATGGTGCATTCCTAGTGGTGA

ACTTTGTTTCCGCTCGGATCACATAGGATGCTGCAGTGGCAAGTGCGCATTCGTCTG

CTTGTAAAACTGCCGTGATGTCTTCTCCTCCCATCTAGTAGTAGTAGGCGGCCGCTC

TAGAGGATCCAAGCTTACGTACGCGTGCATGCGACGTCATAGCTCTTCTATAGTGTC

ACCTAAATTCAATTCACTGGCCGTCGTTTTACAACGTCGTGACTGGGAAAACCCTGG

CGTTACCCAACTTAATCGCCTTGCAGCACATCCCCCTTTCGCCAGCTGGCGTAATAG

CGAAGAGGCCCGCACCGATCGCCCTTCCCAACAGTTTGCGCAGCCTGAATGGCGAA

TGGGACGCGCCCTGTAGCGGCGCATTAAACCGCGGCGGGTGTGGGTGGGTTACGCC

CACGTGACCCGCTACACTTGCCAGCGCCCTANCGCCCCGCTCCTTTCGCTTTCTTTCC

CTTCCTTTCTCGNCACGTTTCGGCCGNTTTTCCCCGTCAAGCTCTTAAATCGGGGGG

CTTCCCTTTAAGGGTTNCCGAATTANTGCTTTACCGGNACCCTTGACCCCCAAAAAA

ACTTGGANTAAGGGGNGATGGNTCNCGTAANTGGGGGCCATCNCCCCTGAANAGA

ACGGTTTTTCNCCCCTTTTGACNGTTGGGNGTTCCNCGGTTTTTAAAAAANGGGACC

TTTTNTTTCCAAAACTGGGAANANACCTAAACCCTATTTTTGGGGCTATTTTTTTGAN

TTTNAAANGGGATTTTGCCCCATTTTNGGCCCTNTTGGGGTAAAAAAAAGAGCCGG

TTTTAAAAAAAATTTTACCCCAAATTTTAACAAAAATTTTTT

Translation:

LRWCIPSGELCFRSDHIGCCSGKCAFVCL (SEQ ID NO:267)

Toxin Sequence:

Leu-Arg-Xaa4-Cys-Ile-Xaa3-Ser-Gly-Xaa1-Leu-Cys-Phe-Arg-Ser-Asp-His-Ile-Gly-Cys-Cys- (SEQ ID NO:268)

Ser-Gly-Lys-Cys-Ala-Phe-Val-Cys-Leu-^

Name: δStriatus 26

Species: *striatus*

Isolated: No

Cloned: Yes

TABLE 1-continued

Sequences of Mature O-Superfamily Conotoxins,
Propeptides and DNA Encoding Propeptides

DNA Sequence:

TTGAGATGGTGCATTCCTAGTGGTGATCTTTGTTTCCGCTCGGATCACATAGGATGC (SEQ ID NO:269)

TGCAGTGGCAAGTGCGCATTCGTCTGCTTGTAA

Translation:

LRWCIPSGDLCFRSDHIGCCSGKCAFVCL (SEQ ID NO:270)

Toxin Sequence:

Xaa4-Cys-Ile-Xaa3-Ser-Gly-Asp-Leu-Cys-Phe-Arg-Ser-Asp-His-Ile-Gly-Cys-Cys-Ser-Gly-Lys- (SEQ ID NO:271)

Cys-Ala-Phe-Val-Cys-Leu-^

Name: δStriatus 106

Species: *striatus*

Isolated: No

Cloned: Yes

DNA Sequence:

TTGAGATGGTGCATTCCTAGTGGTGATCTTTGTTTCCGCTCGGATCACATACAATGC (SEQ ID NO:272)

TGCAGTGGCAAGTGCGCATTCGTCTGCTTGTAA

Translation:

LRWCIPSGDLCFRSDHIQCCSGKCAFVCL (SEQ ID NO:273)

Toxin Sequence:

Xaa4-Cys-Ile-Xaa3-Ser-Gly-Asp-Leu-Cys-Phe-Arg-Ser-Asp-His-Ile-Gln-Cys-Cys-Ser-Gly-Lys- (SEQ ID NO:274)

Cys-Ala-Phe-Val-Cys-Leu-^

Name: O6.3

Species: *obscurus*

Isolated: No

Cloned: Yes

DNA Sequence:

cgatccatctgtccatccatccattcagtcattcgctgccaaactgtaacaaatattcaagtcttgctttctgtttgtgtctgaca (SEQ ID NO:275)

gATTGAGATGGTGCGTTCCTAGCGGTGAAGTTTGTCGCCGCTATGAATTCGTGGGATGCTGCAG

TGGCAAGTGCTTCTTCGTCTGCTCGTAAAACTGTTGTGATGTCTTCTCCTCCCCTC

Translation:

VSDRLRWCVPSGEVCRRYEFVGCCSGKCFFVCS (SEQ ID NO:276)

Toxin Sequence:

Leu-Arg-Xaa4-Cys-vaL-Xaa3-Ser-Gly-Xaa1-Val-Cys-Arg-Arg-Xaa5-Xaa1-Phe-Val-Gly-Cys- (SEQ ID NO:277)

Cys-Ser-Gly-Lys-Cys-Phe-Phe-Val-Cys-Ser-^

Name: R6.3

Species: *radiatus*

Isolated: No

Cloned: Yes

TABLE 1-continued

Sequences of Mature O-Superfamily Conotoxins,
Propeptides and DNA Encoding Propeptides

DNA Sequence:

ctctctctctctctgctggacaggTCGACTCGCTGCTTGCCTGACGGAACGTCTTGCCTTTTTAGTA (SEQ ID NO:278)

GGATCAGATGCTGCGGTACTTGCAGTTCAATCTTAAAGTCATGTGTGAGCTGATCCG

GCGGTTGATCTTCCTCCCTCTGTGCTCCATCCTTTTCTGCCTGAGTCCTCCTTACCTG

AGAGTGGTCATGAACCACTCATCACCTACTCCTCTGGAGGCTTCAGAGGAGCTACAT

TGAAATAAAAGCCGCATTGC

Translation:

RSTRCLPDGTSCLFSRIRCCGTCSSILKSCVS (SEQ ID NO:279)

Toxin Sequence:

Cys-Leu-Xaa3-Asp-Gly-Thr-Ser-Cys-Leu-Phe-Ser-Arg-Ile-Arg-Cys-Cys-Gly-Thr-Cycs-Ser-Ser- (SEQ ID NO:280)

Ile-Leu-Lys-Ser-CysVal-Ser-^

Name: G6.3

Species: *geographus*

Isolated: No

Cloned: Yes

DNA Sequence:

GGATCTTGCACGGTGAATTTCGCTTCATATTTTTCTACTGTCGTCTTTGGCATCATCC (SEQ ID NO:281)

AAAACATCACCAAGATGAAACTGACGTGCATGATGATCGTTGCTGTGCTGTTCTTGA

CCGCCTGGACATTCGTCACGGCTGTGCCTCACTCCAGCGATGTATTGGAGAATCTTT

ATCTGAAGGCACTTCACGAAACGGAAAACCACGAAGCCTCTAAATTGAACGTGAGA

GACGACGAGTGCGAACCTCCTGGAGATTTTTGTGGCTTTTTTAAAATTGGGCCGCCT

TGCTGCAGTGGCTGGTGCTTCCTCTGGTGCGCCTAAAACTGCCGTGATGTCTTCTATT

CCCCTCTGTGCTACCTGGCTTGATCTTTGATTGGCGCGTGCCCTTCAGTGGTTATGAA

CCCCCCTGAGCCGACTCTCTGGGGGCCTCGGGGGTTCAACATCCAAATAAAGCGAC

AACACAATCACAAGTAAAAAA

Translation:

MKLTCMMIVAVLFLTAWTFVTAVPHSSDVLENLYLKALHETENHEASKLNVRDDECEP (SEQ ID NO:282)

PGDFCGFFKIGPPCCSGWCFLWCA

Toxin Sequence:

Asp-Asp-Xaa1-Cys-Xaa1-Xaa3-Xaa3-Gly-Asp-Phe-Cys-Gly-Phe-Phe-Lys-Ile-Gly-Xaa3-Xaa3- (SEQ ID NO:283)

Cys-Cys-Ser-Gly-Xaa4-Cys-Phe-Leu-Xaa4-Cys-Ala-^

Name: Tx6.8

Species: *textile*

Isolated: No

Cloned: Yes

TABLE 1-continued

Sequences of Mature O-Superfamily Conotoxins,
Propeptides and DNA Encoding Propeptides

DNA Sequence:

GCTGCAGGTCGACTCTAGAGGCGTTGGAGAATCTTTATCTGAAGGCACATCATGAA (SEQ ID NO:284)

ATGAACAACCCCGAAGACTCTGAATTGAACAAGAGGTGCTATGATAGTGGGACAAAG

TTGTAACACTGGAAACCAATGCTGCAGTGGCTGGTGCATTTTCGTCTGCCTCTAAAA

CTGCCGTGATGTCTTCTACTCCCCTCTGTGCTACCTACCTGGCTTGATCTTTGATTGG

CGCGTGCCCTTCACTGGTTATGAACCCCTCTGATCCGACTCTCTGGGGGCCTCGGGG

ATCCAACATCAAAATANAGCGACAGCACAATCAC

Translation:

CRSTLEALENLYLKAHHEMNPEDSELNKRCYDSGTSCNTGNQCCSGWCIFVCL (SEQ ID NO:285)

Toxin Sequence:

Cys-Xaa5-Asp-Ser-Gly-Thr-Ser-Cys-Asn-Thr-Gly-Asn-Gln-Cys-Cys-Ser-Gly-Xaa4-Cys-Ile- (SEQ ID NO:286)

--------------------------------

Phe-Val-Cys-Leu-^

Name: Qc6.1

Species: *quercinus*

Isolated: No

Cloned: Yes

DNA Sequence:

GCTTCGTATTTCTCCGCTGTCTTCCTTGGCATCACCCAAAACATCACCAAGATGAAA (SEQ ID NO:287)

CTGACGTGCATGATGATCGTTGCTCTGCTGTTCTTGACCGCCTGGACATTCGTCACG

GCTGTTGACTCCAAAAATGAACTGGAGaACAGAGGAGGATGGGGGCAGGCACGAG

GATGGGGGAAACTTTTTCCGATGGCACGCGACGAAATGAAAAACAGCGAAGTCTCT

AAATTGGACAATAAGAGAAGTGCGCTGCAGCCGGTGAAGCTTGCGTAATACCTAT

CATTGGaAACGTATTTTGCTGCAAAGGCTACTGtCTTTTCGTCTGCATTAGTTAAACT

GCTGTGATGCCTTCTACTCACCTCTGTGCTACCTGGCTTGATCTTTGATTGGCGTGTGC

CCTTCACTGGTTATGAgCTCGTCTGAtCCTACTCTCTGGAGACCTCTGTGGTCCAACAt

CCaAATAAAGCGGcATCCCAATC

Translation:

MKLTCMMIVALLFLTAWTFVTAVDSKNELENRGGWGQAGGWGKLFPMARDEMKNSE (SEQ ID NO:288)

VSKLDNKRKCAAAGEACVIPIIGNVFCCKGYCLFVCIS

Toxin Sequence:

Cys-Ala-Ala-Ala-Gly-Xaa1-Ala-Cys-Val-Ile-Xaa3-Ile-Ile-Gly-Asn-Val-Phe-Cys-Cys-Lys-Gly- (SEQ ID NO:289)

Xaa5-Cys-Leu-Phe-Val-Cys-Ile-Ser-^

--------------------------------

Name: Lp6.5

Species: *leopardus*

Isolated: No

Cloned: Yes

TABLE 1-continued

Sequences of Mature O-Superfamily Conotoxins,
Propeptides and DNA Encoding Propeptides

DNA Sequence:

ATGAAACTGACGTGCGTGGTGATCGTTGCTGTGCTGTTCTTGACCGCCTGGATATTC (SEQ ID NO:290)

ATCACGGCTGATGACTCCACAATGGACTGGAGAATCGTTTTAGGAAGGCACGTGA

CAACATGAAGAACGCCAAGCCTCTACATTAGCCGAGAAGAAAGCGTGTGTTAAC

TTGGTGAGATTTGTGCCACAGGCTTCTTCCTAGACGAGGAATGCTGCACTGGTTCAT

GCCATGTCTTCTGCGTACTATAGTTAAACTGCTGTGATGTCTTCTTCTCCTCCGTG

CTACCTGGCTTGATCTTTGATTGGTGCCTGTCCTTCAGTGGTTGTGAAACCCTCTGAT

CCTACTCTCTGGACGCCTCTGAGGCCCAACATCCAAATAAAGCGACATCCTAATGCC

AAAAAAAAAA

Translation:

MKLTCVVIVAVLKLTAWIFITADDSTNGLENRFKARDNMKNAKASTLAEKKACVELG (SEQ ID NO:291)

EICATGFFLDEECCTGSCHVFCVL

Toxin Sequence:

Ala-Cys-Val-Xaa1-Leu-Gly-Xaa1-Ile-Cys-Ala-Thr-Gly-Phe-Phe-Leu-Asp-Xaa1-Xaa1-Cys-Cys- (SEQ ID NO:292)

Thr-Gly-Ser-Cys-His-Val-Phe-Cys-Val-Leu-^

-------------------------------

Name: Mr6.4

Species: *marmoreus*

Isolated: No

Cloned: Yes

DNA Sequence:

ATGAAACTGACGTGCGTGGTGATCGTTGCTGTGCTGTTCTTGACCGCCTGGACATTT (SEQ ID NO:293)

GCCACGGCTGATGACCCCAGAATGGATTGGAGAATCTTTTTTCGAAGGCACATCA

AATTATGTGATGTGGTTGAACAAAACTGCTGCTATACCTATTGCTTTATTGTAGTCT

AATTATGTGATGTGGTTGAACAAAACTGCTGCTATACCTATTGCTTTATTGTAGTCT

GCCTATAAAACTACCGTGATGTCTTCTACTCCCCTCTGTGCTGCCTGGCTTGATCTTT

GATTGGCGCGTGCCCTTCACTGGTTATGACCCCCCTGATCCGACCTCTGGGG

Translation:

MKLTCVVIVAVLFLTAWTFATADDPRNGLENLFSKAHHEMKNPEASKLNKRCPNTGEL (SEQ ID NO:294)

CDVVEQNCCYTYCFIVVCL

Toxin Sequence:

Cys-Xaa3-Asn-Thr-Gly-Xaa1-Leu-Cys-Asp-Val-Val-Xaa1-Gln-Asn-Cys-Cys-Xaa5-Thr-Xaa5- (SEQ ID NO:295)

Cys-Phe-Ile-Val-Val-Cys-Leu-^

-------------------------------

Name: Qc6.2

Species: *quercinus*

Isolated: No

Cloned: Yes

TABLE 1-continued

Sequences of Mature O-Superfamily Conotoxins,
Propeptides and DNA Encoding Propeptides

DNA Sequence:

GGATCCATGAAACTGACGTGTATGGTGATCGTTGCTGTGCTATTCTTGACCGCCTCG (SEQ ID NO:296)

GCTGATGACTCCAGAAATGGATTCGAGAATCGAAATGGAGAACGCGAAACGAAAACG

AAATGAAGAACCTCGAAGCCTCTAAATTGAACAGGAGAGACGGCGATTGCGTTGAT

GGTGGTGAATTTTGTGGCTTTCCGAAAATTGGAGGGCCATGCTGTAGTGGCTGGTGC

TTTTTCGTCTGCTTATAAAACTGCCATGATGTCTTCTACCCCCCTCTGTGCTACCTGA

CTTGATCTTTGATTGGCGTGTGCCCTTCACTGGTTATGAACCCCTCTGATCCGACTCT

CTGGAGGCCTGGGGGGTCCAACATCCK&ATAAAGCGACAGCAAAAAAAAAAAAAA

AAAAAA

Translation:

MKLTCMVIVAVLFTASADDSRNGFENRNGERNENEMKNLEASKLNRRDGDCVDGGE (SEQ ID NO:297)

FCGFPKIGGPCCSGWCFFVCL

Toxin Sequence:

Asp-Gly-Asp-Cys-Val-Asp-Gly-Gly-Xaa1-Phe-Cys-Gly-Phe-Xaa3-Lys-Ile-Gly-Gly-Xaa3-Cys- (SEQ ID NO:298)

Cys-Ser-Gly-Xaa4-Cys-Phe-Phe-Val-Cys-Leu-^

-------------------------------

Name: Qc6.3

Species: *quercinus*

Isolated: No

Cloned: Yes

DNA Sequence:

GGATCCATGAAACTGACGTGCGTGGTGATCGTTGCTGTGCTATTCTTGACCGCCTTG (SEQ ID NO:299)

GCTGATGACTCCAGAAATGGATTGGAGAATCGAAATGAACAAGAACGAAACGAAA

ACGAAATGAGGGACCGCCGGGACTGCCAAGATAGTGGTGTAGTTTGTGGCTTTCCG

AAACCTGAACCACACTGCTGCAGTGGCTGGTGCCTTTTCGTCTGCGCCTAAAACTGC

CGTGATGTCAAATAAAGCGACAGACAATNAAAAAAAAAAAAAAAAAAAA

Translation:

MKLTCVVIVAVLFLTALADDSRNGLENRNEQERNENEMRDRRDCQDSGVVCGFPKPEP (SEQ ID NO:300)

HCCSGWCLFVCA

Toxin Sequence:

Asp-Cys-Gln-Asp-Ser-Gly-Val-Val-Cys-Gly-Phe-Xaa3-Lys-Xaa3-Xaa1-Xaa3-His-Cys-Cys- (SEQ ID NO:301)

Ser-Gly-Xaa4-Cys-Leu-Phe-Val-Cys-Ala-^

-------------------------------

Name: Ar6.5

Species: *arenatus*

Isolated: No

Cloned: Yes

TABLE 1-continued

Sequences of Mature O-Superfamily Conotoxins,
Propeptides and DNA Encoding Propeptides

DNA Sequence:

GGATCCATGAAACTGACGTGTGTGGTGATCGTTGCTGTGCTGTTCTTGACCGCCTGG (SEQ ID NO:302)

ACATTCGTCACGGCTGACTCCATACGTGCACTGGAGGATTTTTTTGCGAAGGCACGT

GACGAAATGGAAAACAGCGGAGCTTCTCCATTGAACGAGAGAGACTGCCGACCTGT

AGGTCAATATTGTGGCATACCGTATAAGCACAACTGGCGATGCTGCAGTCAGCTTTG

TGCAATTATCTGTGTTTCCTAACCCCTCTGATCCTACTCTCTGAAGACCTCCCGGATT

CAACATCCAAATAAAGCGACATCCCGATNAAAAAAAANGAAAAAAAAAAAAAAAAAA

Translation:

MKLTCVVIVAVLFLTAWTFVTADSIRALEDFFAEKARDEMENSGASPLNERDCRPVGQY (SEQ ID NO:303)

CGIPYKHNWRCCSQLCAIICVS

Toxin Sequence:

Asp-Cys-Arg-Xaa3-Val-Gly-Gln-Xaa5-Cys-Gly-Ile-Xaa3-Xaa5-Lys-His-Asn-Xaa4-Arg-Cys- (SEQ ID NO:304)

Cys-Ser-Gln-Leu-Cys-Ala-Ile-Ile-Cys-Val-Ser-^

------------------------------

Name: Ar6.11

Species: arenatus

Isolated: No

Cloned: Yes

DNA Sequence:

GGATCCATGAAACTGACGTGTGTGGTGATCGTTGTTGTGCTGTTCTTGACCGCCTGG (SEQ ID NO:305)

ACATTCGTCAAGGCTGATGACTCCATAAATGGATTGGAGAATCTTTTTCCGAAGGCA

CGTCACGAAATGAAGAACCCCGAAGCCTCTAAATTGAACGAGAGGTGCCTTGAAAA

GGGTGTACTTTGTGATCCGAGTGCTGGAAACTGCTGTAGTGGCGAATGCGTTTTAGT

CTGCCTCTAAAACTACCGTGATGTCTTCTACTCCCATCTGTGCTACCCCTCGAG

Translation:

MKLTCVVIVVVLFLTAWTFVKADDSINGLENLFPKARHEMKNPEASKLNERCLELGVL (SEQ ID NO:306)

CDPSAGNCCSGECVLVCL

Toxin Sequence:

Cys-Leu-Xaa1-Lys-Gly-Val-Leu-Cys-Asp-Xaa3-Ser-Ala-Gly-Asn-Cys-Cys-Ser-Gly-Xaa1-Cys- (SEQ ID NO:307)

Val-Leu-Val-Cys-Leu-^

------------------------------

Name: Ar6.12

Species: arenatus

Isolated: No

Cloned: Yes

TABLE 1-continued

Sequences of Mature O-Superfamily Conotoxins,
Propeptides and DNA Encoding Propeptides

DNA Sequence:

GGATCCATGAAACTGACGTGCATGGTGATCGTTACTGTGTTGTTCTTGACCGCCTGG (SEQ ID NO:308)

ACATTCGTCACGGCTGATGACTCCAGAAATGAATTGGAGAATCTTTTTCTGAAGGCA

TATCACGAAATGAACTCCGAAGCCTCTAAATTGGACAAGAAAGAGTGCGTTGCTGG

TAGTCACTTTTGTGGTTTTCCGAAAATTGGAGGGCCATGCTGCAGTGGCTGGTGCTT

TTTCGTCTGCTTGTAAACCTGCCGTGATGTCTTCTACTCCCATCTGTGCTACCCCTCG

AG

Translation:

MKLTCMVIVTVLFLTAWTFVTADDSRNELENLFKAYHEMNSEASKLDKKECVAGSHF (SEQ ID NO:309)

CGFPKIGGPCCSGWCFFVCL

Toxin Sequence:

Xaa1-Cys-Val-Ala-Gly-Ser-His-Phe-Cys-Gly-Phe-Xaa3-Lys-Ile-Gly-Gly-Xaa3-Cys-Cys-Ser- (SEQ ID NO:310)

Gly-Xaa4-Cys-Phe-Phe-Val-Cys-Leu-^

---

Name: Ts6.2

Species: *tessulatus*

Isolated: No

Cloned: Yes

DNA Sequence:

GGATCCATGAAACTGACGTGTGTGGTGATCGTTGCTGTGATGTTCTTGACCGCCTGG (SEQ ID NO:311)

ACATTCATCACGGCTGATGACTCCATAAATGGACTGGAGGATAGAGGCATATGGGG

GGAACCTTTGTCGAAGGCACGTGACGAATGAACCCCGAAGTCTCTAAACGGGATT

GCTGGCCTCAATATTGGTTTTGTGGCCTACAGAGGGGATGCTGCCCAGGGACTACTT

GCTTCTTCCTTTGCTTTTAGTGATCTCTTCGACTCCCTTCTGTGCTACCTGGCTTGACC

TTTGATTGGCGCGTGCCCTTCACTGGTTATAAACCCCTCTGTTCCTCCTCTCTGGACG

CTTCGGGGTGTCCAGCATCCMATKAAGCGACGTCCCCAAAAAAAAAAAAAAAA

AA

Translation:

MKLTCVVIVAVMFLTAWTFITADDSINGLEDRGIWGEPLSKARDEMNPEVSKRDCWPQ (SEQ ID NO:312)

YWFCGLQRGCCPGTTCFFLCF

Toxin Sequence:

Asp-Cys-Xaa4-Xaa3-Gln-Xaa5-Xaa4-Phe-Cys-Gly-Leu-Gln-Arg-Gly-Cycs-Cycs-Xaa3-Gly-Thr- (SEQ ID NO:313)

Thr-Cys-Phe-Phe-Leu-Cys-Phe-^

---

Name: Ts6.4

Species: *tessulatus*

Isolated: No

Cloned: Yes

TABLE 1-continued

Sequences of Mature O-Superfamily Conotoxins,
Propeptides and DNA Encoding Propeptides

DNA Sequence:

GGATCCATGAAACTGACGTGCGTGGTGGTCGTTGCTGTGCTGTTCTTGAACGCCTGG (SEQ ID NO:314)

ACATTCGCCACGGCTGTTGACTCCAACATGCACTGGCGKAACTTTTTATGAAGGCA

CGTGACGAAATGTATAACCCCGATGCCACTAAATTGGACGATAAGAGATGGTGCGC

TTTAGATGGTGAACTTTGTATCATACCGGTCATTGGGTCCATATTTTGCTGCCATGGC

ATATGTATGATCTACTGCGTCTAGTTGAACTGCCGTGATGTCTTCTACTCCCCTCTGT

GCTACCCCTGGTTTGATCTTTGATTGCCCTGTGCCCTTCACTGATTATGAATCCCTCT

GATCCTACTCTCTGAAGACCTCTTGGGGTCCAACATCCAAATAAAGCGACATCCCAA

AAAAAAAAAAAAAAAAAA

Translation:

MKLTCVVVVAVLFLNAWTFATAVDSKHALAKLFMKARDEMTNPDATKLDDKRWCA (SEQ ID NO:315)

LDGELCIIPVIGSIFCCHGICMIYCV

Toxin Sequence:

Xaa4-Cys-Ala-Leu-Asp-Gly-Xaa1-Leu-Cys-Ile-Ile-Xaa3-Val-Ile-Gly-Ser-Ile-Phe-Cys-Cys- (SEQ ID NO:316)

His-Gly-Ile-Cys-Met-Ile-Xaa5-Cys-Val-

---

Name: Im6.1

Species: *imperialis*

Isolated: No

Cloned: Yes

DNA Sequence:

GGATCCATGAAACTGACGTGCGTGGTGTTCGTTGCTGTGCCGTTCTTGACCGCCTCG (SEQ ID NO:317)

GTATTCATCACGGCTGATGACTCCAGAAATGGAATCGAGAATCTTCCTCGGATGAG

ACGTCACGAAATGAAGAACCCCAAAGCCTCTAAGTTGAACAAGAGACAGTGCCGTG

TAGAAGGTGAAATTTGTGGCATGCTGTTTGAAGCACAATGCTGCGATGGCTGGTGCT

TTTTCGTCTGCATGTAAAACTGCCGTGATGTCTTCTACTCTCCTCTGTGCTACCTGCC

CTGATCTTTGATTGGCTCGCGCCCTTCATTGGTTATGAACCCCTCTGATCCTACTCTC

TGGAGGCCTCAGGGGTCCAGCATCTAAATAAAGCGACATCACAATCAAAAAAAAA

AAAAAAAAAAA

Translation:

MKLTCVVFVAVPFLTASVFITADDSRNGIENLPRMRRHEMKNPKASKLNKRQCRVEGEI (SEQ ID NO:318)

CGMLFEAQCCDGWCFFVCM

TABLE 1-continued

Sequences of Mature O-Superfamily Conotoxins,
Propeptides and DNA Encoding Propeptides

Toxin Sequence:

Xaa2-Cys-Arg-Val-Xaa1-Gly-Xaa1-Ile-Cys-Gly-Met-Leu-Phe-Xaa1-Ala-Gln-Cys-Cys-Asp-   (SEQ ID NO:319)

Gly-Xaa4-Cys-Phe-Phe-Val-Cys-Met-^

Name: Ca6.5

Species: *caracteristicus*

Isolated: No

Cloned: Yes

DNA Sequence:

GGATCCATGAAACTGACGTGTGTGGTGATCGTTGCTGTGCTGTTCTTGACCGCCTGG   (SEQ ID NO:320)

ACATTCGTCACGGCTGATGACTCCAGAAATGGATTGGAGAATCTTTTTCCGAAGGCA

CGTCACGAAATGAAGAACCCCGAAGCCTCTAAATTGAACAAGAGGTGCGTTGACCC

TGGTGAATTTTGTGGTCCGGGATTTGGAGATTGCTGCACTGGCTTCTGCCTTTTAGTC

TGCATCTAAAACTGCCGTGATGTCTTCTACTCCCATCTGTGCTACCCCTCGAG

Translation:

MKLTCVVIVAVLFLTAWTFVTADDSRNGLENLFPKARHEMKNPEASKLNKRCVDPGEF   (SEQ ID NO:321)

CGPGFGDCCTGFCLLVCI

Toxin Sequence:

Cys-Val-Asp-Xaa3-Gly-Xaa1-Phe-Cys-Gly-Xaa3-Gly-Phe-Gly-Asp-Cys-Cys-Thr-Gly-Phe-Cys-   (SEQ ID NO:322)

Leu-Leu-Val-Cys-Ile-^

-------------------------------

Name: Mf6.2

Species: *miliaris*

Isolated: No

Cloned: Yes

DNA Sequence:

GGATCCATGAAACTGACGTGCGTGGTGATCGTTGCTGTGTTGTTCTTGACCGCCTGG   (SEQ ID NO:323)

ACATTCGTCATGGCTGATGACTCCAGAAATGATTTGGAGAATCTTTTTCTGAAGCA

CGTCATGAAATGAAGAACCCCGAAGCTTCTAAATTGAACAAGAGATGCCTTCCAAA

TGGTGTACTTTGTGATCTGGGATCTCCACCATACTGCTGCAGTGGCTGGTGCGCGAT

CGTCGTCTGCATCTAAAACTGTCGTCATGTCTTCTACTCCCATCTGTGCTACCCCTCG

AG

Translation:

MKLTCVVIVAVLFLTAWTFVMADDSRNDLENLFLKARHEMKNPEASKLNKRCLPNGV   (SEQ ID NO:324)

LCDLGSPPYCCSGWCAIVVCI

Toxin Sequence:

Cys-Leu-Xaa3-Asn-Gly-Val-Leu-Cys-Asp-Leu-Gly-Ser-Xaa3-Xaa3-Xaa5-Cys-Cys-Ser-Gly-   (SEQ ID NO:325)

Xaa4-Cys-Ala-Ila-Ile-Val-Val-Cys-Ile-^

-------------------------------

TABLE 1-continued

Sequences of Mature O-Superfamily Conotoxins,
Propeptides and DNA Encoding Propeptides

Name: Ak6.1

Species: *atlanticus*

Isolated: No

Cloned: Yes

DNA Sequence:

GGATCCATGAAACTGACGTGCGTGGTGATCGTTGCTGTGCTGTTCTTGACCGCCTGG  (SEQ ID NO:326)

ACATTCGTCACGGCTGATGACTCCATAAATGGGTTGGAGAATCTTTTTCCGAAGGCA

CGTCACGAAATGAGGAAACCCGAAGCCTCTAGATCGAGAGGGAGGTGCCGTCCTCG

TGGTATGTTCTGTGGCTTTCCGAAACCTGGACCATACTGCTGCAATGGCTGGTGCTT

TTTCGTCTGCATCTAAAACTGCCGTGATGTGTTCTACTCCCATCTGTGCTACCCCTCG

AG

Translation:

MKLTCVVIVAVLFLTAWTFVTADDSINGLENLFPKARHEMRKPEASRSRGRCRPRGMF  (SEQ ID NO:327)

CGFPKPGPYCCNGWCFFVCI

Toxin Sequence:

Cys-Arg-Xaa3-Arg-Gly-Met-Phe-Cys-Gly-Phe-Xaa3-Lys-Xaa3-Gly-Xaa5-Cys-Cys-Asn-  (SEQ ID NO:328)

Gly-Xaa4-Cys-Phe-Phe-Val-Cys-Ile-

-------------------------------

Name: Lv6.1

Species: *lividus*

Isolated: No

Cloned: Yes

DNA Sequence:

GGATCCATGAAACTGACGTGCGTGGTGATCGTTGCTGTGCTGTTCTTGACCGCCTGG  (SEQ ID NO:329)

ACATTTGCCACGGCTGATGACCCCAGAAATGGATTGGAGAATCTTTTTTCGAAGGCA

CATCACGAAATGAAGAACCCCGAAGCCTCTAAATTGACAAGAGGTGCCCTAACAC

TGGTGAATTATGTGATGTGGTTGAACAAAACTGCTGCTATACCTATTGCTTTATTGT

AGTCTGCCTATAAAACTACCGTGATGTCTTCTACTCCCATCTGTGCTACCCCTCGAG

Translation:

MKLTCVVIVAVLFLTAWTFATADDPRNGLENLFSKAHEMKNPEASKLNKRCPNTGEL  (SEQ ID NO:330)

CDVVEQNCCYTYCFIVVCL

TABLE 1-continued

Sequences of Mature O-Superfamily Conotoxins,
Propeptides and DNA Encoding Propeptides

Toxin Sequence:

Cys-Xaa3-Asn-Thr-Gly-Xaa1-Leu-Cys-Asp-Val-Val-Xaa1-Gln-Asn-Cys-Cys-Xaa5-Thr-Xaa5- (SEQ ID NO:331)

Cys-Phe-Ile-Val-Val-Cys-Leu-^

------------------------------

Name: Pu6.3

Species: *pulicarius*

Isolated: No

Cloned: Yes

DNA Sequence:

GGATCCATGAAACTGACGTGCATGGTGATCGTTGCTGTGCTGTTCTTGACCGCCTGG (SEQ ID NO:332)

ACATTCGTCAAGGCTGATGACTCCAGAAATGGATTGGAGAATCTTTTTCCGAAGGC

ACGTCACGAAATGAAGAACTCCAAAGCCCTCTAAATTAAACAAGAGGTGCGTTGAAG

ATGGTGATTTTTGTGGTCCGGGATATGAAGAGTGCTGCAGTGGCTTCTGCCTTTACG

TCTGCATCTAAAACTGCCGTGATGTCTTCTACTCCCATCTGTGCTACCCCTCGAG

Translation:

MKLTCMVIVAVLFTAWTFVKADDSRNGLENLFPKARHEMKNSKASKLNKRCVEDGD (SEQ ID NO:333)

FCGPGYEECCSGFCLYVCI

Toxin Sequence:

Cys-Val-Xaa1-Asp-Gly-Asp-Phe-Cys-Gly-Xaa3-Gly-Xaa5-Xaa1-Xaa1-Cys-Cys-Ser-Gly-Phe- (SEQ ID NO:334)

Cys-Leu-Xaa5-Val-Cys-Ile-^

------------------------------

Name: Ge6.1

Species: *generalis*

Isolated: No

Cloned: Yes

DNA Sequence:

GGATCCATGAAACTGACGTGTGTGGTGATCGTTGCTGTGCTATTCTTGACCGCCTGG (SEQ ID NO:335)

ACATTCGTCACGGCTGATGACACCAGATATAACTGGAGAATCCTTTTCTGAAGGC

ACGCAACGAACTGCAGAAACACGAAGCCTCTCAACTGAACGAGAGAGGCTGCCTTG

ACCCAGGTTACTTCTGTGGGACGCCGTTTCTTGGAGCATACTGCTGCGGTGGCATTT

GCCTTATTGTCTGCATAGAAACGTAAAGGCTTGATGTCTTCTACTCCCATCTGTGCT

ACCCCTCGAG

Translation:

MKLTCVVIVAVLFLTAWTFVTADDTRYKLENPFLKARNELQKHEASQLNERGCLDPGY (SEQ ID NO:336)

FCGTPFLGAYCCGGICLIVCIET

TABLE 1-continued

Sequences of Mature O-Superfamily Conotoxins,
Propeptides and DNA Encoding Propeptides

Toxin Sequence:

Gly-Cys-Leu-Asp-Xaa3-Gly-Xaa5-Phe-Cys-Gly-Thr-Xaa3-Phe-Leu-Gly-Ala-Xaa5-Cys-Cys- (SEQ ID NO:337)

Gly-Gly-Ile-Cys-Leu-Ile-Val-Cys-Ile-Xaa1-Thr-^

---

Name: Ep6.1

Species: *episcopatus*

Isolated: No

Cloned: Yes

DNA Sequence:

GGATCCATGAAACTGACGTGCGTGGTGATCGTTGCTGTGCTGTTCTTGACCGCCTGG (SEQ ID NO:338)

ACATTTGCCACGGCTGATGACCCCAGAAATGGATTGGGGAATCTTTTTTCGAATGTA

CATCACGAAATGAAGAACCTCGAAGACTCTAAATTGGACAAGAAGTGCCTTGGGTT

TGGTGAAGCTTGTCTTATGCTTTATTCAGACTGCTGCAGCTATTGCGTTGCTCTTGTC

TGCCTATAAAACTACCGTGACGTCTTCTACTCCCCTCTGTGCTACCTGGCTTGATCTT

TGATTGGCGTGTGCGCTTCACTGGTTATGAACCCCTCTGATCCTACTCTCTGAAGAC

CTCTGGGGTCCAACATCCAAATAAAGCGACATCACAAAAAAAAAAAAAAAAAAAA

AA

Translation:

MKLTCVVIVAVLFLTAWTFATADDPRNGLGNLFSNVHHEMKNLEDSKLDKKCLGFGE (SEQ ID NO:339)

ACLMLYSDCCSYCVALVCL

Toxin Sequence:

Cys-Leu-Gly-Phe-Gly-Xaa1-Ala-Cys-Leu-Met-Leu-Xaa5-Ser-Asp-Cys-Cys-Ser-Xaa5-Cys-Val- (SEQ ID NO:340)

Ala-Leu-Val-Cys-Leu-^

---

Name: Ep6.2

Species: *episcopatus*

Isolated: No

Cloned: Yes

DNA Sequence:

GGATCCATGAAACTGACGTGCGTGGTGATCATTGCTGTGCTGTTCTTGACCGCCTGG (SEQ ID NO:341)

ACATTCGTCATGGCTGATGACCCCAGAGATGAACCGGAGGCACGTGACGAAATGAA

CCCCGCAGCCTCTAAATTGAACGAGAGAGGCTGCCTTGCAGTTGATTATTTTTGCGG

CATACCGTTTGTGAGCAACGGGCTATGCTGCAGTGGCAATTGTGTTTTTGTCTGCAC

ACCCCAAGGGAAGTAAAACTGCCGTGACGTCTTCTACTCCCCTCTGTGCTACCTGGC

TABLE 1-continued

Sequences of Mature O-Superfamily Conotoxins,
Propeptides and DNA Encoding Propeptides

TTGATCTTTGATTGGCGTGTGCACTTCACTGGTTATGAACCCCTCTGATCCTACTCTC

TGAAGACCTCTGGGGTCCAACATCCAAATAAAGCGACATCCCAAAAAAAAAAAAA

AAAAAAA

Translation:

MKLTCVVIIAVLFLTAWTFVMADDPRDEPEARDEMNPAASKLNERGCLAVDYFCGIPF  (SEQ ID NO:342)

VSNGLCCSGNCVFVCTPQGK

Toxin Sequence:

Gly-Cys-Leu-Ala-Val-Asp-Xaa5-Phe-Cys-Gly-Ile-Xaa3-Phe-Val-Ser-Asn-Gly-Leu-Cys-Cys-  (SEQ ID NO:343)

Ser-Gly-Asn-Cys-Val-Phe-Val-Cys-Thr-Xaa3-Gln-#

------------------------------

Name: Ac6.1

Species: achatinus

Isolated: No

Cloned: Yes

DNA Sequence:

CGATCCTCTGTCCTCCATCTATTATTATTCGCTGCCAAACTGTGTTAAATATTCAAGT  (SEQ ID NO:344)

CTCTCTTTCTGTTTGTGTCTAACAGGTTGAGATGGTGCATTCCTAGAGGTGATCTTTG

TTTCCCCTCGGATCGCATACAATGCTGCAGTGGCAAGTGCACATTCGTCTGCATGTA

AAACTGCCGTGATGTCTTCTCCTCCCCTC

Translation:

LRWCIPRGDLCFPSDRIQCCSGKCTFVCM  (SEQ ID NO:345)

Toxin Sequence:

Xaa4-Cys-Ile-Xaa3-Arg-Gly-Asp-Leu-Cys-Phe-Xaa3-Ser-Asp-Arg-Ile-Gln-Cys-Ser-Gly-  (SEQ ID NO:346)

Lys-Cys-Thr-Phe-Val-Cys-Met-^

------------------------------

Name: Ac6.2

Species: *achatinus*

Isolated: No

Cloned: Yes

DNA Sequence:

CGATCCTCTGTCCTCCTCCTTCATTCATTCGCTGCCAAACTGTATTAAATATTCGAAT  (SEQ ID NO:347)

CTCTCTTTCTGTTTGTGTCTGACAGATTGAGAGGGTGCGTTCCTAGTGGTGAAATTTG

TTACTTCATGGATCACATAGGATGCTGCAGTGGCAAGTGCACATTCGTCTGCATGTA

AAACTGCCGTGATGTCTTCTCCTCCCATC

TABLE 1-continued

Sequences of Mature O-Superfamily Conotoxins,
Propeptides and DNA Encoding Propeptides

Translation:

LRGCVPSGEICYFMDHIGCCSGKCTFVCM (SEQ ID NO:348)

Toxin Sequence:

Gly-Cys-Val-Xaa3-Ser-Gly-Xaa1-Ile-Cys-Xaa5-Phe-Met-Asp-His-Ile-Gly-Cys-Cys-Ser-Gly- (SEQ ID NO:349)

Lys-Cys-Thr-Phe-Val-Cys-Met-^

------------------------------

Name: Bu6.7

Species: bullatus

Isolated: No

Cloned: Yes

DNA Sequence:

ATGAAACTGACGTGCGTGATGATCGTTACTGTGCTGTTCTTGACCGCCTGGACATTC (SEQ ID NO:350)

GTCAGGCTGATGACTCCACATATGGATTGAAGAATCTTTTGCCGAACGGACGTCAT

GAAATGATGAACCCCGAAGCCCCTAAATTGAACAAGAAAGATGAATGCTCTGCTCC

TGGTGCATTTTGTCTCATCAGGCCAGGACTCTGCTGCAGCGAGTTCTGCTTCTTTGCG

TGTTTTTAGTGACGGTTGATGTCTTCTACTCCCCTC

Translation:

MKLTCVMIVTVLFLTAWTFVTADDSTYGLKNLLPNGRHEMMNPEAPKLNKKDECSAP (SEQ ID NO:351)

GAFCLIRPGLCCSEFCFFACF

Toxin Sequence:

Asp-Xaa1-Cys-Ser-Ala-Xaa3-Gly-Ala-Phe-Cys-Leu-Ile-Arg-Xaa3-Gly-Leu-Cys-Cys-Ser-Xaa1- (SEQ ID NO:352)

Phe-Cys-Phe-Phe-Ala-Cys-Phe-^

------------------------------

Name: Bu6.8

Species: bullatus

Isolated: No

Cloned: Yes

DNA Sequence:

ATGAAACTGACGTGCGTGATGATCGTTACTGTGCTGTTCTTGACCGCCTGGACATTC (SEQ ID NO:353)

GTCACGGCTGATGACTCCAGAGACGCTCCGGATAGTGCAGAAGGATGGGAGAAACT

TTTCTCGGAGGCACGTGACGAAATGAAGAACCGCAAAGACTTTGAATTGAGAGGGT

GCCTTCCTAGGTGGGAATTTTGTCCCATCTTTAAAAAAAACGATTGCTGCAGTGGCA

TATGCATAAGCATCTGCTTGTAAAACTCCGTGATGTCTTCTCTTCCCATC

TABLE 1-continued

Sequences of Mature O-Superfamily Conotoxins,
Propeptides and DNA Encoding Propeptides

Translation:

MKLTCVMIVTVLFLTAWTFVTADDSRDAPDSAEGWEKLFSEARDEMKNRKDFELRGC (SEQ ID NO:354)

LPRWEFCPIFKKNDCCSGICISICL

Toxin Sequence:

Gly-Cys-Leu-Xaa3-Arg-Xaa4-Xaa1-Phe-Cys-Xaa3-Ile-Phe-Lys-Lys-Asn-Asp-Cys-Cys-Ser- (SEQ ID NO:355)

Gly-Ile-Cys-Ile-Ser-Ile-Cys-Leu-^

---

Name: Sx6.4

Species: *striolatus*

Isolated: No

Cloned: Yes

DNA Sequence:

ATGAAACTGACGTGCATGATGATTGTTGCTGTGCTGTTCTTGACCGCCTGGATATTT (SEQ ID NO:356)

GTAATGGCTGATGACTCCAGAAATGGATTGGAGAATCTTCCTCAGACTACACGTCA

CGAAATGAAGAACCCCGAAGCCTCTAAATTGAACCAGACAGACTGCCTTGCTAAAG

ACGCTTTCTGTGCCTGGCCGATACTTGGACCACTGTGCTGCAGTCGCTTGTGCTTAT

ACGTCTGCATGtaaAACTGCCGTGATGTCTTCTACTCCCTC

Translation:

MKLTCMMIVAVLFLTAWIFVMADDSRNGIENLPQTTRHEMKNPEASKLNQTDCLAKD (SEQ ID NO:357)

AFCAWPILGPLCCSRLCLYVCM

Toxin Sequence:

Asp-Cys-Leu-Ala-Lys-Asp-Ala-Phe-Cys-Ala-Xaa4-Xaa3-Ile-Leu-Gly-Xaa3-Leu-Cys-Cys-Ser- (SEQ ID NO:358)

Arg-Leu-Cys-Leu-Xaa5-Val-Cys-Met-^

---

Name: Cn6.9

Species: *consors*

Isolated: No

Cloned: Yes

DNA Sequence:

ATGAAACTGACGTGCATGATGATCGTTGCTGTGCTGTTCTTGACCGCCTGGACATTC (SEQ ID NO:359)

GTCACGGCTGATGACTCCAGAAATGGATTGGAGAATCTTTCTCCGAAGGCACGTCA

CGAAATGAAGAACCCCGAAGCCTCTAAATCGAACAAGAGATATGAGTGCTATTCTA

CTGGTACATTTTGTGGCATCAACGGAGGACTCTGCTGCAGCAACCTTTGCTTATTTT

CGTGTGCTTAACATTTTCGTGATGTCTTCTCCTCCCCTC

Translation:

MKLTCMMIVAVLFLTAWTFVTADDSRNGLENLSPKARHEMKNPEASKSNKRYECYST (SEQ ID NO:360)

GTFCGINGGLCCSNLCLFFVCLTFS

TABLE 1-continued

Sequences of Mature O-Superfamily Conotoxins,
Propeptides and DNA Encoding Propeptides

Toxin Sequence:

Xaa5-Xaa1-Cys-Xaa5-Ser-Thr-Gly-Thr-Phe-Cys-Gly-Ile-Asn-Gly-Gly-Leu-Cys-Cys-Ser-Asn- (SEQ ID NO:361)

Leu-Cys-Leu-Phe-Phe-Val-Cys-Leu-Thr-Phe-Ser-^

---

Name: Cn6.10

Species: *consors*

Isolated: No

Cloned: Yes

DNA Sequence:

ATGAAACTGACGTGCCTGATGATCGTTGCTGTGCTGTTCTTGACCACCTGGACATTC (SEQ ID NO:362)

GTCACGGCTGATGACTCCAGATATGGATTGAAGAATCTTTTTCCGAAGGCACGTCAT

GAAATGAAGAACCCTGAAGCCTCTAAATTGAACAAGAGAGATGGGTGCTATAATGC

TGGTACATTTTGTGGCATCCGTCCAGGACTCTGCTGCAGCGAGTTTTGCTTTTTATGG

TGCATAACATTTGTTGATTCTGGCTAACAGTGTGCGTTGGTTGATGTCTTCTACTCCC

CTC

Translation:

MKLTCLMIVAVLFLTTWTFVTADDSRYGLKNLFPKARHMKNPEASKLNKRDGCYNA (SEQ ID NO:363)

GTFCGIRPGLCCSEFCFLWCITFVDSG

Toxin Sequence:

Asp-Gly-Cys-Xaa5-Asn-Ala-Gly-Thr-Phe-Cys-Gly-Ile-Arg-Xaa3-Gly-Leu-Cys-Cys-Ser-Xaa1- (SEQ ID NO:364)

Phe-Cys-Phe-Leu-Xaa4-Cys-Ile-Thr-Phe-Val-Asp-Ser-#

---

Name: Cr6.6

Species: *circumcisus*

Isolated: No

Cloned: Yes

DNA Sequence:

CGATCCATCTGTCCATCCATCTATTCATTCATTCGCTGCCAAACTGTATTAAATATTC

AAGTCTCTCTTTCTGTTTGTGTCTAACAGATTGAGTAGGTGCATTCCTAGTGGTGATC

TTTGTTTCCCCTCGGATCACATACAATGCTGCAATGCCAAGTGCGCATTCGTCTGCTT

GTAAAACTGCCGTGATGTCTTCTCTTCCCTC (SEQ ID NO:365)

TABLE 1-continued

Sequences of Mature O-Superfamily Conotoxins,
Propeptides and DNA Encoding Propeptides

Translation:

NRLSRCIPSGDLCFPSDHIQCCNAKCAFVCL (SEQ ID NO:366)

Toxin Sequence:

Cys-Ile-Xaa3-Ser-Gly-Asp-Leu-Cys-Phe-Xaa3-Ser-Asp-His-Ile-Gln-Cys-Cys-Asn-Ala-Lys- (SEQ ID NO:367)

Cys-Ala-Phe-Val-Cys-Leu-^

---

Name: Cr6.5

Species: *circumcisus*

Isolated: No

Cloned: Yes

DNA Sequence:

CGATCCATCTGTCCATCCATCTATTCATTCATTCGCTGTCAAACTGTATTAAATATTC (SEQ ID NO:368)

AAGTCTCTCTTTCTGTTTGTGTCTAACAGATTGAGTTGGTGCATTCCTAGTGGTGATC

TTTGTTTCCCCTCGGATCACATACAATGCTGCAGTGCCAAGTGCGCATTCGTCTGCTT

GTAAAACTGCCGTGATGTCTTCTACTCCCCTC

Translation:

NRLSWCIPSGDLCFPSDHIQCCSAKCAFVCL (SEQ ID NO:369)

Toxin Sequence:

Xaa4-Cys-Ile-Xaa3-Ser-Gly-Asp-Leu-Cys-Phe-Xaa3-Ser-Asp-His-Ile-Gln-Cys-Cys-Ser-Ala- (SEQ ID NO:370)

Lys-Cys-Ala-Phe-Val-Cys-Leu-^

---

Name: Cr6.5A

Species: *circumoisus*

Isolated: No

Cloned: Yes

DNA Sequence:

CGATCCATCTGTCCATCCATCTATTCATTCATTCGCTGTCAAACTGTATTAAATATTC (SEQ ID NO:371)

AAGTCTCTCTTTCTGTTTGTGTCTAACAGATTGAGTAGGTGCATTCCTAGTGGTGATC

TTTGTTTCCCCTCGGATCACATACAATGCTGCAGTGCCAAGTGCGCATTCGTCTGCTT

GTAAAACTGCCGTGATGTCTTCTCCTCCCCTC

TABLE 1-continued

Sequences of Mature O-Superfamily Conotoxins,
Propeptides and DNA Encoding Propeptides

Translation:

NRLSRCIPSGDLCFPSDHIQCCSAKCAFVCL (SEQ ID NO:372)

Toxin Sequence:

Cys-Ile-Xaa3-Ser-Gly-Asp-Leu-Cys-Phe-Xaa3-Ser-Asp-His-Ile-Gln-Cys-Cys-Ser-Ala-Lys-Cys- (SEQ ID NO:373)

Ala-Phe-Val-Cys-Leu-^

-------------------------------

Name: Cr6.6A

Species: *circumcisus*

Isolated: No

Cloned: Yes

DNA Sequence:

CGATCCATCTGTCCATCCATCTATTCATTCATTCGCTGCCAAACTGTATTAAATATTC (SEQ ID NO:374)

AAGTCTCTCTTTCTGTTTGTGTCTAACAGATTGAGTAGGTGCATTCCTAGTGGTGATC

TTTGTTTCCCCTCGGATCACATACAATGCTGCAATGCCGAGTGCGCATTCGTCTGCTT

GTAAAACTGCCGTGATGTCTTCTCCTCCCCTC

Translation:

NRLSRCIPSGDLCFPSDHIQCCNAECAFVCL (SEQ ID NO:375)

Toxin Sequence:

Cys-Ile-Xaa3-Ser-Gly-Asp-Leu-Cys-Phe-Xaa3-Ser-Asp-His-Ile-Gln-Cys-Cys-Asn-Ala-Xaa1- (SEQ ID NO:376)

Cys-Ala-Phe-Val-Cys-Leu-^

-------------------------------

Name: Cr6.5B

Species: *circumcisus*

Isolated: No

Cloned: Yes

DNA Sequence:

CGATCCATCTGTCCATCCATCTATTCATTCATTCGCTGTCAAACTGTATTAAATATTC (SEQ ID NO:377)

AAGTCTCTCTTTCTGTTTGTGTCTAACAGATTGAGTTGGTGCATTCCTAGTGGTGATC

TTTGTTTCCCCTCGGATCACATACGATGCTGCAGTGCCAAGTGCGCATTCGTCTGCTT

GTAAAACTGCCGTGATGTCTTCTCTTCCCATC

TABLE 1-continued

Sequences of Mature O-Superfamily Conotoxins,
Propeptides and DNA Encoding Propeptides

Translation:

NRLSWCIPSGDLCFPSDHIRCCSAKCAFVCL (SEQ ID NO:378)

Toxin Sequence:

Xaa4-Cys-Ile-Xaa3-Ser-Gly-Asp-Leu-Cys-Phe-Xaa3-Ser-Asp-His-Ile-Arg-Cys-Cys-Ser-Ala- (SEQ ID NO:379)

Lys-Cys-Ala-Phe-Val-Cys-Leu-^

------------------------------

Name: Cr6.6B

Species: *circumcisus*

Isolated: No

Cloned: Yes

DNA Sequence:

CGATCCATCTGTCCATCCATCTATTCATTCATTCGCTGCCACTGTATTAAATATTC (SEQ ID NO:380)

AAGTCTCTCTTTCTGTTTGTGTCTAACAGATTGAGTAGGTGCATTCCTAGTGGTGATC

TTTGTTTCCCCTCGGATCACATACAATGCTGCAATGCCAAGTGCGCATTCGCCTGCT

TGTAAAACTGCCGTGATGTCTTCTCTTCCCCTC

Translation:

NRLSRCIPSGDLCFPSDHIQCCNAKCAFACL (SEQ ID NO:381)

Toxin Sequence:

Cys-Ile-Xaa3-Ser-Gly-Asp-Leu-Cys-Phe-Xaa3-Ser-Asp-His-Ile-Gln-Cys-Cys-Asn-Ala-Lys- (SEQ ID NO:382)

Cys-Ala-Phe-Ala-Cys-Leu-^

------------------------------

Name: Cr6.6C

Species: *circumoisus*

Isolated: No

Cloned: Yes

DNA Sequence:

CGATCCATCTGTCCATCCATCTATTCATTCATTCGCTGCCAAACTGTATTAAATATTC (SEQ ID NO:383)

AAGTCTCTCTTTCTGTTTGTGTCTAACAGATTGAGTTGGTGCATTCCTAGTGGTGATC

TTTGTTTCCCCTCGGATCACATACAATGCTGCAATGCCAAGTGCGCATTCGTCTGCTT

GTAAAACTGCCGTGATGTCTTCTACTCCCCTC

Translation:

NRLSWCIPSGDLCFPSDHIQCCNAKCAFVCL (SEQ ID NO:384)

TABLE 1-continued

Sequences of Mature O-Superfamily Conotoxins,
Propeptides and DNA Encoding Propeptides

Toxin Sequence:

Xaa4-Cys-Ile-Xaa3-Ser-Gly-Asp-Leu-Cys-Phe-Xaa3-Ser-Asp-His-Ile-Gln-Cys-Cys-Asn-Ala- (SEQ ID NO:385)

Lys-Cys-Ala-Phe-Val-Cys-Leu-^

---

Name: Cr6.7

Species: *circumcisus*

Isolated: No

Cloned: Yes

DNA Sequence:

CGATCCTCTGTCCTCCTCTATTATTATTCGCTGCCAACTGTATTAAATATTCAAGTCT (SEQ ID NO:386)

CTCTTTCTGTTTGTGTCTAACAGATTGAGTTGGTGCATTCCTACTGGTGATCTTTGTT

TCCCCTCGGATCACATACAATGCTGCAGTGGCAAGTGCACATTCGTCTGCATGTAAA

ACTGCCGTGATGTCTTCTCCTCCCCTC

Translation:

NRLSWCIPTGDLCFPSDHIQCCSGKCTFVCM (SEQ ID NO:387)

Toxin Sequence:

Xaa4-Cys-Ile-Xaa3-Thr-Gly-Asp-Leu-Cys-Phe-Xaa3-Ser-Asp-His-Ile-Gln-Cys-Cys-Ser-Gly- (SEQ ID NO:388)

Lys-Cys-Thr-Phe-Val-Cys-Met-^

---

Name: Mn6.3

Species: *monachus*

Isolated: No

Cloned: Yes

DNA Sequence:

ATGAAACTGACGTGCATGATGATCGTTGCTGTGCTGTTCTTGACCGCCTGGACATTC (SEQ ID NO:389)

GTCACGGCTGATGACTCCAGAAATGGATTGGAGAATCTTTCTCCGAAGGCACGTCA

CGAAATGAAGAACCCCGAAGCCTCTAAATCGAACAAGAGATATGAGTGCTATTCTA

CTGGTACATTTTGTGGCATCAACGGAGGACTCTGCTGCAGCAACCTTTGCTTATTTTT

CGTGTGCTTAACATTTTCGTGATGTCTTCTCCTCCCCTC

Translation:

MKLTCMMIVAVLFLTAWTFVTADDSRNGLENLSPKARHEMKNPEASKSNKRYECYST (SEQ ID NO:390)

GTFCGINGGLCCSNLCLFFVCLTFS

TABLE 1-continued

Sequences of Mature O-Superfamily Conotoxins,
Propeptides and DNA Encoding Propeptides

Toxin Sequence:

Xaa5-Xaa1-Cys-Xaa5-Ser-Thr-Gly-Thr-Phe-Cys-Gly-Ile-Asn-Gly-Gly-Leu-Cys-Cys-Ser-Asn- (SEQ ID NO:391)

Leu-Cys-Leu-Phe-Phe-Val-Cys-Leu-Thr-Phe-Ser-^

---

Name: Sm6.5

Species: *stercusmuscarum*

Isolated: No

Cloned: Yes

DNA Sequence:

ATGAAACTGACGTGCATGATGATCGTTGCTGTGCTGTTCTTGACCGCCTGGACATTC (SEQ ID NO:392)

GTCACAGCTGATGACTCCATAAATGGACCGGAGAATAGACGAATATGGGAGAAACT

TTTGTTGAAGGCACGTGACGAAATGAAGAACCCCGAAGCCTCTCAATTGAGATGGT

GCATTCCTAGTGGTGAACTTTGTTTCCGCTCGGATCACATACAATGCTGCAGTGCCA

AGTGCGCATTCGTCTGCTTGTAAAACTACCGTGATGTCTTCTCCTCCCATC

Translation:

MKLTCMMIVAVLFLTAWTFVTADDSINGPENRRIWEKLLLKARDEMKNPEASQLRWCI (SEQ ID NO:393)

PSGELCFRSDHIQCCSAKCAFVCL

Toxin Sequence:

Xaa4-Cys-Ile-Xaa3-Ser-Gly-Xaa1-Leu-Cys-Phe-Arg-Ser-Asp-His-Ile-Gln-Cys-Cys-Ser-Ala- (SEQ ID NO:394)

Lys-Cys-Ala-Phe-Val-Cycs-Leu-^

---

Name: Sm6.6

Species: *stercusmuscarum*

Isolated: No

Cloned: Yes

DNA Sequence:

ATGAAACTGACGTGTGTGATGATCGTTGCTGTGCTGTTCTTGATCGCCTGGACATTC (SEQ ID NO:395)

GTCACGGCTGATGACTCCAGAAATGGATTGAAGAATCTTTTTCCGAAGGCACGTCAT

GAAATGAAGAACCCCGAAGCCTCTAAATTGAACAAGAGAGATGGGTGCTCTAGTGG

TGGTACATTTTGTGGCATCCGTCCAGGACTCTGCTGCAGCGAGTTTTGCTTTCTTTGG

TGCATAACATTTATTGATTGATGTCTTCTATTCCCCTC

TABLE 1-continued

Sequences of Mature O-Superfamily Conotoxins,
Propeptides and DNA Encoding Propeptides

Translation:

MKLTCVMIVAVLFLIAWTFVTADDSRNGLKNLFPKARHEMKNPEASKLNKRDGCSSGG (SEQ ID NO:396)

TFCGIRPGLCCSEFCFLWCITFID

Toxin Sequence:

Asp-Gly-Cys-Ser-Ser-Gly-Gly-Thr-Phe-Cys-Gly-Ile-Arg-Xaa3-Gly-Leu-Cys-Cys-Ser-Xaa1- (SEQ ID NO:397)

Phe-Cys-Phe-Leu-Xaa4-Cys-Ile-Thr-Phe-Ile-Asp-^

---

Name: Sx6.5

Species: *striolatus*

Isolated: No

Cloned: Yes

DNA Sequence:

ATGAAACTGACGTGCATAATGACCGTTGCTGTGCTGTTCTTGACCGCTTGGACATTC (SEQ ID NO:398)

GTCACGGCTGATGACTCCAGAAATGCATTGGAGAATCTTCTTCTGAAGACACGTCA

CGAAGTGGAAAACCCCAAAGCCTCTAGGTCGGGCGGTAGGTGCCGTCCTGGTGGTA

CGGTTTGTGGCTTTCCGAAACCTGGACCATACTGCTGCAGTGGCTGGTGCTTTTTTGT

CTGCGCCTAAACCTGCCGTGATGTCTTCTCCTCCCATC

Translation:

MKLTCIMTVAVLFLTAWTFVTADDSRNGLENLLLKTRIHEVENPKASRSGGRCRGGTV (SEQ ID NO:399)

CGFPKPGPYCCSGWCFFVCA

Toxin Sequence:

Cys-Arg-Xaa3-Gly-Gly-Thr-Val-Cys-Gly-Phe-Xaa3-Lys-Xaa3-Gly-Xaa3-Xaa5-Cys-Cys-Ser- (SEQ ID NO:400)

Gly-Xaa4-Cys-Phe-Phe-Val-Cycs-Ala-^

---

Name: Sx6.6

Species: *striolatus*

Isolated: No

Cloned: Yes

DNA Sequence:

ATGAAACTGACGTGCGTGATGATCGTTGCTGTGCTGTTCTTGACTGCCTGGACATTC (SEQ ID NO:401)

GTCACGGCTGATGACTCCAAAAATGGACTGGAGAATCATTTTTGGAAGGCACGTGA

CGAAATGAAGAACCGCGAAGCCTCTAAATTGGACAAAAAGGAAGCCTGCTATCCGC

CTGGTACTTTTTGTGGCATAAAGCCCGGGCTATGCTGCAGTGAGTTGTGTTTACCGG

CCGTCTGCGTCGGTGGTTAACTGCCGTGATGTCTTCTATTCCCCTC

Translation:

MKLTCVMIVAVLFLTAWTFVTADDSKNGLENHFWKARDEMKNREASKLDKKEACYP (SEQ ID NO:402)

PGTFCGIKPGLCCSELCLPAVCVGG

TABLE 1-continued

Sequences of Mature O-Superfamily Conotoxins,
Propeptides and DNA Encoding Propeptides

Toxin Sequence:

Xaa1-Ala-Cys-Xaa5-Xaa3-Xaa3-Gly-Thr-Phe-Cys-Gly-Ile-Lys-Xaa3-Gly-Leu-Cys-Cys-Ser- (SEQ ID NO:403)

Xaa1-Leu-Cys-Leu-Xaa3-Ala-Val-Cys-Val-Gly-#

------------------------------

Name: Sx6.7

Species: *striolatus*

Isolated: No

Cloned: Yes

DNA Sequence:

ATGAAACTGACGTGTCTGATGGCTGTTGCTGTGCTGTTCTTGACCGCCCGGACATTC (SEQ ID NO:404)

GTCACGGCTGATGACTCCAGAAATGGATTGGAGAATCTTTCTCCGAAGGCACGTCA

CGAAATGAAGAACCCCGAAGCCTCTAAATCGAACAAGAGATATGAGTGCTATTCTA

CTGGTACATTTTGTGGCATCAACGGAGGACTCTGCTGCAGCAACCTTTGCTTATTTT

CGTGTGCTTAACATTTTCGTGATGTCTTCTATCCCCTC

Translation:

MKLTCLMAVAVLFLTARTFVTADDSRNGLENLSPKARHMKNPEASKSNKRYECYST (SEQ ID NO:405)

GTFCGTNGGLCCSNLCLFFVCLTFS

Toxin Sequence:

Xaa5-Xaa1-Cys-Xaa5-Ser-Thr-Gly-Thr-Phe-Cys-Gly-Ile-Asn-Gly-Gly-Leu-Cys-Cys-Ser-Asn- (SEQ ID NO:406)

Leu-Cys-Leu-Phe-Phe-Val-Cys-Leu-Thr-Phe-Ser-^

------------------------------

Name: Sx6.8

Species: *striolatus*

Isolated: No

Cloned: Yes

DNA Sequence:

ATGAAACTGACGTGTATGGTGATCGTCGCCGTGCTGCTCCTGACGACCTGTCATCTC (SEQ ID NO:407)

ATCACAGCTGATGACTCCAGAGGTACGCAGAAGCATCGTTCCCTGAGGTCGACTAC

CAAAGTCTCCAAGTCGACTAGCTGCATGAAAGCCGGGTCTTATTGCGTCGCTACTAC

GAGAATCTGCTGCGGTTATTGCGCTTATTTCGGCAAAATATGTATTGGCTATCCCAA

AAACTGATCCTCCCCCTACTGTGCTCTATCCTTTTCTGCCTGATGTCTTCTCCTCCCC

TC

TABLE 1-continued

Sequences of Mature O-Superfamily Conotoxins,
Propeptides and DNA Encoding Propeptides

Translation:

MKLTCMVIVAVLLLTTCHLITADDSRGTQKHRSLRSTTKVSKSTSCMKAGSYCVATTRI  (SEQ ID NO:408)

CCGYCAYFGKICIGYPKN

Toxin Sequence:

Ser-Thr-Ser-Cys-Met-Lys-Ala-Gly-Ser-Xaa5-Cys-Val-Ala-Thr-Thr-Arg-Ile-Cys-Cys-Gly-Xaa5-  (SEQ ID NO:409)

Cys-Ala-Xaa5-Phe-Gly-Lys-Ile-Cys-Ile-Gly-Xaa5-Xaa3-Lys-Asn-^

Xaa1 is Glu or γ-carboxy-Glu
Xaa2 is Gln or pyro-Glu
Xaa3 is Pro or hydroxy-Pro
Xaa4 is Trp or bromo-Trp
Xaa5 is Tyr, $^{125}$I-Tyr, mono-iodo-Tyr, di-iodo-Tyr, O-sulpho-Tyr or O-phospho-Tyr
Xaa6 is Nle
^ is free carboxyl or amidated C-terminus, preferably free carboxyl
# is free carboxyl or amidated C-terminus, preferably amidated

TABLE 2

Alignment of Conotoxin Peptide Sequences

| | | |
|---|---|---|
| δ-GmVIA [F15Y] | -VKPCRKEGQLCDPIYQN---CCRGWNC--VLF-CV^ | (SEQ ID NO:4) |
| δ-GmVIA [F27Y] | -VKPCRKEGQLCDPIFQN---CCRGWNC--VLY-CV^ | (SEQ ID NO:5) |
| Omaria9 | M---CRREAQLCDPIFQN---CCHGLFC--VLV-CV^ | (SEQ ID NO:8) |
| Tx6.11 | QVKPCRKEHQLCDLIFQN---CCRGWYC--VVLSCT^ | (SEQ ID NO:11) |
| Om6.6 | ----CVPHEGPCNWLTQN---CCSGYNC--IIFFCL^ | (SEQ ID NO:14) |
| Da6.2 | QVKPCRKEHQLCDLIFQN---CCRGWYC--LLRPCI^ | (SEQ ID NO:17) |
| Da6.6 | -VKPCSEEGQLCDPLSQN---CCRGWHC--VLVSCV^ | (SEQ ID NO:22) |
| δ-TxVIA [M8J] | W---CKQSGEXCNLLDQN---CCDGY-C--IVLVCT^ | (SEQ ID NO:24) |
| Da6.4 | ----CLGGGEVCDIFFPQ---CC-GY-C--ILLFCT^ | (SEQ ID NO:37) |
| GmG.5 | ----CRLGAESCDVISQN---CCQGT-C--VFF-CLP^ | (SEQ ID NO:40) |
| Gm6.6 | ----CKQADESCNVFSLD----CCTGL-C--LGF-CVS^ | (SEQ ID NO:43) |
| Gm6.3 | ----CVPYEOPCNWLTQN----CCDEL-C--VFF-CL^ | (SEQ ID NO:46) |
| M6.5 | ----CKQADEPCDVFSLE---CCTGI-C--LGF-CTW^ | (SEQ ID NO:49) |
| Tx6.2 | ----CLDAGEVCDIFFPT---CC-GY-C--ILLFCA^ | (SEQ ID NO:52) |
| Om6.1 | ----CLAEHETCNIFTQN---CCEGV-C--IFI-CVQAPE^ | (SEQ ID NO:57) |
| Om6.3 | ----CIPHFDPCDPIRHT---CCFGL-C--LLIACI^ | (SEQ ID NO:60) |
| Om6.4 | ----CLGFGEACLILYSD---CC-GY-C--VGAICL^ | (SEQ ID NO:63) |
| Au6.1 | ----CKAENELCNIFIQN---CCDGT-C--LLI-CIQNPQ^ | (SEQ ID NO:66) |
| Au6.2 | ----CLEFGELCNFFFPT---CC-GY-C--VLLVCL^ | (SEQ ID NO:69) |
| Da6.5 | ----CAQSSELCDALDSD---CCSGV-C--MVFFCL^ | (SEQ ID NO:72) |
| Di6.4 | ----CLGFGEACLMLYSD---CC-SY-C--VGAVCL^ | (SEQ ID NO:75) |
| Pn6.2 | ----CVKYLDPCDMLRHT---CCFGL-C--VLIACI^ | (SEQ ID NO:78) |
| Pn6.3 | ----CLGFGEVCNFFFPN---CC-SY-C--VALVCL^ | (SEQ ID NO:81) |
| Pn6.4 | ----CIPQFDPCDMVRHT---CCKGL-C--VLIACSKTA^ | (SEQ ID NO:84) |
| Pn6.7 | ----CKAESEACNIITQN---CCDGK-C--LFF-CIQIPE^ | (SEQ ID NO:87) |
| Omaria3 | ----CIDGGEICDIFFPN---CCSGW-C--IILVCA^ | (SEQ ID NO:90) |
| Omaria1 | ----CLDGGEICGILFPS---CCSGW-C--IVLVCA^ | (SEQ ID NO:93) |
| Marm7 | ----CLEFGEVCNFFFPT---CC-GY-C--VLLVCL^ | (SEQ ID NO:96) |
| Marm12 | ----CQEFGEVCNFFFPD---CC-GY-C--VLLLCI^ | (SEQ ID NO:99) |
| Omaria7 | ----CIPHFDPCDPIRHT---CCFGL-C--LLIACI^ | (SEQ ID NO:102) |
| Omaria11 | ----CLEFGEVCNFFFPT---CC-GY-C--VLLVCL^ | (SEQ ID NO:105) |
| O6.5 | SKKQCRQNGEVCDANLAH---CCSGP-C--FLF-CLNQP^ | (SEQ ID NO:108) |
| Af6.8 | ----CTQSGELCDVIDPD---CCNNF-C--IIFFCI^ | (SEQ ID NO:111) |
| KK-2A | ----CAPFLHLCTFFFPN---CCNGY-C--VQFICL^ | (SEQ ID NO:114) |
| KKM1 | ----CLDAGEMCDLFNSK---CCSGW-C--IILFCA^ | (SEQ ID NO:117) |
| KKM4 | ----CLDGGEICGILFPS---CCSGW-C--IVLVCA^ | (SEQ ID NO:120) |
| KKM5 | ----CPNTGELCDVVEQN---CCYTY-C--FIVVCPI^ | (SEQ ID NO:123) |
| KKM6 | -DDECEPPGDFCGFFKIGP-PCCSGW-C--FLW-CA^ | (SEQ ID NO:126) |
| C. striatus S2 | -DDECEPPGDFCGFFKIGP-PCCSGW-C--FLW-CA^ | (SEQ ID NO:129) |
| Om6.5 | -DDDCEPPGNFCGMIKIGP-PCCSGW-C--FFA-CA^ | (SEQ ID NO:132) |
| Au6.3 | -DYDCEPPCNFCGMIKIGP-PCCSGW-C--FFA-CA^ | (SEQ ID NO:135) |
| Marm9 | -DDDCEPPGNFCGMIKIGP-PCCSGW-C--FFA-CA^ | (SEQ ID NO:138) |
| Rg6.4 | -D---CLSKNAFCAWPILGP-LCCSGW-C--LYV-CM^ | (SEQ ID NO:141) |
| R6.5 | -GDDCLAVKKNCGFPKLGG-PCCSGL-C--FFV-CA^ | (SEQ ID NO:144) |
| Rg6.2 | D--CLPRDTFCALPQLGL-LCCSGR-C--LLF-CV^ | (SEQ ID NO:147) |
| A6.5 | -DG-CSNAGAFCG---IHPGLCCSEI-C--IVW-CT^ | (SEQ ID NO:150) |
| δ-PVIA[F9A] | -EA-CYAOGTACG---IKOGLCCSEF-C--LPGVCFG^ | (SEQ ID NO:154) |
| δ-PVIA[I12A] | -EA-CYAOGTFCG---AKOGLCCSEF-C--LPGVCFG^ | (SEQ ID NO:155) |

TABLE 2-continued

Alignment of Conotoxin Peptide Sequences

| | | |
|---|---|---|
| δ-PVIA[TS8] | -EA-CYAOGAFCG---IKOGLCCSEF-C--LPGVCFG^ | (SEQ ID NO:156) |
| M6.3 | -DG-CYNAGTFCG---IRPGLCCSEF-C--FLW-CITFVDS# | (SEQ ID NO:159) |
| M6.6 | -DE-CYPPGTFCG---IKPGLCCSAI-C--LSFVCISF-DF^ | (SEQ ID NO:162) |
| M6.7 | -EA-CYNAGSFCG---IHPGLCCSEF-C--ILW-CITFVDS# | (SEQ ID NO:165) |
| M6.8 | -EA-CYNAGTFCG---IKPGLCCSAI-C--LSFVCTSF-DF^ | (SEQ ID NO:168) |
| E6.4 | -EA-CYPPGTFCG---IKPGLCCSEL-C--LPAVCVG# | (SEQ ID NO:171) |
| P6.4 | -EA-CYPPCTPCG---IKPGLCCSEL-C--LPAVCVG# | (SEQ ID NO:174) |
| δ-SVIE [D1E] | -EG-CSSOGTFCG---IHOGLCCSEP-C--FLW-CITFID^ | (SEQ ID NO:177) |
| δ-SVIE | -DG-CSSGGTFCG---IHOGLCCSEF-C--FLW-CITFID^ | (SEQ ID NO:180) |
| C6.2 | -YG-CSNAGAFCG---IHPGLCCSEL-C--LVW-CT^ | (SEQ ID NO:184) |
| C6.3 | -YG-CSNAGAFCG---IHPGLCCSEL-C--LGW-CT^ | (SEQ ID NO:187) |
| Di6.3 | -YE-CYLLVHFCG---INGGLCCSNL-C--LFFVCLTFS^ | (SEQ ID NO:190) |
| Rg6.1 | -D--CLPDYTICA---FNMGLCCSDK-C--MLV-CLP^ | (SEQ ID NO:193) |
| Rg6.3 | -II-CFPDYMFCG---VNVFLCCSGN-C--LLI-CVP^ | (SEQ ID NO:196) |
| Gm6.2 | ----CYDGGTGCD----SGNQCCSGW-C--IFA-CL^ | (SEQ ID NO:199) |
| Da6.1 | ----CYDGGTGCD----SGNQCCSGW-C--IFV-CL^ | (SEQ ID NO:202) |
| Pn6.6 | ----CFESWVACE----SPKRCCSHV-C--LFV-CT^ | (SEQ ID NO:205) |
| Di6.5 | ----CNEAQEHCT----QNPDCCSES-CNKFVGRCLS--D^ | (SEQ ID NO:208) |
| Af6.10 | ----CYDGGTSCN----TGNQCCSGW-C--IFL-CL^ | (SEQ ID NO:211) |
| Tx6.10 | ----CYDSGTSCN----TGNQCCSGW-C--IFVSCL^ | (SEQ ID NO:214) |
| Gm6.4 | -D--CQALWDYCPVPLLSSGDCCYGLIC--GPFVCIGW^ | (SEQ ID NO:217) |
| Om6.2 | KT--CQRRWDFCPGSLVGVITCCGGLIC--FLFFCV^ | (SEQ ID NO:220) |
| Da6.3 | -D--CQEKWDYCPVPSRYCCDGFIC--PSFFCA^ | (SEQ ID NO:223) |
| Da6.7 | -D--CQCEWEFCIVPLGPVYCCPWLIC--GPFVCVDI^ | (SEQ ID NO:226) |
| Pn6.5 | -G--CLEVDYFCGIPFVNNGLCCSGN-C--VFV-C--TPQ# | (SEQ ID NO:229) |
| Marm6 | ----CLNVDYFCGIPFVNNGLCCSGN-C--VFV-C--TPQ# | (SEQ ID NO:232) |
| Marm15 | -E--CLEADYYCLPFVGNGMECCSGI-C--VFV-CIAQRFKTV^ | (SEQ ID NO:235) |
| Marm10 | -D--CLEPDYVCGIPFVFNGLCCSOI-C--VFI-CIAQKY^ | (SEQ ID NO:238) |
| Marm14 | -A--CSKKWEYCIVPILGFVYCCPGLIC--GPFVCV^ | (SEQ ID NO:241) |
| Omaria14 | -D--CLNVDYFCGIPFVNNGLCCSGN-C--VF--CLHTPREVKLP^ | (SEQ ID NO:244) |
| O6.4 | ----CLVYGTPCDWLTIAGMECCSKK-C--FMM-CW^ | (SEQ ID NO:247) |
| R6.4 | -D--CHEVGEPCGLPIKNGLCCSQI-C--LGV-CAKVF^ | (SEQ ID NO:250) |
| R6.6 | -E--CTANGEFCGISVFGSYLCCSGR-C--VFV-CI^ | (SEQ ID NO:253) |
| R6.7 | -E--CTTNGEFCGISVFASFLCCSGL-C--VFV-CI^ | (SEQ ID NO:256) |
| R6.8 | -K--CFPKNHFCGFVVMLNYLCCSGR-C--IFV-CV^ | (SEQ ID NO:259) |
| Rg6.5 | -S--CLPLDWFCGFNIIGAFLCCSGY-C--LVV-CM^ | (SEQ ID NO:262) |
| De6.2 | -D--CIPGGENC--DVFRPYRCCSGY-C--ILLLCA^ | (SEQ ID NO:265) |
| Striat21 | -LRWCIPSGELC--FRSDHIGCCSGK-C--AFV-CL^ | (SEQ ID NO:268) |
| δStriatus 26 | ---WCIPSGDLC--FRSDHIGCCSGK-C--AFV-CL^ | (SEQ ID NO:271) |
| δStriatus 106 | ---WCIPSGDLC--FRSDHIQCCSGK-C--AFV-CL^ | (SEQ ID NO:274) |
| O6.3 | -LRWCVPSGEVC--RRYEFVGCCSGK-C--FFV-CS^ | (SEQ ID NO:277) |
| R6.3 | ----CLPDGTSC---LFSRIRCC-GT-CSSILKSCVS^ | (SEQ ID NO:280) |
| Ak6.1 (F763) | ----CRPRGMFCGFPKPGPY-CCSGW-CF--IV-CI^ | (SEQ ID NO:328) |
| Ar6.11 (G21) | ----CLEKGVLCD--PSAGN-CCSGE-CV--LV-CL^ | (SEQ ID NO:307) |
| Ar6.12 (G20) | -E--CVAGSHFCGFPKIGGP-CCSGW-CF--FV-CL^ | (SEQ ID NO:310) |
| Ar6.5 (F008) | -D---CRPVGQYCGIPYKHNWRCCSQL-CA--II-CVS^ | (SEQ ID NO:304) |
| Ca6.5 (G211) | ----CVDPGEFCG--PGFGD-CCTGF-CL--LV-CI^ | (SEQ ID NO:322) |
| Ep6.1 (J425) | ----CLGFGEACL--MLYSD--CCS-Y-CV-ALV-CL^ | (SEQ ID NO:340) |
| Ep6.2 (J424) | -G--CLAVDYFCGIPFVSNOLCCSON-CV--FV-CTPQ# | (SEQ ID NO:343) |
| G6.3 | -DDECEPPGDPCGFPKIGPP-CCSGW-CF--LW-CA^ | (SEQ ID NO:283) |
| Ge6.1 (G18) | -G--CLDPGYFCGTPFLGAY-CCGGI-CL--IV-CIET^ | (SEQ ID NO:337) |
| Im6.1 (F076) | Q---CRVEGEICGML-FEAQ-CCDGW-CF--V-CM^ | (SEQ ID NO:319) |
| Lp6.5 (A667) | -A--CVELGEICATGFFLDEECCTGS-CH--VF--CVL^ | (SEQ ID NO:292) |
| Lv6.1 (F775) | ----CPNTGELCDV-VEQN-CCTY-CF-IVV-CL^ | (SEQ ID NO:331) |
| Mf6.2 (G218) | ----CLPNGVLCDL-GSPPYCCSGW-CA-IVV-CI^ | (SEQ ID NO:325) |
| Mr6.4 (A666) | ----CPNTGELCDV--VEQN-CCTY-CF-IVV-CL^ | (SEQ ID NO:295) |
| Pu6.3 (F770) | ----CVEDGDFCG--PGYEE-CCSGP-CL--YV-CI^ | (SEQ ID NO:334) |
| Qc6.1 | ----CAAAGEACVIPIIGNVFCCKGY-CL--FV-CIS^ | (SEQ ID NO:289) |
| Qc6.2 (F024) | -DGDCVDGGEFCGFPKIGGP-CCSGW-CF--FV-CL^ | (SEQ ID NO:298) |
| Qc6.3 (F026) | -D--CQDSGVVCGFPKPEPH-CCSGW-CL--FV-CA^ | (SEQ ID NO:301) |
| Ts6.2 (F078) | -D--CWPQYWFCGLQRG----CCPGTTCF--FL-CF^ | (SEQ ID NO:313) |
| Ts6.4 (F080) | ---WCALDGELCIIPV1GSIFCCHGI-CM--IY-CV^ | (SEQ ID NO:316) |
| Tx6.8 | -----CYDSGTSC---NTGNQ-CCSGW-CI--FV-CL^ | (SEQ ID NO:286) |
| Ac6.1 | W---CIPRGDLC-FPSDRIQ-CCSGK-CTF---VCM^ | (SEQ ID NO:346) |
| Ac6.2 | -G--CVPSCEIC-YFMDHTC-CCSGK-CTF---VCM^ | (SEQ ID NO:349) |
| Bu6.7 | -DE-CSAPGAFCL--IRPGL-CCSEF-C-FF--ACF^ | (SEQ ID NO:352) |
| Bu6.8 | -G--CLPRWEFC-PIFKKND--CCSGI-CIS---ICL' | (SEQ ID NO:355) |
| Cn6.10 | -DG-CYNAGTFCG---IRPGL-CCSEF-C-FL--WCITFVDS# | (SEQ ID NO:364) |
| Cn6.9 | -YE-CYSTGTFCG--INGGL-CCSNL-CLFF--VCLTFS^ | (SEQ ID NO:361) |
| Cr6.5 | W---CIPSGDLC-FPSDHIQ-CCSAK-CAF---VCL^ | (SEQ ID NO:370) |
| Cr6.5A | ----CIPSGDLC-FPSDHIQ-CCSAK-CAF---VCL^ | (SEQ ID NO:373) |
| Cr6.6 | ----CIPSGDLC-FPSDHIQ-CCNAK-CAF---VCL^ | (SEQ ID NO:367) |
| Cr6.6A | ----CIPSGDLC-FPSDHIQ-CCNAE-CAF---VCL^ | (SEQ ID NO:376) |
| Cr6.5B | W---CIPSGDLC-FPSDHIR-CCSAK-CAF---VCL^ | (SEQ ID NO:379) |
| Cr6.6B | ----CIPSCDLC-FPSDHIQ-CCNAK-CAF---ACL^ | (SEQ ID NO:382) |
| Cr6.6C | W---CIPSCDLC-FPSDHIQ-CCNAK-CAF---VCL^ | (SEQ ID NO:285) |
| Cr6.7 | W---CIPTGDLC-FPSDSIQ-CCSGK-CTF---VCM^ | (SEQ ID NO:368) |

TABLE 2-continued

Alignment of Conotoxin Peptide Sequences

| | | |
|---|---|---|
| Mn6.3 | -YE-CYSTGTFCG--INGGL-CCSNL-CLFF--VCLTFS^ | (SEQ ID NO:391) |
| Sm6.5 | W---CIPSGELC-FRSDHIQ-CCSAK-CAF---VCL^ | (SEQ ID NO:394) |
| Sm6.6 | -DC-CSSGGTFCG--IRPGL-CCSEF-C-FL--WCITFID^ | (SEQ ID NO:397) |
| Sx6.4 | -D--CLAKDAFCAWPILGPL-CCSRL-CLY---VCM^ | (SEQ ID NO:358) |
| Sx6.5 | ----CRPGGIVCGFPKPGPY-CCSGW-CFF---VCA^ | (SEQ ID NO:400) |
| Sx6.6 | -EA-CYPPGTFCG--IKPGL-CCSEL-CLPA--VCVG# | (SEQ ID NO:403) |
| Sx6.7 | -YE-CYSTGTFCG--INGGL-CCSNL-CLFF--VCLTFS^ | (SEQ ID NO:406) |
| Sx6.8 | STS-CMKAGSYCVATTR--I-CC-GY-CAYFGKICIGYPKN^ | (SEQ ID NO:409) |

X is Nle

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Barnay, G. et al. (2000). *J. Med. Chem.*
Bitan, G. et al. (1997). *J. Peptide Res.* 49:421–426.
Bodansky et al. (1966). *Chem. Ind.* 38:1597–98.
Cartier, G. E. et al. (1996). *J. Biol. Chem.* 271:7522–7528.
Cornell-Bell, A. H. et al. (1999). Kainate spiral waves and integrins: A signaling system without gap junctions. *Glia,* in press.
Craik, D. J. et al. (2001). *Toxicon* 39:43–60.
Cruz, L. J. at al. (1976). *Verliger* 18:302–308.
Ettinger, L. J. et al. (1978). *Cancer* 41:1270–1273.
Fainzilber, M. et al. (1991). *Eur. J. Biochem.* 202:589–595.
Fainzilber, M. et al. (1995). *J. Biol. Chem.* 270:1123–1129.
Hammerland et al. (1992). *Eur. J. Pharmacol.* 226:239–244.
Hillyard, D. R. et al. (1989). *Biochemistry* 28:358–361.
Horiki, K. et al. (1978). *Chemistry Letters* 165–68.
Hubry, V. et al. (1994). *Reactive Polymers* 22:231–241.
Kapoor (1970). *J. Pharm. Sci.* 59:1–27.
Kornreich, W. D. et al. (1986). U.S. Pat. No. 4,569,967.
Luer, M. S. & Hatton, J. (1993). *Annals Pharmcotherapy* 27:912–921.
Martinez, J. S. et al. (1995). *Biochem.* 34:14519–14526.
McIntosh, J. M. et al. (1982). *Arch. Biochem. Biophys.* 218:329–334.
McIntosh, J. M. et al. (1998). *Methods Enzymol.* 294:605–624.
*Methoden der Organischen Chemie (Houben-Weyl): Synthese von Peptiden,* E. Wunsch (Ed.), Georg Thieme Verlag, Stuttgart, Ger. (1974).
Myers, R. A. et al. (1991). *Biochemistry* 30:9370–9377.
Nakamura, T. et al. (1996). *Protein Sci.* 5:524–530.
Nishiuchi, Y. et al. (1993). Synthesis of gamma-carboxyglutamic acid-containing peptides by the Boc strategy. *Int. J. Pept. Protein Res.* 42:533–538.
Nowak, L. et al. (1984). *Nature* 307:462–465.
Olivera, B. M. et al. (1984). U.S. Pat. No. 4,447,356.
Olivera, B. M. et al. (1985). *Science* 230:1338–1343.
Olivera, B. M. et al. (1990). *Science* 249:257–263.
Olivera, B. M. et al. (1996). U.S. Pat. No. 5,514,774.
Ornstein, et al. (1993). *Biorganic Medicinal Chemistry Letters* 3:43–48.
Plone, M. A. et al. (1996). *Pain* 66:265–70.
Plummer, J. L. et al. (1991). *J Pharmacol Methods* 26:79–87.
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual,* 2nd Ed., Cold Spring Harbor Laboratory, Cold Spring Harbor, N.Y.
Schroder & Lubke (1965). *The Peptides* 1:72–75, Academic Press, NY.
Shon, K.-J. et al. (1994). *Biochemistry* 33:11420–11425.
Stewart and Young, *Solid-Phase Peptide Synthesis,* Freeman & Co., San Francisco, Calif. (1969).
Suh, H. H. et al. (1992). *Eur J Pharmacol* 213:337–41.
Vale et al. (1978). U.S. Pat. No. 4,105,603.
Van de Steen, P. et al. (1998). *Critical Rev. in Biochem. and Mol. Biol.* 33:151–208.
Woolfe, G. and MacDonald, A. (1944). *J. Pharmacol. Exp. Ther.* 80:300–307.
Zafaralla, G. C. et al. (1988). *Biochemistry* 27:7102–7105.
Zhou L. M., et al. (1996). *J. Neurochem.* 66:620–628.
Zimm, S. et al. (1984). *Cancer Res.* 44:1698–1701.
U.S. Pat. No. 3,972,859.
U.S. Pat. No. 3,842,067.
U.S. Pat. No. 3,862,925.
U.S. Pat. No. 5,514,774.
U.S. Pat. No. 5,531,001.
U.S. Pat. No. 5,534,615.
U.S. Pat. No. 5,364,769.
U.S. Pat. No. 5,545,723.
U.S. Pat. No. 5,550,050.
U.S. Pat. No. 5,591,821.
U.S. Pat. No. 5,719,264.
U.S. Pat. No. 5,844,077.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.
PCT Published Application WO 98/03189.
PCT Published Application WO 00/23092.

What is claimed is:

1. A substantially pure O-Superfamily conopeptide comprising the amino acid sequence Xaa1-Cys-Ile-Xaa4-Ser-Gly-Asp-Leu-Cys-Phe-Arg-Ser-Asp-His-Ile-Gly-Cys-Cys-Ser-Gly-Lys-Cys-Ala-Phe-Val-Cys-Leu (SEQ ID NO:271), wherein Xaa1 is Trp or bromo-Trp and Xaa4 is Pro or hydroxy-Pro.

2. The substantially pure O-Superfamily conopeptide of claim 1, wherein Xaa1 is Trp.

3. The substantially pure O-Superfamily conopeptide of claim 1, wherein Xaa4 is Pro.

4. The substantially pure O-Superfamily conopeptide of claim 1, wherein Xaa4 is hydroxy-Pro.

5. The substantially pure O-Superfamily conopeptide of claim 1, wherein Xaa1 is 6-bromo-Trp.

6. A pharmaceutical composition comprising a conotoxin peptide or a pharmaceutically acceptable salt thereof and a pharmaceutically acceptable carrier, said conotoxin peptide being the O-Superfamily conopeptide of claim 1.

7. A method for regulating the flow of sodium through sodium channels in an individual in need thereof which comprises administering a therapeutically effective amount of the O-Superfamily conopeptide of claim 1 or a pharmaceutically acceptable salt thereof.

8. The method of claim 7, wherein said individual in need thereof suffers from a disorder selected from the group consisting of multiple sclerosis, a demyelinating disease, sub-acute sclerosing panencephalomyelitis (SSPE), metachromatic leukodystrophy, Pelizaeus-Merzbacher disease, spinal cord injury, a compression and entrapment neuropathy, and a cardiovascular disorder.

9. The method of claim 7, wherein the demyelinating disease is selected from the group consisting of acute disseminated encephalomyelitis, optic neuromyelitis, adrenoleukodystrophy, acute transverse myelitis and progressive multifocal leukoencephalopathy.

10. The method of claim 7, wherein the compression and entrapment neuropathy is selected from the group consisting of carpal tunnel syndrome and ulnar nerve palsy.

11. The method of claim 7, wherein the cardiovascular disorder is selected from the group consisting of cardiac arrhythmias and congestive heart failure.

12. A method for treating or preventing disorders associated with voltage gated ion channel disorders in which comprises administering to a patient in need thereof a therapeutically effective amount of the O-Superfamily conopeptide of claim 1 or a pharmaceutically acceptable salt thereof.

13. The method of claim 12, wherein said disorder is a neurologic disorder.

14. The method of claim 12, wherein said disorder is a cardiovascular disorder.

15. The substantially pure O-Superfamily conopeptide of claim 1, wherein Xaa1 is Trp and Xaa4 is Pro.

16. A pharmaceutical composition comprising a conotoxin peptide or a pharmaceutically acceptable salt thereof and a pharmaceutically acceptable carrier, said conotoxin peptide being the O-Superfamily conopeptide of claim 15.

17. A substantially pure conotoxin precursor comprising an amino acid sequence Leu-Arg-Trp-Cys-Ile-Pro-Ser-Gly-Asp-Leu-Cys-Phe-Arg-Ser-Asp-His-Ile-Gly-Cys-Cys-Ser-Gly-Lys-Cys-Ala-Phe-Val-Cys-Leu (SEQ ID NO:270).

18. A pharmaceutical composition comprising a conotoxin peptide or a pharmaceutically acceptable salt thereof and a pharmaceutically acceptable carrier, said conotoxin peptide being the conotoxin protein precursor of claim 17.

* * * * *

SEQUENCE LISTING

<160> NUMBER OF SEQ ID NOS: 409

<210> SEQ ID NO 1
<211> LENGTH: 261
<212> TYPE: DNA
<213> ORGANISM: Conus gloriamaris
<220> FEATURE:
<221> NAME/KEY: CDS
<222> LOCATION: (1)..(231)

<400> SEQUENCE: 1

```
atg aaa ctg acg tgc atg atg atc gtt gct gtg ctg ttc ttg acc gcc      48
Met Lys Leu Thr Cys Met Met Ile Val Ala Val Leu Phe Leu Thr Ala
1               5                   10                  15 tgg aca ttc gtc acg gct gat gac tcc gga aat gga atg gag att ctt      96
Trp Thr Phe Val Thr Ala Asp Asp Ser Gly Asn Gly Met Glu Ile Leu
                20                  25                  30 ttt ccg aag gcg ggt cac gaa atg gag aac ctc gaa gtc tct aat cgg     144
Phe Pro Lys Ala Gly His Glu Met Glu Asn Leu Glu Val Ser Asn Arg
            35                  40                  45 gtc aag ccg tgc cgt aaa gaa ggt caa ctt tgt gat ccg ata ttt caa     192
Val Lys Pro Cys Arg Lys Glu Gly Gln Leu Cys Asp Pro Ile Phe Gln
    50                  55                  60 aac tgc tgc cgt ggc tgg aat tgc gtt ctt ttc tgc gtc tgaaactacc      241
Asn Cys Cys Arg Gly Trp Asn Cys Val Leu Phe Cys Val
65                  70                  75 gtgatgtctt ctctcccctc                                                261
```

<210> SEQ ID NO 2
<211> LENGTH: 77
<212> TYPE: PRT
<213> ORGANISM: Conus gloriamaris

<400> SEQUENCE: 2

```
Met Lys Leu Thr Cys Met Met Ile Val Ala Val Leu Phe Leu Thr Ala
1               5                   10                  15

Trp Thr Phe Val Thr Ala Asp Asp Ser Gly Asn Gly Met Glu Ile Leu
                20                  25                  30

Phe Pro Lys Ala Gly His Glu Met Glu Asn Leu Glu Val Ser Asn Arg
            35                  40                  45

Val Lys Pro Cys Arg Lys Glu Gly Gln Leu Cys Asp Pro Ile Phe Gln
    50                  55                  60

Asn Cys Cys Arg Gly Trp Asn Cys Val Leu Phe Cys Val
65                  70                  75
```

<210> SEQ ID NO 3
<211> LENGTH: 29
<212> TYPE: PRT
<213> ORGANISM: Conus gloriamaris
<220> FEATURE:
<221> NAME/KEY: SITE
<222> LOCATION: (1)..(29)
<223> OTHER INFORMATION: Xaa at residues 3 and 13 may be pro or
      hydroxy-Pro; Xaa at residu e 7 may be Glu or gamma-carboxy-Glu;
      Xaa at residue 22 may be Trp
      or bromo-Trp

<400> SEQUENCE: 3

```
Val Lys Xaa Cys Arg Lys Xaa Gly Gln Leu Cys Asp Xaa Ile Phe Gln
1               5                   10                  15

Asn Cys Cys Arg Gly Xaa Asn Cys Val Leu Phe Cys Val
```

-continued

<210> SEQ ID NO 4
<211> LENTGH: 29
<212> TYPE: PRT
<213> ORGANISM: Conus gloriamaris
<220> FEATURE:
<221> NAME/KEY: SITE
<222> LOCATION: (1)..(29)
<223> OTHER INFORMATION: Xaa at residues 3 and 13 may be pro or
      hydroxy-Pro; Xaa at residu e 7 may be Glu or gamma-carboxy-Glu;
      Xaa at residue 15 may be Tyr , 125-I-Tyr, mono-iodo-Tyr,
      di-iodo-Tyr, O-sulpho-Tyr or O-phospn o-Tyr; Xaa at residue 22
      may be Trp or bromo-Trp

<400> SEQUENCE: 4

Val Lys Xaa Cys Arg Lys Xaa Gly Gln Leu Cys Asp Xaa Ile Xaa Gln
1               5                   10                  15

Asn Cys Cys Arg Gly Xaa Asn Cys Val Leu Phe Cys Val
            20                  25

<210> SEQ ID NO 5
<211> LENGTH: 29
<212> TYPE: PRT
<213> ORGANISM: Conus gloriamaris
<220> FEATURE:
<221> NAME/KEY: SITE
<222> LOCATION: (1)..(29)
<223> OTHER INFORMATION: Xaa at residues 3 and 13 may be pro or
      hydroxy-Pro; Xaa at residu e 7 may be Glu or gamma-carboxy-Glu;
      Xaa at residue 22 may be Trp or bromo-Trp; Xaa at residue 27 may
      be Tyr, 125-I-Tyr, mono-iodo -Tyr, di-iodo-Tyr, O-sulpho-Tyr or
      O-phospno-Tyr

<400> SEQUENCE: 5

Val Lys Xaa Cys Arg Lys Xaa Gly Gln Leu Cys Asp Xaa Ile Phe Gln
1               5                   10                  15

Asn Cys Cys Arg Gly Xaa Asn Cys Val Leu Xaa Cys Val
            20                  25

<210> SEQ ID NO 6
<211> LENGTH: 542
<212> TYPE: DNA
<213> ORGANISM: Conus omaria
<220> FEATURE:
<221> NAME/KEY: CDS
<222> LOCATION: (146)..(235)

<400> SEQUENCE: 6
gaagctggta cgcctgcagg taccggtccg gaattcccgg gtcgacatca tcatcatcga      60
tccatctgtc catccatcca ttcattcatt cgctgccaga ctataataaa cattcaagtc    120
tctctttctt tttgtgtctg acaga tcg atc agg atg tgc cgt aga gaa gct      172
                              Ser Ile Arg Met Cys Arg Arg Glu Ala
                                1               5 caa ctt tgt gat ccg att ttt caa aac tgc tgc cat ggc ttg ttt tgc      220
Gln Leu Cys Asp Pro Ile Phe Gln Asn Cys Cys His Gly Leu Phe Cys
 10              15                  20                  25 gtt ttg gtc tgc gtc taaaactacc gtgatgtctt ctcctcccct ctagtagtag      275
Val Leu Val Cys Val
                30 taggcggccg ctctagagga tccaagctta cgtacgcgtg catgcgacgt catagctctt    335 ctatagtgtc acctaaattc aattcactgg ccgtcgtttt acaacgtcgt gactgggaaa    395 accctggcgt tacccaactt aatcgccttg cagcacatcc ccctttcgcc agctggcgta    455

-continued

```
atagcgaaga ggcccgcacc gatcgccctt cccaacagtt gcgcagcctg aatggcgaat      515
gggacgcgcc ctgtagcggc gcattat                                          542
```

<210> SEQ ID NO 7
<211> LENGTH: 30
<212> TYPE: PRT
<213> ORGANISM: Conus omaria

<400> SEQUENCE: 7

```
Ser Ile Arg Met Cys Arg Arg Glu Ala Gln Leu Cys Asp Pro Ile Phe
1               5                   10                  15

Gln Asn Cys Cys His Gly Leu Phe Cys Val Leu Val Cys Val
            20                  25                  30
```

<210> SEQ ID NO 8
<211> LENGTH: 27
<212> TYPE: PRT
<213> ORGANISM: Conus omaria
<220> FEATURE:
<221> NAME/KEY: SITE
<222> LOCATION: (1)..(27)
<223> OTHER INFORMATION: Xaa at residue 5 is Glu or gamma-carboxy-Glu;
    Xaa at residue 11 m ay be Pro or hydroxy-Pro

<400> SEQUENCE: 8

```
Met Cys Arg Arg Xaa Ala Gln Leu Cys Asp Xaa Ile Phe Gln Asn Cys
1               5                   10                  15

Cys His Gly Leu Phe Cys Val Leu Val Cys Val
            20                  25
```

<210> SEQ ID NO 9
<211> LENGTH: 346
<212> TYPE: DNA
<213> ORGANISM: Conus textile
<220> FEATURE:
<221> NAME/KEY: CDS
<222> LOCATION: (25)..(315)

<400> SEQUENCE: 9

```
ggcattacct aaaacatcac caag atg aaa ctg acg tgc atg atg atc gtt         51
                         Met Lys Leu Thr Cys Met Met Ile Val
                           1               5 gct gtg ctg ttc ttg acc gcc tgg aca ttc gtc acg gct gat gac tcc        99
Ala Val Leu Phe Leu Thr Ala Trp Thr Phe Val Thr Ala Asp Asp Ser
 10              15                  20                  25 aga aat gga atg gag aat ctt ttt ccg aag gca ggt cac gaa atg gag       147
Arg Asn Gly Met Glu Asn Leu Phe Pro Lys Ala Gly His Glu Met Glu
                 30                  35                  40 aac ctc gaa gac tct aaa cac agg cac cag gag aga ccg gac acc ggc       195
Asn Leu Glu Asp Ser Lys His Arg His Gln Glu Arg Pro Asp Thr Gly
             45                  50                  55 gac aaa gaa gag atg ctg cta cag aga cag gtc aag ccg tgt cgt aaa       243
Asp Lys Glu Glu Met Leu Leu Gln Arg Gln Val Lys Pro Cys Arg Lys
         60                  65                  70 gaa cat caa ctt tgt gat ctg att ttt caa aac tgc tgc cgt ggc tgg       291
Glu His Gln Leu Cys Asp Leu Ile Phe Gln Asn Cys Cys Arg Gly Trp
     75                  80                  85 tat tgc gtt gtt ctg tct tgc act tgaaagctac ctgatgtgtt ctactcccat      345
Tyr Cys Val Val Leu Ser Cys Thr
 90                  95 c                                                                      346
```

```
<210> SEQ ID NO 10
<211> LENGTH: 97
<212> TYPE: PRT
<213> ORGANISM: Conus textile

<400> SEQUENCE: 10

Met Lys Leu Thr Cys Met Met Ile Val Ala Val Leu Phe Leu Thr Ala
1               5                   10                  15

Trp Thr Phe Val Thr Ala Asp Asp Ser Arg Asn Gly Met Glu Asn Leu
            20                  25                  30

Phe Pro Lys Ala Gly His Glu Met Glu Asn Leu Glu Asp Ser Lys His
        35                  40                  45

Arg His Gln Glu Arg Pro Asp Thr Gly Asp Lys Glu Glu Met Leu Leu
    50                  55                  60

Gln Arg Gln Val Lys Pro Cys Arg Lys Glu His Gln Leu Cys Asp Leu
65                  70                  75                  80

Ile Phe Gln Asn Cys Cys Arg Gly Trp Tyr Cys Val Val Leu Ser Cys
                85                  90                  95

Thr

<210> SEQ ID NO 11
<211> LENGTH: 31
<212> TYPE: PRT
<213> ORGANISM: Conus textile
<220> FEATURE:
<221> NAME/KEY: SITE
<222> LOCATION: (1)..(31)
<223> OTHER INFORMATION: Xaa at residue 1 may be Gln or pyro-Glu; Xaa at
      residue 4 may be Pro or hydroxy-Pro; Xaa at residue 8 may be Glu o
      gamma-carboxy- Glu; Xaa at residue 23 may be Trp or bromo-Trp; Xaa
      at residue 24
<221> NAME/KEY: SITE
<222> LOCATION: (1)..(31)
<223> OTHER INFORMATION: may be Tyr, 125-I-Tyr, mono-iodo-Tyr,
      di-iodo-Tyr, O-sulpho-Tyr or O-phospho-Tyr

<400> SEQUENCE: 11

Xaa Val Lys Xaa Cys Arg Lys Xaa His Gln Leu Cys Asp Leu Ile Phe
1               5                   10                  15

Gln Asn Cys Cys Arg Gly Xaa Xaa Cys Val Val Leu Ser Cys Thr
            20                  25                  30

<210> SEQ ID NO 12
<211> LENGTH: 265
<212> TYPE: DNA
<213> ORGANISM: Conus omaria
<220> FEATURE:
<221> NAME/KEY: CDS
<222> LOCATION: (1)..(234)

<400> SEQUENCE: 12 atg aaa ctg acg tgc ctg atg atc gtt gcc gtg ctg tcc ttg acc ggc      48
Met Lys Leu Thr Cys Leu Met Ile Val Ala Val Leu Ser Leu Thr Gly
1               5                   10                  15 tgg aca ttc gtc acg gct gat gac tct gga aat gga ttg ggg aat ctt      96
Trp Thr Phe Val Thr Ala Asp Asp Ser Gly Asn Gly Leu Gly Asn Leu
            20                  25                  30 ttt tcg aat gca cat cac gaa atg aag aac ccc gaa gcc tct aaa ttg     144
Phe Ser Asn Ala His His Glu Met Lys Asn Pro Glu Ala Ser Lys Leu
        35                  40                  45 aac aag agg tgc gtt cca cac gag ggc cct tgt aat tgg ctt aca caa     192
Asn Lys Arg Cys Val Pro His Glu Gly Pro Cys Asn Trp Leu Thr Gln
    50                  55                  60
```

```
aac tgc tgc agt ggt tat aat tgc atc att ttt ttc tgc cta         234
Asn Cys Cys Ser Gly Tyr Asn Cys Ile Ile Phe Phe Cys Leu
65              70                  75 taaaactacc gtgatgtctt ctcttcccct c                              265
```

<210> SEQ ID NO 13
<211> LENGTH: 78
<212> TYPE: PRT
<213> ORGANISM: Conus omaria

<400> SEQUENCE: 13

```
Met Lys Leu Thr Cys Leu Met Ile Val Ala Val Leu Ser Leu Thr Gly
1               5                   10                  15

Trp Thr Phe Val Thr Ala Asp Asp Ser Gly Asn Gly Leu Gly Asn Leu
            20                  25                  30

Phe Ser Asn Ala His His Glu Met Lys Asn Pro Glu Ala Ser Lys Leu
        35                  40                  45

Asn Lys Arg Cys Val Pro His Glu Gly Pro Cys Asn Trp Leu Thr Gln
    50                  55                  60

Asn Cys Cys Ser Gly Tyr Asn Cys Ile Ile Phe Phe Cys Leu
65              70                  75
```

<210> SEQ ID NO 14
<211> LENGTH: 27
<212> TYPE: PRT
<213> ORGANISM: Conus omaria
<220> FEATURE:
<221> NAME/KEY: SITE
<222> LOCATION: (1)..(27)
<223> OTHER INFORMATION: Xaa at residues 3 and 7 may be Pro or
      hydroxy-Pro; Xaa at residue 5 may be Glu or gamma-carboxy-Glu;
      Xaa at residue 10 may be Trp or bromo-Trp; Xaa at residue 19 may
      be Tyr, 125-I-Tyr, mono-iodo- Tyr, di-iodo-Tyr, O-sulpho-Tyr or
      O-phospho-Tyr

<400> SEQUENCE: 14

```
Cys Val Xaa His Xaa Gly Xaa Cys Asn Xaa Leu Thr Gln Asn Cys Cys
1               5                   10                  15

Ser Gly Xaa Asn Cys Ile Ile Phe Phe Cys Leu
            20                  25
```

<210> SEQ ID NO 15
<211> LENGTH: 321
<212> TYPE: DNA
<213> ORGANISM: Conus dalli
<220> FEATURE:
<221> NAME/KEY: CDS
<222> LOCATION: (1)..(291)

<400> SEQUENCE: 15

```
atg aaa ctg acg tgc ctg ctg atc att gct gtg ctg ttc ttg acc gcc         48
Met Lys Leu Thr Cys Leu Leu Ile Ile Ala Val Leu Phe Leu Thr Ala
1               5                   10                  15 tgg aca ttc gtc acg gct gat gac tcc gga aat gga atg gag aat ctt         96
Trp Thr Phe Val Thr Ala Asp Asp Ser Gly Asn Gly Met Glu Asn Leu
            20                  25                  30 ttt ccg aag gca cgt cac gaa atg gag aac ctc gaa gac tct aaa cac        144
Phe Pro Lys Ala Arg His Glu Met Glu Asn Leu Glu Asp Ser Lys His
        35                  40                  45 agg cac cag gag aga ccg gac acg ggc gac aaa gaa gag atg ctg cta        192
Arg His Gln Glu Arg Pro Asp Thr Gly Asp Lys Glu Glu Met Leu Leu
    50                  55                  60 cag aga cag gtc aag ccg tgt cgt aaa gaa cat caa ctt tgt gat ctg        240
Gln Arg Gln Val Lys Pro Cys Arg Lys Glu His Gln Leu Cys Asp Leu
```

```
Gln Arg Gln Val Lys Pro Cys Arg Lys Glu His Gln Leu Cys Asp Leu
 65                  70                  75                  80 att ttt caa aac tgc tgc cgt ggc tgg tat tgc ttg ctt cgt cct tgc     288
Ile Phe Gln Asn Cys Cys Arg Gly Trp Tyr Cys Leu Leu Arg Pro Cys
                 85                  90                  95 atc tgaaactacc gtgatgtctt ctctcccatc                                321
Ile
```

<210> SEQ ID NO 16
<211> LENGTH: 97
<212> TYPE: PRT
<213> ORGANISM: Conus dalli

<400> SEQUENCE: 16

```
Met Lys Leu Thr Cys Leu Leu Ile Ile Ala Val Leu Phe Leu Thr Ala
  1               5                  10                  15

Trp Thr Phe Val Thr Ala Asp Asp Ser Gly Asn Gly Met Glu Asn Leu
                 20                  25                  30

Phe Pro Lys Ala Arg His Glu Met Glu Asn Leu Glu Asp Ser Lys His
             35                  40                  45

Arg His Gln Glu Arg Pro Asp Thr Gly Asp Lys Glu Glu Met Leu Leu
         50                  55                  60

Gln Arg Gln Val Lys Pro Cys Arg Lys Glu His Gln Leu Cys Asp Leu
 65                  70                  75                  80

Ile Phe Gln Asn Cys Cys Arg Gly Trp Tyr Cys Leu Leu Arg Pro Cys
                 85                  90                  95

Ile
```

<210> SEQ ID NO 17
<211> LENGTH: 31
<212> TYPE: PRT
<213> ORGANISM: Conus dalli
<220> FEATURE:
<221> NAME/KEY: SITE
<222> LOCATION: (1)..(31)
<223> OTHER INFORMATION: Xaa at residue 1 may be Gln or pyro-Glu; Xaa at
      residues 4 and 29 may be Pro or hydroxy-Pro; Xaa at residue 8 may
      be Glu or gamma- carboxy-Glu ; Xaa at residue 23 may be Trp or
      bromo-Trp;
<221> NAME/KEY: SITE
<222> LOCATION: (1)..(31)
<223> OTHER INFORMATION: Xaa at residue 24 may be Tyr, 125-I-Tyr,
      mono-iodo-Tyr, di-iodo-T yr, O-sulpho-Tyr or O-phospho-Tyr

<400> SEQUENCE: 17

```
Xaa Val Lys Xaa Cys Arg Lys Xaa His Gln Leu Cys Asp Leu Ile Phe
  1               5                  10                  15

Gln Asn Cys Cys Arg Gly Xaa Xaa Cys Leu Leu Arg Xaa Cys Ile
                 20                  25                  30
```

<210> SEQ ID NO 18
<211> LENGTH: 321
<212> TYPE: DNA
<213> ORGANISM: Conus dalli
<220> FEATURE:
<221> NAME/KEY: CDS
<222> LOCATION: (1)..(291)

<400> SEQUENCE: 18

```
atg aaa ctg acg tgt atg ctg atc att gct gtg ctg ttc ttg acc gcc      48
Met Lys Leu Thr Cys Met Leu Ile Ile Ala Val Leu Phe Leu Thr Ala
  1               5                  10                  15 tgg aca ttc gtc acg gct gat gac tcc gga aat gga atg gag aat ctt      96
```

```
                                                                    -continued Trp Thr Phe Val Thr Ala Asp Asp Ser Gly Asn Gly Met Glu Asn Leu
        20                  25                  30 ttt ccg aag gca cgt cac gaa atg gag aac ctc gaa gac tct aaa cac       144
Phe Pro Lys Ala Arg His Glu Met Glu Asn Leu Glu Asp Ser Lys His
        35                  40                  45 agg cac cag gag aga ccg gac acg ggc gac aaa gaa gag atg ctg cta       192
Arg His Gln Glu Arg Pro Asp Thr Gly Asp Lys Glu Glu Met Leu Leu
 50                  55                  60 cag aga cgg gtc aag ccg tgc agt gaa gaa ggt caa ctt tgt gat cca       240
Gln Arg Arg Val Lys Pro Cys Ser Glu Glu Gly Gln Leu Cys Asp Pro
 65                  70                  75                  80 ctt tct caa aac tgc tgc cgt ggc tgg cat tgc gtt ctt gtc tct tgc       288
Leu Ser Gln Asn Cys Cys Arg Gly Trp His Cys Val Leu Val Ser Cys
                 85                  90                  95 gtc tgaaactacc gtgatgtctt ctctcccatc                                  321
Val

<210> SEQ ID NO 19
<211> LENGTH: 97
<212> TYPE: PRT
<213> ORGANISM: Conus dalli

<400> SEQUENCE: 19

Met Lys Leu Thr Cys Met Leu Ile Ile Ala Val Leu Phe Leu Thr Ala
1               5                   10                  15

Trp Thr Phe Val Thr Ala Asp Asp Ser Gly Asn Gly Met Glu Asn Leu
            20                  25                  30

Phe Pro Lys Ala Arg His Glu Met Glu Asn Leu Glu Asp Ser Lys His
        35                  40                  45

Arg His Gln Glu Arg Pro Asp Thr Gly Asp Lys Glu Glu Met Leu Leu
    50                  55                  60

Gln Arg Arg Val Lys Pro Cys Ser Glu Glu Gly Gln Leu Cys Asp Pro
65                  70                  75                  80

Leu Ser Gln Asn Cys Cys Arg Gly Trp His Cys Val Leu Val Ser Cys
                85                  90                  95

Val

<210> SEQ ID NO 20
<211> LENGTH: 30
<212> TYPE: PRT
<213> ORGANISM: Conus dalli
<220> FEATURE:
<221> NAME/KEY: SITE
<222> LOCATION: (1)..(30)
<223> OTHER INFORMATION: Xaa at residues 3 and 13 may be Pro or
      hydroxy-Pro; Xaa at residues 6 and 7 may be Glu or
      gamma-carboxy-Glu ; Xaa at residue 22 may be Trp or bromo-Trp

<400> SEQUENCE: 20

Val Lys Xaa Cys Ser Xaa Xaa Gly Gln Leu Cys Asp Xaa Leu Ser Gln
1               5                   10                  15

Asn Cys Cys Arg Gly Xaa His Cys Val Leu Val Ser Cys Val
            20                  25                  30

<210> SEQ ID NO 21
<211> LENGTH: 406
<212> TYPE: DNA
<213> ORGANISM: Conus textile
<220> FEATURE:
<221> NAME/KEY: CDS
<222> LOCATION: (14)..(247)
```

```
<400> SEQUENCE: 21
aaacatcgcc aag atg aaa ctg acg tgc atg atg atc gtt gct gtg ctg              49
            Met Lys Leu Thr Cys Met Met Ile Val Ala Val Leu
              1               5                  10 ttc ttg acc gcc tgg aca ttt gcc acg gct gat gac ccc aga aat gga             97
Phe Leu Thr Ala Trp Thr Phe Ala Thr Ala Asp Asp Pro Arg Asn Gly
         15                  20                  25 ttg ggg aat ctt ttt tcg aat gca cat cac gaa atg aag aac ccc gaa            145
Leu Gly Asn Leu Phe Ser Asn Ala His His Glu Met Lys Asn Pro Glu
     30                  35                  40 gcc tct aaa ttg aac aag agg tgg tgc aaa caa agc ggt gaa atg tgt            193
Ala Ser Lys Leu Asn Lys Arg Trp Cys Lys Gln Ser Gly Glu Met Cys
 45                  50                  55                  60 aat ttg tta gac caa aac tgc tgc gac ggc tat tgc ata gta ctt gtc            241
Asn Leu Leu Asp Gln Asn Cys Cys Asp Gly Tyr Cys Ile Val Leu Val
                 65                  70                  75 tgc aca taaaactgcc gtgatgtctt ctcttcccct ctgtgctacc tggcttgatc             297
Cys Thr tttgattggc gcgtgtcgtt cactggttat gaaccccccc cccccccccc cccccccct           357 tccggctctc tggaggcctc ggggggttcaa catccaaata aagtgacag                     406

<210> SEQ ID NO 22
<211> LENGTH: 78
<212> TYPE: PRT
<213> ORGANISM: Conus textile

<400> SEQUENCE: 22

Met Lys Leu Thr Cys Met Met Ile Val Ala Val Leu Phe Leu Thr Ala
  1               5                  10                  15

Trp Thr Phe Ala Thr Ala Asp Asp Pro Arg Asn Gly Leu Gly Asn Leu
                 20                  25                  30

Phe Ser Asn Ala His His Glu Met Lys Asn Pro Glu Ala Ser Lys Leu
         35                  40                  45

Asn Lys Arg Trp Cys Lys Gln Ser Gly Glu Met Cys Asn Leu Leu Asp
     50                  55                  60

Gln Asn Cys Cys Asp Gly Tyr Cys Ile Val Leu Val Cys Thr
 65                  70                  75

<210> SEQ ID NO 23
<211> LENGTH: 27
<212> TYPE: PRT
<213> ORGANISM: Conus textile
<220> FEATURE:
<221> NAME/KEY: SITE
<222> LOCATION: (1)..(27)
<223> OTHER INFORMATION: Xaa at residue 1 may be Trp or bromo-Trp; Xaa
      at residue 7 may be Glu or gamma-carboxy-Glu; Xaa at residue 20
      may be Tyr, 125-I-Ty r, mono-iodo-Tyr, di-iodo-Tyr, O-sulpho-Tyr
      or O-phospho-Tyr

<400> SEQUENCE: 23

Xaa Cys Lys Gln Asp Gly Xaa Met Cys Asn Leu Leu Asp Gln Asn Cys
  1               5                  10                  15

Cys Asp Gly Xaa Cys Ile Val Leu Val Cys Thr
                 20                  25

<210> SEQ ID NO 24
<211> LENGTH: 27
<212> TYPE: PRT
<213> ORGANISM: Conus textile
<220> FEATURE:
```

```
<221> NAME/KEY: SITE
<222> LOCATION: (1)..(26)
<223> OTHER INFORMATION: Xaa at residue 1 may be Trp or bromo-Trp; Xaa
      at residue 7 may be Glu or gamma-carboxy-Glu;Xaa at residue 9 is
      Nle; Xaa at residue 20 may be Tyr, 125-I-Tyr, mono-iodo-Tyr,
      di-iodo-Tyr, O-sulpho-Tyr or O-phospho-Tyr

<400> SEQUENCE: 24

Xaa Cys Lys Gln Asp Gly Xaa Xaa Cys Asn Leu Leu Asp Gln Asn Cys
1               5                  10                  15

Cys Asp Gly Xaa Cys Ile Val Leu Val Cys Thr
            20                  25

<210> SEQ ID NO 25
<211> LENGTH: 265
<212> TYPE: DNA
<213> ORGANISM: Conus magus
<220> FEATURE:
<221> NAME/KEY: CDS
<222> LOCATION: (1)..(234)

<400> SEQUENCE: 25 atg aaa ctg acg tgt gtg atg atc gtt gct gtg ctg ttc ttg acc gcc      48
Met Lys Leu Thr Cys Val Met Ile Val Ala Val Leu Phe Leu Thr Ala
1               5                   10                  15 tgg aca ttt gcc acg gct gat gac ccc aga aat gga ttg ggg aat ctt      96
Trp Thr Phe Ala Thr Ala Asp Asp Pro Arg Asn Gly Leu Gly Asn Leu
            20                  25                  30 ttt tcg aat gca cat cac gaa atg aag aac ccc gaa gcc tct aaa ttg     144
Phe Ser Asn Ala His His Glu Met Lys Asn Pro Glu Ala Ser Lys Leu
        35                  40                  45 aac aag agg tgg tgc aaa caa agc ggt gaa atg tgt aat ttg tta gac     192
Asn Lys Arg Trp Cys Lys Gln Ser Gly Glu Met Cys Asn Leu Leu Asp
    50                  55                  60 caa aac tgc tgc gac ggc tat tgc ata gta ctt gtc tgc aca             234
Gln Asn Cys Cys Asp Gly Tyr Cys Ile Val Leu Val Cys Thr
65                  70                  75 taaaactgcc gtgatgtctt ctcctcccct c                                  265

<210> SEQ ID NO 26
<211> LENGTH: 78
<212> TYPE: PRT
<213> ORGANISM: Conus magus

<400> SEQUENCE: 26

Met Lys Leu Thr Cys Val Met Ile Val Ala Val Leu Phe Leu Thr Ala
1               5                   10                  15

Trp Thr Phe Ala Thr Ala Asp Asp Pro Arg Asn Gly Leu Gly Asn Leu
            20                  25                  30

Phe Ser Asn Ala His His Glu Met Lys Asn Pro Glu Ala Ser Lys Leu
        35                  40                  45

Asn Lys Arg Trp Cys Lys Gln Ser Gly Glu Met Cys Asn Leu Leu Asp
    50                  55                  60

Gln Asn Cys Cys Asp Gly Tyr Cys Ile Val Leu Val Cys Thr
65                  70                  75

<210> SEQ ID NO 27
<211> LENGTH: 27
<212> TYPE: PRT
<213> ORGANISM: Conus magus
<220> FEATURE:
<221> NAME/KEY: SITE
<222> LOCATION: (1)..(27)
```

-continued

```
<223> OTHER INFORMATION: Xaa at residue 1 may be Trp or bromo-Trp; Xaa
      at residue 7 may be Glu or gamma-carboxy-Glu; Xaa at residue 20
      may be Tyr, 125-I-Tyr, mono-iodo-Tyr, di-iodo-Tyr, O-sulpho-Tyr or
      O-phospho-Tyr

<400> SEQUENCE: 27

Xaa Cys Lys Gln Ser Gly Xaa Met Cys Asn Leu Leu Asp Gln Asn Cys
1               5                   10                  15

Cys Asp Gly Xaa Cys Ile Val Leu Val Cys Thr
            20                  25

<210> SEQ ID NO 28
<211> LENGTH: 27
<212> TYPE: PRT
<213> ORGANISM: Conus textile
<220> FEATURE:
<221> NAME/KEY: SITE
<222> LOCATION: (1)..(27)
<223> OTHER INFORMATION: Xaa at residue 1 may be Trp or bromo-Trp; Xaa
      at residue 7 may be Glu or gamma-carboxy-Glu; Xaa at residue 20
      may be Tyr, 125-I-Tyr, mono-iodo-Tyr, di-iodo-Tyr, O-sulpho-Tyr or
      O-phospho-Tyr

<400> SEQUENCE: 28

Xaa Cys Lys Gln Ser Gly Xaa Met Cys Asn Leu Leu Asp Gln Asn Cys
1               5                   10                  15

Cys Asp Gly Xaa Cys Ile Val Phe Val Cys Thr
            20                  25

<210> SEQ ID NO 29
<211> LENGTH: 265
<212> TYPE: DNA
<213> ORGANISM: Conus distans
<220> FEATURE:
<221> NAME/KEY: CDS
<222> LOCATION: (1)..(234)

<400> SEQUENCE: 29 atg aaa ctg acg tgc ctg atg atc gtt gct gtg ctg ttc ttg acc gcc      48
Met Lys Leu Thr Cys Leu Met Ile Val Ala Val Leu Phe Leu Thr Ala
1               5                   10                  15 tgg aca ttt gcc acg gct gat gac ccc aga aat gga ttg ggg aat ctt      96
Trp Thr Phe Ala Thr Ala Asp Asp Pro Arg Asn Gly Leu Gly Asn Leu
            20                  25                  30 ttt tcg aat gca cat cac gaa atg aag aac ccc gaa gcc tct aaa ttg     144
Phe Ser Asn Ala His His Glu Met Lys Asn Pro Glu Ala Ser Lys Leu
        35                  40                  45 aac aag agg tgg tgc aaa caa agc ggt gaa atg tgt aat ttg tta gac     192
Asn Lys Arg Trp Cys Lys Gln Ser Gly Glu Met Cys Asn Leu Leu Asp
    50                  55                  60 caa aac tgc tgc gac ggc tat tgc ata gta ctt gtc tgc aca             234
Gln Asn Cys Cys Asp Gly Tyr Cys Ile Val Leu Val Cys Thr
65                  70                  75 taaaactgcc gtgatgtctt ctcctcccct c                                  265

<210> SEQ ID NO 30
<211> LENGTH: 78
<212> TYPE: PRT
<213> ORGANISM: Conus distans

<400> SEQUENCE: 30

Met Lys Leu Thr Cys Leu Met Ile Val Ala Val Leu Phe Leu Thr Ala
1               5                   10                  15

Trp Thr Phe Ala Thr Ala Asp Asp Pro Arg Asn Gly Leu Gly Asn Leu
```

```
                    20                  25                  30
Phe Ser Asn Ala His His Glu Met Lys Asn Pro Glu Ala Ser Lys Leu
            35                  40                  45

Asn Lys Arg Trp Cys Lys Gln Ser Gly Glu Met Cys Asn Leu Leu Asp
        50                  55                  60

Gln Asn Cys Cys Asp Gly Tyr Cys Ile Val Leu Val Cys Thr
65                  70                  75

<210> SEQ ID NO 31
<211> LENGTH: 27
<212> TYPE: PRT
<213> ORGANISM: Conus distans
<220> FEATURE:
<221> NAME/KEY: SITE
<222> LOCATION: (1)..(27)
<223> OTHER INFORMATION: Xaa at residue 1 may be Trp or bromo-Trp; Xaa
      at residue 7 may be Glu or gamma-carboxy-Glu; Xaa at residue 20
      may be Tyr, 125-I-Tyr, mono-iodo-Tyr, di-iodo-Tyr, O-sulpho-Tyr or
      O-phospho-Tyr

<400> SEQUENCE: 31

Xaa Cys Lys Gln Ser Gly Xaa Met Cys Asn Leu Leu Asp Gln Asn Cys
1               5                   10                  15

Cys Asp Gly Xaa Cys Ile Val Leu Val Cys Thr
            20                  25

<210> SEQ ID NO 32
<211> LENGTH: 265
<212> TYPE: DNA
<213> ORGANISM: Conus ammiralis
<220> FEATURE:
<221> NAME/KEY: CDS
<222> LOCATION: (1)..(234)

<400> SEQUENCE: 32 atg aaa ctg acg tgc gtg atg atc gtt gct gtg ctg ttc ttg acc gcc        48
Met Lys Leu Thr Cys Val Met Ile Val Ala Val Leu Phe Leu Thr Ala
1               5                   10                  15 tgg aca ttt gcc acg gct gat gac ccc aga aat gga ttg ggg aat ctt        96
Trp Thr Phe Ala Thr Ala Asp Asp Pro Arg Asn Gly Leu Gly Asn Leu
            20                  25                  30 ttt tcg aat gca cat cac gaa atg aag aac ccc gaa gcc tct aaa ttg       144
Phe Ser Asn Ala His His Glu Met Lys Asn Pro Glu Ala Ser Lys Leu
        35                  40                  45 aac aag agg tgg tgc aaa caa agc ggt gaa atg tgt aat ttg tta gac       192
Asn Lys Arg Trp Cys Lys Gln Ser Gly Glu Met Cys Asn Leu Leu Asp
    50                  55                  60 caa aac tgc tgc gag ggc tat tgc ata gta ctt gtc tgc aca              234
Gln Asn Cys Cys Glu Gly Tyr Cys Ile Val Leu Val Cys Thr
65                  70                  75 taaaactgcc gtgatgtctt ctcctcccct c                                    265

<210> SEQ ID NO 33
<211> LENGTH: 78
<212> TYPE: PRT
<213> ORGANISM: Conus ammiralis

<400> SEQUENCE: 33

Met Lys Leu Thr Cys Val Met Ile Val Ala Val Leu Phe Leu Thr Ala
1               5                   10                  15

Trp Thr Phe Ala Thr Ala Asp Asp Pro Arg Asn Gly Leu Gly Asn Leu
            20                  25                  30
```

```
Phe Ser Asn Ala His His Glu Met Lys Asn Pro Glu Ala Ser Lys Leu
        35                  40                  45

Asn Lys Arg Trp Cys Lys Gln Ser Gly Glu Met Cys Asn Leu Leu Asp
    50                  55                  60

Gln Asn Cys Cys Glu Gly Tyr Cys Ile Val Leu Val Cys Thr
65                  70                  75

<210> SEQ ID NO 34
<211> LENGTH: 27
<212> TYPE: PRT
<213> ORGANISM: Conus ammiralis
<220> FEATURE:
<221> NAME/KEY: SITE
<222> LOCATION: (1)..(27)
<223> OTHER INFORMATION: Xaa at residue 1 may be Trp or bromo-Trp;
      Xaa at residues 7 and 18 may be Glu or gamma-carboxy-Glu; Xaa at
      residue 20 may be Tyr,125-I-Tyr, mono-iodo-Tyr, di-iodo-Tyr,
      O-sulpho-Tyr or O-phospho-Tyr

<400> SEQUENCE: 34

Xaa Cys Lys Gln Ser Gly Xaa Met Cys Asn Leu Leu Asp Gln Asn Cys
1               5                  10                  15

Cys Xaa Gly Xaa Cys Ile Val Leu Val Cys Thr
            20                  25

<210> SEQ ID NO 35
<211> LENGTH: 256
<212> TYPE: DNA
<213> ORGANISM: Conus dalli
<220> FEATURE:
<221> NAME/KEY: CDS
<222> LOCATION: (1)..(225)

<400> SEQUENCE: 35 atg aaa ctg acg tgc gtg atg atc gtt gct gtg ctg ttc ttg acc gcc        48
Met Lys Leu Thr Cys Val Met Ile Val Ala Val Leu Phe Leu Thr Ala
1               5                  10                  15 tgg aca ttc gcc acg gct gat gac ccc aga aat gga ttg gag aat ctt        96
Trp Thr Phe Ala Thr Ala Asp Asp Pro Arg Asn Gly Leu Glu Asn Leu
            20                  25                  30 ttt ttg aag gca cat cac gaa atg aac ccc gaa gcc tct aag ttg aat       144
Phe Leu Lys Ala His His Glu Met Asn Pro Glu Ala Ser Lys Leu Asn
        35                  40                  45 gag agg tgc ctt ggt ggt ggt gaa gtt tgt gat atc ttt ttt cca caa       192
Glu Arg Cys Leu Gly Gly Gly Glu Val Cys Asp Ile Phe Phe Pro Gln
    50                  55                  60 tgc tgt ggc tat tgc att ctt ctt ttc tgc aca taaaactacc gtgatgtctt     245
Cys Cys Gly Tyr Cys Ile Leu Leu Phe Cys Thr
65                  70                  75 ctcctcccct c                                                          256

<210> SEQ ID NO 36
<211> LENGTH: 75
<212> TYPE: PRT
<213> ORGANISM: Conus dalli

<400> SEQUENCE: 36

Met Lys Leu Thr Cys Val Met Ile Val Ala Val Leu Phe Leu Thr Ala
1               5                  10                  15

Trp Thr Phe Ala Thr Ala Asp Asp Pro Arg Asn Gly Leu Glu Asn Leu
            20                  25                  30

Phe Leu Lys Ala His His Glu Met Asn Pro Glu Ala Ser Lys Leu Asn
        35                  40                  45
```

```
Glu Arg Cys Leu Gly Gly Gly Glu Val Cys Asp Ile Phe Phe Pro Gln
    50                  55                  60
Cys Cys Gly Tyr Cys Ile Leu Leu Phe Cys Thr
65                  70                  75

<210> SEQ ID NO 37
<211> LENGTH: 25
<212> TYPE: PRT
<213> ORGANISM: Conus dalli
<220> FEATURE:
<221> NAME/KEY: SITE
<222> LOCATION: (1)..(25)
<223> OTHER INFORMATION: Xaa at residue 6 may be Glu or
      gamma-carboxy-Glu; Xaa at residue 13 may be Pro or hydroxy-Pro;Xaa
      at residue 18 may be Tyr, 125-I-Tyr, mono-iodo-Tyr, di-iodo-Tyr,
      O-sulpho-Tyr or O-phospho-Tyr

<400> SEQUENCE: 37

Cys Leu Gly Gly Gly Xaa Val Cys Asp Ile Phe Phe Xaa Gln Cys Cys
1               5                   10                  15
Gly Xaa Cys Ile Leu Leu Phe Cys Thr
            20                  25

<210> SEQ ID NO 38
<211> LENGTH: 441
<212> TYPE: DNA
<213> ORGANISM: Conus gloriamaris
<220> FEATURE:
<221> NAME/KEY: CDS
<222> LOCATION: (70)..(300)

<400> SEQUENCE: 38
gcttgcacgg tgaatttggc ttcacagttt tccactgtcg tctttggcat catctgaaac      60 atcgccaag atg aaa ctg acg tgc atg atg atc gtt gct gtg ctg ttc ttg    111
           Met Lys Leu Thr Cys Met Met Ile Val Ala Val Leu Phe Leu
             1               5                   10 acc gcc tgg aca ttt gcc acg gct gat gac ccc aga aat gga ttg ggg      159
Thr Ala Trp Thr Phe Ala Thr Ala Asp Asp Pro Arg Asn Gly Leu Gly
15                  20                  25                  30
aat att ttt tcg aat gca cat cac gaa atg aag aat ccc gaa gcc tct      207

Asn Ile Phe Ser Asn Ala His His Glu Met Lys Asn Pro Glu Ala Ser
                35                  40                  45
aaa ttg aac aag agg tgc cgt cta ggg gct gaa agt tgt gat gta att      255
Lys Leu Asn Lys Arg Cys Arg Leu Gly Ala Glu Ser Cys Asp Val Ile
            50                  55                  60
tca caa aac tgc tgc caa ggc acg tgc gtt ttt ttc tgc tta cca          300
Ser Gln Asn Cys Cys Gln Gly Thr Cys Val Phe Phe Cys Leu Pro
            65                  70                  75 tgatgtcttc tattctcctc tgtgctacct ggcttgatct ttcattagcg cgtgcctttc    360
actggttatg aaccccctga tccgactctc tggcagcctc ggggttcaa catccaaata     420 aaacgacagc acaatgacaa a                                              441

<210> SEQ ID NO 39
<211> LENGTH: 77
<212> TYPE: PRT
<213> ORGANISM: Conus gloriamaris

<400> SEQUENCE: 39

Met Lys Leu Thr Cys Met Met Ile Val Ala Val Leu Phe Leu Thr Ala
1               5                   10                  15
Trp Thr Phe Ala Thr Ala Asp Asp Pro Arg Asn Gly Leu Gly Asn Ile
            20                  25                  30
```

-continued

Phe Ser Asn Ala His His Glu Met Lys Asn Pro Glu Ala Ser Lys Leu
        35                  40                  45

Asn Lys Arg Cys Arg Leu Gly Ala Glu Ser Cys Asp Val Ile Ser Gln
 50                  55                  60

Asn Cys Cys Gln Gly Thr Cys Val Phe Phe Cys Leu Pro
65                  70                  75

<210> SEQ ID NO 40
<211> LENGTH: 26
<212> TYPE: PRT
<213> ORGANISM: Conus gloriamaris
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 26 may be Pro or hydroxy-Pro

<400> SEQUENCE: 40

Cys Arg Leu Gly Ala Xaa Ser Cys Asp Val Ile Ser Gln Asn Cys Cys
1               5                   10                  15

Gln Gly Thr Cys Val Phe Phe Cys Leu Xaa
            20                  25

<210> SEQ ID NO 41
<211> LENGTH: 446
<212> TYPE: DNA
<213> ORGANISM: Conus gloriamaris
<220> FEATURE:
<221> NAME/KEY: CDS
<222> LOCATION: (74)..(304)

<400> SEQUENCE: 41
ggatccttgc acggtgaatt tggcttcaca gttttccact gtcgtctttc gcatcatcca      60
aaacatcacc aag atg aaa ctg acg tgc atg atg atc gtt gct gtg ctg       109
            Met Lys Leu Thr Cys Met Met Ile Val Ala Val Leu
            1               5                   10 ttc ttg acc gcc tgg aca ttc gcc acg gct gat gac ccc aga aat gga      157
Phe Leu Thr Ala Trp Thr Phe Ala Thr Ala Asp Asp Pro Arg Asn Gly
         15                  20                  25 ttg gag aaa ctt ttt tcg aat aca cat cac gaa atg aag aac ccc gaa      205
Leu Glu Lys Leu Phe Ser Asn Thr His His Glu Met Lys Asn Pro Glu
 30                  35                  40 gcc tct aaa ttg aac aag agg tgc aaa caa gct gat gaa tct tgt aat      253
Ala Ser Lys Leu Asn Lys Arg Cys Lys Gln Ala Asp Glu Ser Cys Asn
45                  50                  55                  60 gta ttt tca ctt gac tgc tgc acc ggc tta tgc ttg gga ttc tgc gta      301
Val Phe Ser Leu Asp Cys Cys Thr Gly Leu Cys Leu Gly Phe Cys Val
                 65                  70                  75 tcg tgatgtcttc tactcccctc tgtgctacct ggcttgatct ttgattggcg           354
Ser tgtgcctttc attggttatg aaccccctg atccgattct ttggcggcct cggggttca      414 acatccaaat aaagcgacag cacaataaaa aa                                  446

<210> SEQ ID NO 42
<211> LENGTH: 77
<212> TYPE: PRT
<213> ORGANISM: Conus gloriamaris

<400> SEQUENCE: 42

Met Lys Leu Thr Cys Met Met Ile Val Ala Val Leu Phe Leu Thr Ala
1               5                   10                  15

```
Trp Thr Phe Ala Thr Ala Asp Asp Pro Arg Asn Gly Leu Glu Lys Leu
            20                  25                  30

Phe Ser Asn Thr His His Glu Met Lys Asn Pro Glu Ala Ser Lys Leu
        35                  40                  45

Asn Lys Arg Cys Lys Gln Ala Asp Glu Ser Cys Asn Val Phe Ser Leu
    50                  55                  60

Asp Cys Cys Thr Gly Leu Cys Leu Gly Phe Cys Val Ser
65                  70                  75
```

```
<210> SEQ ID NO 43
<211> LENGTH: 26
<212> TYPE: PRT
<213> ORGANISM: Conus gloriamaris
<220> FEATURE:
<221> NAME/KEY: SITE
<222> LOCATION: (1)..(26)
<223> OTHER INFORMATION: Xaa at residue 6 may be Glu or
      gamma-carboxy-Glu.

<400> SEQUENCE: 43
```

```
Cys Lys Gln Ala Asp Xaa Ser Cys Asn Val Phe Ser Leu Asp Cys Cys
1               5                   10                  15

Thr Gly Leu Cys Leu Gly Phe Cys Val Ser
            20                  25
```

```
<210> SEQ ID NO 44
<211> LENGTH: 242
<212> TYPE: DNA
<213> ORGANISM: Conus gloriamaris
<220> FEATURE:
<221> NAME/KEY: CDS
<222> LOCATION: (1)..(225)

<400> SEQUENCE: 44
```

```
atg aaa ctg acg tgc atg atg atc gtt gct gtg ctg ttc ttg acc acc      48
Met Lys Leu Thr Cys Met Met Ile Val Ala Val Leu Phe Leu Thr Thr
1               5                   10                  15 tgg aca ttc gcc acg gcc atc acc agg aat gga ttg ggg aat ctt ttt      96
Trp Thr Phe Ala Thr Ala Ile Thr Arg Asn Gly Leu Gly Asn Leu Phe
            20                  25                  30 ccg aag aat cat cac gaa atg aag aac ccc gaa gcc tct aaa ttg aac     144
Pro Lys Asn His His Glu Met Lys Asn Pro Glu Ala Ser Lys Leu Asn
        35                  40                  45 aag agg tgc gtt cca tac gag ggc cct tgt aat tgg ctt aca caa aac     192
Lys Arg Cys Val Pro Tyr Glu Gly Pro Cys Asn Trp Leu Thr Gln Asn
    50                  55                  60 tgc tgc gat gag cta tgc gta ttt ttc tgc cta taaaactagc ctgatgt      242
Cys Cys Asp Glu Leu Cys Val Phe Phe Cys Leu
65                  70                  75
```

```
<210> SEQ ID NO 45
<211> LENGTH: 75
<212> TYPE: PRT
<213> ORGANISM: Conus gloriamaris

<400> SEQUENCE: 45
```

```
Met Lys Leu Thr Cys Met Met Ile Val Ala Val Leu Phe Leu Thr Thr
1               5                   10                  15

Trp Thr Phe Ala Thr Ala Ile Thr Arg Asn Gly Leu Gly Asn Leu Phe
            20                  25                  30

Pro Lys Asn His His Glu Met Lys Asn Pro Glu Ala Ser Lys Leu Asn
        35                  40                  45
```

```
Lys Arg Cys Val Pro Tyr Glu Gly Pro Cys Asn Trp Leu Thr Gln Asn
     50                  55                  60

Cys Cys Asp Glu Leu Cys Val Phe Phe Cys Leu
65                  70                  75

<210> SEQ ID NO 46
<211> LENGTH: 25
<212> TYPE: PRT
<213> ORGANISM: Conus gloriamaris
<220> FEATURE:
<221> NAME/KEY: SITE
<222> LOCATION: (1)..(25)
<223> OTHER INFORMATION: Xaa at residue 2 and 7 may be Pro or
      hydroxy-Pro; Xaa at residue 4 may be Tyr, 125-I-Tyr,
      mono-iodo-Tyr, di-iodo-Tyr, O-sulpho-Tyr or O-phospho-Tyr;
      Xaa at residue 5 and 18 may be Glu or gamma-carboxy-Glu ; Xaa at
      residue 10 may be Trp or bromo-Trp

<400> SEQUENCE: 46

Cys Val Xaa Xaa Xaa Gly Xaa Cys Asn Xaa Leu Thr Gln Asn Cys Cys
1               5                   10                  15

Asp Xaa Leu Cys Val Phe Phe Cys Leu
            20                  25

<210> SEQ ID NO 47
<211> LENGTH: 250
<212> TYPE: DNA
<213> ORGANISM: Conus magus
<220> FEATURE:
<221> NAME/KEY: CDS
<222> LOCATION: (1)..(231)

<400> SEQUENCE: 47 atg aaa ctg acg tgc gtg atg atc gtt gct gtg ctc ttc ttg acc gtc        48
Met Lys Leu Thr Cys Val Met Ile Val Ala Val Leu Phe Leu Thr Val
1               5                   10                  15 tgg aca ttc gcc acg gct gat gac tcc gga aat gga ttg gag aaa ctt        96
Trp Thr Phe Ala Thr Ala Asp Asp Ser Gly Asn Gly Leu Glu Lys Leu
                20                  25                  30 ttt tcg aat gca cat cac gaa atg aag aac ccc gaa gcc tct aaa ttg       144
Phe Ser Asn Ala His His Glu Met Lys Asn Pro Glu Ala Ser Lys Leu
            35                  40                  45 aac aag agg tgc aaa caa gct gat gaa cct tgt gat gta ttt tca ctt       192
Asn Lys Arg Cys Lys Gln Ala Asp Glu Pro Cys Asp Val Phe Ser Leu
        50                  55                  60 gaa tgc tgc acc ggc ata tgt ctt gga ttc tgc acg tgg tgatgtcttc        241
Glu Cys Cys Thr Gly Ile Cys Leu Gly Phe Cys Thr Trp
65                  70                  75 cctcccctc                                                              250

<210> SEQ ID NO 48
<211> LENGTH: 77
<212> TYPE: PRT
<213> ORGANISM: Conus magus

<400> SEQUENCE: 48

Met Lys Leu Thr Cys Val Met Ile Val Ala Val Leu Phe Leu Thr Val
1               5                   10                  15

Trp Thr Phe Ala Thr Ala Asp Asp Ser Gly Asn Gly Leu Glu Lys Leu
                20                  25                  30

Phe Ser Asn Ala His His Glu Met Lys Asn Pro Glu Ala Ser Lys Leu
            35                  40                  45
```

-continued

```
Asn Lys Arg Cys Lys Gln Ala Asp Glu Pro Cys Asp Val Phe Ser Leu
 50                  55                  60
Glu Cys Cys Thr Gly Ile Cys Leu Gly Phe Cys Thr Trp
 65                  70                  75
```

<210> SEQ ID NO 49
<211> LENGTH: 26
<212> TYPE: PRT
<213> ORGANISM: Conus magus
<220> FEATURE:
<221> NAME/KEY: SITE
<222> LOCATION: (1)..(26)
<223> OTHER INFORMATION: Xaa at residue 6 and 14 may be Glu or
    gamma-carboxy-Glu; Xaa at residue 7 may be Pro or hydroxy-Pro; Xaa
    at residue 26may be Trp or bromo-Trp

<400> SEQUENCE: 49

```
Cys Lys Gln Ala Asp Xaa Xaa Cys Asp Val Phe Ser Leu Xaa Cys Cys
 1               5                  10                  15
Thr Gly Ile Cys Leu Gly Phe Cys Thr Xaa
             20                  25
```

<210> SEQ ID NO 50
<211> LENGTH: 434
<212> TYPE: DNA
<213> ORGANISM: Conus textile
<220> FEATURE:
<221> NAME/KEY: CDS
<222> LOCATION: (71)..(295)

<400> SEQUENCE: 50

```
gccttgcacg gtgaatttgg cttcatagtt ttccactgtc gtctttggca tcatccaaaa       60
catcaccaag atg aaa ctg acg tgc atg atg atc gtt gct gtg ctg ttc        109
            Met Lys Leu Thr Cys Met Met Ile Val Ala Val Leu Phe
              1               5                  10 ttg acc gcc tgg aca ttc gcc acg gct gat gac tcc agc aat gga ttg       157
Leu Thr Ala Trp Thr Phe Ala Thr Ala Asp Asp Ser Ser Asn Gly Leu
     15                  20                  25 gag aat ctt ttt ttg aag gca cat cac gaa atg aac ccc gaa gcc tct       205
Glu Asn Leu Phe Leu Lys Ala His His Glu Met Asn Pro Glu Ala Ser
 30                  35                  40                  45 aag ttg aac gag agg tgc ctt gat gct ggt gaa gtt tgt gat att ttt       253
Lys Leu Asn Glu Arg Cys Leu Asp Ala Gly Glu Val Cys Asp Ile Phe
             50                  55                  60 ttt cca aca tgc tgc ggc tat tgc att ctt ctt ttc tgc gca              295
Phe Pro Thr Cys Cys Gly Tyr Cys Ile Leu Leu Phe Cys Ala
             65                  70                  75 taaaactacc gtgatgtctt ctactcccct ctgtgctacc tggcttgatc tttgattggc      355
gcgtacccct cactggttat gaaacccctg atccagctct ctggaggcct cggggggttca     415 acatccaaat aaagcgaca                                                   434
```

<210> SEQ ID NO 51
<211> LENGTH: 75
<212> TYPE: PRT
<213> ORGANISM: Conus textile

<400> SEQUENCE: 51

```
Met Lys Leu Thr Cys Met Met Ile Val Ala Val Leu Phe Leu Thr Ala
 1               5                  10                  15
Trp Thr Phe Ala Thr Ala Asp Asp Ser Ser Asn Gly Leu Glu Asn Leu
             20                  25                  30
```

-continued

```
Phe Leu Lys Ala His His Glu Met Asn Pro Glu Ala Ser Lys Leu Asn
         35                  40                  45

Glu Arg Cys Leu Asp Ala Gly Glu Val Cys Asp Ile Phe Phe Pro Thr
     50                  55                  60

Cys Cys Gly Tyr Cys Ile Leu Leu Phe Cys Ala
65                  70                  75

<210> SEQ ID NO 52
<211> LENGTH: 25
<212> TYPE: PRT
<213> ORGANISM: Conus textile
<220> FEATURE:
<221> NAME/KEY: SITE
<222> LOCATION: (1)..(25)
<223> OTHER INFORMATION: Xaa at residue 6 may be Glu or
      gamma-carboxy-Glu; Xaa at residue 13 may be Pro or hydroxy-Pro;
      Xaa at residue 18 may be Tyr, 125- I-Tyr, mono-iodo-Tyr,
      di-iodo-Tyr, O-sulpho-Tyr or O-phospho-Tyr.

<400> SEQUENCE: 52

Cys Leu Asp Ala Gly Xaa Val Cys Asp Ile Phe Phe Xaa Thr Cys Cys
1               5                   10                  15

Gly Xaa Cys Ile Leu Leu Phe Cys Ala
            20                  25

<210> SEQ ID NO 53
<211> LENGTH: 26
<212> TYPE: PRT
<213> ORGANISM: Conus textile
<220> FEATURE:
<221> NAME/KEY: SITE
<222> LOCATION: (1)..(26)
<223> OTHER INFORMATION: Xaa at residues 3 and 9 may be Glu or
      gamma-carboxy-Glu; Xaa at residue 7 may be Pro or hydroxy-Pro

<400> SEQUENCE: 53

Cys Ile Xaa Gln Phe Asp Xaa Cys Xaa Met Ile Arg His Thr Cys Cys
1               5                   10                  15

Val Gly Val Cys Phe Leu Met Ala Cys Ile
            20                  25

<210> SEQ ID NO 54
<211> LENGTH: 26
<212> TYPE: PRT
<213> ORGANISM: Conus textile
<220> FEATURE:
<221> NAME/KEY: SITE
<222> LOCATION: (1)..(26)
<223> OTHER INFORMATION: Xaa at residues 3, 7 and 13 may be Pro or
      hydroxy-Pro; Xaa at residue 19 may be Tyr, 125-I-Tyr,
      mono-iodo-Tyr, di-iodo-Tyr, O-sulpho-Tyr or O-phospho-Tyr

<400> SEQUENCE: 54

Cys Ala Xaa Phe Leu His Xaa Cys Thr Phe Phe Phe Xaa Asn Cys Cys
1               5                   10                  15

Asn Ser Xaa Cys Val Gln Phe Ile Cys Leu
            20                  25

<210> SEQ ID NO 55
<211> LENGTH: 260
<212> TYPE: DNA
<213> ORGANISM: Conus omaria
<220> FEATURE:
<221> NAME/KEY: CDS
<222> LOCATION: (1)..(240)

<400> SEQUENCE: 55
```

```
atg aaa ctg acg tgc atg atg atc gtt gct gtg ctg ttc ttg acc gcc      48
Met Lys Leu Thr Cys Met Met Ile Val Ala Val Leu Phe Leu Thr Ala
1               5                   10                  15 tgg aca ttc gcc acg gct gat gac ccc aga aat gga ttg gag aat ttt      96
Trp Thr Phe Ala Thr Ala Asp Asp Pro Arg Asn Gly Leu Glu Asn Phe
                20                  25                  30 ttt tcg aag aca caa cac gaa atg aag aac ccc gaa gcc tct aaa ttg     144
Phe Ser Lys Thr Gln His Glu Met Lys Asn Pro Glu Ala Ser Lys Leu
            35                  40                  45 aac aag agg tgc cta gca gaa cat gaa act tgt aat ata ttt aca caa     192
Asn Lys Arg Cys Leu Ala Glu His Glu Thr Cys Asn Ile Phe Thr Gln
        50                  55                  60 aac tgc tgc gaa ggc gtg tgc att ttt atc tgc gta caa gct cca gag     240
Asn Cys Cys Glu Gly Val Cys Ile Phe Ile Cys Val Gln Ala Pro Glu
65                  70                  75                  80 tgatgtcttc tcctcccctc                                                260
```

<210> SEQ ID NO 56
<211> LENGTH: 80
<212> TYPE: PRT
<213> ORGANISM: Conus omaria

<400> SEQUENCE: 56

```
Met Lys Leu Thr Cys Met Met Ile Val Ala Val Leu Phe Leu Thr Ala
1               5                   10                  15

Trp Thr Phe Ala Thr Ala Asp Asp Pro Arg Asn Gly Leu Glu Asn Phe
                20                  25                  30

Phe Ser Lys Thr Gln His Glu Met Lys Asn Pro Glu Ala Ser Lys Leu
            35                  40                  45

Asn Lys Arg Cys Leu Ala Glu His Glu Thr Cys Asn Ile Phe Thr Gln
        50                  55                  60

Asn Cys Cys Glu Gly Val Cys Ile Phe Ile Cys Val Gln Ala Pro Glu
65                  70                  75                  80
```

<210> SEQ ID NO 57
<211> LENGTH: 29
<212> TYPE: PRT
<213> ORGANISM: Conus omaria
<220> FEATURE:
<221> NAME/KEY: SITE
<222> LOCATION: (1)..(29)
<223> OTHER INFORMATION: Xaa at residues 4, 6, 17 and 29 may be Glu or
      gamma-carboxy-Glu; Xaa at residue 28 may be Pro or hydroxy-Pro

<400> SEQUENCE: 57

```
Cys Leu Ala Xaa His Xaa Thr Cys Asn Ile Phe Thr Gln Asn Cys Cys
1               5                   10                  15

Xaa Gly Val Cys Ile Phe Ile Cys Val Gln Ala Xaa Xaa
                20                  25
```

<210> SEQ ID NO 58
<211> LENGTH: 261
<212> TYPE: DNA
<213> ORGANISM: Conus omaria
<220> FEATURE:
<221> NAME/KEY: CDS
<222> LOCATION: (1)..(231)

<400> SEQUENCE: 58

```
atg aaa ctg act gtc atg atg atc gtt gct gtg ctg ttc ttg acc gcc      48
Met Lys Leu Thr Val Met Met Ile Val Ala Val Leu Phe Leu Thr Ala
1               5                   10                  15
```

```
tgg aca ttt gcc acg gct gaa gac ccc aga cat gga ttg gag aat ctt      96
Trp Thr Phe Ala Thr Ala Glu Asp Pro Arg His Gly Leu Glu Asn Leu
            20                  25                  30 ttt tcg aag gca cat cac gaa atg aag aac cct gaa gac tct aaa ttg     144
Phe Ser Lys Ala His His Glu Met Lys Asn Pro Glu Asp Ser Lys Leu
        35                  40                  45 gac aag agg tgc att cca cat ttt gac cct tgt gac ccg ata cgc cac     192
Asp Lys Arg Cys Ile Pro His Phe Asp Pro Cys Asp Pro Ile Arg His
    50                  55                  60 acc tgc tgc ttt ggc ctg tgc cta cta ata gcc tgc atc taaaactgcc     241
Thr Cys Cys Phe Gly Leu Cys Leu Leu Ile Ala Cys Ile
65                  70                  75 gtgatgtctt ctctcccatc                                                261

<210> SEQ ID NO 59
<211> LENGTH: 77
<212> TYPE: PRT
<213> ORGANISM: Conus omaria

<400> SEQUENCE: 59

Met Lys Leu Thr Val Met Met Ile Val Ala Val Leu Phe Leu Thr Ala
1               5                   10                  15

Trp Thr Phe Ala Thr Ala Glu Asp Pro Arg His Gly Leu Glu Asn Leu
            20                  25                  30

Phe Ser Lys Ala His His Glu Met Lys Asn Pro Glu Asp Ser Lys Leu
        35                  40                  45

Asp Lys Arg Cys Ile Pro His Phe Asp Pro Cys Asp Pro Ile Arg His
    50                  55                  60

Thr Cys Cys Phe Gly Leu Cys Leu Leu Ile Ala Cys Ile
65                  70                  75

<210> SEQ ID NO 60
<211> LENGTH: 26
<212> TYPE: PRT
<213> ORGANISM: Conus omaria
<220> FEATURE:
<221> NAME/KEY: SITE
<222> LOCATION: (1)..(26)
<223> OTHER INFORMATION: Xaa at residues 3, 7 and 10 may be Pro or
      hydroxy-Pro.

<400> SEQUENCE: 60

Cys Ile Xaa His Phe Asp Xaa Cys Asp Xaa Ile Arg His Thr Cys Cys
1               5                   10                  15

Phe Gly Leu Cys Leu Leu Ile Ala Cys Ile
            20                  25

<210> SEQ ID NO 61
<211> LENGTH: 259
<212> TYPE: DNA
<213> ORGANISM: Conus omaria
<220> FEATURE:
<221> NAME/KEY: CDS
<222> LOCATION: (1)..(228)

<400> SEQUENCE: 61 atg aaa ctg acg tgc gtg atg acc gtt gct gtg ctg ttc ttg acc gcc      48
Met Lys Leu Thr Cys Val Met Thr Val Ala Val Leu Phe Leu Thr Ala
1               5                   10                  15 tgg aca ttc gtc acg gct gaa gac ccc aga gat gga ttg aag aat ctt     96
Trp Thr Phe Val Thr Ala Glu Asp Pro Arg Asp Gly Leu Lys Asn Leu
            20                  25                  30
```

```
tta tca aat gca cat aac gaa atg aag aac ccc gaa gcc tct aca ttg      144
Leu Ser Asn Ala His Asn Glu Met Lys Asn Pro Glu Ala Ser Thr Leu
        35                  40                  45 aac gag agg tgc ctt ggg ttt ggt gaa gct tgt ctt ata ctt tat tca      192
Asn Glu Arg Cys Leu Gly Phe Gly Glu Ala Cys Leu Ile Leu Tyr Ser
 50                  55                  60 gac tgc tgc ggc tat tgc gtt ggt gct atc tgc cta taaaactacc           238
Asp Cys Cys Gly Tyr Cys Val Gly Ala Ile Cys Leu
 65                  70                  75 gtgatgtctt ctcctccct c                                               259
```

<210> SEQ ID NO 62
<211> LENGTH: 76
<212> TYPE: PRT
<213> ORGANISM: Conus omaria

<400> SEQUENCE: 62

```
Met Lys Leu Thr Cys Val Met Thr Val Ala Val Leu Phe Leu Thr Ala
 1               5                  10                  15

Trp Thr Phe Val Thr Ala Glu Asp Pro Arg Asp Gly Leu Lys Asn Leu
             20                  25                  30

Leu Ser Asn Ala His Asn Glu Met Lys Asn Pro Glu Ala Ser Thr Leu
        35                  40                  45

Asn Glu Arg Cys Leu Gly Phe Gly Glu Ala Cys Leu Ile Leu Tyr Ser
 50                  55                  60

Asp Cys Cys Gly Tyr Cys Val Gly Ala Ile Cys Leu
 65                  70                  75
```

<210> SEQ ID NO 63
<211> LENGTH: 25
<212> TYPE: PRT
<213> ORGANISM: Conus omaria
<220> FEATURE:
<221> NAME/KEY: SITE
<222> LOCATION: (1)..(25)
<223> OTHER INFORMATION: Xaa at residue m6 ay be Glu or
      gamma-carboxy-Glu; Xaa at residues 12 and 18 may be Tyr,
      125-I-Tyr, mono-iodo-Tyr, di-iodo-Tyr, O-sulpho-Tyr or
      O-phospho-Tyr

<400> SEQUENCE: 63

```
Cys Leu Gly Phe Gly Xaa Ala Cys Leu Ile Leu Xaa Ser Asp Cys Cys
 1               5                  10                  15

Gly Xaa Cys Val Gly Ala Ile Cys Leu
             20                  25
```

<210> SEQ ID NO 64
<211> LENGTH: 262
<212> TYPE: DNA
<213> ORGANISM: Conus aulicus
<220> FEATURE:
<221> NAME/KEY: CDS
<222> LOCATION: (1)..(240)

<400> SEQUENCE: 64

```
atg aaa ctg acg tgt gtg atc gtt gct gtg ctg ttc ttg acc gcc          48
Met Lys Leu Thr Cys Val Met Ile Val Ala Val Leu Phe Leu Thr Ala
 1               5                  10                  15 tgg aca ttc gcc acg gct gat gac ccc aga aat gga ttg gag aat ctt      96
Trp Thr Phe Ala Thr Ala Asp Asp Pro Arg Asn Gly Leu Glu Asn Leu
             20                  25                  30 ttt tcg aag aca caa cac aaa atg aag aac ccc gaa gcc tct aaa ttg      144
```

```
Phe Ser Lys Thr Gln His Lys Met Lys Asn Pro Glu Ala Ser Lys Leu
        35                  40                  45 aac aag agg tgc aaa gca gaa aat gaa ctt tgt aat ata ttt ata caa      192
Asn Lys Arg Cys Lys Ala Glu Asn Glu Leu Cys Asn Ile Phe Ile Gln
 50                  55                  60 aac tgc tgc gac ggg acg tgc ctt ctt atc tgc ata caa aat cca cag      240
Asn Cys Cys Asp Gly Thr Cys Leu Leu Ile Cys Ile Gln Asn Pro Gln
65                  70                  75                  80 tgatgtcttc tctcctaccc tc                                             262
```

<210> SEQ ID NO 65
<211> LENGTH: 80
<212> TYPE: PRT
<213> ORGANISM: Conus aulicus

<400> SEQUENCE: 65

```
Met Lys Leu Thr Cys Val Met Ile Val Ala Val Leu Phe Leu Thr Ala
 1               5                  10                  15

Trp Thr Phe Ala Thr Ala Asp Asp Pro Arg Asn Gly Leu Glu Asn Leu
                20                  25                  30

Phe Ser Lys Thr Gln His Lys Met Lys Asn Pro Glu Ala Ser Lys Leu
        35                  40                  45

Asn Lys Arg Cys Lys Ala Glu Asn Glu Leu Cys Asn Ile Phe Ile Gln
 50                  55                  60

Asn Cys Cys Asp Gly Thr Cys Leu Leu Ile Cys Ile Gln Asn Pro Gln
65                  70                  75                  80
```

<210> SEQ ID NO 66
<211> LENGTH: 29
<212> TYPE: PRT
<213> ORGANISM: Conus aulicus
<220> FEATURE:
<221> NAME/KEY: SITE
<222> LOCATION: (1)..(29)
<223> OTHER INFORMATION: Xaa at residues 4 and 6may be Glu or
      gamma-carboxy-Glu; Xaa at residue 28 may be Pro or hydroxy-Pro

<400> SEQUENCE: 66

```
Cys Lys Ala Xaa Asn Xaa Leu Cys Asn Ile Phe Ile Gln Asn Cys Cys
 1               5                  10                  15

Asp Gly Thr Cys Leu Leu Ile Cys Ile Gln Asn Xaa Gln
                20                  25
```

<210> SEQ ID NO 67
<211> LENGTH: 258
<212> TYPE: DNA
<213> ORGANISM: Conus aulicus
<220> FEATURE:
<221> NAME/KEY: CDS
<222> LOCATION: (1)..(228)

<400> SEQUENCE: 67

```
atg aaa ctg acg tgc gtg atg atc gtt gct gtg ctg ttc ttg acc gcc       48
Met Lys Leu Thr Cys Val Met Ile Val Ala Val Leu Phe Leu Thr Ala
 1               5                  10                  15 tgg aca ttt gcc acg gct gat gac ccc aga aat gga ttg gat aat cgt       96
Trp Thr Phe Ala Thr Ala Asp Asp Pro Arg Asn Gly Leu Asp Asn Arg
                20                  25                  30 ttt tcg aag gca cgt cac gaa atg aat aac cgc aga gcc tct aaa ttg      144
Phe Ser Lys Ala Arg His Glu Met Asn Asn Arg Arg Ala Ser Lys Leu
        35                  40                  45 aac aag agg tgc ctt gag ttt ggt gaa ctt tgt aat ttt ttt ttc cca      192
```

```
Asn Lys Arg Cys Leu Glu Phe Gly Glu Leu Cys Asn Phe Phe Pro
 50                  55                  60 acc tgc tgc ggc tat tgc gtt ctt ctt gtc tgc cta taaactaccg        238
Thr Cys Cys Gly Tyr Cys Val Leu Leu Val Cys Leu
 65                  70                  75 tgatgtcttc tcttcccctc                                             258
```

<210> SEQ ID NO 68
<211> LENGTH: 76
<212> TYPE: PRT
<213> ORGANISM: Conus aulicus

<400> SEQUENCE: 68

```
Met Lys Leu Thr Cys Val Met Ile Val Ala Val Leu Phe Leu Thr Ala
 1               5                  10                  15

Trp Thr Phe Ala Thr Ala Asp Asp Pro Arg Asn Gly Leu Asp Asn Arg
                20                  25                  30

Phe Ser Lys Ala Arg His Glu Met Asn Asn Arg Arg Ala Ser Lys Leu
            35                  40                  45

Asn Lys Arg Cys Leu Glu Phe Gly Glu Leu Cys Asn Phe Phe Pro
 50                  55                  60

Thr Cys Cys Gly Tyr Cys Val Leu Leu Val Cys Leu
 65                  70                  75
```

<210> SEQ ID NO 69
<211> LENGTH: 25
<212> TYPE: PRT
<213> ORGANISM: Conus aulicus
<220> FEATURE:
<221> NAME/KEY: SITE
<222> LOCATION: (1)..(25)
<223> OTHER INFORMATION: Xaa at residues 3 and 6 may be Glu or
      gamma-carboxy-Glu; Xaa at residue 13 may be Pro or hydroxy-Pro;
      Xaa at residue 18 may be Tyr, 125-I-Tyr, mono-iodo-Tyr,
      di-iodo-Tyr, O-sulpho-Tyr or O-phospho-Tyr

<400> SEQUENCE: 69

```
Cys Leu Xaa Phe Gly Xaa Leu Cys Asn Phe Phe Xaa Thr Cys Cys
 1               5                  10                  15

Gly Xaa Cys Val Leu Leu Val Cys Leu
            20                  25
```

<210> SEQ ID NO 70
<211> LENGTH: 263
<212> TYPE: DNA
<213> ORGANISM: Conus dalli
<220> FEATURE:
<221> NAME/KEY: CDS
<222> LOCATION: (1)..(231)

<400> SEQUENCE: 70

```
atg aaa ctg acg tgt gtg atg atc gtt gct gtg ctg ttc ttg acc gcc    48
Met Lys Leu Thr Cys Val Met Ile Val Ala Val Leu Phe Leu Thr Ala
 1               5                  10                  15 tgg aca ttt gtc atg gct gat gac tcc gga aat gga ttg gaa aat ctg    96
Trp Thr Phe Val Met Ala Asp Asp Ser Gly Asn Gly Leu Glu Asn Leu
                20                  25                  30 ttt tcg aag gca cat cac gaa atg aag aac cct gaa gcc tct aaa ttg   144
Phe Ser Lys Ala His His Glu Met Lys Asn Pro Glu Ala Ser Lys Leu
            35                  40                  45 aac aag agg tgc gct caa agc agt gaa tta tgt gat gcg ctg gac tca   192
Asn Lys Arg Cys Ala Gln Ser Ser Glu Leu Cys Asp Ala Leu Asp Ser
 50                  55                  60
```

```
gac tgc tgc agt ggt gtt tgc atg gta ttt ttc tgc cta taaaactgcc          241
Asp Cys Cys Ser Gly Val Cys Met Val Phe Phe Cys Leu
 65                  70                  75 gtgatgtctt ctctatcccc tc                                                 263
```

<210> SEQ ID NO 71
<211> LENGTH: 77
<212> TYPE: PRT
<213> ORGANISM: Conus dalli

<400> SEQUENCE: 71

```
Met Lys Leu Thr Cys Val Met Ile Val Ala Val Leu Phe Leu Thr Ala
 1               5                  10                  15

Trp Thr Phe Val Met Ala Asp Asp Ser Gly Asn Gly Leu Glu Asn Leu
             20                  25                  30

Phe Ser Lys Ala His His Glu Met Lys Asn Pro Glu Ala Ser Lys Leu
         35                  40                  45

Asn Lys Arg Cys Ala Gln Ser Ser Glu Leu Cys Asp Ala Leu Asp Ser
     50                  55                  60

Asp Cys Cys Ser Gly Val Cys Met Val Phe Phe Cys Leu
 65                  70                  75
```

<210> SEQ ID NO 72
<211> LENGTH: 26
<212> TYPE: PRT
<213> ORGANISM: Conus dalli
<220> FEATURE:
<221> NAME/KEY: SITE
<222> LOCATION: (1)..(26)
<223> OTHER INFORMATION: Xaa at residue 6 may be Glu or
      gamma-carboxy-Glu.

<400> SEQUENCE: 72

```
Cys Ala Gln Ser Ser Xaa Leu Cys Asp Ala Leu Asp Ser Asp Cys Cys
 1               5                  10                  15

Ser Gly Val Cys Met Val Phe Phe Cys Leu
             20                  25
```

<210> SEQ ID NO 73
<211> LENGTH: 259
<212> TYPE: DNA
<213> ORGANISM: Conus distans
<220> FEATURE:
<221> NAME/KEY: CDS
<222> LOCATION: (1)..(228)

<400> SEQUENCE: 73

```
atg aaa ctg acg tgc gtg atg acc gtt gct gtg ctg ttc ttg acc gcc          48
Met Lys Leu Thr Cys Val Met Thr Val Ala Val Leu Phe Leu Thr Ala
 1               5                  10                  15 tgg aca ttc gtc acg gct gaa gac ccc aga gat gga ttg agg aat ctt          96
Trp Thr Phe Val Thr Ala Glu Asp Pro Arg Asp Gly Leu Arg Asn Leu
             20                  25                  30 tta tcg aat gca cgt cat gaa atg aag aac ccc gaa gcc tct aaa ttg         144
Leu Ser Asn Ala Arg His Glu Met Lys Asn Pro Glu Ala Ser Lys Leu
         35                  40                  45 aac gag agg tgc ctt ggg ttt ggt gaa gct tgt ctt atg ctt tat tca         192
Asn Glu Arg Cys Leu Gly Phe Gly Glu Ala Cys Leu Met Leu Tyr Ser
     50                  55                  60 gac tgc tgc agc tat tgc gtt ggt gct gtc tgc cta taaaactacc              238
Asp Cys Cys Ser Tyr Cys Val Gly Ala Val Cys Leu
 65                  70                  75
```

```
gtgatgtctt ctactcccat c                                              259
```

<210> SEQ ID NO 74
<211> LENGTH: 76
<212> TYPE: PRT
<213> ORGANISM: Conus distans

<400> SEQUENCE: 74

```
Met Lys Leu Thr Cys Val Met Thr Val Ala Val Leu Phe Leu Thr Ala
1               5                   10                  15

Trp Thr Phe Val Thr Ala Glu Asp Pro Arg Asp Gly Leu Arg Asn Leu
            20                  25                  30

Leu Ser Asn Ala Arg His Glu Met Lys Asn Pro Glu Ala Ser Lys Leu
        35                  40                  45

Asn Glu Arg Cys Leu Gly Phe Gly Glu Ala Cys Leu Met Leu Tyr Ser
    50                  55                  60

Asp Cys Cys Ser Tyr Cys Val Gly Ala Val Cys Leu
65                  70                  75
```

<210> SEQ ID NO 75
<211> LENGTH: 25
<212> TYPE: PRT
<213> ORGANISM: Conus distans
<220> FEATURE:
<221> NAME/KEY: SITE
<222> LOCATION: (1)..(25)
<223> OTHER INFORMATION: Xaa at residue 6 may be Glu or
      gamma-carboxy-Glu; Xaa at residues 12 and 18 may be Tyr,
      125-I-Tyr, mono-iodo-Tyr, di-iodo-Tyr, O-sulpho-Tyr or
      O-phospho-Tyr

<400> SEQUENCE: 75

```
Cys Leu Gly Phe Gly Xaa Ala Cys Leu Met Leu Xaa Ser Asp Cys Cys
1               5                   10                  15

Ser Xaa Cys Val Gly Ala Val Cys Leu
            20                  25
```

<210> SEQ ID NO 76
<211> LENGTH: 262
<212> TYPE: DNA
<213> ORGANISM: Conus pennaceus
<220> FEATURE:
<221> NAME/KEY: CDS
<222> LOCATION: (1)..(231)

<400> SEQUENCE: 76

```
atg aaa ctg acg tgc ctg atg acc gtt gct gtg ctg ttc ttg acc gcc      48
Met Lys Leu Thr Cys Leu Met Thr Val Ala Val Leu Phe Leu Thr Ala
1               5                   10                  15 tgg aca ttt gcc acg gct gaa gac ccc aga aat gga ttg gag aat ctt      96
Trp Thr Phe Ala Thr Ala Glu Asp Pro Arg Asn Gly Leu Glu Asn Leu
            20                  25                  30 ttt tcg aag gca cat cac gaa atg aag aac cct gaa gac tct aaa ttg     144
Phe Ser Lys Ala His His Glu Met Lys Asn Pro Glu Asp Ser Lys Leu
        35                  40                  45 gac aag agg tgc gtt aaa tat ctt gac cct tgt gac atg tta cgc cac     192
Asp Lys Arg Cys Val Lys Tyr Leu Asp Pro Cys Asp Met Leu Arg His
    50                  55                  60 acc tgc tgc ttt ggc ctg tgc gta cta ata gcc tgc atc taaaactgcc     241
Thr Cys Cys Phe Gly Leu Cys Val Leu Ile Ala Cys Ile
65                  70                  75 gtgatgtctt ctactcccat c                                             262
```

<210> SEQ ID NO 77
<211> LENGTH: 77
<212> TYPE: PRT
<213> ORGANISM: Conus pennaceus

<400> SEQUENCE: 77

Met Lys Leu Thr Cys Leu Met Thr Val Ala Val Leu Phe Leu Thr Ala
1               5                   10                  15

Trp Thr Phe Ala Thr Ala Glu Asp Pro Arg Asn Gly Leu Glu Asn Leu
            20                  25                  30

Phe Ser Lys Ala His His Glu Met Lys Asn Pro Glu Ser Lys Leu
        35                  40                  45

Asp Lys Arg Cys Val Lys Tyr Leu Asp Pro Cys Asp Met Leu Arg His
    50                  55                  60

Thr Cys Cys Phe Gly Leu Cys Val Leu Ile Ala Cys Ile
65                  70                  75

<210> SEQ ID NO 78
<211> LENGTH: 26
<212> TYPE: PRT
<213> ORGANISM: Conus pennaceus
<220> FEATURE:
<221> NAME/KEY: SITE
<222> LOCATION: (1)..(26)
<223> OTHER INFORMATION: Xaa at residue 4 may be Tyr, 125-I-Tyr,
      mono-iodo-Tyr, di-iodo-Tyr, O-sulpho-Tyr or O-phospho-Tyr; Xaa at
      residue 7 may be Pro or hydroxy-Pro

<400> SEQUENCE: 78

Cys Val Lys Xaa Leu Asp Xaa Cys Asp Met Leu Arg His Thr Cys Cys
1               5                   10                  15

Phe Gly Leu Cys Val Leu Ile Ala Cys Ile
            20                  25

<210> SEQ ID NO 79
<211> LENGTH: 259
<212> TYPE: DNA
<213> ORGANISM: Conus pennaceus
<220> FEATURE:
<221> NAME/KEY: CDS
<222> LOCATION: (1)..(228)

<400> SEQUENCE: 79 atg aaa ctg acg tgt gtg atg atc gtt gct gtg ctg ttc ttg acc gcc        48
Met Lys Leu Thr Cys Val Met Ile Val Ala Val Leu Phe Leu Thr Ala
1               5                   10                  15 tgg aca ttt gcc acg gct gat gac ccc aga aat gga ttg ggg aat ctt        96
Trp Thr Phe Ala Thr Ala Asp Asp Pro Arg Asn Gly Leu Gly Asn Leu
            20                  25                  30 ttt tcg aat gca cat cac gaa atg aag aac ccc gaa gct tct aaa ttg       144
Phe Ser Asn Ala His His Glu Met Lys Asn Pro Glu Ala Ser Lys Leu
        35                  40                  45 aac gag agg tgc ctt ggg ttt ggt gaa gtt tgc aat ttc ttt ttt cca       192
Asn Glu Arg Cys Leu Gly Phe Gly Glu Val Cys Asn Phe Phe Phe Pro
    50                  55                  60 aac tgc tgc agc tat tgc gtt gct ctt gtc tgc cta taaaactacc            238
Asn Cys Cys Ser Tyr Cys Val Ala Leu Val Cys Leu
65                  70                  75 gtgatgtctt ctattcccct c                                               259

<210> SEQ ID NO 80

<211> LENGTH: 76
<212> TYPE: PRT
<213> ORGANISM: Conus pennaceus

<400> SEQUENCE: 80

Met Lys Leu Thr Cys Val Met Ile Val Ala Val Leu Phe Leu Thr Ala
1               5                   10                  15

Trp Thr Phe Ala Thr Ala Asp Asp Pro Arg Asn Gly Leu Gly Asn Leu
            20                  25                  30

Phe Ser Asn Ala His His Glu Met Lys Asn Pro Glu Ala Ser Lys Leu
        35                  40                  45

Asn Glu Arg Cys Leu Gly Phe Gly Glu Val Cys Asn Phe Phe Phe Pro
    50                  55                  60

Asn Cys Cys Ser Tyr Cys Val Ala Leu Val Cys Leu
65                  70                  75

<210> SEQ ID NO 81
<211> LENGTH: 25
<212> TYPE: PRT
<213> ORGANISM: Conus pennaceus
<220> FEATURE:
<221> NAME/KEY: SITE
<222> LOCATION: (1)..(25)
<223> OTHER INFORMATION: Xaa at residue 6 may be Glu or
      gamma-carboxy-Glu; Xaa at residue 13 may be Pro or hydroxy-Pro;
      Xaa at residue 18 may be Tyr, 125-I-Tyr, mono-iodo-Tyr,
      di-iodo-Tyr, O-sulpho-Tyr or O-phospho-Tyr

<400> SEQUENCE: 81

Cys Leu Gly Phe Gly Xaa Val Cys Asn Phe Phe Xaa Asn Cys Cys
1               5                   10                  15

Ser Xaa Cys Val Ala Leu Val Cys Leu
            20                  25

<210> SEQ ID NO 82
<211> LENGTH: 260
<212> TYPE: DNA
<213> ORGANISM: Conus pennaceus
<220> FEATURE:
<221> NAME/KEY: CDS
<222> LOCATION: (1)..(240)

<400> SEQUENCE: 82 atg aaa ctg acg tgc gtg atg ctc gtt gct gtg ctg ttc ttg acc gcc     48
Met Lys Leu Thr Cys Val Met Leu Val Ala Val Leu Phe Leu Thr Ala
1               5                   10                  15 tgg aca ttc gcc acg gct gat gac tcc agc aat gga ctg gag aat ctt     96
Trp Thr Phe Ala Thr Ala Asp Asp Ser Ser Asn Gly Leu Glu Asn Leu
            20                  25                  30 ttt tcg aag gca cat cac gaa atg aag aac ccc gaa gcc tct aaa ttg    144
Phe Ser Lys Ala His His Glu Met Lys Asn Pro Glu Ala Ser Lys Leu
        35                  40                  45 aac aag agg tgc att cca caa ttt gat cct tgt gac atg gta cgt cac    192
Asn Lys Arg Cys Ile Pro Gln Phe Asp Pro Cys Asp Met Val Arg His
    50                  55                  60 act tgc tgc aaa ggg ttg tgc gta cta ata gcc tgc tct aaa act gcg    240
Thr Cys Cys Lys Gly Leu Cys Val Leu Ile Ala Cys Ser Lys Thr Ala
65                  70                  75                  80 tgatgtcttc atctccctc                                                260

<210> SEQ ID NO 83
<211> LENGTH: 80
<212> TYPE: PRT

<213> ORGANISM: Conus pennaceus

<400> SEQUENCE: 83

Met Lys Leu Thr Cys Val Met Leu Val Ala Val Leu Phe Leu Thr Ala
1               5                   10                  15

Trp Thr Phe Ala Thr Ala Asp Asp Ser Ser Asn Gly Leu Glu Asn Leu
                20                  25                  30

Phe Ser Lys Ala His His Glu Met Lys Asn Pro Glu Ala Ser Lys Leu
            35                  40                  45

Asn Lys Arg Cys Ile Pro Gln Phe Asp Pro Cys Asp Met Val Arg His
        50                  55                  60

Thr Cys Cys Lys Gly Leu Cys Val Leu Ile Ala Cys Ser Lys Thr Ala
65                  70                  75                  80

<210> SEQ ID NO 84
<211> LENGTH: 29
<212> TYPE: PRT
<213> ORGANISM: Conus pennaceus
<220> FEATURE:
<221> NAME/KEY: SITE
<222> LOCATION: (1)..(29)
<223> OTHER INFORMATION: Xaa at residues 3 and 7 may be Pro or
      hydroxy-Pro.

<400> SEQUENCE: 84

Cys Ile Xaa Gln Phe Asp Xaa Cys Asp Met Val Arg His Thr Cys Cys
1               5                   10                  15

Lys Gly Leu Cys Val Leu Ile Ala Cys Ser Lys Thr Ala
            20                  25

<210> SEQ ID NO 85
<211> LENGTH: 260
<212> TYPE: DNA
<213> ORGANISM: Conus pennaceus
<220> FEATURE:
<221> NAME/KEY: CDS
<222> LOCATION: (1)..(240)

<400> SEQUENCE: 85

```
atg aaa ctg acg tgc ttg atg atc gtt gct gtg ctg ttc ttg acc gcc        48
Met Lys Leu Thr Cys Leu Met Ile Val Ala Val Leu Phe Leu Thr Ala
1               5                   10                  15 tgg aca ttc gcc acg gct gat gac ccc aga aat gga ttg gag aat ttt        96
Trp Thr Phe Ala Thr Ala Asp Asp Pro Arg Asn Gly Leu Glu Asn Phe
                20                  25                  30 ttt tcg aag aca caa cac gaa atg aag aac ccc gaa gcc tct aaa ttg       144
Phe Ser Lys Thr Gln His Glu Met Lys Asn Pro Glu Ala Ser Lys Leu
            35                  40                  45 aac aag agg tgc aaa gca gaa agt gaa gct tgt aat ata att aca caa       192
Asn Lys Arg Cys Lys Ala Glu Ser Glu Ala Cys Asn Ile Ile Thr Gln
        50                  55                  60 aac tgc tgc gac ggc aag tgc ctt ttt ttc tgc ata caa att cca gag       240
Asn Cys Cys Asp Gly Lys Cys Leu Phe Phe Cys Ile Gln Ile Pro Glu
65                  70                  75                  80 tgatgtcttc tcctcccatc                                                 260
```

<210> SEQ ID NO 86
<211> LENGTH: 80
<212> TYPE: PRT
<213> ORGANISM: Conus pennaceus

<400> SEQUENCE: 86

```
Met Lys Leu Thr Cys Leu Met Ile Val Ala Val Leu Phe Leu Thr Ala
1               5                   10                  15

Trp Thr Phe Ala Thr Ala Asp Asp Pro Arg Asn Gly Leu Glu Asn Phe
            20                  25                  30

Phe Ser Lys Thr Gln His Glu Met Lys Asn Pro Glu Ala Ser Lys Leu
        35                  40                  45

Asn Lys Arg Cys Lys Ala Glu Ser Glu Ala Cys Asn Ile Ile Thr Gln
50                  55                      60

Asn Cys Cys Asp Gly Lys Cys Leu Phe Phe Cys Ile Gln Ile Pro Glu
65                  70                  75                  80
```

<210> SEQ ID NO 87
<211> LENGTH: 29
<212> TYPE: PRT
<213> ORGANISM: Conus pennaceus
<220> FEATURE:
<221> NAME/KEY: SITE
<222> LOCATION: (1)..(29)
<223> OTHER INFORMATION: Xaa at residues 4, 6 and 29 may be Glu or
      gamma-carboxy-Glu; Xaa at residue 28 may be Pro or hydroxy-Pro

<400> SEQUENCE: 87

```
Cys Lys Ala Xaa Ser Xaa Ala Cys Asn Ile Ile Thr Gln Asn Cys Cys
1               5                   10                  15

Asp Gly Lys Cys Leu Phe Phe Cys Ile Gln Ile Xaa Xaa
            20                  25
```

<210> SEQ ID NO 88
<211> LENGTH: 632
<212> TYPE: DNA
<213> ORGANISM: Conus omaria
<220> FEATURE:
<221> NAME/KEY: CDS
<222> LOCATION: (110)..(199)

<400> SEQUENCE: 88

```
ggtcgacatc atcatcatca tcgatccatc tgtccatcca tccattcatt cattcgctgc      60
cagactgtca taaatattcg agtctctcct tctgtttgta tctgacaga ttg aac aag     118
                                                    Leu Asn Lys
                                                      1 agg tgc att gac ggt ggt gaa att tgt gat att ttt ttt cca aac tgc       166
Arg Cys Ile Asp Gly Gly Glu Ile Cys Asp Ile Phe Phe Pro Asn Cys
      5                  10                  15 tgc agt ggg tgg tgc att att ctc gtc tgc gca tgaaactacc gtgatgtctt    219
Cys Ser Gly Trp Cys Ile Ile Leu Val Cys Ala
20                  25                  30 ctactcccct ctagtagtag taggcggccg ctctagagga tccaagctta cgtacgcgtg    279
catgcgacgt catagctctt ctatagtgtc acctaaattc aattcactgg ccgtcgtttt    339
acaacgtcgt gactgggaaa accctggcgt tacccaactt aatcgccttg cagcacatcc    399 cccttcgcc agctggcgta atagcgaaga ggcccgcacc gatcgccctt ccaacagttt     459
gcgcagcctg aatggcgaat gggacgcgcc ctgtagcggc gcattaagcg cggcgggtgt    519
ggtgggtacg cgcagcgtga ccggtacact tgccagcgcc ctagcgcccg ctccttttgc    579
tttcttccct tcctttctcg ccaccgttcg cccggggttt tcccgtcaag ctc           632
```

<210> SEQ ID NO 89
<211> LENGTH: 30
<212> TYPE: PRT
<213> ORGANISM: Conus omaria

```
-continued

<400> SEQUENCE: 89

Leu Asn Lys Arg Cys Ile Asp Gly Gly Glu Ile Cys Asp Ile Phe Phe
1               5                   10                  15

Pro Asn Cys Cys Ser Gly Trp Cys Ile Ile Leu Val Cys Ala
            20                  25                  30

<210> SEQ ID NO 90
<211> LENGTH: 26
<212> TYPE: PRT
<213> ORGANISM: Conus omaria
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 13 may be Pro or hydroxy-Pro;
      Xaa at residue 19 mo-Trp

<400> SEQUENCE: 90

Cys Ile Asp Gly Gly Xaa Ile Cys Asp Ile Phe Phe Xaa Asn Cys Cys
1               5                   10                  15

Ser Gly Xaa Cys Ile Ile Leu Val Cys Ala
            20                  25

<210> SEQ ID NO 91
<211> LENGTH: 650
<212> TYPE: DNA
<213> ORGANISM: Conus omaria
<220> FEATURE:
<221> NAME/KEY: CDS
<222> LOCATION: (107)..(196)

<400> SEQUENCE: 91
ggtcgacatc atcatcatcg atccatctgt ccatccatcc attcattcat tcgctgccag      60
actgtcataa atattcgagt ctctccttct gtttgtatct gacaga ttg aac aag        115
                                                   Leu Asn Lys
                                                   1 agg tgc ctt gac ggt ggt gaa att tgt ggt att ttg ttt cca agc tgc       163
Arg Cys Leu Asp Gly Gly Glu Ile Cys Gly Ile Leu Phe Pro Ser Cys
    5                   10                  15 tgc agt ggg tgg tgc att gtt ctc gtc tgc gca tgaaactacc gtgatgtctt    216
Cys Ser Gly Trp Cys Ile Val Leu Val Cys Ala
20                  25                  30 ctactcccct ctagtagtag taggcggccg ctctagagga tccaagctta cgtacgcgtg     276
catgcgacgt catagctctt ctatagtgtc acctaaattc aattcactgg ccgtcgtttt     336
acaacgtcgt gactgggaaa accctggcgt tacccaactt aatcgccttg cagcacatcc     396
ccctttcgcc agctggcgta atagcgaaga ggcccgcacc gatcgccctt cccaacaagt     456
tgcgcagcct gaatggcgaa tgggacgcgc cctgtagcgg cgcattaagc gcggcgggtg     516
tggtggttac gcgcaccgtg accgctacac ttgccagcgc cctagccgcc cgctcctttc     576
gctttcttcc cttcctttct cgcacgttcg gccggctttc cccgtcaagc tctaaatcgg     636
gggcttccct ttta                                                      650

<210> SEQ ID NO 92
<211> LENGTH: 30
<212> TYPE: PRT
<213> ORGANISM: Conus omaria

<400> SEQUENCE: 92

Leu Asn Lys Arg Cys Leu Asp Gly Gly Glu Ile Cys Gly Ile Leu Phe
1               5                   10                  15
```

```
Pro Ser Cys Cys Ser Gly Trp Cys Ile Val Leu Val Cys Ala
            20                  25                  30

<210> SEQ ID NO 93
<211> LENGTH: 26
<212> TYPE: PRT
<213> ORGANISM: Conus omaria
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 13 may be Pro or hydroxy-Pro;
      Xaa at residue 19 may be Trp or bromo-Trp

<400> SEQUENCE: 93

Cys Leu Asp Gly Gly Xaa Ile Cys Gly Ile Leu Phe Xaa Ser Cys Cys
1               5                   10                  15

Ser Gly Xaa Cys Ile Val Leu Val Cys Ala
            20                  25

<210> SEQ ID NO 94
<211> LENGTH: 618
<212> TYPE: DNA
<213> ORGANISM: Conus marmoreus
<220> FEATURE:
<221> NAME/KEY: CDS
<222> LOCATION: (107)..(193)

<400> SEQUENCE: 94
ggtcgacatc atcatcatcg atccatctgt ccatccatcc atccattcat tcgctgccag     60
actgtaataa atattcgagt ctctctttct gtttgtatct gacaga ttg aac aag       115
                                                  Leu Asn Lys
                                                    1 agg tgc ctt gag ttt ggt gaa gtt tgt aat ttt ttt ttc cca acc tgc      163
Arg Cys Leu Glu Phe Gly Glu Val Cys Asn Phe Phe Phe Pro Thr Cys
      5              10                  15 tgc ggc tat tgc gtt ctt ctt gtc tgc cta taaaactacc gtgatgtctt        213
Cys Gly Tyr Cys Val Leu Leu Val Cys Leu
20                  25 ctactcccct ctagtagtag taggcggccg ctctagagga tccaagctta cgtacgcgtg    273
catgcgacgt catagctctt ctatagtgtc acctaaattc aattcactgg ccgtcgtttt    333
acaacgtcgt gactgggaaa accctggcgt tacccaactt aatcgccttg cagcacatcc    393
cccttccgcc agctggcgta atagcgaaga ggcccgcacc gatcgccctt cccaacagtt    453
gcgcagcctg aatggcgaat gggacgcgcc ctgtagcggc gcattaagcg cggcgggtgt    513
ggtggttacg cgcagcgtga ccgctacact tgcagcgccc tagcgcccgc tcctttcgct    573
ttcttccctt cctttctcgc cacgttcgcc ggctttcccc gtcaa                   618

<210> SEQ ID NO 95
<211> LENGTH: 29
<212> TYPE: PRT
<213> ORGANISM: Conus marmoreus

<400> SEQUENCE: 95

Leu Asn Lys Arg Cys Leu Glu Phe Gly Glu Val Cys Asn Phe Phe Phe
1               5                   10                  15

Pro Thr Cys Cys Gly Tyr Cys Val Leu Leu Val Cys Leu
            20                  25

<210> SEQ ID NO 96
```

-continued

```
<211> LENGTH: 25
<212> TYPE: PRT
<213> ORGANISM: Conus marmoreus
<220> FEATURE:
<221> NAME/KEY: SITE
<222> LOCATION: (1)..(25)
<223> OTHER INFORMATION: Xaa at residues 3 and 6 may be Glu or
      gamma-carboxy-Glu; Xaa at residue 13 may be Pro or hydroxy-Pro;
      Xaa at residue 18 may be Tyr, 125-I-Tyr, mono-iodo-Tyr,
      di-iodo-Tyr, O-sulpho-Tyr or O-phospho-Tyr

<400> SEQUENCE: 96

Cys Leu Xaa Phe Gly Xaa Val Cys Asn Phe Phe Xaa Thr Cys Cys
1               5                   10                  15

Gly Xaa Cys Val Leu Leu Val Cys Leu
            20                  25

<210> SEQ ID NO 97
<211> LENGTH: 444
<212> TYPE: DNA
<213> ORGANISM: Conus marmoreus
<220> FEATURE:
<221> NAME/KEY: CDS
<222> LOCATION: (150)..(236)

<400> SEQUENCE: 97
gaaagctggt acgcctgcag gtaccggtcc ggaattcccg ggtcgacatc atcatcatca      60
tcgatccatc tgtccatcca tccattcatt cattcgctgc cagactgtaa taaatattcg     120
agtttctcct tctgtttgta tctgacagg ttg aac aag agg tgc caa gag ttc      173
                                  Leu Asn Lys Arg Cys Gln Glu Phe
                                    1               5 ggt gaa gtt tgt aat ttt ttt ttc cca gac tgc tgc ggc tat tgc gtt      221
Gly Glu Val Cys Asn Phe Phe Phe Pro Asp Cys Cys Gly Tyr Cys Val
        10                  15                  20 ctt tta ctc tgc ata taaaactacc gtgatgtctt ctcttcccat ctagtagtag      276
Leu Leu Leu Cys Ile
25 tagtagtagt aggcggccgc tctagaggat ccaagcttac gtacgcgtgc atgcgacgtc     336 atagctcttc tatagtgtca cctaaattca attcactggc cgtcgtttta caaccgtcgt     396 gactgggaaa accctggcgt tcccaactta attcgccttg cagcacat                 444

<210> SEQ ID NO 98
<211> LENGTH: 29
<212> TYPE: PRT
<213> ORGANISM: Conus marmoreus

<400> SEQUENCE: 98

Leu Asn Lys Arg Cys Gln Glu Phe Gly Glu Val Cys Asn Phe Phe
1               5                   10                  15

Pro Asp Cys Cys Gly Tyr Cys Val Leu Leu Leu Cys Ile
            20                  25

<210> SEQ ID NO 99
<211> LENGTH: 25
<212> TYPE: PRT
<213> ORGANISM: Conus marmoreus
<220> FEATURE:
<221> NAME/KEY: SITE
<222> LOCATION: (1)..(25)
<223> OTHER INFORMATION: Xaa at residues 3 and 6 may be Glu or
      gamma-carboxy-Glu; Xaa at residue 13 may be Pro or hydroxy-Pro;
      Xaa at residue 18may be Tyr,125-I-Tyr, mono-iodo-Tyr, di-iodo-Tyr,
      O-sulpho-Tyr or O-phospho-Tyr
```

```
<400> SEQUENCE: 99

Cys Gln Xaa Phe Gly Xaa Val Cys Asn Phe Phe Phe Xaa Asp Cys Cys
1               5                   10                  15

Gly Xaa Cys Val Leu Leu Leu Cys Ile
            20                  25

<210> SEQ ID NO 100
<211> LENGTH: 545
<212> TYPE: DNA
<213> ORGANISM: Conus omaria
<220> FEATURE:
<221> NAME/KEY: CDS
<222> LOCATION: (153)..(242)
<221> NAME/KEY: misc_feature
<222> LOCATION: (1)..(545)
<223> OTHER INFORMATION: n may be any nucleotide

<400> SEQUENCE: 100
ttttgaagcn ggtacgcctg caggtaccgg tccggaattc ccgggtcgac atcatcatca      60
tcatcgatcc atctgtccat ccatccattc attcattcgc taccagactg taataaatat    120
tcgggtctct ctttctgttt gtatctgaca ga ttg gac aag agg tgc att cca      173
                                   Leu Asp Lys Arg Cys Ile Pro
                                     1               5 cat ttt gac cct tgt gac ccg ata cgc cac acc tgc tgc ttt ggc ctg      221
His Phe Asp Pro Cys Asp Pro Ile Arg His Thr Cys Cys Phe Gly Leu
            10                  15                  20 tgc cta cta ata gcc tgc atc taaaactgcc gtgatgtctt ctcctcccct         272
Cys Leu Leu Ile Ala Cys Ile
        25          30 ctagtagtag taggcggccg ctctagagga tccaagctta cgtacgcgtg catgcgacgt    332
catagctctt ctatagtgtc acctaaattc aattcactgg ccgtcgtttt acaacgtcgt    392
gactgggaaa accctggcgt tacccaactt aatcgccttg cagcacatcc ccctttcgcc    452
agctggcgta atagcgaaga ggcccgcacc gatcgccctt cccaacagtt gcgcagcctg    512
aatggcgaat gggacgcgcc ctgtagcggc gct                                 545

<210> SEQ ID NO 101
<211> LENGTH: 30
<212> TYPE: PRT
<213> ORGANISM: Conus omaria

<400> SEQUENCE: 101

Leu Asp Lys Arg Cys Ile Pro His Phe Asp Pro Cys Asp Pro Ile Arg
1               5                   10                  15

His Thr Cys Cys Phe Gly Leu Cys Leu Leu Ile Ala Cys Ile
            20                  25                  30

<210> SEQ ID NO 102
<211> LENGTH: 26
<212> TYPE: PRT
<213> ORGANISM: Conus omaria
<220> FEATURE:
<221> NAME/KEY: SITE
<222> LOCATION: (1)..(26)
<223> OTHER INFORMATION: Xaa at residues 3, 7 and 10 may be Pro or
      hydroxy-Pro.

<400> SEQUENCE: 102

Cys Ile Xaa His Phe Asp Xaa Cys Asp Xaa Ile Arg His Thr Cys Cys
1               5                   10                  15

Phe Gly Leu Cys Leu Leu Ile Ala Cys Ile
            20                  25
```

```
<210> SEQ ID NO 103
<211> LENGTH: 534
<212> TYPE: DNA
<213> ORGANISM: Conus omaria
<220> FEATURE:
<221> NAME/KEY: CDS
<222> LOCATION: (140)..(226)

<400> SEQUENCE: 103
ggtacgcctg caggtaccgg tccggaattc ccgggtcgac atcatcatca tcgatccatc      60
tgtccatcca tccattcttt catttgctgc cagactgtaa taaatattcg agtctctctt     120
tctgtttgta tctgacaga ttg aac aag agg tgc ctt gag ttt ggt gaa gtt     172
                     Leu Asn Lys Arg Cys Leu Glu Phe Gly Glu Val
                      1               5                  10 tgt aat ttt ttt ttc cca acc tgc tgc ggc tat tgc gtt ctt ctt gtc     220
Cys Asn Phe Phe Phe Pro Thr Cys Cys Gly Tyr Cys Val Leu Leu Val
             15                  20                  25 tgc cta taaaactacc gtgatgtctt ctcttcccct ctagtagtag taggcggccg       276
Cys Leu ctctagagga tccaagctta cgtacgcgtg catgcgacgt catagctctt ctatagtgtc     336
acctaaattc aattcactgg ccgtcgtttt acaacgtcgt gactgggaaa accctggcgt     396
tacccaactt aatcgccttg cagcacatcc ccctttcgcc agctggcgta atagcgaaga     456
ggcccgcacc gatcgccctt cccaacagtt gcgcagcctg aatggcgaat gggacgcgcc     516
ctgtagcggc gcattaag                                                   534

<210> SEQ ID NO 104
<211> LENGTH: 29
<212> TYPE: PRT
<213> ORGANISM: Conus omaria

<400> SEQUENCE: 104

Leu Asn Lys Arg Cys Leu Glu Phe Gly Glu Val Cys Asn Phe Phe Phe
 1               5                  10                  15

Pro Thr Cys Cys Gly Tyr Cys Val Leu Leu Val Cys Leu
             20                  25

<210> SEQ ID NO 105
<211> LENGTH: 25
<212> TYPE: PRT
<213> ORGANISM: Conus omaria
<220> FEATURE:
<221> NAME/KEY: SITE
<222> LOCATION: (1)..(25)
<223> OTHER INFORMATION: Xaa at residues 3 and 6 may be Glu or
      gamma-carboxy-Glu; Xaa at residue13  may be Pro or hydroxy-Pro;
      Xaa at residue 18 may be Tyr, 125-I-Tyr, mono-iodo-Tyr,
      di-iodo-Tyr, O-sulpho-Tyr or O-phospho-Tyr

<400> SEQUENCE: 105

Cys Leu Xaa Phe Gly Xaa Val Cys Asn Phe Phe Phe Xaa Thr Cys Cys
 1               5                  10                  15

Gly Xaa Cys Val Leu Leu Val Cys Leu
             20                  25

<210> SEQ ID NO 106
<211> LENGTH: 200
<212> TYPE: DNA
<213> ORGANISM: Conus obscurus
<220> FEATURE:
```

```
<221> NAME/KEY: CDS
<222> LOCATION: (73)..(180)

<400> SEQUENCE: 106
cgatccatct gtccatccat ccattcgttc gttcgctgcc aaactgtaat aaataaccga     60
gtctctctgt tt gta tct gac aga tcg aaa aag caa tgc cgt caa aat ggt    111
              Val Ser Asp Arg Ser Lys Lys Gln Cys Arg Gln Asn Gly
                1               5                  10 gaa gtg tgt gat gcg aat ttg gca cac tgc tgc agt ggc ccg tgt ttt      159
Glu Val Cys Asp Ala Asn Leu Ala His Cys Cys Ser Gly Pro Cys Phe
         15                  20                  25 ctc ttc tgt cta aac cag ccg tgatgtcttc tactcccctc                    200
Leu Phe Cys Leu Asn Gln Pro
 30              35

<210> SEQ ID NO 107
<211> LENGTH: 36
<212> TYPE: PRT
<213> ORGANISM: Conus obscurus

<400> SEQUENCE: 107

Val Ser Asp Arg Ser Lys Lys Gln Cys Arg Gln Asn Gly Glu Val Cys
 1               5                  10                  15

Asp Ala Asn Leu Ala His Cys Cys Ser Gly Pro Cys Phe Leu Phe Cys
             20                  25                  30

Leu Asn Gln Pro
         35

<210> SEQ ID NO 108
<211> LENGTH: 32
<212> TYPE: PRT
<213> ORGANISM: Conus obscurus
<220> FEATURE:
<221> NAME/KEY: SITE
<222> LOCATION: (1)..(32)
<223> OTHER INFORMATION: Xaa at residue 10 may be Glu or
      gamma-carboxy-Glu; Xaa at residues 23 and 32 may be Pro or
      hydroxy-Pro

<400> SEQUENCE: 108

Ser Lys Lys Gln Cys Arg Gln Asn Gly Xaa Val Cys Asp Ala Asn Leu
 1               5                  10                  15

Ala His Cys Cys Ser Gly Xaa Cys Phe Leu Phe Cys Leu Asn Gln Xaa
             20                  25                  30

<210> SEQ ID NO 109
<211> LENGTH: 262
<212> TYPE: DNA
<213> ORGANISM: Conus ammiralis
<220> FEATURE:
<221> NAME/KEY: CDS
<222> LOCATION: (1)..(231)

<400> SEQUENCE: 109 atg aaa ctg acg tgc gtg atg atc att gct gtg ctg ttc ttg acc gcc      48
Met Lys Leu Thr Cys Val Met Ile Ile Ala Val Leu Phe Leu Thr Ala
 1               5                  10                  15 tgg aca ttt gcc acg gct gat gac tcc gga aat gga ttg gaa aat ctt      96
Trp Thr Phe Ala Thr Ala Asp Asp Ser Gly Asn Gly Leu Glu Asn Leu
             20                  25                  30 ttt tcg aag gca cat cac gaa atg aag aac ccc aaa gcc tct aaa ttg     144
Phe Ser Lys Ala His His Glu Met Lys Asn Pro Lys Ala Ser Lys Leu
         35                  40                  45
```

```
aac aag agg tgc act caa agc ggt gaa ctt tgt gat gtg ata gac cca      192
Asn Lys Arg Cys Thr Gln Ser Gly Glu Leu Cys Asp Val Ile Asp Pro
     50                  55                  60 gac tgc tgc aat aat ttt tgc att ata ttt ttc tgc ata taaaactgcc       241
Asp Cys Cys Asn Asn Phe Cys Ile Ile Phe Phe Cys Ile
65                  70                  75 gtgatgtctt ctactccct c                                                262

<210> SEQ ID NO 110
<211> LENGTH: 77
<212> TYPE: PRT
<213> ORGANISM: Conus ammiralis

<400> SEQUENCE: 110

Met Lys Leu Thr Cys Val Met Ile Ile Ala Val Leu Phe Leu Thr Ala
1               5                   10                  15

Trp Thr Phe Ala Thr Ala Asp Asp Ser Gly Asn Gly Leu Glu Asn Leu
            20                  25                  30

Phe Ser Lys Ala His His Glu Met Lys Asn Pro Lys Ala Ser Lys Leu
        35                  40                  45

Asn Lys Arg Cys Thr Gln Ser Gly Glu Leu Cys Asp Val Ile Asp Pro
    50                  55                  60

Asp Cys Cys Asn Asn Phe Cys Ile Ile Phe Phe Cys Ile
65                  70                  75

<210> SEQ ID NO 111
<211> LENGTH: 26
<212> TYPE: PRT
<213> ORGANISM: Conus ammiralis
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 13 may be Pro or hydroxy-Pro

<400> SEQUENCE: 111

Cys Thr Gln Ser Gly Xaa Leu Cys Asp Val Ile Asp Xaa Asp Cys Cys
1               5                   10                  15

Asn Asn Phe Cys Ile Ile Phe Phe Cys Ile
            20                  25

<210> SEQ ID NO 112
<211> LENGTH: 286
<212> TYPE: DNA
<213> ORGANISM: Conus textile
<220> FEATURE:
<221> NAME/KEY: CDS
<222> LOCATION: (25)..(255)

<400> SEQUENCE: 112
ggcattacct aaaacatcac caaa atg aaa ctg acg tgc atg atg atc gtt       51
                          Met Lys Leu Thr Cys Met Met Ile Val
                          1               5 gct gtg ctg ttc ttg acc gcc tgg aca ttc gcc acg gct gat gac tcc      99
Ala Val Leu Phe Leu Thr Ala Trp Thr Phe Ala Thr Ala Asp Asp Ser
10                  15                  20                  25 gga aat gga ttg gag aaa ctt ttt tcg aat gca cat cac gaa atg aag     147
Gly Asn Gly Leu Glu Lys Leu Phe Ser Asn Ala His His Glu Met Lys
                30                  35                  40 aac ccc gaa gcc tct aat ttg aac aag agg tgc gct cct ttt ctt cac     195
Asn Pro Glu Ala Ser Asn Leu Asn Lys Arg Cys Ala Pro Phe Leu His
            45                  50                  55
```

```
ctt tgt acc ttt ttc ttc cca aac tgc tgc aac ggc tat tgc gtt caa       243
Leu Cys Thr Phe Phe Phe Pro Asn Cys Cys Asn Gly Tyr Cys Val Gln
            60                  65                  70 ttt atc tgc cta taaaactact gtgatgtctt ctattcccct c                    286
Phe Ile Cys Leu
    75
```

<210> SEQ ID NO 113
<211> LENGTH: 77
<212> TYPE: PRT
<213> ORGANISM: Conus textile

<400> SEQUENCE: 113

```
Met Lys Leu Thr Cys Met Met Ile Val Ala Val Leu Phe Leu Thr Ala
1               5                   10                  15

Trp Thr Phe Ala Thr Ala Asp Asp Ser Gly Asn Gly Leu Glu Lys Leu
                20                  25                  30

Phe Ser Asn Ala His His Glu Met Lys Asn Pro Glu Ala Ser Asn Leu
            35                  40                  45

Asn Lys Arg Cys Ala Pro Phe Leu His Leu Cys Thr Phe Phe Phe Pro
        50                  55                  60

Asn Cys Cys Asn Gly Tyr Cys Val Gln Phe Ile Cys Leu
65                  70                  75
```

<210> SEQ ID NO 114
<211> LENGTH: 26
<212> TYPE: PRT
<213> ORGANISM: Conus textile
<220> FEATURE:
<221> NAME/KEY: SITE
<222> LOCATION: (1)..(26)
<223> OTHER INFORMATION: Xaa at residues 3 and 13 may be Pro or
      hydroxy-Pro; Xaa at residue 19 may be Tyr, 125-I-Tyr,
      mono-iodo-Tyr, di-iodo-Tyr, O-sulpho-Tyr or O-phospho-Tyr

<400> SEQUENCE: 114

```
Cys Ala Xaa Phe Leu His Leu Cys Thr Phe Phe Phe Xaa Asn Cys Cys
1               5                   10                  15

Asn Gly Xaa Cys Val Gln Phe Ile Cys Leu
            20                  25
```

<210> SEQ ID NO 115
<211> LENGTH: 484
<212> TYPE: DNA
<213> ORGANISM: Conus marmoreus
<220> FEATURE:
<221> NAME/KEY: CDS
<222> LOCATION: (74)..(304)

<400> SEQUENCE: 115

```
ggatcctagc acagtgaatt tggcttcaca gttttccact gtcgtctttg gcatcatcca     60 aacatcacc aag atg aaa ctg acg tgc atg atg atc gtt gct gtg ctg        109
           Met Lys Leu Thr Cys Met Met Ile Val Ala Val Leu
           1               5                   10 ttc ttg acc gcc tgg aca ttt gcc acg gct gat gac ccc aga aat gga     157
Phe Leu Thr Ala Trp Thr Phe Ala Thr Ala Asp Asp Pro Arg Asn Gly
            15                  20                  25 ttg gag aat ctt ttt tcg aag gca cat cac gaa atg aag aac ccc aaa     205
Leu Glu Asn Leu Phe Ser Lys Ala His His Glu Met Lys Asn Pro Lys
        30                  35                  40 gac tct aaa ttg aac aag agg tgc ctt gac gct ggt gaa atg tgt gat     253
Asp Ser Lys Leu Asn Lys Arg Cys Leu Asp Ala Gly Glu Met Cys Asp
45                  50                  55                  60
```

-continued

| | |
|---|---|
| ctt ttt aat tca aaa tgc tgc agt ggg tgg tgc att att ctc ttc tgc<br>Leu Phe Asn Ser Lys Cys Cys Ser Gly Trp Cys Ile Ile Leu Phe Cys<br>               65                                70                      75 | 301 |
| gca   taaaactacc gtgatgtctt ctactcccct ctgtgctacc tggcttgatc<br>Ala | 354 |
| tttgattggc gcgtgccctt cactggttat gaaccccct gatccgactc tctggcggcc | 414 |
| tcggggttc aacatccaaa taaagccgac acgatactga cgtagaaaaa aaaaaaaaa | 474 |
| aaaaaaaaaa | 484 |

<210> SEQ ID NO 116
<211> LENGTH: 77
<212> TYPE: PRT
<213> ORGANISM: Conus marmoreus

<400> SEQUENCE: 116

Met Lys Leu Thr Cys Met Met Ile Val Ala Val Leu Phe Leu Thr Ala
1               5                   10                  15

Trp Thr Phe Ala Thr Ala Asp Asp Pro Arg Asn Gly Leu Glu Asn Leu
            20                  25                  30

Phe Ser Lys Ala His His Glu Met Lys Asn Pro Lys Asp Ser Lys Leu
        35                  40                  45

Asn Lys Arg Cys Leu Asp Ala Gly Glu Met Cys Asp Leu Phe Asn Ser
    50                  55                  60

Lys Cys Cys Ser Gly Trp Cys Ile Ile Leu Phe Cys Ala
65                  70                  75

<210> SEQ ID NO 117
<211> LENGTH: 26
<212> TYPE: PRT
<213> ORGANISM: Conus marmoreus
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 19 may be Trp or bromo-Trp

<400> SEQUENCE: 117

Cys Leu Asp Ala Gly Xaa Met Cys Asp Leu Phe Asn Ser Lys Cys Cys
1               5                   10                  15

Ser Gly Xaa Cys Ile Ile Leu Phe Cys Ala
            20                  25

<210> SEQ ID NO 118
<211> LENGTH: 427
<212> TYPE: DNA
<213> ORGANISM: Conus marmoreus
<220> FEATURE:
<221> NAME/KEY: CDS
<222> LOCATION: (19)..(249)

<400> SEQUENCE: 118

| | |
|---|---|
| gccgaaaaca tcaccaag atg aaa ctg acg agc atg atg atc gtt gct gtg<br>                                    Met Lys Leu Thr Ser Met Met Ile Val Ala Val<br>                                        1                       5                         10 | 51 |
| ctg ttc ttg acc gcc tgg aca ttc gtc acg gct gac gac tcc gga aat<br>Leu Phe Leu Thr Ala Trp Thr Phe Val Thr Ala Asp Asp Ser Gly Asn<br>               15                          20                          25 | 99 |
| gga ttg gag aat ctt ttt tcg aag gca cat cac gag atg aag aac ccc<br>Gly Leu Glu Asn Leu Phe Ser Lys Ala His His Glu Met Lys Asn Pro<br>        30                          35                          40 | 147 |
| aaa gac tct aaa ttg aac aag agg tgc ctt gac ggt ggt gaa att tgt | 195 |

-continued

```
Lys Asp Ser Lys Leu Asn Lys Arg Cys Leu Asp Gly Gly Glu Ile Cys
         45                  50                  55 ggt att ttg ttt cca agc tgc tgc agt ggg tgg tgc att gtt ctc gtc      243
Gly Ile Leu Phe Pro Ser Cys Cys Ser Gly Trp Cys Ile Val Leu Val
 60                  65                  70                  75 tgc gca tgaaactacc gtgatgtctt ctactcccct ctgtgctacc tggcttgatc       299
Cys Ala tttgattggc gcgtgccctt cactggttat gaaccccct gatccgactc tctggcggcc     359 tcggggttc aacatccaaa taaagcgaca cgacaatgac aaaaaaaaaa aaaaaaaaa      419 aaaaaaaa                                                             427

<210> SEQ ID NO 119
<211> LENGTH: 77
<212> TYPE: PRT
<213> ORGANISM: Conus marmoreus

<400> SEQUENCE: 119

Met Lys Leu Thr Ser Met Met Ile Val Ala Val Leu Phe Leu Thr Ala
 1               5                  10                  15

Trp Thr Phe Val Thr Ala Asp Asp Ser Gly Asn Gly Leu Glu Asn Leu
             20                  25                  30

Phe Ser Lys Ala His His Glu Met Lys Asn Pro Lys Asp Ser Lys Leu
         35                  40                  45

Asn Lys Arg Cys Leu Asp Gly Gly Glu Ile Cys Gly Ile Leu Phe Pro
     50                  55                  60

Ser Cys Cys Ser Gly Trp Cys Ile Val Leu Val Cys Ala
 65                  70                  75

<210> SEQ ID NO 120
<211> LENGTH: 26
<212> TYPE: PRT
<213> ORGANISM: Conus marmoreus
<220> FEATURE:
<221> NAME/KEY: SITE
<222> LOCATION: (1)..(26)
<223> OTHER INFORMATION: Xaa at residue 6 may be Glu or
      gamma-carboxy-Glu; Xaa at residue 13 may be Pro or hydroxy-Pro;
      Xaa at residue 19 may be Trp or bromo-Trp

<400> SEQUENCE: 120

Cys Leu Asp Gly Gly Xaa Ile Cys Gly Ile Leu Phe Xaa Ser Cys Cys
 1               5                  10                  15

Ser Gly Xaa Cys Ile Val Leu Val Cys Ala
             20                  25

<210> SEQ ID NO 121
<211> LENGTH: 470
<212> TYPE: DNA
<213> ORGANISM: Conus marmoreus
<220> FEATURE:
<221> NAME/KEY: CDS
<222> LOCATION: (70)..(303)

<400> SEQUENCE: 121
gctagcacag tgaatttggc ttcacagttt tccactgtcg tctttggcat catccaaaac    60 atcaccaag atg aaa ctg acg tgc atg atg atc gaa gca gag ctg ttc ttg    111
           Met Lys Leu Thr Cys Met Met Ile Glu Ala Glu Leu Phe Leu
            1               5                  10 acc gcc tgg aca ttt gcc acg gct gat gac ccc aga aat gga ttg gag     159
Thr Ala Trp Thr Phe Ala Thr Ala Asp Asp Pro Arg Asn Gly Leu Glu
 15                  20                  25                  30
```

```
aat ctt ttt tcg aag gca cat cac gaa atg aag aac ccc gaa gcc tct      207
Asn Leu Phe Ser Lys Ala His His Glu Met Lys Asn Pro Glu Ala Ser
             35                  40                  45 aaa ttg aac aag agg tgc cct aac act ggt gaa tta tgt gat gtg gtt      255
Lys Leu Asn Lys Arg Cys Pro Asn Thr Gly Glu Leu Cys Asp Val Val
         50                  55                  60 gaa caa aac tgc tgc tat acc tat tgc ttt att gta gtc tgc cct ata      303
Glu Gln Asn Cys Cys Tyr Thr Tyr Cys Phe Ile Val Val Cys Pro Ile
     65                  70                  75 taactaccgt gatgtcttct actccctct gtgctgcctg gcttgatctt tgattggcgc      363
gtgcccttca ctggttatga acccccctga tccgactctc ttgcggcctc aggggttcaa     423
catccaaata aagcgacacg aaaatgaaaa aaaaaaaaaa aaaaaaa                    470

<210> SEQ ID NO 122
<211> LENGTH: 78
<212> TYPE: PRT
<213> ORGANISM: Conus marmoreus

<400> SEQUENCE: 122

Met Lys Leu Thr Cys Met Met Ile Glu Ala Glu Leu Phe Leu Thr Ala
1               5                   10                  15

Trp Thr Phe Ala Thr Ala Asp Asp Pro Arg Asn Gly Leu Glu Asn Leu
            20                  25                  30

Phe Ser Lys Ala His His Glu Met Lys Asn Pro Glu Ala Ser Lys Leu
        35                  40                  45

Asn Lys Arg Cys Pro Asn Thr Gly Glu Leu Cys Asp Val Val Glu Gln
    50                  55                  60

Asn Cys Cys Tyr Thr Tyr Cys Phe Ile Val Val Cys Pro Ile
65                  70                  75

<210> SEQ ID NO 123
<211> LENGTH: 27
<212> TYPE: PRT
<213> ORGANISM: Conus marmoreus
<220> FEATURE:
<221> NAME/KEY: SITE
<222> LOCATION: (1)..(27)
<223> OTHER INFORMATION: Xaa at residues 2 and 26 may be Pro or
      hydroxy-Pro; Xaa at residues 6 and 12 may be Glu or
      gamma-carboxy-Glu; Xaa at residues 17 and 19 may be Tyr,
      125-I-Tyr, mono-iodo-Tyr, di-iodo-Tyr, O-sulpho-Tyr or
      O-phospho-Tyr

<400> SEQUENCE: 123

Cys Xaa Asn Thr Gly Xaa Leu Cys Asp Val Val Xaa Gln Asn Cys Cys
1               5                   10                  15

Xaa Thr Xaa Cys Phe Ile Val Val Cys Xaa Ile
            20                  25

<210> SEQ ID NO 124
<211> LENGTH: 470
<212> TYPE: DNA
<213> ORGANISM: Conus marmoreus
<220> FEATURE:
<221> NAME/KEY: CDS
<222> LOCATION: (67)..(312)

<400> SEQUENCE: 124
ttgcacggtg aatttcgctt atattttct actgtcgtct ttggcatcat ccaaacatc      60 accaag atg aaa ctg acg tgc atg atg atc gtt gct gtg ctg ttc ttg     108
       Met Lys Leu Thr Cys Met Met Ile Val Ala Val Leu Phe Leu
```

```
                 1               5                   10
acc gcc tgg aca ttc gtc acg gct gtg cct cac tcc agc gat gta ttg       156
Thr Ala Trp Thr Phe Val Thr Ala Val Pro His Ser Ser Asp Val Leu
 15                  20                  25                  30 gag aat ctt tat ctg aag gca ctt cac gaa acg gaa aac cac gaa gcc       204
Glu Asn Leu Tyr Leu Lys Ala Leu His Glu Thr Glu Asn His Glu Ala
                 35                  40                  45 tct aaa ttg aac gtg aga gac gac gag tgc gaa cct cct gga gat ttt       252
Ser Lys Leu Asn Val Arg Asp Asp Glu Cys Glu Pro Pro Gly Asp Phe
             50                  55                  60 tgt ggc ttt ttt aaa att ggg ccg cct tgc tgc agt ggc tgg tgc ttc       300
Cys Gly Phe Phe Lys Ile Gly Pro Pro Cys Cys Ser Gly Trp Cys Phe
         65                  70                  75 ctc tgg tgc gcc taaaactgcc gtgatgtctt ctattcccct ctgtgctacc           352
Leu Trp Cys Ala
         80 tggcttgatc tttgattggc gcgtgccctt cagtggttat gaaccccct gatccgactc      412 tctgggggcc tcggggttc aacatccaaa taaagctgac aacacaataa aaaaaaaa        470

<210> SEQ ID NO 125
<211> LENGTH: 82
<212> TYPE: PRT
<213> ORGANISM: Conus marmoreus

<400> SEQUENCE: 125

Met Lys Leu Thr Cys Met Met Ile Val Ala Val Leu Phe Leu Thr Ala
 1               5                  10                  15

Trp Thr Phe Val Thr Ala Val Pro His Ser Ser Asp Val Leu Glu Asn
                 20                  25                  30

Leu Tyr Leu Lys Ala Leu His Glu Thr Glu Asn His Glu Ala Ser Lys
             35                  40                  45

Leu Asn Val Arg Asp Asp Glu Cys Glu Pro Pro Gly Asp Phe Cys Gly
         50                  55                  60

Phe Phe Lys Ile Gly Pro Pro Cys Cys Ser Gly Trp Cys Phe Leu Trp
 65                  70                  75                  80

Cys Ala

<210> SEQ ID NO 126
<211> LENGTH: 30
<212> TYPE: PRT
<213> ORGANISM: Conus marmoreus
<220> FEATURE:
<221> NAME/KEY: SITE
<222> LOCATION: (1)..(30)
<223> OTHER INFORMATION: Xaa at residues 3 and 5 may be Glu or
      gamma-carboxy-Glu; Xaa at residues 6, 7, 18 and 19 may be Pro or
      hydroxy-Pro; Xaa at residues 24 and 28 may be Trp or bromo-Trp

<400> SEQUENCE: 126

Asp Asp Xaa Cys Xaa Xaa Xaa Gly Asp Phe Cys Gly Phe Phe Lys Ile
 1               5                  10                  15

Gly Xaa Xaa Cys Cys Ser Gly Xaa Cys Phe Leu Xaa Cys Ala
             20                  25                  30

<210> SEQ ID NO 127
<211> LENGTH: 277
<212> TYPE: DNA
<213> ORGANISM: Conus striatus
<220> FEATURE:
<221> NAME/KEY: CDS
<222> LOCATION: (1)..(246)
```

-continued

```
<400> SEQUENCE: 127 atg aaa ctg acg tgt gtg atg atc gtt gct gtg ctg ttc ttg acc gcc         48
Met Lys Leu Thr Cys Val Met Ile Val Ala Val Leu Phe Leu Thr Ala
1               5                   10                  15 tgg aca ttc gtc acg gct gtg cct cac tcc agc gat gca ttg gag aat         96
Trp Thr Phe Val Thr Ala Val Pro His Ser Ser Asp Ala Leu Glu Asn
            20                  25                  30 ctt tat ctg aag gca ctt cac gaa acg gaa aac cac gaa gcc tct aaa        144
Leu Tyr Leu Lys Ala Leu His Glu Thr Glu Asn His Glu Ala Ser Lys
        35                  40                  45 ttg aac gtg aga gac gac gag tgc gaa cct cct gga gat ttt tgt ggc        192
Leu Asn Val Arg Asp Asp Glu Cys Glu Pro Pro Gly Asp Phe Cys Gly
    50                  55                  60 ttt ttt aaa att ggg ccg cct tgc tgc agt ggc tgg tgc ttc ctc tgg        240
Phe Phe Lys Ile Gly Pro Pro Cys Cys Ser Gly Trp Cys Phe Leu Trp
65                  70                  75                  80 tgc gca taaaactgcc gtgatgtctt ctcctcccct c                             277
Cys Ala <210> SEQ ID NO 128
<211> LENGTH: 82
<212> TYPE: PRT
<213> ORGANISM: Conus striatus

<400> SEQUENCE: 128

Met Lys Leu Thr Cys Val Met Ile Val Ala Val Leu Phe Leu Thr Ala
1               5                   10                  15

Trp Thr Phe Val Thr Ala Val Pro His Ser Ser Asp Ala Leu Glu Asn
            20                  25                  30

Leu Tyr Leu Lys Ala Leu His Glu Thr Glu Asn His Glu Ala Ser Lys
        35                  40                  45

Leu Asn Val Arg Asp Asp Glu Cys Glu Pro Pro Gly Asp Phe Cys Gly
    50                  55                  60

Phe Phe Lys Ile Gly Pro Pro Cys Cys Ser Gly Trp Cys Phe Leu Trp
65                  70                  75                  80

Cys Ala

<210> SEQ ID NO 129
<211> LENGTH: 30
<212> TYPE: PRT
<213> ORGANISM: Conus striatus
<220> FEATURE:
<221> NAME/KEY: SITE
<222> LOCATION: (1)..(30)
<223> OTHER INFORMATION: Xaa at residues 3 and 5 may be Glu or
      gamma-carboxy-Glu; Xaa at residues 6, 7, 18 and 19 may be Pro or
      hydroxy-Pro; Xaa at residues 24 and 28 may be Trp or bromo-Trp

<400> SEQUENCE: 129

Asp Asp Xaa Cys Xaa Xaa Xaa Gly Asp Phe Cys Gly Phe Phe Lys Ile
1               5                   10                  15

Gly Xaa Xaa Cys Cys Ser Gly Xaa Cys Phe Leu Xaa Cys Ala
            20                  25                  30

<210> SEQ ID NO 130
<211> LENGTH: 277
<212> TYPE: DNA
<213> ORGANISM: Conus omaria
<220> FEATURE:
<221> NAME/KEY: CDS
<222> LOCATION: (1)..(246)
```

-continued

```
<400> SEQUENCE: 130 atg aaa ctg acg tgc gtg atg atc gtt gct gtg ctg ttc ttg acc gcc        48
Met Lys Leu Thr Cys Val Met Ile Val Ala Val Leu Phe Leu Thr Ala
1               5                   10                  15 tgg aca ttc gtc acg gct gtg cct cac tcc agc aat gca ttg gaa aat        96
Trp Thr Phe Val Thr Ala Val Pro His Ser Ser Asn Ala Leu Glu Asn
            20                  25                  30 ctt tat ctg aag gca cgt cac gaa atg gaa aac ccc gaa gcc tct aaa       144
Leu Tyr Leu Lys Ala Arg His Glu Met Glu Asn Pro Glu Ala Ser Lys
        35                  40                  45 ttg aac acg aga gac gac gat tgc gaa cct cct gga aat ttt tgt ggc       192
Leu Asn Thr Arg Asp Asp Asp Cys Glu Pro Pro Gly Asn Phe Cys Gly
    50                  55                  60 atg ata aaa att ggg ccg cct tgc tgc agt ggc tgg tgc ttt ttc gcc       240
Met Ile Lys Ile Gly Pro Pro Cys Cys Ser Gly Trp Cys Phe Phe Ala
65                  70                  75                  80 tgc gcc taaaactgcc gtgatgtctt ctcctcccct c                            277
Cys Ala <210> SEQ ID NO 131
<211> LENGTH: 82
<212> TYPE: PRT
<213> ORGANISM: Conus omaria

<400> SEQUENCE: 131

Met Lys Leu Thr Cys Val Met Ile Val Ala Val Leu Phe Leu Thr Ala
1               5                   10                  15

Trp Thr Phe Val Thr Ala Val Pro His Ser Ser Asn Ala Leu Glu Asn
            20                  25                  30

Leu Tyr Leu Lys Ala Arg His Glu Met Glu Asn Pro Glu Ala Ser Lys
        35                  40                  45

Leu Asn Thr Arg Asp Asp Asp Cys Glu Pro Pro Gly Asn Phe Cys Gly
    50                  55                  60

Met Ile Lys Ile Gly Pro Pro Cys Cys Ser Gly Trp Cys Phe Phe Ala
65                  70                  75                  80

Cys Ala

<210> SEQ ID NO 132
<211> LENGTH: 30
<212> TYPE: PRT
<213> ORGANISM: Conus omaria
<220> FEATURE:
<221> NAME/KEY: SITE
<222> LOCATION: (1)..(30)
<223> OTHER INFORMATION: Xaa at residue 5 may be Glu or
      gamma-carboxy-Glu; Xaa at residues 6, 7, 18 and 19 may be Pro or
      hydroxy-Pro; Xaa at residue 24 maybe Trp or bromo-Trp

<400> SEQUENCE: 132

Asp Asp Asp Cys Xaa Xaa Xaa Gly Asn Phe Cys Gly Met Ile Lys Ile
1               5                   10                  15

Gly Xaa Xaa Cys Cys Ser Gly Xaa Cys Phe Phe Ala Cys Ala
            20                  25                  30

<210> SEQ ID NO 133
<211> LENGTH: 277
<212> TYPE: DNA
<213> ORGANISM: Conus aulicus
<220> FEATURE:
<221> NAME/KEY: CDS
<222> LOCATION: (1)..(246)
```

-continued

```
<400> SEQUENCE: 133 atg aaa ctg acg tgc ctg atg ata gtt gct gtg ctg ttc ttg acc gcc    48
Met Lys Leu Thr Cys Leu Met Ile Val Ala Val Leu Phe Leu Thr Ala
1               5                   10                  15 tgg aca ttc gtc acg gct gtg cct cac tcc agc aat gca ttg gag aat    96
Trp Thr Phe Val Thr Ala Val Pro His Ser Ser Asn Ala Leu Glu Asn
                20                  25                  30 ctt tat ctg aag gca cgt cac gaa atg gaa aac ccc gaa gcc tct aaa   144
Leu Tyr Leu Lys Ala Arg His Glu Met Glu Asn Pro Glu Ala Ser Lys
            35                  40                  45 ttg aac acg aga gac tac gat tgc gaa cct cct gga aat ttt tgt ggc   192
Leu Asn Thr Arg Asp Tyr Asp Cys Glu Pro Pro Gly Asn Phe Cys Gly
        50                  55                  60 atg ata aaa att ggg ccg cct tgc tgc agt ggc tgg tgc ttt ttc gcc   240
Met Ile Lys Ile Gly Pro Pro Cys Cys Ser Gly Trp Cys Phe Phe Ala
65                  70                  75                  80 tgc gcc taaaactgcc gtgatgtctt ctcctcccct c                        277
Cys Ala

<210> SEQ ID NO 134
<211> LENGTH: 82
<212> TYPE: PRT
<213> ORGANISM: Conus aulicus

<400> SEQUENCE: 134

Met Lys Leu Thr Cys Leu Met Ile Val Ala Val Leu Phe Leu Thr Ala
1               5                   10                  15

Trp Thr Phe Val Thr Ala Val Pro His Ser Ser Asn Ala Leu Glu Asn
                20                  25                  30

Leu Tyr Leu Lys Ala Arg His Glu Met Glu Asn Pro Glu Ala Ser Lys
            35                  40                  45

Leu Asn Thr Arg Asp Tyr Asp Cys Glu Pro Pro Gly Asn Phe Cys Gly
        50                  55                  60

Met Ile Lys Ile Gly Pro Pro Cys Cys Ser Gly Trp Cys Phe Phe Ala
65                  70                  75                  80

Cys Ala

<210> SEQ ID NO 135
<211> LENGTH: 30
<212> TYPE: PRT
<213> ORGANISM: Conus aulicus
<220> FEATURE:
<221> NAME/KEY: SITE
<222> LOCATION: (1)..(30)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 5 may be Glu or gamma-carboxy-Glu; Xaa at residues 6, 7,
      18 and 19 may be Pro or
      hydroxy-Pro; Xaa at residue 24 may be Trp or bromo-Trp

<400> SEQUENCE: 135

Asp Xaa Asp Cys Xaa Xaa Xaa Gly Asn Phe Cys Gly Met Ile Lys Ile
1               5                   10                  15

Gly Xaa Xaa Cys Cys Ser Gly Xaa Cys Phe Phe Ala Cys Ala
            20                  25                  30

<210> SEQ ID NO 136
<211> LENGTH: 685
<212> TYPE: DNA
<213> ORGANISM: Conus marmoreus
<220> FEATURE:
```

```
<221> NAME/KEY: CDS
<222> LOCATION: (111)..(212)

<400> SEQUENCE: 136
ggtcgacatc atcatcatca tcgatccatc tgtccatcca tctattcatt cattcgtggc      60
caaactgtaa taataatgc aagtctctct ttctgtttgt atctgacaga ttg aac        116
                                                       Leu Asn
                                                         1 acg aga gac gac gat tgc gaa cct cct gga aat ttt tgt ggc atg ata      164
Thr Arg Asp Asp Asp Cys Glu Pro Pro Gly Asn Phe Cys Gly Met Ile
        5                   10                  15 aaa att ggg ccg cct tgc tgc agt ggc tgg tgc ttt ttc gcc tgc gcc      212
Lys Ile Gly Pro Pro Cys Cys Ser Gly Trp Cys Phe Phe Ala Cys Ala
 20                  25                  30 taaaactgcc gtgatgtctt ctcttcccct ctagtagtag taggcggccg ctctagagga    272
tccaagctta cgtacgcgtg catgcgacgt catagctctt ctatagtgtc acctaaattc    332
aattcactgg ccgtcgtttt acaacgtcgt gactgggaaa accctggcgt tacccaactt    392
aatcgccttg cagcacatcc ccctttcgcc agctggcgta atagcgaaga ggcccgcacc    452
gatcgccctt cccaacagtt gcgcagcctg aatggcgaat gggacgcgcc ctgtagcggc    512
gcattaagcg cggcgggtgt ggtggttacg ccgcagccgt gacccgctac acttgccagc    572
gccctagcgc ccgctccttt cgctttcttc cttcctttct cgccacgttc gccggctttt    632
cccgtcaagc tctaaatcgg gggctccttt agggtccgat ttaagtgctt tac            685

<210> SEQ ID NO 137
<211> LENGTH: 34
<212> TYPE: PRT
<213> ORGANISM: Conus marmoreus

<400> SEQUENCE: 137

Leu Asn Thr Arg Asp Asp Asp Cys Glu Pro Pro Gly Asn Phe Cys Gly
 1               5                  10                  15

Met Ile Lys Ile Gly Pro Pro Cys Cys Ser Gly Trp Cys Phe Phe Ala
             20                  25                  30

Cys Ala

<210> SEQ ID NO 138
<211> LENGTH: 30
<212> TYPE: PRT
<213> ORGANISM: Conus marmoreus
<220> FEATURE:
<221> NAME/KEY: SITE
<222> LOCATION: (1)..(30)
<223> OTHER INFORMATION: Xaa at residue 5 may be Glu or
      gamma-carboxy-Glu; Xaa at residues 6, 7, 18 and 19 may be Pro or
      hydroxy-Pro; Xaa at residue 24 maybe Trp or bromo-Trp

<400> SEQUENCE: 138

Asp Asp Asp Cys Xaa Xaa Xaa Gly Asn Phe Cys Gly Met Ile Lys Ile
 1               5                  10                  15

Gly Xaa Xaa Cys Cys Ser Gly Xaa Cys Phe Phe Ala Cys Ala
             20                  25                  30

<210> SEQ ID NO 139
<211> LENGTH: 126
<212> TYPE: DNA
<213> ORGANISM: Conus regius
<220> FEATURE:
<221> NAME/KEY: CDS
<222> LOCATION: (1)..(96)
```

```
<400> SEQUENCE: 139 ttg aac cag aga gac tgc ctt agt aaa aac gct ttc tgt gcc tgg ccg      48
Leu Asn Gln Arg Asp Cys Leu Ser Lys Asn Ala Phe Cys Ala Trp Pro
1               5                   10                  15 ata ctt gga cca ctg tgc tgc agt ggc tgg tgc tta tac gtc tgc atg      96
Ile Leu Gly Pro Leu Cys Cys Ser Gly Trp Cys Leu Tyr Val Cys Met
            20                  25                  30 taaaactgcc gtgatgtctt ctatcccctc                                    126

<210> SEQ ID NO 140
<211> LENGTH: 32
<212> TYPE: PRT
<213> ORGANISM: Conus regius

<400> SEQUENCE: 140

Leu Asn Gln Arg Asp Cys Leu Ser Lys Asn Ala Phe Cys Ala Trp Pro
1               5                   10                  15

Ile Leu Gly Pro Leu Cys Cys Ser Gly Trp Cys Leu Tyr Val Cys Met
            20                  25                  30

<210> SEQ ID NO 141
<211> LENGTH: 28
<212> TYPE: PRT
<213> ORGANISM: Conus regius
<220> FEATURE:
<221> NAME/KEY: SITE
<222> LOCATION: (1)..(28)
<223> OTHER INFORMATION: Xaa at residues 11 and 22 may be Trp or
      bromo-Trp; Xaa at residues 12 and 16 may be Pro or hydroxy-Pro;
      Xaa at residue 25 may be Tyr, 125-I-Tyr, mono-iodo-Tyr,
      di-iodo-Tyr, O-sulpho-Tyr or O-phos
      pho-Tyr

<400> SEQUENCE: 141

Asp Cys Leu Ser Lys Asn Ala Phe Cys Ala Xaa Xaa Ile Leu Gly Xaa
1               5                   10                  15

Leu Cys Cys Ser Gly Xaa Cys Leu Xaa Val Cys Met
            20                  25

<210> SEQ ID NO 142
<211> LENGTH: 133
<212> TYPE: DNA
<213> ORGANISM: Conus radiatus
<220> FEATURE:
<221> NAME/KEY: CDS
<222> LOCATION: (2)..(103)

<400> SEQUENCE: 142 a ttg aac aag aaa ggt gat gac tgc ctt gct gtt aaa aaa aat tgt ggc    49
  Leu Asn Lys Lys Gly Asp Asp Cys Leu Ala Val Lys Lys Asn Cys Gly
  1               5                   10                  15 ttt cca aaa ctt gga ggg cca tgc tgc agt ggc ttg tgc ttt ttc gtc      97
Phe Pro Lys Leu Gly Gly Pro Cys Cys Ser Gly Leu Cys Phe Phe Val
                20                  25                  30 tgc gcc taaaactgcc gtgatgtctt ctcctcccct                            133
Cys Ala

<210> SEQ ID NO 143
<211> LENGTH: 34
<212> TYPE: PRT
<213> ORGANISM: Conus radiatus

<400> SEQUENCE: 143
```

```
Leu Asn Lys Lys Gly Asp Asp Cys Leu Ala Val Lys Lys Asn Cys Gly
1               5                   10                  15

Phe Pro Lys Leu Gly Gly Pro Cys Cys Ser Gly Leu Cys Phe Phe Val
                20                  25                  30

Cys Ala

<210> SEQ ID NO 144
<211> LENGTH: 30
<212> TYPE: PRT
<213> ORGANISM: Conus radiatus
<220> FEATURE:
<221> NAME/KEY: SITE
<222> LOCATION: (1)..(30)
<223> OTHER INFORMATION: Xaa at residues 14 and 19 may be Pro or
      hydroxy-Pro.

<400> SEQUENCE: 144

Gly Asp Asp Cys Leu Ala Val Lys Lys Asn Cys Gly Phe Xaa Lys Leu
1               5                   10                  15

Gly Gly Xaa Cys Cys Ser Gly Leu Cys Phe Phe Val Cys Ala
                20                  25                  30

<210> SEQ ID NO 145
<211> LENGTH: 127
<212> TYPE: DNA
<213> ORGANISM: Conus regius
<220> FEATURE:
<221> NAME/KEY: CDS
<222> LOCATION: (1)..(96)

<400> SEQUENCE: 145 ttg aat cag agc gac tgc ctt cct aga gac aca ttc tgt gcc ttg ccg      48
Leu Asn Gln Ser Asp Cys Leu Pro Arg Asp Thr Phe Cys Ala Leu Pro
1               5                   10                  15 caa ctt gga cta ctg tgc tgc agt ggc cgg tgc tta ctc ttc tgc gtg      96
Gln Leu Gly Leu Leu Cys Cys Ser Gly Arg Cys Leu Leu Phe Cys Val
                20                  25                  30 taaaactgcc gtgatgtctt ctcctcccct c                                   127

<210> SEQ ID NO 146
<211> LENGTH: 32
<212> TYPE: PRT
<213> ORGANISM: Conus regius

<400> SEQUENCE: 146

Leu Asn Gln Ser Asp Cys Leu Pro Arg Asp Thr Phe Cys Ala Leu Pro
1               5                   10                  15

Gln Leu Gly Leu Leu Cys Cys Ser Gly Arg Cys Leu Leu Phe Cys Val
                20                  25                  30

<210> SEQ ID NO 147
<211> LENGTH: 28
<212> TYPE: PRT
<213> ORGANISM: Conus regius
<220> FEATURE:
<221> NAME/KEY: SITE
<222> LOCATION: (1)..(28)
<223> OTHER INFORMATION: Xaa at residues 4 and 12 may be Pro or
      hydroxy-Pro.

<400> SEQUENCE: 147

Asp Cys Leu Xaa Arg Asp Thr Phe Cys Ala Leu Xaa Gln Leu Gly Leu
1               5                   10                  15
```

Leu Cys Cys Ser Gly Arg Cys Leu Leu Phe Cys Val
              20                  25

<210> SEQ ID NO 148
<211> LENGTH: 345
<212> TYPE: DNA
<213> ORGANISM: Conus aurisiacus
<220> FEATURE:
<221> NAME/KEY: CDS
<222> LOCATION: (1)..(234)

<400> SEQUENCE: 148

```
atg aaa ctg acg tgc gtg atg acc gtt gct gtg ctg ttc ttg acc gcc      48
Met Lys Leu Thr Cys Val Met Thr Val Ala Val Leu Phe Leu Thr Ala
1               5                   10                  15 tgg aca ttc gtc acg gct gat gac tcc aga aat gga ctg aag aat ctt      96
Trp Thr Phe Val Thr Ala Asp Asp Ser Arg Asn Gly Leu Lys Asn Leu
                20                  25                  30 ttt ccg aag gca cgt cat gaa atg aag aac ccc gaa gcc tct aaa ttg     144
Phe Pro Lys Ala Arg His Glu Met Lys Asn Pro Glu Ala Ser Lys Leu
            35                  40                  45 aac aag aga gat ggg tgc tct aat gct ggt gca ttt tgt ggc atc cat     192
Asn Lys Arg Asp Gly Cys Ser Asn Ala Gly Ala Phe Cys Gly Ile His
        50                  55                  60 cca gga ctc tgc tgc agc gag att tgc att gtt tgg tgc aca             234
Pro Gly Leu Cys Cys Ser Glu Ile Cys Ile Val Trp Cys Thr
65                  70                  75 tgagtcgtat tctgctggta cattttgtgg cttcaacgga ggactctgct gcagcaacct   294
ttgcttattt ttcgtgtgct taacatattc gtgatgtctt ctactcccat c            345
```

<210> SEQ ID NO 149
<211> LENGTH: 78
<212> TYPE: PRT
<213> ORGANISM: Conus aurisiacus

<400> SEQUENCE: 149

Met Lys Leu Thr Cys Val Met Thr Val Ala Val Leu Phe Leu Thr Ala
1               5                   10                  15

Trp Thr Phe Val Thr Ala Asp Asp Ser Arg Asn Gly Leu Lys Asn Leu
                20                  25                  30

Phe Pro Lys Ala Arg His Glu Met Lys Asn Pro Glu Ala Ser Lys Leu
            35                  40                  45

Asn Lys Arg Asp Gly Cys Ser Asn Ala Gly Ala Phe Cys Gly Ile His
        50                  55                  60

Pro Gly Leu Cys Cys Ser Glu Ile Cys Ile Val Trp Cys Thr
65                  70                  75

<210> SEQ ID NO 150
<211> LENGTH: 27
<212> TYPE: PRT
<213> ORGANISM: Conus aurisiacus
<220> FEATURE:
<221> NAME/KEY: SITE
<222> LOCATION: (1)..(27)
<223> OTHER INFORMATION: Xaa at residue 14 may be Pro or hydroxy-Pro;
      Xaa at residue 20 may be Glu or gamma-carboxy-Glu; Xaa at residue
      25 may be Trp or bromo-Trp

<400> SEQUENCE: 150

Asp Gly Cys Ser Asn Ala Gly Ala Phe Cys Gly Ile His Xaa Gly Leu
1               5                   10                  15

Cys Cys Ser Xaa Ile Cys Ile Val Xaa Cys Thr
            20                  25

```
<210> SEQ ID NO 151
<211> LENGTH: 412
<212> TYPE: DNA
<213> ORGANISM: Conus purpurascens
<220> FEATURE:
<221> NAME/KEY: CDS
<222> LOCATION: (1)..(243)

<400> SEQUENCE: 151 atg aaa ctg acg tgc gtg atg atc gtt gct gtg ctg ttc ttg act gcc      48
Met Lys Leu Thr Cys Val Met Ile Val Ala Val Leu Phe Leu Thr Ala
1               5                   10                  15 tgg aca ttc gtc acg gct gat gac tcc aaa aat gga ctg gag aat cat      96
Trp Thr Phe Val Thr Ala Asp Asp Ser Lys Asn Gly Leu Glu Asn His
            20                  25                  30 ttt tgg aag gca cgt gac gaa atg aag aac cgc gaa gcc tct aaa ttg     144
Phe Trp Lys Ala Arg Asp Glu Met Lys Asn Arg Glu Ala Ser Lys Leu
35                  40                  45 gac aaa aag gaa gcc tgc tat gcg cct ggt act ttt tgt ggc ata aag     192
Asp Lys Lys Glu Ala Cys Tyr Ala Pro Gly Thr Phe Cys Gly Ile Lys
    50                  55                  60 ccc ggg cta tgc tgc agt gag ttt tgt ctc ccg ggc gtc tgc ttc ggt     240
Pro Gly Leu Cys Cys Ser Glu Phe Cys Leu Pro Gly Val Cys Phe Gly
65                  70                  75                  80 ggt taactgccgt gatgtcttct actcccctct gtgctacctg gcttgatctt          293
Gly
tgatcggcgt gtgcccttca ctggttatga acccactgat cttacctctc ttgaaggacc   353
tctggggtcc agcatccaaa taagcgacat cccaatgaaa aaaaaaaaa aaaaaaaa      412

<210> SEQ ID NO 152
<211> LENGTH: 81
<212> TYPE: PRT
<213> ORGANISM: Conus purpurascens

<400> SEQUENCE: 152

Met Lys Leu Thr Cys Val Met Ile Val Ala Val Leu Phe Leu Thr Ala
1               5                   10                  15

Trp Thr Phe Val Thr Ala Asp Asp Ser Lys Asn Gly Leu Glu Asn His
            20                  25                  30

Phe Trp Lys Ala Arg Asp Glu Met Lys Asn Arg Glu Ala Ser Lys Leu
        35                  40                  45

Asp Lys Lys Glu Ala Cys Tyr Ala Pro Gly Thr Phe Cys Gly Ile Lys
    50                  55                  60

Pro Gly Leu Cys Cys Ser Glu Phe Cys Leu Pro Gly Val Cys Phe Gly
65                  70                  75                  80

Gly

<210> SEQ ID NO 153
<211> LENGTH: 29
<212> TYPE: PRT
<213> ORGANISM: Conus purpurascens
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 6, 14 and 24 may be Pro or hydroxy-Pro

<400> SEQUENCE: 153
```

-continued

```
Xaa Ala Cys Xaa Ala Xaa Gly Thr Phe Cys Gly Ile Lys Xaa Gly Leu
1               5                   10                  15

Cys Cys Ser Xaa Phe Cys Leu Xaa Gly Val Cys Phe Gly
            20                  25
```

<210> SEQ ID NO 154
<211> LENGTH: 29
<212> TYPE: PRT
<213> ORGANISM: Conus purpurascens
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 6, 14 and 24 may be Pro or hydroxy-Pro

<400> SEQUENCE: 154

```
Xaa Ala Cys Xaa Ala Xaa Gly Thr Ala Cys Gly Ile Lys Xaa Gly Leu
1               5                   10                  15

Cys Cys Ser Xaa Phe Cys Leu Xaa Gly Val Cys Phe Gly
            20                  25
```

<210> SEQ ID NO 155
<211> LENGTH: 29
<212> TYPE: PRT
<213> ORGANISM: Conus purpurascens
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 6, 14 and 24 may be Pro or hydroxy-Pro

<400> SEQUENCE: 155

```
Xaa Ala Cys Xaa Ala Xaa Gly Thr Phe Cys Gly Ala Lys Xaa Gly Leu
1               5                   10                  15

Cys Cys Ser Xaa Phe Cys Leu Xaa Gly Val Cys Phe Gly
            20                  25
```

<210> SEQ ID NO 156
<211> LENGTH: 29
<212> TYPE: PRT
<213> ORGANISM: Conus purpurascens
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 6, 14 and 24 may be Pro or hydroxy-Pro

<400> SEQUENCE: 156

```
Xaa Ala Cys Xaa Ala Xaa Gly Ala Phe Cys Gly Ile Lys Xaa Gly Leu
1               5                   10                  15

Cys Cys Ser Xaa Phe Cys Leu Xaa Gly Val Cys Phe Gly
            20                  25
```

<210> SEQ ID NO 157
<211> LENGTH: 289
<212> TYPE: DNA
<213> ORGANISM: Conus magus
<220> FEATURE:
<221> NAME/KEY: CDS
<222> LOCATION: (1)..(252)

<400> SEQUENCE: 157

```
atg aaa ctg acg tgc gtg atg atc gtt gct gtg ctg ttc ttg acc acc      48
Met Lys Leu Thr Cys Val Met Ile Val Ala Val Leu Phe Leu Thr Thr
1               5                   10                  15 tgg aca ttc gtc acg gct gat gac tcc aga tat gga ttg aag aat ctt      96
Trp Thr Phe Val Thr Ala Asp Asp Ser Arg Tyr Gly Leu Lys Asn Leu
                20                  25                  30 ttt ccg aag gca cgt cat gaa atg aag aac cct gaa gcc tct aaa ttg     144
Phe Pro Lys Ala Arg His Glu Met Lys Asn Pro Glu Ala Ser Lys Leu
        35                  40                  45 aac aag aga gat ggg tgc tat aat gct ggt aca ttt tgt ggc atc cgt     192
Asn Lys Arg Asp Gly Cys Tyr Asn Ala Gly Thr Phe Cys Gly Ile Arg
50                  55                  60 cca gga ctc tgc tgc agc gag ttt tgc ttt tta tgg tgc ata aca ttt     240
Pro Gly Leu Cys Cys Ser Glu Phe Cys Phe Leu Trp Cys Ile Thr Phe
65                  70                  75                  80 gtt gat tct ggc taacagtgtg cgttggttag tgtcttctcc tcccctc            289
Val Asp Ser Gly
```

<210> SEQ ID NO 158
<211> LENGTH: 84
<212> TYPE: PRT
<213> ORGANISM: Conus magus

<400> SEQUENCE: 158

Met Lys Leu Thr Cys Val Met Ile Val Ala Val Leu Phe Leu Thr Thr
1               5                   10                  15

Trp Thr Phe Val Thr Ala Asp Asp Ser Arg Tyr Gly Leu Lys Asn Leu
                20                  25                  30

Phe Pro Lys Ala Arg His Glu Met Lys Asn Pro Glu Ala Ser Lys Leu
        35                  40                  45

Asn Lys Arg Asp Gly Cys Tyr Asn Ala Gly Thr Phe Cys Gly Ile Arg
50                  55                  60

Pro Gly Leu Cys Cys Ser Glu Phe Cys Phe Leu Trp Cys Ile Thr Phe
65                  70                  75                  80

Val Asp Ser Gly

<210> SEQ ID NO 159
<211> LENGTH: 32
<212> TYPE: PRT
<213> ORGANISM: Conus magus
<220> FEATURE:
<221> NAME/KEY: SITE
<222> LOCATION: (1)..(32)
<223> OTHER INFORMATION: Xaa at residue 4 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro; Xaa at residue 20 may be Glu
      or gamma-carboxy-Glu; Xaa at residue 25 may be Trp or bromo-Trp

<400> SEQUENCE: 159

Asp Gly Cys Xaa Asn Ala Gly Thr Phe Cys Gly Ile Arg Xaa Gly Leu
1               5                   10                  15

Cys Cys Ser Xaa Phe Cys Phe Leu Xaa Cys Ile Thr Phe Val Asp Ser
                20                  25                  30

<210> SEQ ID NO 160
<211> LENGTH: 273
<212> TYPE: DNA
<213> ORGANISM: Conus magus
<220> FEATURE:
<221> NAME/KEY: CDS
<222> LOCATION: (1)..(249)

```
<400> SEQUENCE: 160 atg aaa ctg acg tgc gtg atg atc gtt gct gtg ctg ttc ttg acc acc      48
Met Lys Leu Thr Cys Val Met Ile Val Ala Val Leu Phe Leu Thr Thr
1               5                   10                  15 tgg aca ttc gtc acg gct gat gac tcc aga tat gga ttg aag aat ctt      96
Trp Thr Phe Val Thr Ala Asp Asp Ser Arg Tyr Gly Leu Lys Asn Leu
            20                  25                  30 ttt ccg aag gca cgt cat gaa atg aag aac cct gaa gcc tct aaa ttg     144
Phe Pro Lys Ala Arg His Glu Met Lys Asn Pro Glu Ala Ser Lys Leu
        35                  40                  45 aac aag aga gat gaa tgc tat cct cct ggt aca ttt tgt ggc atc aaa     192
Asn Lys Arg Asp Glu Cys Tyr Pro Pro Gly Thr Phe Cys Gly Ile Lys
    50                  55                  60 cca gga ctt tgc tgc agc gcg ata tgc tta tcg ttt gtc tgc ata tca     240
Pro Gly Leu Cys Cys Ser Ala Ile Cys Leu Ser Phe Val Cys Ile Ser
65                  70                  75                  80 ttt gat ttt tgattgatgt cttctcctcc cctc                              273
Phe Asp Phe <210> SEQ ID NO 161
<211> LENGTH: 83
<212> TYPE: PRT
<213> ORGANISM: Conus magus

<400> SEQUENCE: 161

Met Lys Leu Thr Cys Val Met Ile Val Ala Val Leu Phe Leu Thr Thr
1               5                   10                  15

Trp Thr Phe Val Thr Ala Asp Asp Ser Arg Tyr Gly Leu Lys Asn Leu
            20                  25                  30

Phe Pro Lys Ala Arg His Glu Met Lys Asn Pro Glu Ala Ser Lys Leu
        35                  40                  45

Asn Lys Arg Asp Glu Cys Tyr Pro Pro Gly Thr Phe Cys Gly Ile Lys
    50                  55                  60

Pro Gly Leu Cys Cys Ser Ala Ile Cys Leu Ser Phe Val Cys Ile Ser
65                  70                  75                  80

Phe Asp Phe

<210> SEQ ID NO 162
<211> LENGTH: 32
<212> TYPE: PRT
<213> ORGANISM: Conus magus
<220> FEATURE:
<221> NAME/KEY: SITE
<222> LOCATION: (1)..(32)
<223> OTHER INFORMATION: Xaa at residue 2 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 5, 6and 14 may be Pro or hydro
      xy-Pro

<400> SEQUENCE: 162

Asp Xaa Cys Xaa Xaa Xaa Gly Thr Phe Cys Gly Ile Lys Xaa Gly Leu
1               5                   10                  15

Cys Cys Ser Ala Ile Cys Leu Ser Phe Val Cys Ile Ser Phe Asp Phe
            20                  25                  30

<210> SEQ ID NO 163
<211> LENGTH: 289
<212> TYPE: DNA
<213> ORGANISM: Conus magus
<220> FEATURE:
```

```
<221> NAME/KEY: CDS
<222> LOCATION: (1)..(252)

<400> SEQUENCE: 163 atg aaa ctg acg tgc gtg atg atc gtt gct gta ctg ttc ttg acc gcc        48
Met Lys Leu Thr Cys Val Met Ile Val Ala Val Leu Phe Leu Thr Ala
1               5                   10                  15 tgg aca ttc gtc acg gct gat gac tcc aga tat gga ctg aag gat ctg        96
Trp Thr Phe Val Thr Ala Asp Asp Ser Arg Tyr Gly Leu Lys Asp Leu
            20                  25                  30 ttt ccg aag gaa cgt cat gaa atg aag aac ccc gaa gcc tct aaa ttg       144
Phe Pro Lys Glu Arg His Glu Met Lys Asn Pro Glu Ala Ser Lys Leu
        35                  40                  45 aac cag aga gaa gcc tgc tat aat gct ggt tca ttt tgt ggc atc cat       192
Asn Gln Arg Glu Ala Cys Tyr Asn Ala Gly Ser Phe Cys Gly Ile His
    50                  55                  60 cca gga ctc tgc tgc agc gag ttt tgc att ctt tgg tgc ata aca ttt       240
Pro Gly Leu Cys Cys Ser Glu Phe Cys Ile Leu Trp Cys Ile Thr Phe
65                  70                  75                  80 gtt gat tct ggc taactgtgtg cgttggttga tgtcttctcc tcccatc              289
Val Asp Ser Gly <210> SEQ ID NO 164
<211> LENGTH: 84
<212> TYPE: PRT
<213> ORGANISM: Conus magus

<400> SEQUENCE: 164

Met Lys Leu Thr Cys Val Met Ile Val Ala Val Leu Phe Leu Thr Ala
1               5                   10                  15

Trp Thr Phe Val Thr Ala Asp Asp Ser Arg Tyr Gly Leu Lys Asp Leu
            20                  25                  30

Phe Pro Lys Glu Arg His Glu Met Lys Asn Pro Glu Ala Ser Lys Leu
        35                  40                  45

Asn Gln Arg Glu Ala Cys Tyr Asn Ala Gly Ser Phe Cys Gly Ile His
    50                  55                  60

Pro Gly Leu Cys Cys Ser Glu Phe Cys Ile Leu Trp Cys Ile Thr Phe
65                  70                  75                  80

Val Asp Ser Gly

<210> SEQ ID NO 165
<211> LENGTH: 32
<212> TYPE: PRT
<213> ORGANISM: Conus magus
<220> FEATURE:
<221> NAME/KEY: SITE
<222> LOCATION: (1)..(32)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro; Xaa at residue 25 may be Trp
      or bromo-Trp

<400> SEQUENCE: 165

Xaa Ala Cys Xaa Asn Ala Gly Ser Phe Cys Gly Ile His Xaa Gly Leu
1               5                   10                  15

Cys Cys Ser Xaa Phe Cys Ile Leu Xaa Cys Ile Thr Phe Val Asp Ser
            20                  25                  30

<210> SEQ ID NO 166
<211> LENGTH: 271
<212> TYPE: DNA
```

```
<213> ORGANISM: Conus magus
<220> FEATURE:
<221> NAME/KEY: CDS
<222> LOCATION: (1)..(249)

<400> SEQUENCE: 166 atg aaa ctg acg tgc atg atg atc gtt gct gta ctg ttc ttg acc gcc      48
Met Lys Leu Thr Cys Met Met Ile Val Ala Val Leu Phe Leu Thr Ala
1               5                   10                  15 tgg aca ttc gtc acg gct gat gac tcc aga tat gga ctg aag gat ctg      96
Trp Thr Phe Val Thr Ala Asp Asp Ser Arg Tyr Gly Leu Lys Asp Leu
            20                  25                  30 ttt ccg aag gaa cgt cat gaa atg aag aac ccc gaa gcc tct aaa ttg     144
Phe Pro Lys Glu Arg His Glu Met Lys Asn Pro Glu Ala Ser Lys Leu
        35                  40                  45 aac cag aga gaa gcc tgc tat aat gct ggt aca ttt tgt ggc atc aaa     192
Asn Gln Arg Glu Ala Cys Tyr Asn Ala Gly Thr Phe Cys Gly Ile Lys
    50                  55                  60 cca gga ctt tgc tgc agc gcg ata tgc tta tcg ttt gtc tgc ata tca     240
Pro Gly Leu Cys Cys Ser Ala Ile Cys Leu Ser Phe Val Cys Ile Ser
65                  70                  75                  80 ttt gat ttg attgatgtct tctcctcccc tc                                 271
Phe Asp Leu <210> SEQ ID NO 167
<211> LENGTH: 83
<212> TYPE: PRT
<213> ORGANISM: Conus magus

<400> SEQUENCE: 167

Met Lys Leu Thr Cys Met Met Ile Val Ala Val Leu Phe Leu Thr Ala
1               5                   10                  15

Trp Thr Phe Val Thr Ala Asp Asp Ser Arg Tyr Gly Leu Lys Asp Leu
            20                  25                  30

Phe Pro Lys Glu Arg His Glu Met Lys Asn Pro Glu Ala Ser Lys Leu
        35                  40                  45

Asn Gln Arg Glu Ala Cys Tyr Asn Ala Gly Thr Phe Cys Gly Ile Lys
    50                  55                  60

Pro Gly Leu Cys Cys Ser Ala Ile Cys Leu Ser Phe Val Cys Ile Ser
65                  70                  75                  80

Phe Asp Leu

<210> SEQ ID NO 168
<211> LENGTH: 32
<212> TYPE: PRT
<213> ORGANISM: Conus magus
<220> FEATURE:
<221> NAME/KEY: SITE
<222> LOCATION: (1)..(32)
<223> OTHER INFORMATION: Xaa at residue 1 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro

<400> SEQUENCE: 168

Xaa Ala Cys Xaa Asn Ala Gly Thr Phe Cys Gly Ile Lys Xaa Gly Leu
1               5                   10                  15

Cys Cys Ser Ala Ile Cys Leu Ser Phe Val Cys Ile Ser Phe Asp Phe
            20                  25                  30

<210> SEQ ID NO 169
```

-continued

```
<211> LENGTH: 272
<212> TYPE: DNA
<213> ORGANISM: Conus ermineus
<220> FEATURE:
<221> NAME/KEY: CDS
<222> LOCATION: (1)..(243)

<400> SEQUENCE: 169 atg aaa ctg acg tgc gtg atg atc gtt gct gtg ctg ttc ttg act gcc      48
Met Lys Leu Thr Cys Val Met Ile Val Ala Val Leu Phe Leu Thr Ala
1               5                   10                  15 tgg aca ttc gtc acg gct gat gac tcc aaa aat gga ctg gag aat cat      96
Trp Thr Phe Val Thr Ala Asp Asp Ser Lys Asn Gly Leu Glu Asn His
            20                  25                  30 ttt tgg aag gca cgt gac gaa atg aag aac cgc gaa gcc tct aaa ttg     144
Phe Trp Lys Ala Arg Asp Glu Met Lys Asn Arg Glu Ala Ser Lys Leu
        35                  40                  45 gac aaa aag gaa gcc tgc tat ccg cct ggt act ttt tgt ggc ata aag     192
Asp Lys Lys Glu Ala Cys Tyr Pro Pro Gly Thr Phe Cys Gly Ile Lys
    50                  55                  60 ccc ggg cta tgc tgc agt gag ttg tgt tta ccg gcc gtc tgc gtc ggt     240
Pro Gly Leu Cys Cys Ser Glu Leu Cys Leu Pro Ala Val Cys Val Gly
65                  70                  75                  80 ggt taactgccgt gatgtcttct cctcccctc                                  272
Gly

<210> SEQ ID NO 170
<211> LENGTH: 81
<212> TYPE: PRT
<213> ORGANISM: Conus ermineus

<400> SEQUENCE: 170

Met Lys Leu Thr Cys Val Met Ile Val Ala Val Leu Phe Leu Thr Ala
1               5                   10                  15

Trp Thr Phe Val Thr Ala Asp Asp Ser Lys Asn Gly Leu Glu Asn His
            20                  25                  30

Phe Trp Lys Ala Arg Asp Glu Met Lys Asn Arg Glu Ala Ser Lys Leu
        35                  40                  45

Asp Lys Lys Glu Ala Cys Tyr Pro Pro Gly Thr Phe Cys Gly Ile Lys
    50                  55                  60

Pro Gly Leu Cys Cys Ser Glu Leu Cys Leu Pro Ala Val Cys Val Gly
65                  70                  75                  80

Gly

<210> SEQ ID NO 171
<211> LENGTH: 29
<212> TYPE: PRT
<213> ORGANISM: Conus ermineus
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 5, 6, 14 and 24 may be Pro or hydroxy-Pro

<400> SEQUENCE: 171

Xaa Ala Cys Xaa Xaa Xaa Gly Thr Phe Cys Gly Ile Lys Xaa Gly Leu
1               5                   10                  15

Cys Cys Ser Xaa Leu Cys Leu Xaa Ala Val Cys Val Gly
            20                  25
```

-continued

```
<210> SEQ ID NO 172
<211> LENGTH: 272
<212> TYPE: DNA
<213> ORGANISM: Conus purpurascens
<220> FEATURE:
<221> NAME/KEY: CDS
<222> LOCATION: (1)..(243)

<400> SEQUENCE: 172 atg aaa ctg acg tgc atg atg atc gtt gct gtg ctg ttc ttg act gcc      48
Met Lys Leu Thr Cys Met Met Ile Val Ala Val Leu Phe Leu Thr Ala
1               5                   10                  15 tgg aca ttc gtc acg gct gat gac tcc aaa aat gga ctg gag aat cat      96
Trp Thr Phe Val Thr Ala Asp Asp Ser Lys Asn Gly Leu Glu Asn His
            20                  25                  30 ttt tgg aag gca cgt gac gaa atg aag aac cgc gaa gcc tct aaa ttg     144
Phe Trp Lys Ala Arg Asp Glu Met Lys Asn Arg Glu Ala Ser Lys Leu
        35                  40                  45 gac aaa aag gaa gcc tgc tat ccg cct ggt act ttt tgt ggc ata aag     192
Asp Lys Lys Glu Ala Cys Tyr Pro Pro Gly Thr Phe Cys Gly Ile Lys
50                  55                  60 ccc ggg cta tgc tgc agt gag ttg tgt tta ccg gcc gtc tgc gtc ggt     240
Pro Gly Leu Cys Cys Ser Glu Leu Cys Leu Pro Ala Val Cys Val Gly
65                  70                  75                  80 ggt taactgccgt gatgtcttct cctcccctc                                  272
Gly

<210> SEQ ID NO 173
<211> LENGTH: 81
<212> TYPE: PRT
<213> ORGANISM: Conus purpurascens

<400> SEQUENCE: 173

Met Lys Leu Thr Cys Met Met Ile Val Ala Val Leu Phe Leu Thr Ala
1               5                   10                  15

Trp Thr Phe Val Thr Ala Asp Asp Ser Lys Asn Gly Leu Glu Asn His
            20                  25                  30

Phe Trp Lys Ala Arg Asp Glu Met Lys Asn Arg Glu Ala Ser Lys Leu
        35                  40                  45

Asp Lys Lys Glu Ala Cys Tyr Pro Pro Gly Thr Phe Cys Gly Ile Lys
50                  55                  60

Pro Gly Leu Cys Cys Ser Glu Leu Cys Leu Pro Ala Val Cys Val Gly
65                  70                  75                  80

Gly

<210> SEQ ID NO 174
<211> LENGTH: 29
<212> TYPE: PRT
<213> ORGANISM: Conus purpurascens
<220> FEATURE:
<221> NAME/KEY: SITE
<222> LOCATION: (1)..(29)
<223> OTHER INFORMATION: Xaa at residues 1 and 20 may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 14 and 24 may be Pro orhydroxy-Pro

<400> SEQUENCE: 174

Xaa Ala Cys Xaa Xaa Xaa Gly Thr Phe Cys Gly Ile Lys Xaa Gly Leu
1               5                   10                  15

Cys Cys Ser Xaa Leu Cys Leu Xaa Ala Val Cys Val Gly
            20                  25
```

-continued

```
<210> SEQ ID NO 175
<211> LENGTH: 266
<212> TYPE: DNA
<213> ORGANISM: Conus striatus
<220> FEATURE:
<221> NAME/KEY: CDS
<222> LOCATION: (1)..(246)

<400> SEQUENCE: 175 atg aaa ctg acg tgc gtg atg atc gtt gct gtg ctg ttc ttg acc act       48
Met Lys Leu Thr Cys Val Met Ile Val Ala Val Leu Phe Leu Thr Thr
1               5                  10                  15 tgg aca ttc gtc acg gct gat gac tcc aga tat gga ttg aag aat ctt       96
Trp Thr Phe Val Thr Ala Asp Asp Ser Arg Tyr Gly Leu Lys Asn Leu
                20                  25                  30 ttt ccg aag gca cgt cat gaa atg aag aac ccc gaa gcc tct aaa ttg      144
Phe Pro Lys Ala Arg His Glu Met Lys Asn Pro Glu Ala Ser Lys Leu
            35                  40                  45 aac aag aga gaa ggg tgc tct agt ggt ggt aca ttt tgt ggc atc cat      192
Asn Lys Arg Glu Gly Cys Ser Ser Gly Gly Thr Phe Cys Gly Ile His
        50                  55                  60 cca gga ctc tgc tgc agc gag ttt tgc ttt ctt tgg tgc ata aca ttt      240
Pro Gly Leu Cys Cys Ser Glu Phe Cys Phe Leu Trp Cys Ile Thr Phe
65                  70                  75                  80 att gat tgatgtcttc tcctcccctc                                        266
Ile Asp <210> SEQ ID NO 176
<211> LENGTH: 82
<212> TYPE: PRT
<213> ORGANISM: Conus striatus

<400> SEQUENCE: 176

Met Lys Leu Thr Cys Val Met Ile Val Ala Val Leu Phe Leu Thr Thr
1               5                  10                  15

Trp Thr Phe Val Thr Ala Asp Asp Ser Arg Tyr Gly Leu Lys Asn Leu
                20                  25                  30

Phe Pro Lys Ala Arg His Glu Met Lys Asn Pro Glu Ala Ser Lys Leu
            35                  40                  45

Asn Lys Arg Glu Gly Cys Ser Ser Gly Gly Thr Phe Cys Gly Ile His
        50                  55                  60

Pro Gly Leu Cys Cys Ser Glu Phe Cys Phe Leu Trp Cys Ile Thr Phe
65                  70                  75                  80

Ile Asp

<210> SEQ ID NO 177
<211> LENGTH: 31
<212> TYPE: PRT
<213> ORGANISM: Conus striatus
<220> FEATURE:
<221> NAME/KEY: SITE
<222> LOCATION: (1)..(31)
<223> OTHER INFORMATION: Xaa at residues 1 and 20 may be Glu or
      gamma-carboxy-Glu; Xaa at residue 14 may be Pro or hydroxy-Pro;
      Xaa at residue 25 may be Trp or bromo-Trp

<400> SEQUENCE: 177

Xaa Gly Cys Ser Ser Gly Gly Thr Phe Cys Gly Ile His Xaa Gly Leu
1               5                  10                  15

Cys Cys Ser Xaa Phe Cys Phe Leu Xaa Cys Ile Thr Phe Ile Asp
                20                  25                  30
```

-continued

```
<210> SEQ ID NO 178
<211> LENGTH: 266
<212> TYPE: DNA
<213> ORGANISM: Conus striatus
<220> FEATURE:
<221> NAME/KEY: CDS
<222> LOCATION: (1)..(246)

<400> SEQUENCE: 178 atg aaa ctg acg tgc gtg atg atc gtt gct gtg ctg ttc ttg acc act      48
Met Lys Leu Thr Cys Val Met Ile Val Ala Val Leu Phe Leu Thr Thr
1               5                   10                  15 tgg aca ttc gtc acg gct gat gac tcc aga tat gga ttg aag aat ctt      96
Trp Thr Phe Val Thr Ala Asp Asp Ser Arg Tyr Gly Leu Lys Asn Leu
                20                  25                  30 ttt ccg aag gca cgt cat gaa atg aag aac ccc gaa gcc tct aaa ttg     144
Phe Pro Lys Ala Arg His Glu Met Lys Asn Pro Glu Ala Ser Lys Leu
            35                  40                  45 aac aag aga gat ggg tgc tct agt ggt ggt aca ttt tgt ggc atc cat     192
Asn Lys Arg Asp Gly Cys Ser Ser Gly Gly Thr Phe Cys Gly Ile His
        50                  55                  60 cca gga ctc tgc tgc agc gag ttt tgc ttt ctt tgg tgc ata aca ttt     240
Pro Gly Leu Cys Cys Ser Glu Phe Cys Phe Leu Trp Cys Ile Thr Phe
65                  70                  75                  80 att gat tgatgtcttc tcctcccctc                                        266
Ile Asp <210> SEQ ID NO 179
<211> LENGTH: 82
<212> TYPE: PRT
<213> ORGANISM: Conus striatus

<400> SEQUENCE: 179

Met Lys Leu Thr Cys Val Met Ile Val Ala Val Leu Phe Leu Thr Thr
1               5                   10                  15

Trp Thr Phe Val Thr Ala Asp Asp Ser Arg Tyr Gly Leu Lys Asn Leu
                20                  25                  30

Phe Pro Lys Ala Arg His Glu Met Lys Asn Pro Glu Ala Ser Lys Leu
            35                  40                  45

Asn Lys Arg Asp Gly Cys Ser Ser Gly Gly Thr Phe Cys Gly Ile His
        50                  55                  60

Pro Gly Leu Cys Cys Ser Glu Phe Cys Phe Leu Trp Cys Ile Thr Phe
65                  70                  75                  80

Ile Asp

<210> SEQ ID NO 180
<211> LENGTH: 31
<212> TYPE: PRT
<213> ORGANISM: Conus striatus
<220> FEATURE:
<221> NAME/KEY: SITE
<222> LOCATION: (1)..(31)
<223> OTHER INFORMATION: Xaa at residue 20 may be Glu or
      gamma-carboxy-Glu; Xaa at residue 14 may be Pro or hydroxy-Pro;
      Xaa at residue 25 may be Trp or bromo-Trp

<400> SEQUENCE: 180

Asp Gly Cys Ser Ser Gly Gly Thr Phe Cys Gly Ile His Xaa Gly Leu
1               5                   10                  15

Cys Cys Ser Xaa Phe Cys Phe Leu Xaa Cys Ile Thr Phe Ile Asp
                20                  25                  30
```

```
<210> SEQ ID NO 181
<211> LENGTH: 31
<212> TYPE: PRT
<213> ORGANISM: Conus striolatus
<220> FEATURE:
<221> NAME/KEY: SITE
<222> LOCATION: (1)..(31)
<223> OTHER INFORMATION: Xaa at residues 6 and 14 may be Pro or
      hydroxy-Pro; Xaa at residue 31may be Glu or gamma-carboxy-Glu

<400> SEQUENCE: 181

Ser Lys Cys Phe Ser Xaa Gly Thr Phe Cys Gly Ile Lys Xaa Gly Leu
1               5                   10                  15

Cys Cys Ser Val Arg Cys Phe Ser Leu Phe Cys Ile Ser Phe Xaa
            20                  25                  30

<210> SEQ ID NO 182
<211> LENGTH: 345
<212> TYPE: DNA
<213> ORGANISM: Conus catus
<220> FEATURE:
<221> NAME/KEY: CDS
<222> LOCATION: (1)..(234)

<400> SEQUENCE: 182 atg aaa ctg acg tgc atg atg atc gtt gct gtg ctg ttc ttg acc gcc      48
Met Lys Leu Thr Cys Met Met Ile Val Ala Val Leu Phe Leu Thr Ala
1               5                   10                  15 tgg aca ttc gtc acg gct gat gac tcc aga aat gga ctg aag aat ctt      96
Trp Thr Phe Val Thr Ala Asp Asp Ser Arg Asn Gly Leu Lys Asn Leu
            20                  25                  30 ttt ccg aag gca cgt cat gaa atg aag aac ccc gaa gcc tct aaa ttg     144
Phe Pro Lys Ala Arg His Glu Met Lys Asn Pro Glu Ala Ser Lys Leu
        35                  40                  45 aac aag aga tat ggg tgc tct aat gct ggt gca ttt tgt ggc atc cat     192
Asn Lys Arg Tyr Gly Cys Ser Asn Ala Gly Ala Phe Cys Gly Ile His
    50                  55                  60 cca gga ctc tgc tgc agc gag ctt tgc ctg gtt tgg tgc aca             234
Pro Gly Leu Cys Cys Ser Glu Leu Cys Leu Val Trp Cys Thr
65                  70                  75 tgagtgctat tcttctggta cattttgtgg cttcaacgga ggactctgct gcagcaacct   294
ttgcttattt tcgtgtgctt aacatttcgt gatgtcttct ctattcccct c            345

<210> SEQ ID NO 183
<211> LENGTH: 78
<212> TYPE: PRT
<213> ORGANISM: Conus catus

<400> SEQUENCE: 183

Met Lys Leu Thr Cys Met Met Ile Val Ala Val Leu Phe Leu Thr Ala
1               5                   10                  15

Trp Thr Phe Val Thr Ala Asp Asp Ser Arg Asn Gly Leu Lys Asn Leu
            20                  25                  30

Phe Pro Lys Ala Arg His Glu Met Lys Asn Pro Glu Ala Ser Lys Leu
        35                  40                  45

Asn Lys Arg Tyr Gly Cys Ser Asn Ala Gly Ala Phe Cys Gly Ile His
    50                  55                  60

Pro Gly Leu Cys Cys Ser Glu Leu Cys Leu Val Trp Cys Thr
65                  70                  75

<210> SEQ ID NO 184
```

```
<211> LENGTH: 27
<212> TYPE: PRT
<213> ORGANISM: Conus catus
<220> FEATURE:
<221> NAME/KEY: SITE
<222> LOCATION: (1)..(27)
<223> OTHER INFORMATION: Xaa at residue 1 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro; Xaa at residue 20 may be Glu
      or gamma-carboxy-Glu; Xaa at residue 25 may be Trp or bromo-Trp

<400> SEQUENCE: 184

Xaa Gly Cys Ser Asn Ala Gly Ala Phe Cys Gly Ile His Xaa Gly Leu
1               5                   10                  15

Cys Cys Ser Xaa Leu Cys Leu Val Xaa Cys Thr
            20                  25

<210> SEQ ID NO 185
<211> LENGTH: 345
<212> TYPE: DNA
<213> ORGANISM: Conus catus
<220> FEATURE:
<221> NAME/KEY: CDS
<222> LOCATION: (1)..(234)

<400> SEQUENCE: 185 atg aaa ctg acg tgt atg atg atc gtt gct gtg ctg ttc ttg acc gcc      48
Met Lys Leu Thr Cys Met Met Ile Val Ala Val Leu Phe Leu Thr Ala
1               5                   10                  15 tgg aca ttc gtc acg gct gat gac tcc aga tat gga ctg aag aat ctt      96
Trp Thr Phe Val Thr Ala Asp Asp Ser Arg Tyr Gly Leu Lys Asn Leu
            20                  25                  30 ttt ccg aag gca cgt cat gaa atg aag aac ccc gaa gcc tct aaa ttg     144
Phe Pro Lys Ala Arg His Glu Met Lys Asn Pro Glu Ala Ser Lys Leu
        35                  40                  45 aac aag aga tat ggg tgc tct aat gct ggt gca ttt tgt ggc atc cat     192
Asn Lys Arg Tyr Gly Cys Ser Asn Ala Gly Ala Phe Cys Gly Ile His
    50                  55                  60 cca gga ctc tgc tgc agc gag ctt tgc ctg ggt tgg tgc aca             234
Pro Gly Leu Cys Cys Ser Glu Leu Cys Leu Gly Trp Cys Thr
65                  70                  75 tgagtgctat tctactggta cattttgtgg cttcaacgga ggactctgct gcagcaacct   294
ttgcttattt tcgtgtgctt aacatttcgt gatgtcttct ctattcccct c            345

<210> SEQ ID NO 186
<211> LENGTH: 78
<212> TYPE: PRT
<213> ORGANISM: Conus catus

<400> SEQUENCE: 186

Met Lys Leu Thr Cys Met Met Ile Val Ala Val Leu Phe Leu Thr Ala
1               5                   10                  15

Trp Thr Phe Val Thr Ala Asp Asp Ser Arg Tyr Gly Leu Lys Asn Leu
            20                  25                  30

Phe Pro Lys Ala Arg His Glu Met Lys Asn Pro Glu Ala Ser Lys Leu
        35                  40                  45

Asn Lys Arg Tyr Gly Cys Ser Asn Ala Gly Ala Phe Cys Gly Ile His
    50                  55                  60

Pro Gly Leu Cys Cys Ser Glu Leu Cys Leu Gly Trp Cys Thr
65                  70                  75

<210> SEQ ID NO 187
```

```
<211> LENGTH: 27
<212> TYPE: PRT
<213> ORGANISM: Conus catus
<220> FEATURE:
<221> NAME/KEY: SITE
<222> LOCATION: (1)..(27)
<223> OTHER INFORMATION: Xaa at residue 1 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro; Xaa at residue 20 may be Glu
      or gamma-carboxy-Glu; Xaa at residue 25 may be Trp or bromo-Trp

<400> SEQUENCE: 187

Xaa Gly Cys Ser Asn Ala Gly Ala Phe Cys Gly Ile His Xaa Gly Leu
1               5                  10                  15

Cys Cys Ser Xaa Leu Cys Leu Gly Xaa Cys Thr
            20                  25

<210> SEQ ID NO 188
<211> LENGTH: 266
<212> TYPE: DNA
<213> ORGANISM: Conus distans
<220> FEATURE:
<221> NAME/KEY: CDS
<222> LOCATION: (1)..(246)

<400> SEQUENCE: 188 atg aaa ctg acg tgt ctg atg atc gtt gct gtg ctg ttc ttg acc gcc      48
Met Lys Leu Thr Cys Leu Met Ile Val Ala Val Leu Phe Leu Thr Ala
1               5                  10                  15 tgg aca ttc gtc acg gct gat gac tcc aga aat gga ttg gag aat ctc      96
Trp Thr Phe Val Thr Ala Asp Asp Ser Arg Asn Gly Leu Glu Asn Leu
            20                  25                  30 tct ccg aag gca cct cac gaa atg aag aac ccc gaa gcc tct aaa tcg     144
Ser Pro Lys Ala Pro His Glu Met Lys Asn Pro Glu Ala Ser Lys Ser
        35                  40                  45 aac aag aga tat gag tgc tat cta ctg gta cat ttt tgt ggc atc aac     192
Asn Lys Arg Tyr Glu Cys Tyr Leu Leu Val His Phe Cys Gly Ile Asn
    50                  55                  60 gga gga ctc tgc tgc agc aac ctt tgc tta ttt ttc gtg tgc tta aca     240
Gly Gly Leu Cys Cys Ser Asn Leu Cys Leu Phe Phe Val Cys Leu Thr
65                  70                  75                  80 ttt tcg tgatgtcttc tcctcccatc                                       266
Phe Ser

<210> SEQ ID NO 189
<211> LENGTH: 82
<212> TYPE: PRT
<213> ORGANISM: Conus distans

<400> SEQUENCE: 189

Met Lys Leu Thr Cys Leu Met Ile Val Ala Val Leu Phe Leu Thr Ala
1               5                  10                  15

Trp Thr Phe Val Thr Ala Asp Asp Ser Arg Asn Gly Leu Glu Asn Leu
            20                  25                  30

Ser Pro Lys Ala Pro His Glu Met Lys Asn Pro Glu Ala Ser Lys Ser
        35                  40                  45

Asn Lys Arg Tyr Glu Cys Tyr Leu Leu Val His Phe Cys Gly Ile Asn
    50                  55                  60

Gly Gly Leu Cys Cys Ser Asn Leu Cys Leu Phe Phe Val Cys Leu Thr
65                  70                  75                  80

Phe Ser
```

```
<210> SEQ ID NO 190
<211> LENGTH: 31
<212> TYPE: PRT
<213> ORGANISM: Conus distans
<220> FEATURE:
<221> NAME/KEY: SITE
<222> LOCATION: (1)..(31)
<223> OTHER INFORMATION: Xaa at residues 1 and 4 may be Tyr, 125-I-Tyr,
      mono-iodo-Tyr, di-iodo-Tyr, O-sulpho-Tyr or O-phospho-Tyr; Xaa at
      residue 2 may be Glu or gamma-carboxy-Glu

<400> SEQUENCE: 190

Xaa Xaa Cys Xaa Leu Leu Val His Phe Cys Gly Ile Asn Gly Gly Leu
1               5                   10                  15

Cys Cys Ser Asn Leu Cys Leu Phe Phe Val Cys Leu Thr Phe Ser
            20                  25                  30

<210> SEQ ID NO 191
<211> LENGTH: 113
<212> TYPE: DNA
<213> ORGANISM: Conus regius
<220> FEATURE:
<221> NAME/KEY: CDS
<222> LOCATION: (1)..(93)

<400> SEQUENCE: 191 ttg agc aag aga gac tgc ctt cct gac tac acg att tgt gcc ttc aat          48
Leu Ser Lys Arg Asp Cys Leu Pro Asp Tyr Thr Ile Cys Ala Phe Asn
1               5                   10                  15 atg ggt ctg tgc tgc agc gac aag tgc atg ctc gtc tgc ctg ccg              93
Met Gly Leu Cys Cys Ser Asp Lys Cys Met Leu Val Cys Leu Pro
            20                  25                  30 tgatgtcttc tcctcccctc                                                    113

<210> SEQ ID NO 192
<211> LENGTH: 31
<212> TYPE: PRT
<213> ORGANISM: Conus regius

<400> SEQUENCE: 192

Leu Ser Lys Arg Asp Cys Leu Pro Asp Tyr Thr Ile Cys Ala Phe Asn
1               5                   10                  15

Met Gly Leu Cys Cys Ser Asp Lys Cys Met Leu Val Cys Leu Pro
            20                  25                  30

<210> SEQ ID NO 193
<211> LENGTH: 27
<212> TYPE: PRT
<213> ORGANISM: Conus regius
<220> FEATURE:
<221> NAME/KEY: SITE
<222> LOCATION: (1)..(27)
<223> OTHER INFORMATION: Xaa at residues 5 and 27 may be Pro or
      hydroxy-Pro; Xaa at residue 7 may be Tyr, 125-I-Tyr,
      mono-iodo-Tyr, di-iodo-Tyr, O-sulpho-Tyr or O-phospho-Tyr

<400> SEQUENCE: 193

Asp Cys Leu Xaa Asp Xaa Thr Ile Cys Ala Phe Asn Met Gly Leu Cys
1               5                   10                  15

Cys Ser Asp Lys Cys Met Leu Val Cys Leu Xaa
            20                  25

<210> SEQ ID NO 194
<211> LENGTH: 116
<212> TYPE: DNA
<213> ORGANISM: Conus regius
```

```
-continued

<220> FEATURE:
<221> NAME/KEY: CDS
<222> LOCATION: (1)..(96)

<400> SEQUENCE: 194 ttg aac aag aga atc atc tgc ttt cct gac tac atg ttt tgt ggc gtc     48
Leu Asn Lys Arg Ile Ile Cys Phe Pro Asp Tyr Met Phe Cys Gly Val
1               5                  10                  15 aat gtg ttt ctg tgc tgc agt ggc aac tgc ctt ctc atc tgc gtg ccg     96
Asn Val Phe Leu Cys Cys Ser Gly Asn Cys Leu Leu Ile Cys Val Pro
            20                  25                  30 tgatgtcttc tactcccctc                                               116

<210> SEQ ID NO 195
<211> LENGTH: 32
<212> TYPE: PRT
<213> ORGANISM: Conus regius

<400> SEQUENCE: 195

Leu Asn Lys Arg Ile Ile Cys Phe Pro Asp Tyr Met Phe Cys Gly Val
1               5                  10                  15

Asn Val Phe Leu Cys Cys Ser Gly Asn Cys Leu Leu Ile Cys Val Pro
            20                  25                  30

<210> SEQ ID NO 196
<211> LENGTH: 28
<212> TYPE: PRT
<213> ORGANISM: Conus regius
<220> FEATURE:
<221> NAME/KEY: SITE
<222> LOCATION: (1)..(28)
<223> OTHER INFORMATION: Xaa at residues 5 and 28 may be Pro or
      hydroxy-Pro; Xaa at residue 7 may be Tyr, 125-I-Tyr,
      mono-iodo-Tyr, di-iodo-Tyr, O-sulpho-Tyr or
      O-phospho-Tyr

<400> SEQUENCE: 196

Ile Ile Cys Gly Xaa Asp Xaa Met Phe Cys Gly Val Asn Val Phe Leu
1               5                  10                  15

Cys Cys Ser Gly Asn Cys Leu Leu Ile Cys Val Xaa
            20                  25

<210> SEQ ID NO 197
<211> LENGTH: 259
<212> TYPE: DNA
<213> ORGANISM: Conus gloriamaris
<220> FEATURE:
<221> NAME/KEY: CDS
<222> LOCATION: (1)..(228)

<400> SEQUENCE: 197 atg aaa ctg acg tgc atg atg atc gtt gct gtg ctg ttc ttg acc gcc     48
Met Lys Leu Thr Cys Met Met Ile Val Ala Val Leu Phe Leu Thr Ala
1               5                  10                  15 tgg aca ttc gtc acg gct gtg cct cac tcc agc aat gcg ttg gag aat     96
Trp Thr Phe Val Thr Ala Val Pro His Ser Ser Asn Ala Leu Glu Asn
            20                  25                  30 ctt tat ctg aag gca cat cat gaa atg aac aac ccc gaa gac tct gaa    144
Leu Tyr Leu Lys Ala His His Glu Met Asn Asn Pro Glu Asp Ser Glu
        35                  40                  45 ttg aac aag agg tgc tat gat ggt ggg aca ggt tgt gac tct gga aac    192
Leu Asn Lys Arg Cys Tyr Asp Gly Gly Thr Gly Cys Asp Ser Gly Asn
    50                  55                  60 caa tgc tgc agt ggc tgg tgc att ttc gcc tgc ctc taaaactgtc         238
```

```
Gln Cys Cys Ser Gly Trp Cys Ile Phe Ala Cys Leu
65                  70                  75 gtgatgtctt ctcctcccct c                                              259
```

```
<210> SEQ ID NO 198
<211> LENGTH: 76
<212> TYPE: PRT
<213> ORGANISM: Conus gloriamaris

<400> SEQUENCE: 198
```

```
Met Lys Leu Thr Cys Met Met Ile Val Ala Val Leu Phe Leu Thr Ala
1               5                   10                  15

Trp Thr Phe Val Thr Ala Val Pro His Ser Ser Asn Ala Leu Glu Asn
                20                  25                  30

Leu Tyr Leu Lys Ala His His Glu Met Asn Asn Pro Glu Asp Ser Glu
            35                  40                  45

Leu Asn Lys Arg Cys Tyr Asp Gly Gly Thr Gly Cys Asp Ser Gly Asn
        50                  55                  60

Gln Cys Cys Ser Gly Trp Cys Ile Phe Ala Cys Leu
65                  70                  75
```

```
<210> SEQ ID NO 199
<211> LENGTH: 24
<212> TYPE: PRT
<213> ORGANISM: Conus gloriamaris
<220> FEATURE:
<221> NAME/KEY: SITE
<222> LOCATION: (1)..(24)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 18 may be Trp or bromo-Trp

<400> SEQUENCE: 199
```

```
Cys Xaa Asp Gly Gly Thr Gly Cys Asp Ser Gly Asn Gln Cys Cys Ser
1               5                   10                  15

Gly Xaa Cys Ile Phe Ala Cys Leu
            20
```

```
<210> SEQ ID NO 200
<211> LENGTH: 258
<212> TYPE: DNA
<213> ORGANISM: Conus dalli
<220> FEATURE:
<221> NAME/KEY: CDS
<222> LOCATION: (1)..(228)

<400> SEQUENCE: 200
```

```
atg aaa ctg acg tgc att atg atc gtt gct gtg ctg ttc ttg acc gcc        48
Met Lys Leu Thr Cys Ile Met Ile Val Ala Val Leu Phe Leu Thr Ala
1               5                   10                  15 tgg aca ttc gtc acg gct gtg cct cac tcc agc aat gcg ttg gag aat        96
Trp Thr Phe Val Thr Ala Val Pro His Ser Ser Asn Ala Leu Glu Asn
                20                  25                  30 ctt tat ctg aag gca cat cat gaa atg aac aac ccc gag gac tct gaa       144
Leu Tyr Leu Lys Ala His His Glu Met Asn Asn Pro Glu Asp Ser Glu
            35                  40                  45 ttg aac aag agg tgc tat gat ggt ggg aca ggt tgt gac tct gga aac       192
Leu Asn Lys Arg Cys Tyr Asp Gly Gly Thr Gly Cys Asp Ser Gly Asn
        50                  55                  60 caa tgc tgc agt ggc tgg tgc att ttc gtc tgc ctc taaaactgcc            238
Gln Cys Cys Ser Gly Trp Cys Ile Phe Val Cys Leu
65                  70                  75
```
gtgatgtctt ctctcccatc                                                       258

<210> SEQ ID NO 201
<211> LENGTH: 76
<212> TYPE: PRT
<213> ORGANISM: Conus dalli

<400> SEQUENCE: 201

Met Lys Leu Thr Cys Ile Met Ile Val Ala Val Leu Phe Leu Thr Ala
1               5                   10                  15

Trp Thr Phe Val Thr Ala Val Pro His Ser Ser Asn Ala Leu Glu Asn
            20                  25                  30

Leu Tyr Leu Lys Ala His His Glu Met Asn Asn Pro Glu Asp Ser Glu
        35                  40                  45

Leu Asn Lys Arg Cys Tyr Asp Gly Gly Thr Gly Cys Asp Ser Gly Asn
    50                  55                  60

Gln Cys Cys Ser Gly Trp Cys Ile Phe Val Cys Leu
65                  70                  75

<210> SEQ ID NO 202
<211> LENGTH: 24
<212> TYPE: PRT
<213> ORGANISM: Conus dalli
<220> FEATURE:
<221> NAME/KEY: SITE
<222> LOCATION: (1)..(24)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 18 may be Trp or bromo-Trp

<400> SEQUENCE: 202

Cys Xaa Asp Gly Gly Thr Gly Cys Asp Ser Gly Asn Gln Cys Cys Ser
1               5                   10                  15

Gly Xaa Cys Ile Phe Val Cys Leu
            20

<210> SEQ ID NO 203
<211> LENGTH: 259
<212> TYPE: DNA
<213> ORGANISM: Conus pennaceus
<220> FEATURE:
<221> NAME/KEY: CDS
<222> LOCATION: (1)..(228)

<400> SEQUENCE: 203 atg aaa ctg acg tgc gtg atg atc gtt gct gtg ctg ttc ttg acc gcc      48
Met Lys Leu Thr Cys Val Met Ile Val Ala Val Leu Phe Leu Thr Ala
1               5                   10                  15 tgg aca gtc gtc acg gct gtg cct cac tcc aac aag cgg ttg gcg aat      96
Trp Thr Val Val Thr Ala Val Pro His Ser Asn Lys Arg Leu Ala Asn
            20                  25                  30 ctt tat ctg aag gca cgt cac gaa atg aaa aac ccc gaa gcc tct aat     144
Leu Tyr Leu Lys Ala Arg His Glu Met Lys Asn Pro Glu Ala Ser Asn
        35                  40                  45 gtg gac aag agg tgc ttt gag agt tgg gta gct tgt gag tct cca aaa     192
Val Asp Lys Arg Cys Phe Glu Ser Trp Val Ala Cys Glu Ser Pro Lys
    50                  55                  60 cga tgc tgc agt cac gtg tgc ctt ttc gtc tgc acc tgaaactgcc          238
Arg Cys Cys Ser His Val Cys Leu Phe Val Cys Thr
65                  70                  75 gtgatgtctt ctcctccccct c                                            259

<210> SEQ ID NO 204
<211> LENGTH: 76
<212> TYPE: PRT
<213> ORGANISM: Conus pennaceus

<400> SEQUENCE: 204

Met Lys Leu Thr Cys Val Met Ile Val Ala Val Leu Phe Leu Thr Ala
1               5                   10                  15

Trp Thr Val Val Thr Ala Val Pro His Ser Asn Lys Arg Leu Ala Asn
            20                  25                  30

Leu Tyr Leu Lys Ala Arg His Glu Met Lys Asn Pro Glu Ala Ser Asn
        35                  40                  45

Val Asp Lys Arg Cys Phe Glu Ser Trp Val Ala Cys Glu Ser Pro Lys
    50                  55                  60

Arg Cys Cys Ser His Val Cys Leu Phe Val Cys Thr
65                  70                  75

<210> SEQ ID NO 205
<211> LENGTH: 24
<212> TYPE: PRT
<213> ORGANISM: Conus pennaceus
<220> FEATURE:
<221> NAME/KEY: SITE
<222> LOCATION: (1)..(24)
<223> OTHER INFORMATION: Xaa at residues 3 and 9 may be Glu or
      gamma-carboxy-Glu; Xaa at residue 5 may be Trp or bromo-Trp; Xaa
      at residue 11 may be Pro or hydroxy-Pro

<400> SEQUENCE: 205

Cys Phe Xaa Ser Xaa Val Ala Cys Xaa Ser Xaa Lys Arg Cys Cys Ser
1               5                   10                  15

His Val Cys Leu Phe Val Cys Thr
            20

<210> SEQ ID NO 206
<211> LENGTH: 253
<212> TYPE: DNA
<213> ORGANISM: Conus distans
<220> FEATURE:
<221> NAME/KEY: CDS
<222> LOCATION: (1)..(228)

<400> SEQUENCE: 206 atg aaa ctg acg tgt atg ttg atc atc gct gtg ctg ttc ctg acg gcc       48
Met Lys Leu Thr Cys Met Leu Ile Ile Ala Val Leu Phe Leu Thr Ala
1               5                   10                  15 tgt caa ctc tct aca aat gcg agt tac gcc aga agt aag cag aag cat       96
Cys Gln Leu Ser Thr Asn Ala Ser Tyr Ala Arg Ser Lys Gln Lys His
            20                  25                  30 cgt gtt ctg agg tcg act gac aaa aac tcc aag ttg acc cag cgt tgc      144
Arg Val Leu Arg Ser Thr Asp Lys Asn Ser Lys Leu Thr Gln Arg Cys
        35                  40                  45 aat gaa gct caa gaa cat tgc act caa aat cct gac tgc tgc agt gag      192
Asn Glu Ala Gln Glu His Cys Thr Gln Asn Pro Asp Cys Cys Ser Glu
    50                  55                  60 tct tgc aat aag ttt gtc ggc aga tgc ttg tca gac tgatctgatg           238
Ser Cys Asn Lys Phe Val Gly Arg Cys Leu Ser Asp
65                  70                  75 tcttctcctc ccatc                                                      253

<210> SEQ ID NO 207
<211> LENGTH: 76
<212> TYPE: PRT

<213> ORGANISM: Conus distans

<400> SEQUENCE: 207

Met Lys Leu Thr Cys Met Leu Ile Ile Ala Val Leu Phe Leu Thr Ala
1               5                   10                  15

Cys Gln Leu Ser Thr Asn Ala Ser Tyr Ala Arg Ser Lys Gln Lys His
                20                  25                  30

Arg Val Leu Arg Ser Thr Asp Lys Asn Ser Lys Leu Thr Gln Arg Cys
            35                  40                  45

Asn Glu Ala Gln Glu His Cys Thr Gln Asn Pro Asp Cys Cys Ser Glu
        50                  55                  60

Ser Cys Asn Lys Phe Val Gly Arg Cys Leu Ser Asp
65                  70                  75

<210> SEQ ID NO 208
<211> LENGTH: 29
<212> TYPE: PRT
<213> ORGANISM: Conus distans
<220> FEATURE:
<221> NAME/KEY: SITE
<222> LOCATION: (1)..(29)
<223> OTHER INFORMATION: Xaa at residues 3, 6 and 17  may be Glu or
      gamma-carboxy-Glu; Xaa at residue 12 may be Pro or hydroxy-Pro

<400> SEQUENCE: 208

Cys Asn Xaa Ala Gln Xaa His Cys Thr Gln Asn Xaa Asp Cys Cys Ser
1               5                   10                  15

Xaa Ser Cys Asn Lys Phe Val Gly Arg Cys Leu Ser Asp
            20                  25

<210> SEQ ID NO 209
<211> LENGTH: 259
<212> TYPE: DNA
<213> ORGANISM: Conus ammiralis
<220> FEATURE:
<221> NAME/KEY: CDS
<222> LOCATION: (1)..(228)

<400> SEQUENCE: 209 atg aaa ctg acg tgc ctg atg atc gtt gct gtg ctg ttc ttg acc gcc        48
Met Lys Leu Thr Cys Leu Met Ile Val Ala Val Leu Phe Leu Thr Ala
1               5                   10                  15 tgg aca ttc gtc acg gct gtg cct gac tcc agc aat gcg ttg gag aat        96
Trp Thr Phe Val Thr Ala Val Pro Asp Ser Ser Asn Ala Leu Glu Asn
                20                  25                  30 ctt tat ctg aag gca cat cat gaa atg aac aac ccc gaa gac tct gaa       144
Leu Tyr Leu Lys Ala His His Glu Met Asn Asn Pro Glu Asp Ser Glu
            35                  40                  45 ttg aac aag agg tgc tat gat ggt ggg aca agt tgt aac act gga aac       192
Leu Asn Lys Arg Cys Tyr Asp Gly Gly Thr Ser Cys Asn Thr Gly Asn
        50                  55                  60 caa tgc tgc agt ggc tgg tgc att ttc ctc tgc ctc taaaactgcc            238
Gln Cys Cys Ser Gly Trp Cys Ile Phe Leu Cys Leu
65                  70                  75 gtgatgtctt ctcttcccct c                                                259

<210> SEQ ID NO 210
<211> LENGTH: 76
<212> TYPE: PRT
<213> ORGANISM: Conus ammiralis

<400> SEQUENCE: 210

```
Met Lys Leu Thr Cys Leu Met Ile Val Ala Val Leu Phe Leu Thr Ala
1               5                   10                  15

Trp Thr Phe Val Thr Ala Val Pro Asp Ser Ser Asn Ala Leu Glu Asn
            20                  25                  30

Leu Tyr Leu Lys Ala His His Glu Met Asn Asn Pro Glu Asp Ser Glu
        35                  40                  45

Leu Asn Lys Arg Cys Tyr Asp Gly Gly Thr Ser Cys Asn Thr Gly Asn
    50                  55                      60

Gln Cys Cys Ser Gly Trp Cys Ile Phe Leu Cys Leu
65                  70                  75
```

```
<210> SEQ ID NO 211
<211> LENGTH: 24
<212> TYPE: PRT
<213> ORGANISM: Conus ammiralis
<220> FEATURE:
<221> NAME/KEY: SITE
<222> LOCATION: (1)..(24)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 18 may be Trp or bromo-Trp

<400> SEQUENCE: 211
```

```
Cys Xaa Asp Gly Gly Thr Ser Cys Asn Thr Gly Asn Gln Cys Cys Ser
1               5                   10                  15

Gly Xaa Cys Ile Phe Leu Cys Leu
        20
```

```
<210> SEQ ID NO 212
<211> LENGTH: 286
<212> TYPE: DNA
<213> ORGANISM: Conus textile
<220> FEATURE:
<221> NAME/KEY: CDS
<222> LOCATION: (25)..(255)

<400> SEQUENCE: 212
```

```
ggcattacct aaaacatcac caag atg aaa ctg acg tgc atg atg atc gtt          51
                          Met Lys Leu Thr Cys Met Met Ile Val
                          1               5 gct gtg ctg ttc ttg acc gcc tgg aca ttc gtc acg gct gcg cct cac        99
Ala Val Leu Phe Leu Thr Ala Trp Thr Phe Val Thr Ala Ala Pro His
10                  15                  20                  25 tcc agc aat gcg ttg gag aat ctt tat ctg aag gca cat cat gaa atg       147
Ser Ser Asn Ala Leu Glu Asn Leu Tyr Leu Lys Ala His His Glu Met
                30                  35                  40 aac aac ccc gaa gcc tct gaa ttg aac aag agg tgc tat gat agt ggg       195
Asn Asn Pro Glu Ala Ser Glu Leu Asn Lys Arg Cys Tyr Asp Ser Gly
            45                  50                  55 aca agt tgt aac act gga aac caa tgc tgc agt ggc tgg tgc att ttc       243
Thr Ser Cys Asn Thr Gly Asn Gln Cys Cys Ser Gly Trp Cys Ile Phe
        60                  65                  70 gtc tct tgc ctc taaaactacc gtgatgtctt ctcctcccct c                    286
Val Ser Cys Leu
    75
```

```
<210> SEQ ID NO 213
<211> LENGTH: 77
<212> TYPE: PRT
<213> ORGANISM: Conus textile

<400> SEQUENCE: 213

Met Lys Leu Thr Cys Met Met Ile Val Ala Val Leu Phe Leu Thr Ala
```

```
                1               5                  10                 15
Trp Thr Phe Val Thr Ala Ala Pro His Ser Ser Asn Ala Leu Glu Asn
                    20                 25                 30

Leu Tyr Leu Lys Ala His His Glu Met Asn Asn Pro Glu Ala Ser Glu
            35                 40                 45

Leu Asn Lys Arg Cys Tyr Asp Ser Gly Thr Ser Cys Asn Thr Gly Asn
        50                 55                 60

Gln Cys Cys Ser Gly Trp Cys Ile Phe Val Ser Cys Leu
65                  70                 75

<210> SEQ ID NO 214
<211> LENGTH: 25
<212> TYPE: PRT
<213> ORGANISM: Conus textile
<220> FEATURE:
<221> NAME/KEY: SITE
<222> LOCATION: (1)..(25)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 18 may be Trp or bromo-Trp

<400> SEQUENCE: 214

Cys Xaa Asp Ser Gly Thr Ser Cys Asn Thr Gly Asn Gln Cys Cys Ser
1               5                  10                 15

Gly Xaa Cys Ile Phe Val Ser Cys Leu
            20                 25

<210> SEQ ID NO 215
<211> LENGTH: 272
<212> TYPE: DNA
<213> ORGANISM: Conus gloriamaris
<220> FEATURE:
<221> NAME/KEY: CDS
<222> LOCATION: (1)..(252)

<400> SEQUENCE: 215 atg aaa ctg acg tgc atg atg atc gtt gct gtg ctg ttc ctg aca gcc         48
Met Lys Leu Thr Cys Met Met Ile Val Ala Val Leu Phe Leu Thr Ala
1               5                  10                 15 tgg acg cta gtc atg gct gat gac tcc aac aat gga ctg gcg aat ctt         96
Trp Thr Leu Val Met Ala Asp Asp Ser Asn Asn Gly Leu Ala Asn Leu
                20                 25                 30 ttt tcg aaa tca cgt gac gaa atg gag gac ccc gaa gct tct aaa ttg        144
Phe Ser Lys Ser Arg Asp Glu Met Glu Asp Pro Glu Ala Ser Lys Leu
            35                 40                 45 gag aaa agg gat tgc caa gca cta tgg gat tat tgt cca gta ccg ctc        192
Glu Lys Arg Asp Cys Gln Ala Leu Trp Asp Tyr Cys Pro Val Pro Leu
        50                 55                 60 ttg tca tcg ggt gat tgc tgc tat ggc tta atc tgt ggc cct ttc gtc        240
Leu Ser Ser Gly Asp Cys Cys Tyr Gly Leu Ile Cys Gly Pro Phe Val
65                  70                 75                 80 tgc att gga tgg tgatgtcttc tactcccatc                                  272
Cys Ile Gly Trp <210> SEQ ID NO 216
<211> LENGTH: 84
<212> TYPE: PRT
<213> ORGANISM: Conus gloriamaris

<400> SEQUENCE: 216

Met Lys Leu Thr Cys Met Met Ile Val Ala Val Leu Phe Leu Thr Ala
1               5                  10                 15
```

```
Trp Thr Leu Val Met Ala Asp Asp Ser Asn Asn Gly Leu Ala Asn Leu
             20                  25                  30

Phe Ser Lys Ser Arg Asp Glu Met Glu Asp Pro Glu Ala Ser Lys Leu
         35                  40                  45

Glu Lys Arg Asp Cys Gln Ala Leu Trp Asp Tyr Cys Pro Val Pro Leu
 50                  55                  60

Leu Ser Ser Gly Asp Cys Cys Tyr Gly Leu Ile Cys Gly Pro Phe Val
 65                  70                  75                  80

Cys Ile Gly Trp

<210> SEQ ID NO 217
<211> LENGTH: 33
<212> TYPE: PRT
<213> ORGANISM: Conus gloriamaris
<220> FEATURE:
<221> NAME/KEY: SITE
<222> LOCATION: (1)..(33)
<223> OTHER INFORMATION: Xaa at residues 6 and 33 may be Trp or
      bromo-Trp; Xaa at residues 8 and 21 may be Tyr, 125-I-Tyr,
      mono-iodo-Tyr, di-iodo-Tyr, O-sulpho-Tyr or O-phospho-Tyr; Xaa at
      residues 10, 12 and 27 may be Pro or hydroxy-Pro

<400> SEQUENCE: 217

Asp Cys Gln Ala Leu Xaa Asp Xaa Cys Xaa Val Xaa Leu Leu Ser Ser
 1               5                  10                  15

Gly Asp Cys Cys Xaa Gly Leu Ile Cys Gly Xaa Phe Val Cys Ile Gly
             20                  25                  30

Xaa

<210> SEQ ID NO 218
<211> LENGTH: 275
<212> TYPE: DNA
<213> ORGANISM: Conus omaria
<220> FEATURE:
<221> NAME/KEY: CDS
<222> LOCATION: (1)..(249)

<400> SEQUENCE: 218 atg aaa ctg acg tgc ctg atg atc gtt gct gtg ctg ttc ttg acc gcc        48
Met Lys Leu Thr Cys Leu Met Ile Val Ala Val Leu Phe Leu Thr Ala
 1               5                  10                  15 tgg aca ttc gtc atg gct gat gac tcc aac aat gga ctg gca aat ctt        96
Trp Thr Phe Val Met Ala Asp Asp Ser Asn Asn Gly Leu Ala Asn Leu
             20                  25                  30 ttc tcg aaa tca cgt gac gaa atg gag gat acc gat cct tct aaa ttg       144
Phe Ser Lys Ser Arg Asp Glu Met Glu Asp Thr Asp Pro Ser Lys Leu
         35                  40                  45 gag aac aga aaa act tgc caa aga agg tgg gat ttt tgt cca gga tcg       192
Glu Asn Arg Lys Thr Cys Gln Arg Arg Trp Asp Phe Cys Pro Gly Ser
 50                  55                  60 ctc gtt gga gtg ata act tgc tgc ggt ggc tta atc tgt ttt ctg ttc       240
Leu Val Gly Val Ile Thr Cys Cys Gly Gly Leu Ile Cys Phe Leu Phe
 65                  70                  75                  80 ttc tgc gtt tgatagtgat gctcttctcc tcccct                              275
Phe Cys Val <210> SEQ ID NO 219
<211> LENGTH: 83
<212> TYPE: PRT
<213> ORGANISM: Conus omaria

<400> SEQUENCE: 219
```

```
Met Lys Leu Thr Cys Leu Met Ile Val Ala Val Leu Phe Leu Thr Ala
1               5                   10                  15

Trp Thr Phe Val Met Ala Asp Asp Ser Asn Asn Gly Leu Ala Asn Leu
                20                  25                  30

Phe Ser Lys Ser Arg Asp Glu Met Glu Asp Thr Asp Pro Ser Lys Leu
            35                  40                  45

Glu Asn Arg Lys Thr Cys Gln Arg Arg Trp Asp Phe Cys Pro Gly Ser
        50                  55                  60

Leu Val Gly Val Ile Thr Cys Gly Gly Leu Ile Cys Phe Leu Phe
65                  70                  75                  80

Phe Cys Val
```

<210> SEQ ID NO 220
<211> LENGTH: 32
<212> TYPE: PRT
<213> ORGANISM: Conus omaria
<220> FEATURE:
<221> NAME/KEY: SITE
<222> LOCATION: (1)..(32)
<223> OTHER INFORMATION: Xaa at residue 7 may be Trp or bromo-Trp; Xaa
      at residue 10 may be Pro or hydroxy-Pro

<400> SEQUENCE: 220

```
Lys Thr Cys Gln Arg Arg Xaa Asp Phe Cys Xaa Gly Ser Leu Val Gly
1               5                   10                  15

Val Ile Thr Cys Cys Gly Gly Leu Ile Cys Phe Leu Phe Cys Val
                20                  25                  30
```

<210> SEQ ID NO 221
<211> LENGTH: 274
<212> TYPE: DNA
<213> ORGANISM: Conus dalli
<220> FEATURE:
<221> NAME/KEY: CDS
<222> LOCATION: (1)..(246)

<400> SEQUENCE: 221

```
atg aaa ctg acg tgt gtg atg atc gtt gct gtg ctg ttc ctg aca gcc    48
Met Lys Leu Thr Cys Val Met Ile Val Ala Val Leu Phe Leu Thr Ala
1               5                   10                  15 tgg acg cta gtc atg gct gat gac tcc aac aat gga ctg gcg aat ctt    96
Trp Thr Leu Val Met Ala Asp Asp Ser Asn Asn Gly Leu Ala Asn Leu
                20                  25                  30 ttt tcg aaa tta cgt gac gaa atg gag gac ccc gaa ggt tct aaa ttg   144
Phe Ser Lys Leu Arg Asp Glu Met Glu Asp Pro Glu Gly Ser Lys Leu
            35                  40                  45 gag aaa aag gat tgc caa gaa aaa tgg gat tat tgt cca gta ccg ttc   192
Glu Lys Lys Asp Cys Gln Glu Lys Trp Asp Tyr Cys Pro Val Pro Phe
        50                  55                  60 ttg gga tcg agg tat tgc tgc gat ggc ttt atc tgt cca tct ttc ttc   240
Leu Gly Ser Arg Tyr Cys Cys Asp Gly Phe Ile Cys Pro Ser Phe Phe
65                  70                  75                  80 tgc gct tgatagtgat gtcttctcta ttcccctc                            274
Cys Ala
```

<210> SEQ ID NO 222
<211> LENGTH: 82
<212> TYPE: PRT
<213> ORGANISM: Conus dalli

<400> SEQUENCE: 222

Met Lys Leu Thr Cys Val Met Ile Val Ala Val Leu Phe Leu Thr Ala

```
                1               5                      10                      15
              Trp Thr Leu Val Met Ala Asp Asp Ser Asn Asn Gly Leu Ala Asn Leu
                                20                      25                      30

Phe Ser Lys Leu Arg Asp Glu Met Glu Asp Pro Glu Gly Ser Lys Leu
                                35                      40                      45

Glu Lys Lys Asp Cys Gln Glu Lys Trp Asp Tyr Cys Pro Val Pro Phe
                                50                      55                      60

Leu Gly Ser Arg Tyr Cys Cys Asp Gly Phe Ile Cys Pro Ser Phe Phe
              65                      70                      75                      80

Cys Ala

<210> SEQ ID NO 223
<211> LENGTH: 31
<212> TYPE: PRT
<213> ORGANISM: Conus dalli
<220> FEATURE:
<221> NAME/KEY: SITE
<222> LOCATION: (1)..(31)
<223> OTHER INFORMATION: Xaa at residue 4 may be Glu or
      gamma-carboxy-Glu; Xaa at residue 6 may be Trp or bromo-Trp; Xaa
      at residues 8 and 18 may be Tyr, 125-I-Tyr, mono-iodo-Tyr,
      di-iodo-Tyr, O-sulpho-Tyr or O-phospho-Tyr; Xaa at residues 10, 12
      and 26 may be Pro or hydroxy-Pro

<400> SEQUENCE: 223

Asp Cys Gln Xaa Lys Xaa Asp Xaa Cys Xaa Val Xaa Phe Leu Gly Ser
1               5                      10                      15

Arg Xaa Cys Cys Asp Gly Phe Ile Cys Xaa Ser Phe Phe Cys Ala
                20                      25                      30

<210> SEQ ID NO 224
<211> LENGTH: 271
<212> TYPE: DNA
<213> ORGANISM: Conus dalli
<220> FEATURE:
<221> NAME/KEY: CDS
<222> LOCATION: (1)..(252)

<400> SEQUENCE: 224 atg aaa ctg acg tgc gtg atg atc gtt gct gtg ttg ttc ctg aca gcc        48
Met Lys Leu Thr Cys Val Met Ile Val Ala Val Leu Phe Leu Thr Ala
1               5                      10                      15 tgg acg cta gtc atg gct gat gac tcc aac aat gga ctg gcg aat cat        96
Trp Thr Leu Val Met Ala Asp Asp Ser Asn Asn Gly Leu Ala Asn His
                20                      25                      30 ttt tgg aaa tca cgt gac gaa atg gag gac cct gaa gct tct aaa ttg       144
Phe Trp Lys Ser Arg Asp Glu Met Glu Asp Pro Glu Ala Ser Lys Leu
                35                      40                      45 gag aaa agg gat tgc caa ggc gaa tgg gag ttt tgt ata gta ccg gtc       192
Glu Lys Arg Asp Cys Gln Gly Glu Trp Glu Phe Cys Ile Val Pro Val
        50                      55                      60 ctt gga ttt gtg tat tgc tgc ccc tgg ctt atc tgt ggc cct ttc gtc       240
Leu Gly Phe Val Tyr Cys Cys Pro Trp Leu Ile Cys Gly Pro Phe Val
65                      70                      75                      80 tgc gtt gat atc tgatgtcttc tatcccctc                                  271
Cys Val Asp Ile <210> SEQ ID NO 225
<211> LENGTH: 84
<212> TYPE: PRT
<213> ORGANISM: Conus dalli

<400> SEQUENCE: 225
```

```
Met Lys Leu Thr Cys Val Met Ile Val Ala Val Leu Phe Leu Thr Ala
1               5                   10                  15

Trp Thr Leu Val Met Ala Asp Asp Ser Asn Asn Gly Leu Ala Asn His
            20                  25                  30

Phe Trp Lys Ser Arg Asp Glu Met Glu Asp Pro Glu Ala Ser Lys Leu
        35                  40                  45

Glu Lys Arg Asp Cys Gln Gly Glu Trp Glu Phe Cys Ile Val Pro Val
    50                  55                  60

Leu Gly Phe Val Tyr Cys Cys Pro Trp Leu Ile Cys Gly Pro Phe Val
65                  70                  75                  80

Cys Val Asp Ile
```

<210> SEQ ID NO 226
<211> LENGTH: 33
<212> TYPE: PRT
<213> ORGANISM: Conus dalli
<220> FEATURE:
<221> NAME/KEY: SITE
<222> LOCATION: (1)..(33)
<223> OTHER INFORMATION: Xaa at residues 5 and 7 may be Glu or
      gamma-carboxy-Glu; Xaa at residues 6 and 22 may be Trp or
      bromo-Trp; Xaa at residues 12, 21 and 27 may be Pro or
      hydroxy-Pro;
<221> NAME/KEY: SITE
<222> LOCATION: (1)..(33)
<223> OTHER INFORMATION: Xaa at residue 18 may be Tyr, 125-I-Tyr,
      mono-iodo-Tyr, di-iodo-Tyr, O-sulpho-Tyr or O-phospho-Tyr

<400> SEQUENCE: 226

```
Asp Cys Gln Gly Xaa Xaa Xaa Phe Cys Ile Val Xaa Val Leu Gly Phe
1               5                   10                  15

Val Xaa Cys Cys Xaa Xaa Leu Ile Cys Gly Xaa Phe Val Cys Val Asp
            20                  25                  30

Ile
```

<210> SEQ ID NO 227
<211> LENGTH: 265
<212> TYPE: DNA
<213> ORGANISM: Conus pennaceus
<220> FEATURE:
<221> NAME/KEY: CDS
<222> LOCATION: (1)..(234)

<400> SEQUENCE: 227

```
atg aaa ctg acg tgc ctg atg atc att gct gtg ctg ttc ttg acc gcc      48
Met Lys Leu Thr Cys Leu Met Ile Ile Ala Val Leu Phe Leu Thr Ala
1               5                   10                  15 tgg aca ttc gtc atg gct gat gac ccc aga gat gaa ccg gag gca cgt      96
Trp Thr Phe Val Met Ala Asp Asp Pro Arg Asp Glu Pro Glu Ala Arg
            20                  25                  30 gac gaa atg aac ccc gca gcc tct aaa ttg aac gag aga ggc tgc ctt     144
Asp Glu Met Asn Pro Ala Ala Ser Lys Leu Asn Glu Arg Gly Cys Leu
        35                  40                  45 gaa gtt gat tat ttt tgc ggc ata ccg ttt gtg aac aac ggg cta tgc     192
Glu Val Asp Tyr Phe Cys Gly Ile Pro Phe Val Asn Asn Gly Leu Cys
    50                  55                  60 tgc agt ggc aat tgt gtt ttt gtc tgc aca ccc caa ggg aag             234
Cys Ser Gly Asn Cys Val Phe Val Cys Thr Pro Gln Gly Lys
65                  70                  75 taaaactgct gtgatgtctt ctcttcccat c                                   265
```

```
<210> SEQ ID NO 228
<211> LENGTH: 78
<212> TYPE: PRT
<213> ORGANISM: Conus pennaceus

<400> SEQUENCE: 228

Met Lys Leu Thr Cys Leu Met Ile Ile Ala Val Leu Phe Leu Thr Ala
1               5                   10                  15

Trp Thr Phe Val Met Ala Asp Asp Pro Arg Asp Glu Pro Glu Ala Arg
            20                  25                  30

Asp Glu Met Asn Pro Ala Ala Ser Lys Leu Asn Glu Arg Gly Cys Leu
        35                  40                  45

Glu Val Asp Tyr Phe Cys Gly Ile Pro Phe Val Asn Asn Gly Leu Cys
    50                  55                  60

Cys Ser Gly Asn Cys Val Phe Val Cys Thr Pro Gln Gly Lys
65                  70                  75

<210> SEQ ID NO 229
<211> LENGTH: 31
<212> TYPE: PRT
<213> ORGANISM: Conus pennaceus
<220> FEATURE:
<221> NAME/KEY: SITE
<222> LOCATION: (1)..(31)
<223> OTHER INFORMATION: Xaa at residue 4 may be Glu or
      gamma-carboxy-Glu; Xaa at residue 7 may be Tyr, 125-I-Tyr,
      mono-iodo-Tyr, di-iodo-Tyr, O-sulpho-Tyr or O-phospho-Tyr; Xaa at
      residues 12 and 30 may be Pro or hydroxy-Pro

<400> SEQUENCE: 229

Gly Cys Leu Xaa Val Asp Xaa Phe Cys Gly Ile Xaa Phe Val Asn Asn
1               5                   10                  15

Gly Leu Cys Cys Ser Gly Asn Cys Val Phe Val Cys Thr Xaa Gln
            20                  25                  30

<210> SEQ ID NO 230
<211> LENGTH: 428
<212> TYPE: DNA
<213> ORGANISM: Conus marmoreus
<220> FEATURE:
<221> NAME/KEY: CDS
<222> LOCATION: (122)..(229)

<400> SEQUENCE: 230
ggtcgacatc atcatcatcg atccatctgt ccatccatct gtccatccat ccattcattc      60
attcactgcc aaactgtcat aaatatttga gtctctcttt ctgttttat ctgacagatt      120 g aac gag aga gac tgc ctt aat gtt gat tat ttt tgc ggc ata ccg ttt     169
  Asn Glu Arg Asp Cys Leu Asn Val Asp Tyr Phe Cys Gly Ile Pro Phe
  1               5                   10                  15 gtg aac aac ggg cta tgc tgc agt ggc aat tgt gtt ttt gtc tgc aca        217
Val Asn Asn Gly Leu Cys Cys Ser Gly Asn Cys Val Phe Val Cys Thr
            20                  25                  30 ccc caa ggg aag taaaactgcc gtgatgtctt ctcttcccct ctagtagtag            269
Pro Gln Gly Lys
        35 taggcggccg ctctagagga tccaagctta cgtacgcgtg catgcgacgt catagctctt      329 ctatagtgtc acctaaattc aattcactgg ccgtccgttt tacaacgtcg tgactgggaa      389 aaccctggcg ttacccaact taatcgcctt gcagcacat                             428

<210> SEQ ID NO 231
<211> LENGTH: 36
```

```
<212> TYPE: PRT
<213> ORGANISM: Conus marmoreus

<400> SEQUENCE: 231

Asn Glu Arg Asp Cys Leu Asn Val Asp Tyr Phe Cys Gly Ile Pro Phe
1               5                   10                  15

Val Asn Asn Gly Leu Cys Cys Ser Gly Asn Cys Val Phe Val Cys Thr
            20                  25                  30

Pro Gln Gly Lys
        35

<210> SEQ ID NO 232
<211> LENGTH: 30
<212> TYPE: PRT
<213> ORGANISM: Conus marmoreus
<220> FEATURE:
<221> NAME/KEY: SITE
<222> LOCATION: (1)..(30)
<223> OTHER INFORMATION: Xaa at residue 6 may be Tyr, 125-I-Tyr,
      mono-iodo-Tyr, di-iodo-Tyr, O-sulpho-Tyr or O-phospho-Tyr; Xaa at
      residues 11 and 29 may be Pro or hydroxy-Pro

<400> SEQUENCE: 232

Cys Leu Asn Val Asp Xaa Phe Cys Gly Ile Xaa Phe Val Asn Asn Gly
1               5                   10                  15

Leu Cys Cys Ser Gly Asn Cys Val Phe Val Cys Thr Xaa Gln
            20                  25                  30

<210> SEQ ID NO 233
<211> LENGTH: 227
<212> TYPE: DNA
<213> ORGANISM: Conus marmoreus
<220> FEATURE:
<221> NAME/KEY: CDS
<222> LOCATION: (105)..(224)

<400> SEQUENCE: 233
tcgacatcat catcatcgat ccatctgtcc atccatccat tcattcattc gctgccaaac      60
tgtcataaat atttgagtct ctctttctgt ttttatctga caga ttg gac aag aga     116
                                                 Leu Asp Lys Arg
                                                   1 gag tgc ctg gaa gct gat tat tat tgc gtc tta ccg ttt gtg ggc aac      164
Glu Cys Leu Glu Ala Asp Tyr Tyr Cys Val Leu Pro Phe Val Gly Asn
5                10                  15                  20 ggg atg tgc tgc agt ggc att tgt gtt ttt gtc tgc ata gcc caa cgc      212
Gly Met Cys Cys Ser Gly Ile Cys Val Phe Val Cys Ile Ala Gln Arg
                25                  30                  35 ttt aaa acc gtc tga                                                  227
Phe Lys Thr Val
        40

<210> SEQ ID NO 234
<211> LENGTH: 40
<212> TYPE: PRT
<213> ORGANISM: Conus marmoreus

<400> SEQUENCE: 234

Leu Asp Lys Arg Glu Cys Leu Glu Ala Asp Tyr Tyr Cys Val Leu Pro
1               5                   10                  15

Phe Val Gly Asn Gly Met Cys Cys Ser Gly Ile Cys Val Phe Val Cys
            20                  25                  30

Ile Ala Gln Arg Phe Lys Thr Val
        35                  40
```

```
<210> SEQ ID NO 235
<211> LENGTH: 36
<212> TYPE: PRT
<213> ORGANISM: Conus marmoreus
<220> FEATURE:
<221> NAME/KEY: SITE
<222> LOCATION: (1)..(36)
<223> OTHER INFORMATION: Xaa at residues 1 and 4 may be Glu or
      gamma-carboxy-Glu; Xaa at residues 7 and 8 may be Tyr, 125-I-Tyr,
      mono-iodo-Tyr, di-iodo-Tyr, O-sulpho-Tyr or O-phospho-Tyr; Xaa at
      residue 12 may be Pro or hydroxy-Pro

<400> SEQUENCE: 235

Xaa Cys Leu Xaa Ala Asp Xaa Xaa Cys Val Leu Xaa Phe Val Gly Asn
1               5                   10                  15

Gly Met Cys Cys Ser Gly Ile Cys Val Phe Val Cys Ile Ala Gln Arg
            20                  25                  30

Phe Lys Thr Val
        35

<210> SEQ ID NO 236
<211> LENGTH: 525
<212> TYPE: DNA
<213> ORGANISM: Conus marmoreus
<220> FEATURE:
<221> NAME/KEY: CDS
<222> LOCATION: (131)..(241)

<400> SEQUENCE: 236
gtaccggtcc ggaattcccg ggtcgacatc atcatcatcg atccatctgt ccatccatcc      60
atccattcat tcattcgctg ccaaactgtc ataaacattt gagtctctct ttctgttttt     120
atctgacaga ttg aac gag aga gac tgc ctt gaa cct gat tat gtt tgc       169
            Leu Asn Glu Arg Asp Cys Leu Glu Pro Asp Tyr Val Cys
              1               5                   10 ggc ata ccg ttt gtg ttc aac ggg cta tgc tgc agt gga att tgt gtt      217
Gly Ile Pro Phe Val Phe Asn Gly Leu Cys Cys Ser Gly Ile Cys Val
        15                  20                  25 ttt atc tgc ata gcc caa aag tat taaaacgccg tgatgtcttc tattcccatc     271
Phe Ile Cys Ile Ala Gln Lys Tyr
30              35 tagtagtagt aggcggccgc tctagaggat ccaagcttac gtacgcgtgc atgcgacgtc     331
atagctcttc tatagtgtca cctaaattca attcactggc cgtcgtttta caacgtcgtg     391
actgggaaaa ccctggcgtt acccaactta atcgccttgc agcacatccc cctttcgcca     451
gctggcgtaa tagccgaaga ggcccgcacc gatcgccctt cccaacagtt gcgcagcctg     511
aatggcgaat gggg                                                       525

<210> SEQ ID NO 237
<211> LENGTH: 37
<212> TYPE: PRT
<213> ORGANISM: Conus marmoreus

<400> SEQUENCE: 237

Leu Asn Glu Arg Asp Cys Leu Glu Pro Asp Tyr Val Cys Gly Ile Pro
1               5                   10                  15

Phe Val Phe Asn Gly Leu Cys Cys Ser Gly Ile Cys Val Phe Ile Cys
            20                  25                  30

Ile Ala Gln Lys Tyr
        35
```

```
<210> SEQ ID NO 238
<211> LENGTH: 33
<212> TYPE: PRT
<213> ORGANISM: Conus marmoreus
<220> FEATURE:
<221> NAME/KEY: SITE
<222> LOCATION: (1)..(33)
<223> OTHER INFORMATION: Xaa at residue 4 may be Glu or
      gamma-carboxy-Glu; Xaa at residues 5 and 12 may be Pro or
      hydroxy-Pro; Xaa at residues 7 and 33 maybe Tyr, 125-I-Tyr,
      mono-iodo-Tyr, di-iodo-Tyr, O-sulpho-Tyr or O-phospho-Tyr

<400> SEQUENCE: 238

Asp Cys Leu Xaa Xaa Asp Xaa Val Cys Gly Ile Xaa Phe Val Phe Asn
1               5                   10                  15

Gly Leu Cys Cys Ser Gly Ile Cys Val Phe Ile Cys Ile Ala Gln Lys
            20                  25                  30

Xaa

<210> SEQ ID NO 239
<211> LENGTH: 537
<212> TYPE: DNA
<213> ORGANISM: Conus marmoreus
<220> FEATURE:
<221> NAME/KEY: CDS
<222> LOCATION: (146)..(247)

<400> SEQUENCE: 239
ggtacgcctg caggtaccgg tccggaattc ccgggtcgac atcatcatca tcatcgatcc      60
atctgtccat ccatctattc attcattcgc tgtcaaactg taatacatat tagaatctct    120
ctttctgttt gtatctgaca gattg gag aaa agg gcg tgc agc aaa aaa tgg      172
                            Glu Lys Arg Ala Cys Ser Lys Lys Trp
                              1               5 gaa tat tgt ata gta ccg atc ctt gga ttc gta tat tgc tgc cct ggc      220
Glu Tyr Cys Ile Val Pro Ile Leu Gly Phe Val Tyr Cys Cys Pro Gly
10                  15                  20                  25 tta atc tgt ggt cct ttc gtc tgc gtt tgatagtgat gtcttctcct            267
Leu Ile Cys Gly Pro Phe Val Cys Val
                30 cccatctagt agtagtaggc ggccgctcta gaggatccaa gcttacgtac gcgtgcatgc    327 gacgtcatag ctcttctata gtgtcaccta aattcaattc actggccgtc gttttacaac    387 gtcgtgactg ggaaaaccct ggcgttaccc aacttaatcg ccttgcagca catcccctt     447 tcgccagctg gcgtaataag cgaagaggcc cgcaccgatc gcccttccca acagttgcgc    507 agcctgaatg gcgaatggg acgcgccctg                                       537

<210> SEQ ID NO 240
<211> LENGTH: 34
<212> TYPE: PRT
<213> ORGANISM: Conus marmoreus

<400> SEQUENCE: 240

Glu Lys Arg Ala Cys Ser Lys Lys Trp Glu Tyr Cys Ile Val Pro Ile
1               5                   10                  15

Leu Gly Phe Val Tyr Cys Cys Pro Gly Leu Ile Cys Gly Pro Phe Val
            20                  25                  30

Cys Val

<210> SEQ ID NO 241
<211> LENGTH: 31
```

```
<212> TYPE: PRT
<213> ORGANISM: Conus marmoreus
<220> FEATURE:
<221> NAME/KEY: SITE
<222> LOCATION: (1)..(31)
<223> OTHER INFORMATION: Xaa at residue 6 may be Trp or bromo-Trp; Xaa
      at residue 7 may be Glu or gamma-carboxy-Glu; Xaa at residues 8
      and 18 may be Tyr, 125-I-Tyr, mono-iodo-Tyr, di-iodo-Tyr,
      O-sulpho-Tyr or O-phospho-Tyr; Xaa at residues 12, 21 and 27 may
      be Pro or hydroxy-Pro

<400> SEQUENCE: 241

Ala Cys Ser Lys Lys Xaa Xaa Xaa Cys Ile Val Xaa Ile Leu Gly Phe
1               5                   10                  15

Val Xaa Cys Cys Xaa Gly Leu Ile Cys Gly Xaa Phe Val Cys Val
            20                  25                  30

<210> SEQ ID NO 242
<211> LENGTH: 552
<212> TYPE: DNA
<213> ORGANISM: Conus omaria
<220> FEATURE:
<221> NAME/KEY: CDS
<222> LOCATION: (149)..(271)

<400> SEQUENCE: 242
aaagccggta cgcctgcagg taccggtccg gaattcccgg gtcgacatca tcatcatcat      60
cgatccatct gtccatccat ccattcattc attcactgcc aaactgtcat aaatatttga    120
gtctctcttt ctgtttttat ctgacaga ttg aac gag aga gac tgc ctt aat       172
                              Leu Asn Glu Arg Asp Cys Leu Asn
                                1               5 gtt gat tat ttt tgt ggc ata ccg ttt gtg aac aac ggg cta tgc tgc      220
Val Asp Tyr Phe Cys Gly Ile Pro Phe Val Asn Asn Gly Leu Cys Cys
    10              15                  20 agt ggc aat tgt gtt ttt tgt ctg cac acc cca agg gaa gta aaa ctg      268
Ser Gly Asn Cys Val Phe Cys Leu His Thr Pro Arg Glu Val Lys Leu
25              30                  35                  40 ccg tgatgtcttc tcttcccctc tagtagtagt aggcggccgc tctagaggat           321
Pro ccaagcttac gtacgcgtgc atgcgacgtc atagctcttc tatagtgtca cctaaattca    381
attcactggc cgtcgtttta caacgtcgtg actgggaaaa ccctggcgtt acccaactta    441
atcgccttgc agcacatccc cctttcgcca gctggcgtaa tagcgaagag gcccgcaccg    501 atcgccttc ccaacagttg cgcagcctga atggcgaatg ggacgcgccc t              552

<210> SEQ ID NO 243
<211> LENGTH: 41
<212> TYPE: PRT
<213> ORGANISM: Conus omaria

<400> SEQUENCE: 243

Leu Asn Glu Arg Asp Cys Leu Asn Val Asp Tyr Phe Cys Gly Ile Pro
1               5                   10                  15

Phe Val Asn Asn Gly Leu Cys Cys Ser Gly Asn Cys Val Phe Cys Leu
            20                  25                  30

His Thr Pro Arg Glu Val Lys Leu Pro
        35                  40

<210> SEQ ID NO 244
<211> LENGTH: 37
<212> TYPE: PRT
<213> ORGANISM: Conus omaria
```

```
<220> FEATURE:
<221> NAME/KEY: SITE
<222> LOCATION: (1)..(37)
<223> OTHER INFORMATION: Xaa at residue 7 may be Tyr, 125-I-Tyr,
      mono-iodo-Tyr, di-iodo-Tyr, O-sulpho-Tyr or O-phospho-Tyr; Xaa at
      residues 12, 31 and 37 may be Pro or hydroxy-Pro; Xaa at residue
      33 may be Glu or gamma-carboxy-Glu

<400> SEQUENCE: 244

Asp Cys Leu Asn Val Asp Xaa Phe Cys Gly Ile Xaa Phe Val Asn Asn
1               5                   10                  15

Gly Leu Cys Cys Ser Gly Asn Cys Val Phe Cys Leu His Thr Xaa Arg
            20                  25                  30

Xaa Val Lys Leu Xaa
        35

<210> SEQ ID NO 245
<211> LENGTH: 212
<212> TYPE: DNA
<213> ORGANISM: Conus obscurus
<220> FEATURE:
<221> NAME/KEY: CDS
<222> LOCATION: (86)..(181)

<400> SEQUENCE: 245
cgatccatct gtccatccat ccattcattc attcattgcc aaactgtaac aaatattcaa      60
gtctctcttt ctgtttgtgt ctgac aga tcg aaa cgg tgc ctt gtt tac ggt       112
                           Arg Ser Lys Arg Cys Leu Val Tyr Gly
                             1               5 aca cct tgt gac tgg ctg acc att gcg ggt atg gag tgc tgc agt aaa       160
Thr Pro Cys Asp Trp Leu Thr Ile Ala Gly Met Glu Cys Cys Ser Lys
 10              15                  20                  25 aag tgc ttt atg atg tgc tgg taaaactgcc gtgatgtctt ctactcccct c        212
Lys Cys Phe Met Met Cys Trp
                30

<210> SEQ ID NO 246
<211> LENGTH: 32
<212> TYPE: PRT
<213> ORGANISM: Conus obscurus

<400> SEQUENCE: 246

Arg Ser Lys Arg Cys Leu Val Tyr Gly Thr Pro Cys Asp Trp Leu Thr
1               5                   10                  15

Ile Ala Gly Met Glu Cys Cys Ser Lys Lys Cys Phe Met Met Cys Trp
            20                  25                  30

<210> SEQ ID NO 247
<211> LENGTH: 28
<212> TYPE: PRT
<213> ORGANISM: Conus obscurus
<220> FEATURE:
<221> NAME/KEY: SITE
<222> LOCATION: (1)..(28)
<223> OTHER INFORMATION: Xaa at residue 4 may be Tyr, 125-I-Tyr,
      mono-iodo-Tyr, di-iodo-Tyr, O-sulpho-Tyr or O-phospho-Tyr; Xaa at
      residue 7 may be Pro or hydroxy-Pro; Xaa at residues 10 and 28 may
      be Trp or bromo-Trp; Xaa at residue 17 may be Glu or
      gamma-carboxy-Glu

<400> SEQUENCE: 247

Cys Leu Val Xaa Gly Thr Xaa Cys Asp Xaa Leu Thr Ile Ala Gly Met
1               5                   10                  15

Xaa Cys Cys Ser Lys Lys Cys Phe Met Met Cys Xaa
            20                  25
```

<210> SEQ ID NO 248
<211> LENGTH: 139
<212> TYPE: DNA
<213> ORGANISM: Conus radiatus
<220> FEATURE:
<221> NAME/KEY: CDS
<222> LOCATION: (2)..(109)

<400> SEQUENCE: 248

```
attg aac cag aga gac tgc cat gaa gtt ggt gaa ttt tgt ggc tta ccg      49
     Leu Asn Gln Arg Asp Cys His Glu Val Gly Glu Phe Cys Gly Leu Pro
     1               5                  10                  15 tta ata aag aac ggg cta tgc tgc agt cag att tgt tta ggt gtc tgc       97
Leu Ile Lys Asn Gly Leu Cys Cys Ser Gln Ile Cys Leu Gly Val Cys
             20                  25                  30 gca aaa gtg ttt taaaactgcc gtgatgtctt ctactcccat                      139
Ala Lys Val Phe
        35
```

<210> SEQ ID NO 249
<211> LENGTH: 36
<212> TYPE: PRT
<213> ORGANISM: Conus radiatus

<400> SEQUENCE: 249

```
Leu Asn Gln Arg Asp Cys His Glu Val Gly Glu Phe Cys Gly Leu Pro
1               5                  10                  15

Leu Ile Lys Asn Gly Leu Cys Cys Ser Gln Ile Cys Leu Gly Val Cys
            20                  25                  30

Ala Lys Val Phe
        35
```

<210> SEQ ID NO 250
<211> LENGTH: 32
<212> TYPE: PRT
<213> ORGANISM: Conus radiatus
<220> FEATURE:
<221> NAME/KEY: SITE
<222> LOCATION: (1)..(32)
<223> OTHER INFORMATION: Xaa at residues 4 and 7 may be Glu or
      gamma-carboxy-Glu; Xaa at residue 12 may be Pro or hydroxy-Pro

<400> SEQUENCE: 250

```
Asp Cys His Xaa Val Gly Xaa Phe Cys Gly Leu Xaa Leu Ile Lys Asn
1               5                  10                  15

Gly Leu Cys Cys Ser Gln Ile Cys Leu Gly Val Cys Ala Lys Val Phe
            20                  25                  30
```

<210> SEQ ID NO 251
<211> LENGTH: 133
<212> TYPE: DNA
<213> ORGANISM: Conus radiatus
<220> FEATURE:
<221> NAME/KEY: CDS
<222> LOCATION: (2)..(100)

<400> SEQUENCE: 251

```
a tta gac aag aaa gag tgc act gcc aat ggt gaa ttt tgt ggc ata tcg     49
  Leu Asp Lys Lys Glu Cys Thr Ala Asn Gly Glu Phe Cys Gly Ile Ser
  1               5                  10                  15 gtc ttt gga agc tac cta tgc tgc agt ggc cgg tgt gta ttc gtc tgc       97
Val Phe Gly Ser Tyr Leu Cys Cys Ser Gly Arg Cys Val Phe Val Cys
            20                  25                  30
```

-continued

```
atc tagttgaact gccgtgatgt cttctactcc cct                              133
Ile
```

<210> SEQ ID NO 252
<211> LENGTH: 33
<212> TYPE: PRT
<213> ORGANISM: Conus radiatus

<400> SEQUENCE: 252

```
Leu Asp Lys Lys Glu Cys Thr Ala Asn Gly Glu Phe Cys Gly Ile Ser
1               5                   10                  15

Val Phe Gly Ser Tyr Leu Cys Cys Ser Gly Arg Cys Val Phe Val Cys
            20                  25                  30

Ile
```

<210> SEQ ID NO 253
<211> LENGTH: 29
<212> TYPE: PRT
<213> ORGANISM: Conus radiatus
<220> FEATURE:
<221> NAME/KEY: SITE
<222> LOCATION: (1)..(29)
<223> OTHER INFORMATION: Xaa at residues 1 and 7 may be Glu or
      gamma-carboxy-Glu; Xaa at residue 17 may be Tyr, 125-I-Tyr,
      mono-iodo-Tyr, di-iodo-Tyr, O-sulpho-Tyr or O-phospho-Tyr

<400> SEQUENCE: 253

```
Xaa Cys Thr Ala Asn Gly Xaa Phe Cys Gly Ile Ser Val Phe Gly Ser
1               5                   10                  15

Xaa Leu Cys Cys Ser Gly Arg Cys Val Phe Val Cys Ile
            20                  25
```

<210> SEQ ID NO 254
<211> LENGTH: 133
<212> TYPE: DNA
<213> ORGANISM: Conus radiatus
<220> FEATURE:
<221> NAME/KEY: CDS
<222> LOCATION: (2)..(100)

<400> SEQUENCE: 254

```
a ttg gac aag aaa gag tgc act acc aat ggt gaa ttt tgt ggc ata tcg      49
  Leu Asp Lys Lys Glu Cys Thr Thr Asn Gly Glu Phe Cys Gly Ile Ser
  1               5                   10                  15 gtc ttt gca agc ttc cta tgc tgc agt ggc ctg tgt gta ttc gtc tgc       97
Val Phe Ala Ser Phe Leu Cys Cys Ser Gly Leu Cys Val Phe Val Cys
            20                  25                  30 atc tagctgaact gccgtgatgt cttctcttcc cct                              133
Ile
```

<210> SEQ ID NO 255
<211> LENGTH: 33
<212> TYPE: PRT
<213> ORGANISM: Conus radiatus

<400> SEQUENCE: 255

```
Leu Asp Lys Lys Glu Cys Thr Thr Asn Gly Glu Phe Cys Gly Ile Ser
1               5                   10                  15

Val Phe Ala Ser Phe Leu Cys Cys Ser Gly Leu Cys Val Phe Val Cys
            20                  25                  30

Ile
```

<210> SEQ ID NO 256

```
<211> LENGTH: 29
<212> TYPE: PRT
<213> ORGANISM: Conus radiatus
<220> FEATURE:
<221> NAME/KEY: SITE
<222> LOCATION: (1)..(29)
<223> OTHER INFORMATION: Xaa at residues 1 and 7 may be Glu or
      gamma-carboxy-Glu.

<400> SEQUENCE: 256

Xaa Cys Thr Thr Asn Gly Xaa Phe Cys Gly Ile Ser Val Phe Ala Ser
1               5                  10                  15

Phe Leu Cys Cys Ser Gly Leu Cys Val Phe Val Cys Ile
            20                  25

<210> SEQ ID NO 257
<211> LENGTH: 133
<212> TYPE: DNA
<213> ORGANISM: Conus radiatus
<220> FEATURE:
<221> NAME/KEY: CDS
<222> LOCATION: (2)..(100)

<400> SEQUENCE: 257 a ttg gac aag aga aaa tgc ttt ccc aaa aat cat ttt tgt ggc ttt gtg      49
  Leu Asp Lys Arg Lys Cys Phe Pro Lys Asn His Phe Cys Gly Phe Val
  1               5                  10                  15 gtg atg ctg aac tac cta tgc tgc agt ggc cgg tgt ata ttc gtc tgc       97
Val Met Leu Asn Tyr Leu Cys Cys Ser Gly Arg Cys Ile Phe Val Cys
            20                  25                  30 gtc tagttgaact gccgtgatgt cttctactcc cat                             133
Val

<210> SEQ ID NO 258
<211> LENGTH: 33
<212> TYPE: PRT
<213> ORGANISM: Conus radiatus

<400> SEQUENCE: 258

Leu Asp Lys Arg Lys Cys Phe Pro Lys Asn His Phe Cys Gly Phe Val
1               5                  10                  15

Val Met Leu Asn Tyr Leu Cys Cys Ser Gly Arg Cys Ile Phe Val Cys
            20                  25                  30

Val

<210> SEQ ID NO 259
<211> LENGTH: 29
<212> TYPE: PRT
<213> ORGANISM: Conus radiatus
<220> FEATURE:
<221> NAME/KEY: SITE
<222> LOCATION: (1)..(29)
<223> OTHER INFORMATION: Xaa at residue 4 may be Pro or hydroxy-Pro;
      Xaa at residue 17 maybe Tyr, 125-I-Tyr, mono-iodo-Tyr,
      di-iodo-Tyr, O-sulpho-Tyr or O-phospho-Tyr

<400> SEQUENCE: 259

Lys Cys Phe Xaa Lys Asn His Phe Cys Gly Phe Val Val Met Leu Asn
1               5                  10                  15

Xaa Leu Cys Cys Ser Gly Arg Cys Ile Phe Val Cys Val
            20                  25

<210> SEQ ID NO 260
<211> LENGTH: 130
<212> TYPE: DNA
```

```
<213> ORGANISM: Conus regius
<220> FEATURE:
<221> NAME/KEY: CDS
<222> LOCATION: (1)..(99)

<400> SEQUENCE: 260 ttg aac aag aga agc tgc ctt cct cta gac tgg ttt tgt ggc ttc aat    48
Leu Asn Lys Arg Ser Cys Leu Pro Leu Asp Trp Phe Cys Gly Phe Asn
1               5                   10                  15 ata att gga gcg ttt ctg tgc tgt agt ggc tac tgc ctt gtc gtc tgc    96
Ile Ile Gly Ala Phe Leu Cys Cys Ser Gly Tyr Cys Leu Val Val Cys
            20                  25                  30 atg taaaactgcc gtgatgtctt ctcctccct c                             130
Met

<210> SEQ ID NO 261
<211> LENGTH: 33
<212> TYPE: PRT
<213> ORGANISM: Conus regius

<400> SEQUENCE: 261

Leu Asn Lys Arg Ser Cys Leu Pro Leu Asp Trp Phe Cys Gly Phe Asn
1               5                   10                  15

Ile Ile Gly Ala Phe Leu Cys Cys Ser Gly Tyr Cys Leu Val Val Cys
            20                  25                  30

Met

<210> SEQ ID NO 262
<211> LENGTH: 29
<212> TYPE: PRT
<213> ORGANISM: Conus regius
<220> FEATURE:
<221> NAME/KEY: SITE
<222> LOCATION: (1)..(29)
<223> OTHER INFORMATION: Xaa at residue 4 may be Pro or hydroxy-Pro; Xaa
      at residue 7 maybe Trp or bromo-Trp; Xaa at residue 23 may be Tyr,
      125-I-Tyr, mono-iodo-Tyr, di-iodo-Tyr, O-sulpho-Tyr or
      O-phospho-Tyr

<400> SEQUENCE: 262

Ser Cys Leu Xaa Leu Asp Xaa Phe Cys Gly Phe Asn Ile Ile Gly Ala
1               5                   10                  15

Phe Leu Cys Cys Ser Gly Xaa Cys Leu Val Val Cys Met
            20                  25

<210> SEQ ID NO 263
<211> LENGTH: 319
<212> TYPE: DNA
<213> ORGANISM: Conus delessertii
<220> FEATURE:
<221> NAME/KEY: CDS
<222> LOCATION: (1)..(285)

<400> SEQUENCE: 263 atg aaa ctg acg tgt ctg ctg atc gtt gct gtg ctg gtc ttg gca gcc    48
Met Lys Leu Thr Cys Leu Leu Ile Val Ala Val Leu Val Leu Ala Ala
1               5                   10                  15 tgt cag ttc atc gta gct ggc gac tcg agt gat ggc cag gag aat cct    96
Cys Gln Phe Ile Val Ala Gly Asp Ser Ser Asp Gly Gln Glu Asn Pro
            20                  25                  30 gct ctg agg tca cct agc gat tcc tct ggg aaa atg tca tca atg aag   144
Ala Leu Arg Ser Pro Ser Asp Ser Ser Gly Lys Met Ser Ser Met Lys
        35                  40                  45 cgc ttc cag aca cgg ctg atg gtg ggg caa tct gca tcg aaa aga cca   192
```

```
Arg Phe Gln Thr Arg Leu Met Val Gly Gln Ser Ala Ser Lys Arg Pro
 50                  55                  60 agc aag agg gac tgc atc ccc ggc ggc gaa aat tgt gat gta ttc cga    240
Ser Lys Arg Asp Cys Ile Pro Gly Gly Glu Asn Cys Asp Val Phe Arg
 65                  70                  75                  80 cca tac cgg tgc tgc agt gga tat tgc ata cta ctc ctt tgc gca        285
Pro Tyr Arg Cys Cys Ser Gly Tyr Cys Ile Leu Leu Leu Cys Ala
                 85                  90                  95 tgataaagct gccttgatgt cttctcctcc cctc                              319
```

<210> SEQ ID NO 264
<211> LENGTH: 95
<212> TYPE: PRT
<213> ORGANISM: Conus delessertii

<400> SEQUENCE: 264

```
Met Lys Leu Thr Cys Leu Leu Ile Val Ala Val Leu Val Leu Ala Ala
  1               5                  10                  15

Cys Gln Phe Ile Val Ala Gly Asp Ser Ser Asp Gly Gln Glu Asn Pro
                 20                  25                  30

Ala Leu Arg Ser Pro Ser Asp Ser Ser Gly Lys Met Ser Ser Met Lys
             35                  40                  45

Arg Phe Gln Thr Arg Leu Met Val Gly Gln Ser Ala Ser Lys Arg Pro
 50                  55                  60

Ser Lys Arg Asp Cys Ile Pro Gly Gly Glu Asn Cys Asp Val Phe Arg
 65                  70                  75                  80

Pro Tyr Arg Cys Cys Ser Gly Tyr Cys Ile Leu Leu Leu Cys Ala
                 85                  90                  95
```

<210> SEQ ID NO 265
<211> LENGTH: 28
<212> TYPE: PRT
<213> ORGANISM: Conus delessertii
<220> FEATURE:
<221> NAME/KEY: SITE
<222> LOCATION: (1)..(28)
<223> OTHER INFORMATION: Xaa at residues 4 and 14 may be Pro or
     hydroxy-Pro; Xaa at residue 7 may be Glu or gamma-carboxy-Glu; Xaa
     at residues 15 and 21 may be Tyr, 125-I-Tyr, mono-iodo-Tyr,
     di-iodo-Tyr, O-sulpho-Tyr or O-phospho-Tyr

<400> SEQUENCE: 265

```
Asp Cys Ile Xaa Gly Gly Xaa Asn Cys Asp Val Phe Arg Xaa Xaa Arg
  1               5                  10                  15

Cys Cys Ser Gly Xaa Cys Ile Leu Leu Leu Cys Ala
                 20                  25
```

<210> SEQ ID NO 266
<211> LENGTH: 1009
<212> TYPE: DNA
<213> ORGANISM: Conus striatus
<220> FEATURE:
<221> NAME/KEY: CDS
<222> LOCATION: (147)..(233)
<221> NAME/KEY: misc_feature
<222> LOCATION: (1)..(1009)
<223> OTHER INFORMATION: n may ba any nucleotide

<400> SEQUENCE: 266

```
gctggttcgc ctgcaggtac cggtccggaa ttcccgggtc gacatcatca tcatcgatcc      60
atctgtccat ccatctattc attcattcat tcgctgccaa actgtattaa atattcaagt     120
ctctctttct gtttgtgtct aacaga ttg aga tgg tgc att cct agt ggt gaa     173
```

```
                 Leu Arg Trp Cys Ile Pro Ser Gly Glu
                  1               5 ctt tgt ttc cgc tcg gat cac ata gga tgc tgc agt ggc aag tgc gca      221
Leu Cys Phe Arg Ser Asp His Ile Gly Cys Cys Ser Gly Lys Cys Ala
 10              15                  20                  25 ttc gtc tgc ttg taaaactgcc gtgatgtctt ctcctcccat ctagtagtag           273
Phe Val Cys Leu taggcggccg ctctagagga tccaagctta cgtacgcgtg catgcgacgt catagctctt      333
ctatagtgtc acctaaattc aattcactgg ccgtcgtttt acaacgtcgt gactgggaaa      393
accctggcgt tacccaactt aatcgccttg cagcacatcc ccctttcgcc agctggcgta      453
atagcgaaga ggcccgcacc gatcgccctt cccaacagtt tgcgcagcct gaatggcgaa      513
tgggacgcgc cctgtagcgg cgcattaaac gcggcgggt gtgggtgggt tacgcccacg       573
tgacccgcta cacttgccag cgccctancg ccccgctcct ttcgctttct ttcccttcct      633
ttctcgncac gtttcggccg nttttccccg tcaagctctt aaatcggggg gcttcccttt      693
aagggttncc gaattantgc tttaccggna ccettgaccc ccaaaaaaac ttggantaag      753
gggngatggn tcncgtaant gggggccatc ncccctgaan agaacggttt ttcncccctt     813
ttgacngttg ggngttccnc ggttttaaa aaangggacc ttttnttcc aaaactggga       873 ananacctaa accctatttt tggggctatt tttttgantt tnaaanggga ttttgcccca     933
ttttnggccc tnttggggta aaaaaagag ccggttttaa aaaaattt accccaaatt        993 ttaacaaaaa tttttt                                                    1009

<210> SEQ ID NO 267
<211> LENGTH: 29
<212> TYPE: PRT
<213> ORGANISM: Conus striatus

<400> SEQUENCE: 267

Leu Arg Trp Cys Ile Pro Ser Gly Glu Leu Cys Phe Arg Ser Asp His
 1               5                  10                  15

Ile Gly Cys Cys Ser Gly Lys Cys Ala Phe Val Cys Leu
             20                  25

<210> SEQ ID NO 268
<211> LENGTH: 29
<212> TYPE: PRT
<213> ORGANISM: Conus striatus
<220> FEATURE:
<221> NAME/KEY: SITE
<222> LOCATION: (1)..(29)
<223> OTHER INFORMATION: Xaa at residue3  may be Trp or bromo-Trp; Xaa
      at residue 6 may be Pro or hydroxy-Pro; Xaa at residue 9 may be
      Glu or gamma-carboxy-Glu

<400> SEQUENCE: 268

Leu Arg Xaa Cys Ile Xaa Ser Gly Xaa Leu Cys Phe Arg Ser Asp His
 1               5                  10                  15

Ile Gly Cys Cys Ser Gly Lys Cys Ala Phe Val Cys Leu
             20                  25

<210> SEQ ID NO 269
<211> LENGTH: 90
<212> TYPE: DNA
<213> ORGANISM: Conus striatus
<220> FEATURE:
<221> NAME/KEY: CDS
<222> LOCATION: (1)..(87)
```

-continued

```
<400> SEQUENCE: 269 ttg aga tgg tgc att cct agt ggt gat ctt tgt ttc cgc tcg gat cac      48
Leu Arg Trp Cys Ile Pro Ser Gly Asp Leu Cys Phe Arg Ser Asp His
1               5                   10                  15 ata gga tgc tgc agt ggc aag tgc gca ttc gtc tgc ttg taa              90
Ile Gly Cys Cys Ser Gly Lys Cys Ala Phe Val Cys Leu
            20                  25

<210> SEQ ID NO 270
<211> LENGTH: 29
<212> TYPE: PRT
<213> ORGANISM: Conus striatus

<400> SEQUENCE: 270

Leu Arg Trp Cys Ile Pro Ser Gly Asp Leu Cys Phe Arg Ser Asp His
1               5                   10                  15

Ile Gly Cys Cys Ser Gly Lys Cys Ala Phe Val Cys Leu
            20                  25

<210> SEQ ID NO 271
<211> LENGTH: 27
<212> TYPE: PRT
<213> ORGANISM: Conus striatus
<220> FEATURE:
<221> NAME/KEY: SITE
<222> LOCATION: (1)..(27)
<223> OTHER INFORMATION: Xaa at residue 1 may be Trp or bromo-Trp; Xaa
      at residue 4 may be Pro or hydroxy-Pro

<400> SEQUENCE: 271

Xaa Cys Ile Xaa Ser Gly Asp Leu Cys Phe Arg Ser Asp His Ile Gly
1               5                   10                  15

Cys Cys Ser Gly Lys Cys Ala Phe Val Cys Leu
            20                  25

<210> SEQ ID NO 272
<211> LENGTH: 90
<212> TYPE: DNA
<213> ORGANISM: Conus striatus
<220> FEATURE:
<221> NAME/KEY: CDS
<222> LOCATION: (1)..(87)

<400> SEQUENCE: 272 ttg aga tgg tgc att cct agt ggt gat ctt tgt ttc cgc tcg gat cac      48
Leu Arg Trp Cys Ile Pro Ser Gly Asp Leu Cys Phe Arg Ser Asp His
1               5                   10                  15 ata caa tgc tgc agt ggc aag tgc gca ttc gtc tgc ttg taa              90
Ile Gln Cys Cys Ser Gly Lys Cys Ala Phe Val Cys Leu
            20                  25

<210> SEQ ID NO 273
<211> LENGTH: 29
<212> TYPE: PRT
<213> ORGANISM: Conus striatus

<400> SEQUENCE: 273

Leu Arg Trp Cys Ile Pro Ser Gly Asp Leu Cys Phe Arg Ser Asp His
1               5                   10                  15

Ile Gln Cys Cys Ser Gly Lys Cys Ala Phe Val Cys Leu
            20                  25

<210> SEQ ID NO 274
<211> LENGTH: 27
```

```
<212> TYPE: PRT
<213> ORGANISM: Conus striatus
<220> FEATURE:
<221> NAME/KEY: SITE
<222> LOCATION: (1)..(27)
<223> OTHER INFORMATION: Xaa at residue1 may be Trp or bromo-Trp; Xaa at
      residue 4 may be Pro or hydroxy-Pro

<400> SEQUENCE: 274

Xaa Cys Ile Xaa Ser Gly Asp Leu Cys Phe Arg Ser Asp His Ile Gln
1               5                   10                  15

Cys Cys Ser Gly Lys Cys Ala Phe Val Cys Leu
            20                  25

<210> SEQ ID NO 275
<211> LENGTH: 206
<212> TYPE: DNA
<213> ORGANISM: Conus obscurus
<220> FEATURE:
<221> NAME/KEY: CDS
<222> LOCATION: (77)..(175)

<400> SEQUENCE: 275
cgatccatct gtccatccat ccattcagtc attcgctgcc aaactgtaac aaatattcaa      60
gtcttgcttt ctgtttg tg tct gac aga ttg aga tgg tgc gtt cct agc ggt    112
                    Val Ser Asp Arg Leu Arg Trp Cys Val Pro Ser Gly
                     1               5                   10 gaa gtt tgt cgc cgc tat gaa ttc gtg gga tgc tgc agt ggc aag tgc      160
Glu Val Cys Arg Arg Tyr Glu Phe Val Gly Cys Cys Ser Gly Lys Cys
            15                  20                  25 ttc ttc gtc tgc tcg taaaactgtt gtgatgtctt ctcctcccct c               206
Phe Phe Val Cys Ser
    30

<210> SEQ ID NO 276
<211> LENGTH: 33
<212> TYPE: PRT
<213> ORGANISM: Conus obscurus

<400> SEQUENCE: 276

Val Ser Asp Arg Leu Arg Trp Cys Val Pro Ser Gly Glu Val Cys Arg
1               5                   10                  15

Arg Tyr Glu Phe Val Gly Cys Cys Ser Gly Lys Cys Phe Phe Val Cys
            20                  25                  30

Ser

<210> SEQ ID NO 277
<211> LENGTH: 29
<212> TYPE: PRT
<213> ORGANISM: Conus obscurus
<220> FEATURE:
<221> NAME/KEY: SITE
<222> LOCATION: (1)..(29)
<223> OTHER INFORMATION: Xaa at residue 3 may be Trp or bromo-Trp; Xaa
      at residue 6 may be Pro or hydroxy-Pro; Xaa at residues 9 and 15
      may be Glu or gamma-carboxy-Glu; Xaa at residue 14 may be Tyr,
      125-I-Tyr, mono-iodo-Tyr, di-iodo-Tyr, O-sulpho-Tyr or
      O-phospho-Tyr

<400> SEQUENCE: 277

Leu Arg Xaa Cys Val Xaa Ser Gly Xaa Val Cys Arg Arg Xaa Xaa Phe
1               5                   10                  15

Val Gly Cys Cys Ser Gly Lys Cys Phe Phe Val Cys Ser
            20                  25
```

```
<210> SEQ ID NO 278
<211> LENGTH: 259
<212> TYPE: DNA
<213> ORGANISM: Conus radiatus
<220> FEATURE:
<221> NAME/KEY: CDS
<222> LOCATION: (22)..(117)

<400> SEQUENCE: 278
ctctctctct ctctgctgga c agg tcg act cgc tgc ttg cct gac gga acg         51
                        Arg Ser Thr Arg Cys Leu Pro Asp Gly Thr
                        1               5                   10 tct tgc ctt ttt agt agg atc aga tgc tgc ggt act tgc agt tca atc         99
Ser Cys Leu Phe Ser Arg Ile Arg Cys Cys Gly Thr Cys Ser Ser Ile
                15                  20                  25 tta aag tca tgt gtg agc tgatccggcg gttgatcttc ctccctctgt                147
Leu Lys Ser Cys Val Ser
            30 gctccatcct tttctgcctg agtcctcctt acctgagagt ggtcatgaac cactcatcac       207 ctactcctct ggaggcttca gaggagctac attgaaataa aagccgcatt gc               259

<210> SEQ ID NO 279
<211> LENGTH: 32
<212> TYPE: PRT
<213> ORGANISM: Conus radiatus

<400> SEQUENCE: 279

Arg Ser Thr Arg Cys Leu Pro Asp Gly Thr Ser Cys Leu Phe Ser Arg
1               5                   10                  15

Ile Arg Cys Cys Gly Thr Cys Ser Ser Ile Leu Lys Ser Cys Val Ser
                20                  25                  30

<210> SEQ ID NO 280
<211> LENGTH: 28
<212> TYPE: PRT
<213> ORGANISM: Conus radiatus
<220> FEATURE:
<221> NAME/KEY: SITE
<222> LOCATION: (1)..(28)
<223> OTHER INFORMATION: Xaa at residue 3 may be Pro or hydroxy-Pro.

<400> SEQUENCE: 280

Cys Leu Xaa Asp Gly Thr Ser Cys Leu Phe Ser Arg Ile Arg Cys Cys
1               5                   10                  15

Gly Thr Cys Ser Ser Ile Leu Lys Ser Cys Val Ser
                20                  25

<210> SEQ ID NO 281
<211> LENGTH: 478
<212> TYPE: DNA
<213> ORGANISM: Conus geographus
<220> FEATURE:
<221> NAME/KEY: CDS
<222> LOCATION: (73)..(318)

<400> SEQUENCE: 281
ggatcttgca cggtgaattt cgcttcatat ttttctactg tcgtctttgg catcatccaa        60
aacatcacca ag atg aaa ctg acg tgc atg atg atc gtt gct gtg ctg ttc      111
              Met Lys Leu Thr Cys Met Met Ile Val Ala Val Leu Phe
              1               5                   10 ttg acc gcc tgg aca ttc gtc acg gct gtg cct cac tcc agc gat gta        159
Leu Thr Ala Trp Thr Phe Val Thr Ala Val Pro His Ser Ser Asp Val
            15                  20                  25
```

-continued

```
ttg gag aat ctt tat ctg aag gca ctt cac gaa acg gaa aac cac gaa      207
Leu Glu Asn Leu Tyr Leu Lys Ala Leu His Glu Thr Glu Asn His Glu
30                  35                  40                  45 gcc tct aaa ttg aac gtg aga gac gac gag tgc gaa cct cct gga gat      255
Ala Ser Lys Leu Asn Val Arg Asp Asp Glu Cys Glu Pro Pro Gly Asp
                50                  55                  60 ttt tgt ggc ttt ttt aaa att ggg ccg cct tgc tgc agt ggc tgg tgc      303
Phe Cys Gly Phe Phe Lys Ile Gly Pro Pro Cys Cys Ser Gly Trp Cys
            65                  70                  75 ttc ctc tgg tgc gcc taaaactgcc gtgatgtctt ctattcccct ctgtgctacc      358
Phe Leu Trp Cys Ala
        80 tggcttgatc tttgattggc gcgtgccctt cagtggttat gaaccccccct gagccgactc    418 tctgggggcc tcgggggttc aacatccaaa taaagcgaca acacaatcac aagtaaaaaa    478

<210> SEQ ID NO 282
<211> LENGTH: 82
<212> TYPE: PRT
<213> ORGANISM: Conus geographus

<400> SEQUENCE: 282

Met Lys Leu Thr Cys Met Met Ile Val Ala Val Leu Phe Leu Thr Ala
1               5                   10                  15

Trp Thr Phe Val Thr Ala Val Pro His Ser Ser Asp Val Leu Glu Asn
            20                  25                  30

Leu Tyr Leu Lys Ala Leu His Glu Thr Glu Asn His Glu Ala Ser Lys
        35                  40                  45

Leu Asn Val Arg Asp Asp Glu Cys Glu Pro Pro Gly Asp Phe Cys Gly
    50                  55                  60

Phe Phe Lys Ile Gly Pro Pro Cys Cys Ser Gly Trp Cys Phe Leu Trp
65                  70                  75                  80

Cys Ala

<210> SEQ ID NO 283
<211> LENGTH: 30
<212> TYPE: PRT
<213> ORGANISM: Conus geographus
<220> FEATURE:
<221> NAME/KEY: SITE
<222> LOCATION: (1)..(30)
<223> OTHER INFORMATION: Xaa at residues 3and 5 may be Glu or
      gamma-carboxy-Glu; Xaa at residues 6, 7, 18 and 19 may be Pro or
      hydroxy-Pro; Xaa at residues 24 and 28 may be Trp or bromo-Trp

<400> SEQUENCE: 283

Asp Asp Xaa Cys Xaa Xaa Xaa Gly Asp Phe Cys Gly Phe Phe Lys Ile
1               5                   10                  15

Gly Xaa Xaa Cys Cys Ser Gly Xaa Cys Phe Leu Xaa Cys Ala
            20                  25                  30

<210> SEQ ID NO 284
<211> LENGTH: 318
<212> TYPE: DNA
<213> ORGANISM: Conus textile
<220> FEATURE:
<221> NAME/KEY: CDS
<222> LOCATION: (3)..(164)
<221> NAME/KEY: misc_feature
<222> LOCATION: (1)..(318)
<223> OTHER INFORMATION: n may be any nucleotide

<400> SEQUENCE: 284
```

```
gc tgc agg tcg act cta gag gcg ttg gag aat ctt tat ctg aag gca      47
   Cys Arg Ser Thr Leu Glu Ala Leu Glu Asn Leu Tyr Leu Lys Ala
   1               5                   10                  15 cat cat gaa atg aac aac ccc gaa gac tct gaa ttg aac aag agg tgc     95
His His Glu Met Asn Asn Pro Glu Asp Ser Glu Leu Asn Lys Arg Cys
                    20                  25                  30 tat gat agt ggg aca agt tgt aac act gga aac caa tgc tgc agt ggc    143
Tyr Asp Ser Gly Thr Ser Cys Asn Thr Gly Asn Gln Cys Cys Ser Gly
            35                  40                  45 tgg tgc att ttc gtc tgc ctc taaaactgcc gtgatgtctt ctactcccct       194
Trp Cys Ile Phe Val Cys Leu
            50 ctgtgctacc tacctggctt gatctttgat tggcgcgtgc ccttcactgg ttatgaaccc  254 ctctgatccg actctctggg ggcctcgggg atccaacatc aaaatanagc gacagcacaa  314 tcac                                                               318

<210> SEQ ID NO 285
<211> LENGTH: 54
<212> TYPE: PRT
<213> ORGANISM: Conus textile

<400> SEQUENCE: 285

Cys Arg Ser Thr Leu Glu Ala Leu Glu Asn Leu Tyr Leu Lys Ala His
1               5                   10                  15

His Glu Met Asn Asn Pro Glu Asp Ser Glu Leu Asn Lys Arg Cys Tyr
                20                  25                  30

Asp Ser Gly Thr Ser Cys Asn Thr Gly Asn Gln Cys Cys Ser Gly Trp
            35                  40                  45

Cys Ile Phe Val Cys Leu
            50

<210> SEQ ID NO 286
<211> LENGTH: 24
<212> TYPE: PRT
<213> ORGANISM: Conus textile
<220> FEATURE:
<221> NAME/KEY: SITE
<222> LOCATION: (1)..(24)
<223> OTHER INFORMATION: Xaa at residue 2 may be Tyr, 125-I-Tyr,
      mono-iodo-Tyr, di-iodo-Tyr, O-sulpho-Tyr or O-phospho-Tyr; Xaa at
      residue 18 may be Trp or bromo-Trp

<400> SEQUENCE: 286

Cys Xaa Asp Ser Gly Thr Ser Cys Asn Thr Gly Asn Gln Cys Cys Ser
1               5                   10                  15

Gly Xaa Cys Ile Phe Val Cys Leu
            20

<210> SEQ ID NO 287
<211> LENGTH: 480
<212> TYPE: DNA
<213> ORGANISM: Conus quercinus
<220> FEATURE:
<221> NAME/KEY: CDS
<222> LOCATION: (52)..(333)

<400> SEQUENCE: 287
gcttcgtatt tctccgctgt cttccttggc atcacccaaa acatcaccaa g atg aaa   57
                                                         Met Lys
                                                         1 ctg acg tgc atg atg atc gtt gct ctg ctg ttc ttg acc gcc tgg aca   105
Leu Thr Cys Met Met Ile Val Ala Leu Leu Phe Leu Thr Ala Trp Thr
```

```
                5                   10                  15
ttc gtc acg gct gtt gac tcc aaa aat gaa ctg gag aac aga gga gga       153
Phe Val Thr Ala Val Asp Ser Lys Asn Glu Leu Glu Asn Arg Gly Gly
        20                  25                  30 tgg ggg cag gca gga gga tgg ggg aaa ctt ttt ccg atg gca cgc gac       201
Trp Gly Gln Ala Gly Gly Trp Gly Lys Leu Phe Pro Met Ala Arg Asp
 35              40                  45                      50 gaa atg aaa aac agc gaa gtc tct aaa ttg gac aat aag aga aag tgc       249
Glu Met Lys Asn Ser Glu Val Ser Lys Leu Asp Asn Lys Arg Lys Cys
                  55                  60                  65 gct gca gcc ggt gaa gct tgc gta ata cct atc att gga aac gta ttt       297
Ala Ala Ala Gly Glu Ala Cys Val Ile Pro Ile Ile Gly Asn Val Phe
         70                  75                  80 tgc tgc aaa ggc tac tgt ctt ttc gtc tgc att agt taaactgctg            343
Cys Cys Lys Gly Tyr Cys Leu Phe Val Cys Ile Ser
             85                  90 tgatgccttc tactcacctc tgtgctacct ggcttgatct ttgattggcg tgtgcccttc     403
actggttatg agctcgtctg atcctactct ctggagacct ctgtggtcca acatccaaat    463
aaagcggcat cccaatg                                                    480

<210> SEQ ID NO 288
<211> LENGTH: 94
<212> TYPE: PRT
<213> ORGANISM: Conus quercinus

<400> SEQUENCE: 288

Met Lys Leu Thr Cys Met Met Ile Val Ala Leu Leu Phe Leu Thr Ala
1               5                   10                  15

Trp Thr Phe Val Thr Ala Val Asp Ser Lys Asn Glu Leu Glu Asn Arg
            20                  25                  30

Gly Gly Trp Gly Gln Ala Gly Gly Trp Gly Lys Leu Phe Pro Met Ala
        35                  40                  45

Arg Asp Glu Met Lys Asn Ser Glu Val Ser Lys Leu Asp Asn Lys Arg
    50                  55                  60

Lys Cys Ala Ala Ala Gly Glu Ala Cys Val Ile Pro Ile Ile Gly Asn
65                  70                  75                  80

Val Phe Cys Cys Lys Gly Tyr Cys Leu Phe Val Cys Ile Ser
                85                  90

<210> SEQ ID NO 289
<211> LENGTH: 29
<212> TYPE: PRT
<213> ORGANISM: Conus quercinus
<220> FEATURE:
<221> NAME/KEY: SITE
<222> LOCATION: (1)..(29)
<223> OTHER INFORMATION: Xaa at residue 6 may be Glu or
      gamma-carboxy-Glu; Xaa at residue 11 may be Pro or hydroxy-Pro;
      Xaa at residue 22 may be Tyr, 125-I-Tyr, mono-iodo-Tyr,
      di-iodo-Tyr, O-sulpho-Tyr or O-phospho-Tyr

<400> SEQUENCE: 289

Cys Ala Ala Ala Gly Xaa Ala Cys Val Ile Xaa Ile Ile Gly Asn Val
1               5                   10                  15

Phe Cys Cys Lys Gly Xaa Cys Leu Phe Val Cys Ile Ser
            20                  25

<210> SEQ ID NO 290
<211> LENGTH: 410
<212> TYPE: DNA
```

```
<213> ORGANISM: Conus leopardus
<220> FEATURE:
<221> NAME/KEY: CDS
<222> LOCATION: (1)..(246)

<400> SEQUENCE: 290 atg aaa ctg acg tgc gtg gtg atc gtt gct gtg ctg ttc ttg acc gcc        48
Met Lys Leu Thr Cys Val Val Ile Val Ala Val Leu Phe Leu Thr Ala
1               5                   10                  15 tgg ata ttc atc acg gct gat gac tcc aca aat gga ctg gag aat cgt        96
Trp Ile Phe Ile Thr Ala Asp Asp Ser Thr Asn Gly Leu Glu Asn Arg
                20                  25                  30 ttt agg aag gca cgt gac aac atg aag aac gcc aaa gcc tct aca tta       144
Phe Arg Lys Ala Arg Asp Asn Met Lys Asn Ala Lys Ala Ser Thr Leu
            35                  40                  45 gcc gag aag aaa gcg tgt gtt ga

```
<210> SEQ ID NO 293
<211> LENGTH: 336
<212> TYPE: DNA
<213> ORGANISM: Conus marmoreus
<220> FEATURE:
<221> NAME/KEY: CDS
<222> LOCATION: (1)..(231)

<400> SEQUENCE: 293 atg aaa ctg acg tgc gtg gtg atc gtt gct gtg ctg ttc ttg acc gcc      48
Met Lys Leu Thr Cys Val Val Ile Val Ala Val Leu Phe Leu Thr Ala
1               5                   10                  15 tgg aca ttt gcc acg gct gat gac ccc aga aat gga ttg gag aat ctt      96
Trp Thr Phe Ala Thr Ala Asp Asp Pro Arg Asn Gly Leu Glu Asn Leu
            20                  25                  30 ttt tcg aag gca cat cac gaa atg aag aac ccc gaa gcc tct aaa ttg     144
Phe Ser Lys Ala His His Glu Met Lys Asn Pro Glu Ala Ser Lys Leu
        35                  40                  45 aac aag agg tgc cct aac act ggt gaa tta tgt gat gtg gtt gaa caa     192
Asn Lys Arg Cys Pro Asn Thr Gly Glu Leu Cys Asp Val Val Glu Gln
    50                  55                  60 aac tgc tgc tat acc tat tgc ttt att gta gtc tgc cta taaaactacc      241
Asn Cys Cys Tyr Thr Tyr Cys Phe Ile Val Val Cys Leu
65                  70                  75 gtgatgtctt ctactcccct ctgtgctgcc tggcttgatc tttgattggc gcgtgccctt   301
cactggttat gaccccctg atccgacctc tgggg                               336

<210> SEQ ID NO 294
<211> LENGTH: 77
<212> TYPE: PRT
<213> ORGANISM: Conus marmoreus

<400> SEQUENCE: 294

Met Lys Leu Thr Cys Val Val Ile Val Ala Val Leu Phe Leu Thr Ala
1               5                   10                  15

Trp Thr Phe Ala Thr Ala Asp Asp Pro Arg Asn Gly Leu Glu Asn Leu
            20                  25                  30

Phe Ser Lys Ala His His Glu Met Lys Asn Pro Glu Ala Ser Lys Leu
        35                  40                  45

Asn Lys Arg Cys Pro Asn Thr Gly Glu Leu Cys Asp Val Val Glu Gln
    50                  55                  60

Asn Cys Cys Tyr Thr Tyr Cys Phe Ile Val Val Cys Leu
65                  70                  75

<210> SEQ ID NO 295
<211> LENGTH: 26
<212> TYPE: PRT
<213> ORGANISM: Conus marmoreus
<220> FEATURE:
<221> NAME/KEY: SITE
<222> LOCATION: (1)..(26)
<223> OTHER INFORMATION: Xaa at residue 2 may be Pro or hydroxy-Pro; Xaa
      at residues 6 and 12 may be Glu or gamma-carboxy-Glu; Xaa at
      residues 17 and 19 maybe Tyr, 125-I-Tyr, mono-iodo-Tyr,
      di-iodo-Tyr, O-sulpho-Tyr or O-phospho-Tyr

<400> SEQUENCE: 295

Cys Xaa Asn Thr Gly Xaa Leu Cys Asp Val Val Xaa Gln Asn Cys Cys
1               5                   10                  15

Xaa Thr Xaa Cys Phe Ile Val Val Cys Leu
            20                  25

<210> SEQ ID NO 296
```

```
<211> LENGTH: 402
<212> TYPE: DNA
<213> ORGANISM: Conus quercinus
<220> FEATURE:
<221> NAME/KEY: CDS
<222> LOCATION: (7)..(240)

<400> SEQUENCE: 296 ggatcc atg aaa ctg acg tgt atg gtg atc gtt gct gtg cta ttc ttg         48
       Met Lys Leu Thr Cys Met Val Ile Val Ala Val Leu Phe Leu
         1               5                  10 acc gcc tcg gct gat gac tcc aga aat gga ttc gag aat cga aat gga        96
Thr Ala Ser Ala Asp Asp Ser Arg Asn Gly Phe Glu Asn Arg Asn Gly
 15              20                  25                  30 gaa cga aac gaa aac gaa atg aag aac ctc gaa gcc tct aaa ttg aac       144
Glu Arg Asn Glu Asn Glu Met Lys Asn Leu Glu Ala Ser Lys Leu Asn
                 35                  40                  45 agg aga gac ggc gat tgc gtt gat ggt ggt gaa ttt tgt ggc ttt ccg       192
Arg Arg Asp Gly Asp Cys Val Asp Gly Gly Glu Phe Cys Gly Phe Pro
             50                  55                  60 aaa att gga ggg cca tgc tgt agt ggc tgg tgc ttt ttc gtc tgc tta       240
Lys Ile Gly Gly Pro Cys Cys Ser Gly Trp Cys Phe Phe Val Cys Leu
         65                  70                  75 taaaactgcc atgatgtctt ctaccccct ctgtgctacc tgacttgatc tttgattggc      300
gtgtgccctt cactggttat gaaccctct gatccgactc tctggaggcc tcggggtcc       360 aacatccaaa taaagcgaca gcaaaaaaaa aaaaaaaaa aa                         402

<210> SEQ ID NO 297
<211> LENGTH: 78
<212> TYPE: PRT
<213> ORGANISM: Conus quercinus

<400> SEQUENCE: 297

Met Lys Leu Thr Cys Met Val Ile Val Ala Val Leu Phe Leu Thr Ala
  1               5                  10                  15

Ser Ala Asp Asp Ser Arg Asn Gly Phe Glu Asn Arg Asn Gly Glu Arg
             20                  25                  30

Asn Glu Asn Glu Met Lys Asn Leu Glu Ala Ser Lys Leu Asn Arg Arg
         35                  40                  45

Asp Gly Asp Cys Val Asp Gly Gly Glu Phe Cys Gly Phe Pro Lys Ile
     50                  55                  60

Gly Gly Pro Cys Cys Ser Gly Trp Cys Phe Phe Val Cys Leu
 65                  70                  75

<210> SEQ ID NO 298
<211> LENGTH: 30
<212> TYPE: PRT
<213> ORGANISM: Conus quercinus
<220> FEATURE:
<221> NAME/KEY: SITE
<222> LOCATION: (1)..(30)
<223> OTHER INFORMATION: Xaa at residue 9 may be Glu or
      gamma-carboxy-Glu; Xaa at residues 14 and 19may be Pro or
      hydroxy-Pro; Xaa at residue 24 may be Trp or bromo-Trp

<400> SEQUENCE: 298

Asp Gly Asp Cys Val Asp Gly Gly Xaa Phe Cys Gly Phe Xaa Lys Ile
  1               5                  10                  15

Gly Gly Xaa Cys Cys Ser Gly Xaa Cys Phe Phe Val Cys Leu
             20                  25                  30
```

-continued

<210> SEQ ID NO 299
<211> LENGTH: 274
<212> TYPE: DNA
<213> ORGANISM: Conus quercinus
<220> FEATURE:
<221> NAME/KEY: CDS
<222> LOCATION: (7)..(216)
<221> NAME/KEY: misc_feature
<222> LOCATION: (1)..(274)
<223> OTHER INFORMATION: n may be any nucleotide

<400> SEQUENCE: 299

```
ggatcc atg aaa ctg acg tgc gtg gtg atc gtt gct gtg cta ttc ttg        48
       Met Lys Leu Thr Cys Val Val Ile Val Ala Val Leu Phe Leu
       1               5                  10 acc gcc ttg gct gat gac tcc aga aat gga ttg gag aat cga aat gaa        96
Thr Ala Leu Ala Asp Asp Ser Arg Asn Gly Leu Glu Asn Arg Asn Glu
15                  20                  25                  30 caa gaa cga aac gaa aac gaa atg agg gac cgc cgg gac tgc caa gat       144
Gln Glu Arg Asn Glu Asn Glu Met Arg Asp Arg Arg Asp Cys Gln Asp
                35                  40                  45 agt ggt gta gtt tgt ggc ttt ccg aaa cct gaa cca cac tgc tgc agt       192
Ser Gly Val Val Cys Gly Phe Pro Lys Pro Glu Pro His Cys Cys Ser
            50                  55                  60 ggc tgg tgc ctt ttc gtc tgc gcc taaaactgcc gtgatgtcaa ataaagcgac      246
Gly Trp Cys Leu Phe Val Cys Ala
        65                  70 agacaatnaa aaaaaaaaaa aaaaaaa                                         274
```

<210> SEQ ID NO 300
<211> LENGTH: 70
<212> TYPE: PRT
<213> ORGANISM: Conus quercinus

<400> SEQUENCE: 300

Met Lys Leu Thr Cys Val Val Ile Val Ala Val Leu Phe Leu Thr Ala
1               5                  10                  15

Leu Ala Asp Asp Ser Arg Asn Gly Leu Glu Asn Arg Asn Glu Gln Glu
            20                  25                  30

Arg Asn Glu Asn Glu Met Arg Asp Arg Arg Asp Cys Gln Asp Ser Gly
        35                  40                  45

Val Val Cys Gly Phe Pro Lys Pro Glu Pro His Cys Cys Ser Gly Trp
    50                  55                  60

Cys Leu Phe Val Cys Ala
65                  70

<210> SEQ ID NO 301
<211> LENGTH: 28
<212> TYPE: PRT
<213> ORGANISM: Conus quercinus
<220> FEATURE:
<221> NAME/KEY: SITE
<222> LOCATION: (1)..(28)
<223> OTHER INFORMATION: Xaa at residues 12, 14 and 16 may be Pro or
      hydroxy-Pro; Xaa at residue15 may be Glu or gamma-carboxy-Glu; Xaa
      at residue 22 may b
      e Trp or bromo-Trp

<400> SEQUENCE: 301

Asp Cys Gln Asp Ser Gly Val Val Cys Gly Phe Xaa Lys Xaa Xaa Xaa
1               5                  10                  15

His Cys Cys Ser Gly Xaa Cys Leu Phe Val Cys Ala
            20                  25

-continued

```
<210> SEQ ID NO 302
<211> LENGTH: 340
<212> TYPE: DNA
<213> ORGANISM: Conus arenatus
<220> FEATURE:
<221> NAME/KEY: CDS
<222> LOCATION: (7)..(246)
<221> NAME/KEY: misc_feature
<222> LOCATION: (1)..(340)
<223> OTHER INFORMATION: n may be any nucleotide

<400> SEQUENCE: 302 ggatcc atg aaa ctg acg tgt gtg gtg atc gtt gct gtg ctg ttc ttg       48
       Met Lys Leu Thr Cys Val Val Ile Val Ala Val Leu Phe Leu
       1               5                  10 acc gcc tgg aca ttc gtc acg gct gac tcc ata cgt gca ctg gag gat      96
Thr Ala Trp Thr Phe Val Thr Ala Asp Ser Ile Arg Ala Leu Glu Asp
15              20                  25                  30 ttt ttt gcg aag gca cgt gac gaa atg gaa aac agc gga gct tct cca     144
Phe Phe Ala Lys Ala Arg Asp Glu Met Glu Asn Ser Gly Ala Ser Pro
                35                  40                  45 ttg aac gag aga gac tgc cga cct gta ggt caa tat tgt ggc ata ccg     192
Leu Asn Glu Arg Asp Cys Arg Pro Val Gly Gln Tyr Cys Gly Ile Pro
            50                  55                  60 tat aag cac aac tgg cga tgc tgc agt cag ctt tgt gca att atc tgt     240
Tyr Lys His Asn Trp Arg Cys Cys Ser Gln Leu Cys Ala Ile Ile Cys
        65                  70                  75 gtt tcc taaccctct gatcctactc tctgaagacc tccgggattc aacatccaaa       296
Val Ser
    80 taaagcgaca tcccgatnaa aaaaaangaa aaaaaaaaa aaaa                     340

<210> SEQ ID NO 303
<211> LENGTH: 80
<212> TYPE: PRT
<213> ORGANISM: Conus arenatus

<400> SEQUENCE: 303

Met Lys Leu Thr Cys Val Val Ile Val Ala Val Leu Phe Leu Thr Ala
1               5                   10                  15

Trp Thr Phe Val Thr Ala Asp Ser Ile Arg Ala Leu Glu Asp Phe Phe
            20                  25                  30

Ala Lys Ala Arg Asp Glu Met Glu Asn Ser Gly Ala Ser Pro Leu Asn
        35                  40                  45

Glu Arg Asp Cys Arg Pro Val Gly Gln Tyr Cys Gly Ile Pro Tyr Lys
    50                  55                  60

His Asn Trp Arg Cys Cys Ser Gln Leu Cys Ala Ile Ile Cys Val Ser
65                  70                  75                  80

<210> SEQ ID NO 304
<211> LENGTH: 30
<212> TYPE: PRT
<213> ORGANISM: Conus arenatus
<220> FEATURE:
<221> NAME/KEY: SITE
<222> LOCATION: (1)..(30)
<223> OTHER INFORMATION: Xaa at residues 4 and 12 may be Pro
      orhydroxy-Pro; Xaa at residues 8 and 13 may be Tyr, 125-I-Tyr,
      mono-iodo-Tyr, di-iodo-Tyr, O-sulpho-Tyr or O-phospho-Tyr; Xaa at
      residue 17 may be Trp or bromo-Trp

<400> SEQUENCE: 304

Asp Cys Arg Xaa Val Gly Gln Xaa Cys Gly Ile Xaa Xaa Lys His Asn
```

```
                1               5              10              15
Xaa Arg Cys Cys Ser Gln Leu Cys Ala Ile Ile Cys Val Ser
                20                              25                              30

<210> SEQ ID NO 305
<211> LENGTH: 281
<212> TYPE: DNA
<213> ORGANISM: Conus arenatus
<220> FEATURE:
<221> NAME/KEY: CDS
<222> LOCATION: (7)..(234)

<400> SEQUENCE: 305 ggatcc atg aaa ctg acg tgt gtg gtg atc gtt gtt gtg ctg ttc ttg            48
       Met Lys Leu Thr Cys Val Val Ile Val Val Val Leu Phe Leu
       1               5                              10 acc gcc tgg aca ttc gtc aag gct gat gac tcc ata aat gga ttg gag           96
Thr Ala Trp Thr Phe Val Lys Ala Asp Asp Ser Ile Asn Gly Leu Glu
15                  20                              25                  30 aat ctt ttt ccg aag gca cgt cac gaa atg aag aac ccc gaa gcc tct          144
Asn Leu Phe Pro Lys Ala Arg His Glu Met Lys Asn Pro Glu Ala Ser
                35                              40                              45 aaa ttg aac gag agg tgc ctt gaa aag ggt gta ctt tgt gat ccg agt          192
Lys Leu Asn Glu Arg Cys Leu Glu Lys Gly Val Leu Cys Asp Pro Ser
            50                              55                              60 gct gga aac tgc tgt agt ggc gaa tgc gtt tta gtc tgc ctc                  234
Ala Gly Asn Cys Cys Ser Gly Glu Cys Val Leu Val Cys Leu
        65                              70                              75 taaaactacc gtgatgtctt ctactcccat ctgtgctacc cctcgag                      281

<210> SEQ ID NO 306
<211> LENGTH: 76
<212> TYPE: PRT
<213> ORGANISM: Conus arenatus

<400> SEQUENCE: 306

Met Lys Leu Thr Cys Val Val Ile Val Val Val Leu Phe Leu Thr Ala
1               5                              10                              15

Trp Thr Phe Val Lys Ala Asp Asp Ser Ile Asn Gly Leu Glu Asn Leu
                20                              25                              30

Phe Pro Lys Ala Arg His Glu Met Lys Asn Pro Glu Ala Ser Lys Leu
            35                              40                              45

Asn Glu Arg Cys Leu Glu Lys Gly Val Leu Cys Asp Pro Ser Ala Gly
        50                              55                              60

Asn Cys Cys Ser Gly Glu Cys Val Leu Val Cys Leu
65                              70                              75

<210> SEQ ID NO 307
<211> LENGTH: 25
<212> TYPE: PRT
<213> ORGANISM: Conus arenatus
<220> FEATURE:
<221> NAME/KEY: SITE
<222> LOCATION: (1)..(25)
<223> OTHER INFORMATION: Xaa at residues 3 and 19 may be Glu or
      gamma-carboxy-Glu; Xaa at residue 10 may be Pro or hydroxy-Pro

<400> SEQUENCE: 307

Cys Leu Xaa Lys Gly Val Leu Cys Asp Xaa Ser Ala Gly Asn Cys Cys
1               5                              10                              15

Ser Gly Xaa Cys Val Leu Val Cys Leu
                20                              25
```

<210> SEQ ID NO 308
<211> LENGTH: 287
<212> TYPE: DNA
<213> ORGANISM: Conus arenatus
<220> FEATURE:
<221> NAME/KEY: CDS
<222> LOCATION: (7)..(240)

<400> SEQUENCE: 308

```
ggatcc atg aaa ctg acg tgc atg gtg atc gtt act gtg ttg ttc ttg        48
       Met Lys Leu Thr Cys Met Val Ile Val Thr Val Leu Phe Leu
       1               5                  10 acc gcc tgg aca ttc gtc acg gct gat gac tcc aga aat gaa ttg gag        96
Thr Ala Trp Thr Phe Val Thr Ala Asp Asp Ser Arg Asn Glu Leu Glu
15              20                  25                  30 aat ctt ttt ctg aag gca tat cac gaa atg aac tcc gaa gcc tct aaa       144
Asn Leu Phe Leu Lys Ala Tyr His Glu Met Asn Ser Glu Ala Ser Lys
                35                  40                  45 ttg gac aag aaa gag tgc gtt gct ggt agt cac ttt tgt ggt ttt ccg       192
Leu Asp Lys Lys Glu Cys Val Ala Gly Ser His Phe Cys Gly Phe Pro
            50                  55                  60 aaa att gga ggg cca tgc tgc agt ggc tgg tgc ttt ttc gtc tgc ttg       240
Lys Ile Gly Gly Pro Cys Cys Ser Gly Trp Cys Phe Phe Val Cys Leu
        65                  70                  75 taaacctgcc gtgatgtctt ctactcccat ctgtgctacc cctcgag                   287
```

<210> SEQ ID NO 309
<211> LENGTH: 78
<212> TYPE: PRT
<213> ORGANISM: Conus arenatus

<400> SEQUENCE: 309

```
Met Lys Leu Thr Cys Met Val Ile Val Thr Val Leu Phe Leu Thr Ala
1               5                   10                  15

Trp Thr Phe Val Thr Ala Asp Asp Ser Arg Asn Glu Leu Glu Asn Leu
                20                  25                  30

Phe Leu Lys Ala Tyr His Glu Met Asn Ser Glu Ala Ser Lys Leu Asp
            35                  40                  45

Lys Lys Glu Cys Val Ala Gly Ser His Phe Cys Gly Phe Pro Lys Ile
        50                  55                  60

Gly Gly Pro Cys Cys Ser Gly Trp Cys Phe Phe Val Cys Leu
65                  70                  75
```

<210> SEQ ID NO 310
<211> LENGTH: 28
<212> TYPE: PRT
<213> ORGANISM: Conus arenatus
<220> FEATURE:
<221> NAME/KEY: SITE
<222> LOCATION: (1)..(28)
<223> OTHER INFORMATION: Xaa at residue 1 may be Glu or
      gamma-carboxy-Glu; Xaa at residues 12 and 17 may be Pro or
      hydroxy-Pro; Xaa at residue 22 may be Trp or bromo-Trp

<400> SEQUENCE: 310

```
Xaa Cys Val Ala Gly Ser His Phe Cys Gly Phe Xaa Lys Ile Gly Gly
1               5                   10                  15

Xaa Cys Cys Ser Gly Xaa Cys Phe Phe Val Cys Leu
            20                  25
```

<210> SEQ ID NO 311

```
<211> LENGTH: 400
<212> TYPE: DNA
<213> ORGANISM: Conus tessulatus
<220> FEATURE:
<221> NAME/KEY: CDS
<222> LOCATION: (7)..(243)

<400> SEQUENCE: 311 ggatcc atg aaa ctg acg tgt gtg gtg atc gtt gct gtg atg ttc ttg         48
       Met Lys Leu Thr Cys Val Val Ile Val Ala Val Met Phe Leu
       1               5                   10 acc gcc tgg aca ttc atc acg gct gat gac tcc ata aat gga ctg gag        96
Thr Ala Trp Thr Phe Ile Thr Ala Asp Asp Ser Ile Asn Gly Leu Glu
15              20                  25                  30 gat aga ggc ata tgg ggg gaa cct ttg tcg aag gca cgt gac gaa atg       144
Asp Arg Gly Ile Trp Gly Glu Pro Leu Ser Lys Ala Arg Asp Glu Met
                35                  40                  45 aac ccc gaa gtc tct aaa cgg gat tgc tgg cct caa tat tgg ttt tgt       192
Asn Pro Glu Val Ser Lys Arg Asp Cys Trp Pro Gln Tyr Trp Phe Cys
            50                  55                  60 ggc cta cag agg gga tgc tgc cca ggg act act tgc ttc ttc ctt tgc       240
Gly Leu Gln Arg Gly Cys Cys Pro Gly Thr Thr Cys Phe Phe Leu Cys
        65                  70                  75 ttt tagtgatctc ttcgactccc ttctgtgcta cctggcttga cctttgattg            293
Phe gcgcgtgccc ttcactggtt ataaacccct ctgttcctcc tctctggacg cttcggggtg     353
tccagcatcc aaataaagcg acgtccccaa aaaaaaaaaa aaaaaaa                   400

<210> SEQ ID NO 312
<211> LENGTH: 79
<212> TYPE: PRT
<213> ORGANISM: Conus tessulatus

<400> SEQUENCE: 312

Met Lys Leu Thr Cys Val Val Ile Val Ala Val Met Phe Leu Thr Ala
1               5                   10                  15

Trp Thr Phe Ile Thr Ala Asp Asp Ser Ile Asn Gly Leu Glu Asp Arg
            20                  25                  30

Gly Ile Trp Gly Glu Pro Leu Ser Lys Ala Arg Asp Glu Met Asn Pro
        35                  40                  45

Glu Val Ser Lys Arg Asp Cys Trp Pro Gln Tyr Trp Phe Cys Gly Leu
    50                  55                  60

Gln Arg Gly Cys Cys Pro Gly Thr Thr Cys Phe Phe Leu Cys Phe
65                  70                  75

<210> SEQ ID NO 313
<211> LENGTH: 26
<212> TYPE: PRT
<213> ORGANISM: Conus tessulatus
<220> FEATURE:
<221> NAME/KEY: SITE
<222> LOCATION: (1)..(26)
<223> OTHER INFORMATION: Xaa at residues 3 and 7 may be Trp or
      bromo-Trp;
      Xaa at residues 4 and 17 may be Pro or hydroxy-Pro; Xaa at residue
      6 may be Tyr, 125-I-Tyr, mono-iodo-Tyr, di-iodo-Tyr, O-sulpho-Tyr
      or O-phospho-Tyr

<400> SEQUENCE: 313

Asp Cys Xaa Xaa Gln Xaa Xaa Phe Cys Gly Leu Gln Arg Gly Cys Cys
1               5                   10                  15

Xaa Gly Thr Thr Cys Phe Phe Leu Cys Phe
```

<210> SEQ ID NO 314
<211> LENGTH: 419
<212> TYPE: DNA
<213> ORGANISM: Conus tessulatus
<220> FEATURE:
<221> NAME/KEY: CDS
<222> LOCATION: (7)..(249)

<400> SEQUENCE: 314

```
ggatcc atg aaa ctg acg tgc gtg gtg gtc gtt gct gtg ctg ttc ttg         48
       Met Lys Leu Thr Cys Val Val Val Val Ala Val Leu Phe Leu
       1               5                  10 aac gcc tgg aca ttc gcc acg gct gtt gac tcc aaa cat gca ctg gcg         96
Asn Ala Trp Thr Phe Ala Thr Ala Val Asp Ser Lys His Ala Leu Ala
15              20                  25                  30 aaa ctt ttt atg aag gca cgt gac gaa atg tat aac ccc gat gcc act        144
Lys Leu Phe Met Lys Ala Arg Asp Glu Met Tyr Asn Pro Asp Ala Thr
                35                  40                  45 aaa ttg gac gat aag aga tgg tgc gct tta gat ggt gaa ctt tgt atc        192
Lys Leu Asp Asp Lys Arg Trp Cys Ala Leu Asp Gly Glu Leu Cys Ile
    50                  55                  60 ata ccg gtc att ggg tcc ata ttt tgc tgc cat ggc ata tgt atg atc        240
Ile Pro Val Ile Gly Ser Ile Phe Cys Cys His Gly Ile Cys Met Ile
65                  70                  75 tac tgc gtc tagttgaact gccgtgatgt cttctactcc cctctgtgct                289
Tyr Cys Val
    80 acccctggtt tgatctttga ttgccctgtg cccttcactg attatgaatc cctctgatcc      349 tactctctga agacctcttg gggtccaaca tccaaataaa gcgacatccc aaaaaaaaaa      409 aaaaaaaaa                                                              419
```

<210> SEQ ID NO 315
<211> LENGTH: 81
<212> TYPE: PRT
<213> ORGANISM: Conus tessulatus

<400> SEQUENCE: 315

```
Met Lys Leu Thr Cys Val Val Val Val Ala Val Leu Phe Leu Asn Ala
1               5                  10                  15

Trp Thr Phe Ala Thr Ala Val Asp Ser Lys His Ala Leu Ala Lys Leu
            20                  25                  30

Phe Met Lys Ala Arg Asp Glu Met Tyr Asn Pro Asp Ala Thr Lys Leu
        35                  40                  45

Asp Asp Lys Arg Trp Cys Ala Leu Asp Gly Glu Leu Cys Ile Ile Pro
    50                  55                  60

Val Ile Gly Ser Ile Phe Cys Cys His Gly Ile Cys Met Ile Tyr Cys
65                  70                  75                  80

Val
```

<210> SEQ ID NO 316
<211> LENGTH: 29
<212> TYPE: PRT
<213> ORGANISM: Conus tessulatus
<220> FEATURE:
<221> NAME/KEY: SITE
<222> LOCATION: (1)..(29)
<223> OTHER INFORMATION: Xaa at residue 1 may be Trp or bromo-Trp;
      Xaa at residue 7 maybe Glu or gamma-carboxy-Glu; Xaa at residue 12

```
        may be Pro or hydroxy-Pro; Xaa at residue 27 may be Tyr,
        125-I-Tyr, mono-iodo-Tyr, di-iodo-Tyr, O-sulpho-Tyr or
        O-phospho-Tyr

<400> SEQUENCE: 316

Xaa Cys Ala Leu Asp Gly Xaa Leu Cys Ile Ile Xaa Val Ile Gly Ser
1               5                   10                  15

Ile Phe Cys Cys His Gly Ile Cys Met Ile Xaa Cys Val
            20                  25

<210> SEQ ID NO 317
<211> LENGTH: 408
<212> TYPE: DNA
<213> ORGANISM: Conus imperialis
<220> FEATURE:
<221> NAME/KEY: CDS
<222> LOCATION: (7)..(240)

<400> SEQUENCE: 317 ggatcc atg aaa ctg acg tgc gtg gtg ttc gtt gct gtg ccg ttc ttg        48
       Met Lys Leu Thr Cys Val Val Phe Val Ala Val Pro Phe Leu
         1               5                   10 acc gcc tcg gta ttc atc acg gct gat gac tcc aga aat gga atc gag       96
Thr Ala Ser Val Phe Ile Thr Ala Asp Asp Ser Arg Asn Gly Ile Glu
 15                  20                  25                  30 aat ctt cct cgg atg aga cgt cac gaa atg aag aac ccc aaa gcc tct      144
Asn Leu Pro Arg Met Arg Arg His Glu Met Lys Asn Pro Lys Ala Ser
                 35                  40                  45 aag ttg aac aag aga cag tgc cgt gta gaa ggt gaa att tgt ggc atg      192
Lys Leu Asn Lys Arg Gln Cys Arg Val Glu Gly Glu Ile Cys Gly Met
         50                  55                  60 ctg ttt gaa gca caa tgc tgc gat ggc tgg tgc ttt ttc gtc tgc atg      240
Leu Phe Glu Ala Gln Cys Cys Asp Gly Trp Cys Phe Phe Val Cys Met
     65                  70                  75 taaaactgcc gtgatgtctt ctactctcct ctgtgctacc tgccctgatc tttgattggc    300
tcgcgccctt cattggttat gaaccctct gatcctactc tctggaggcc tcagggtcc      360 agcatctaaa taaagcgaca tcacaatcaa aaaaaaaaa aaaaaaaa                  408

<210> SEQ ID NO 318
<211> LENGTH: 78
<212> TYPE: PRT
<213> ORGANISM: Conus imperialis

<400> SEQUENCE: 318

Met Lys Leu Thr Cys Val Val Phe Val Ala Val Pro Phe Leu Thr Ala
1               5                   10                  15

Ser Val Phe Ile Thr Ala Asp Asp Ser Arg Asn Gly Ile Glu Asn Leu
            20                  25                  30

Pro Arg Met Arg Arg His Glu Met Lys Asn Pro Lys Ala Ser Lys Leu
        35                  40                  45

Asn Lys Arg Gln Cys Arg Val Glu Gly Glu Ile Cys Gly Met Leu Phe
    50                  55                  60

Glu Ala Gln Cys Cys Asp Gly Trp Cys Phe Phe Val Cys Met
65                  70                  75

<210> SEQ ID NO 319
<211> LENGTH: 27
<212> TYPE: PRT
<213> ORGANISM: Conus imperialis
<220> FEATURE:
<221> NAME/KEY: SITE
```

-continued

<222> LOCATION: (1)..(27)
<223> OTHER INFORMATION: Xaa at residue 1 may be Gln or pyro-Glu; Xaa at residues 5, 7 and 14 may be Glu or gamma-carboxy-Glu; Xaa at residue 21 may be Trp or bromo-Trp

<400> SEQUENCE: 319

```
Xaa Cys Arg Val Xaa Gly Xaa Ile Cys Gly Met Leu Phe Xaa Ala Gln
1               5                   10                  15

Cys Cys Asp Gly Xaa Cys Phe Phe Val Cys Met
            20                  25
```

<210> SEQ ID NO 320
<211> LENGTH: 281
<212> TYPE: DNA
<213> ORGANISM: Conus caracteristicus
<220> FEATURE:
<221> NAME/KEY: CDS
<222> LOCATION: (7)..(234)

<400> SEQUENCE: 320

```
ggatcc atg aaa ctg acg tgt gtg gtg atc gtt gct gtg ctg ttc ttg        48
       Met Lys Leu Thr Cys Val Val Ile Val Ala Val Leu Phe Leu
       1               5                   10 acc gcc tgg aca ttc gtc acg gct gat gac tcc aga aat gga ttg gag       96
Thr Ala Trp Thr Phe Val Thr Ala Asp Asp Ser Arg Asn Gly Leu Glu
15                  20                  25                  30 aat ctt ttt ccg aag gca cgt cac gaa atg aag aac ccc gaa gcc tct      144
Asn Leu Phe Pro Lys Ala Arg His Glu Met Lys Asn Pro Glu Ala Ser
                35                  40                  45 aaa ttg aac aag agg tgc gtt gac cct ggt gaa ttt tgt ggt ccg gga      192
Lys Leu Asn Lys Arg Cys Val Asp Pro Gly Glu Phe Cys Gly Pro Gly
            50                  55                  60 ttt gga gat tgc tgc act ggc ttc tgc ctt tta gtc tgc atc              234
Phe Gly Asp Cys Cys Thr Gly Phe Cys Leu Leu Val Cys Ile
        65                  70                  75 taaaactgcc gtgatgtctt ctactcccat ctgtgctacc cctcgag                  281
```

<210> SEQ ID NO 321
<211> LENGTH: 76
<212> TYPE: PRT
<213> ORGANISM: Conus caracteristicus

<400> SEQUENCE: 321

```
Met Lys Leu Thr Cys Val Val Ile Val Ala Val Leu Phe Leu Thr Ala
1               5                   10                  15

Trp Thr Phe Val Thr Ala Asp Asp Ser Arg Asn Gly Leu Glu Asn Leu
            20                  25                  30

Phe Pro Lys Ala Arg His Glu Met Lys Asn Pro Glu Ala Ser Lys Leu
        35                  40                  45

Asn Lys Arg Cys Val Asp Pro Gly Glu Phe Cys Gly Pro Gly Phe Gly
    50                  55                  60

Asp Cys Cys Thr Gly Phe Cys Leu Leu Val Cys Ile
65                  70                  75
```

<210> SEQ ID NO 322
<211> LENGTH: 25
<212> TYPE: PRT
<213> ORGANISM: Conus caracteristicus
<220> FEATURE:
<221> NAME/KEY: SITE
<222> LOCATION: (1)..(25)
<223> OTHER INFORMATION: Xaa at residues 4 and 10 may be Pro or hydroxy-Pro; Xaa at residue 6 may be Glu or gamma-carboxy-Glu

```
<400> SEQUENCE: 322

Cys Val Asp Xaa Gly Xaa Phe Cys Gly Xaa Gly Phe Gly Asp Cys Cys
1               5                   10                  15

Thr Gly Phe Cys Leu Leu Val Cys Ile
            20                  25

<210> SEQ ID NO 323
<211> LENGTH: 287
<212> TYPE: DNA
<213> ORGANISM: Conus miliaris
<220> FEATURE:
<221> NAME/KEY: CDS
<222> LOCATION: (7)..(240)

<400> SEQUENCE: 323 ggatcc atg aaa ctg acg tgc gtg gtg atc gtt gct gtg ttg ttc ttg        48
       Met Lys Leu Thr Cys Val Val Ile Val Ala Val Leu Phe Leu
       1               5                   10 acc gcc tgg aca ttc gtc atg gct gat gac tcc aga aat gat ttg gag       96
Thr Ala Trp Thr Phe Val Met Ala Asp Asp Ser Arg Asn Asp Leu Glu
15              20                  25                  30 aat ctt ttt ctg aag gca cgt cat gaa atg aag aac ccc gaa gct tct      144
Asn Leu Phe Leu Lys Ala Arg His Glu Met Lys Asn Pro Glu Ala Ser
                35                  40                  45 aaa ttg aac aag aga tgc ctt cca aat ggt gta ctt tgt gat ctg gga      192
Lys Leu Asn Lys Arg Cys Leu Pro Asn Gly Val Leu Cys Asp Leu Gly
            50                  55                  60 tct cca cca tac tgc tgc agt ggc tgg tgc gcg atc gtc gtc tgc atc      240
Ser Pro Pro Tyr Cys Cys Ser Gly Trp Cys Ala Ile Val Val Cys Ile
        65                  70                  75 taaaactgtc gtcatgtctt ctactcccat ctgtgctacc cctcgag                  287

<210> SEQ ID NO 324
<211> LENGTH: 78
<212> TYPE: PRT
<213> ORGANISM: Conus miliaris

<400> SEQUENCE: 324

Met Lys Leu Thr Cys Val Val Ile Val Ala Val Leu Phe Leu Thr Ala
1               5                   10                  15

Trp Thr Phe Val Met Ala Asp Asp Ser Arg Asn Asp Leu Glu Asn Leu
            20                  25                  30

Phe Leu Lys Ala Arg His Glu Met Lys Asn Pro Glu Ala Ser Lys Leu
        35                  40                  45

Asn Lys Arg Cys Leu Pro Asn Gly Val Leu Cys Asp Leu Gly Ser Pro
    50                  55                  60

Pro Tyr Cys Cys Ser Gly Trp Cys Ala Ile Val Val Cys Ile
65                  70                  75

<210> SEQ ID NO 325
<211> LENGTH: 27
<212> TYPE: PRT
<213> ORGANISM: Conus miliaris
<220> FEATURE:
<221> NAME/KEY: SITE
<222> LOCATION: (1)..(27)
<223> OTHER INFORMATION: Xaa at residues 3, 13 and 14 may be Pro or
      hydroxy-Pro; Xaa at residue 15 may be Tyr, 125-I-Tyr,
      mono-iodo-Tyr, di-iodo-Tyr, O-sulpho-Tyr or O-phospho-Tyr; Xaa at
      residue 20 may be Trp or bromo-Trp

<400> SEQUENCE: 325
```

```
Cys Leu Xaa Asn Gly Val Leu Cys Asp Leu Gly Ser Xaa Xaa Xaa Cys
1               5                   10                  15

Cys Ser Gly Xaa Cys Ala Ile Val Val Cys Ile
            20                  25
```

<210> SEQ ID NO 326
<211> LENGTH: 287
<212> TYPE: DNA
<213> ORGANISM: Conus atlanticus
<220> FEATURE:
<221> NAME/KEY: CDS
<222> LOCATION: (7)..(240)

<400> SEQUENCE: 326

```
ggatcc atg aaa ctg acg tgc gtg gtg atc gtt gct gtg ctg ttc ttg        48
       Met Lys Leu Thr Cys Val Val Ile Val Ala Val Leu Phe Leu
       1               5                   10 acc gcc tgg aca ttc gtc acg gct gat gac tcc ata aat ggg ttg gag       96
Thr Ala Trp Thr Phe Val Thr Ala Asp Asp Ser Ile Asn Gly Leu Glu
15              20                  25                  30 aat ctt ttt ccg aag gca cgt cac gaa atg agg aaa ccc gaa gcc tct      144
Asn Leu Phe Pro Lys Ala Arg His Glu Met Arg Lys Pro Glu Ala Ser
                35                  40                  45 aga tcg aga ggg agg tgc cgt cct cgt ggt atg ttc tgt ggc ttt ccg      192
Arg Ser Arg Gly Arg Cys Arg Pro Arg Gly Met Phe Cys Gly Phe Pro
            50                  55                  60 aaa cct gga cca tac tgc tgc aat ggc tgg tgc ttt ttc gtc tgc atc      240
Lys Pro Gly Pro Tyr Cys Cys Asn Gly Trp Cys Phe Phe Val Cys Ile
        65                  70                  75 taaaactgcc gtgatgtgtt ctactcccat ctgtgctacc cctcgag                  287
```

<210> SEQ ID NO 327
<211> LENGTH: 78
<212> TYPE: PRT
<213> ORGANISM: Conus atlanticus

<400> SEQUENCE: 327

```
Met Lys Leu Thr Cys Val Val Ile Val Ala Val Leu Phe Leu Thr Ala
1               5                   10                  15

Trp Thr Phe Val Thr Ala Asp Asp Ser Ile Asn Gly Leu Glu Asn Leu
            20                  25                  30

Phe Pro Lys Ala Arg His Glu Met Arg Lys Pro Glu Ala Ser Arg Ser
        35                  40                  45

Arg Gly Arg Cys Arg Pro Arg Gly Met Phe Cys Gly Phe Pro Lys Pro
    50                  55                  60

Gly Pro Tyr Cys Cys Asn Gly Trp Cys Phe Phe Val Cys Ile
65                  70                  75
```

<210> SEQ ID NO 328
<211> LENGTH: 27
<212> TYPE: PRT
<213> ORGANISM: Conus atlanticus
<220> FEATURE:
<221> NAME/KEY: SITE
<222> LOCATION: (1)..(27)
<223> OTHER INFORMATION: Xaa at residues 3, 11, 13 and 15 may be Pro or
      hydroxy-Pro; Xaa at residue16 may be Tyr, 125-I-Tyr,
      mono-iodo-Tyr, di-iodo-Tyr, O-sulpho-Tyr or O-phospho-Tyr; Xaa at
      residue 21 may be Trp or bromo-Trp

<400> SEQUENCE: 328

Cys Arg Xaa Arg Gly Met Phe Cys Gly Phe Xaa Lys Xaa Gly Xaa Xaa
```

```
            1               5                  10                 15
Cys Cys Asn Gly Xaa Cys Phe Phe Val Cys Ile
            20                 25
```

<210> SEQ ID NO 329
<211> LENGTH: 284
<212> TYPE: DNA
<213> ORGANISM: Conus lividus
<220> FEATURE:
<221> NAME/KEY: CDS
<222> LOCATION: (7)..(237)

<400> SEQUENCE: 329

```
ggatcc atg aaa ctg acg tgc gtg gtg atc gtt gct gtg ctg ttc ttg        48
       Met Lys Leu Thr Cys Val Val Ile Val Ala Val Leu Phe Leu
       1               5                   10 acc gcc tgg aca ttt gcc acg gct gat gac ccc aga aat gga ttg gag        96
Thr Ala Trp Thr Phe Ala Thr Ala Asp Asp Pro Arg Asn Gly Leu Glu
15           20                  25                  30 aat ctt ttt tcg aag gca cat cac gaa atg aag aac ccc gaa gcc tct       144
Asn Leu Phe Ser Lys Ala His His Glu Met Lys Asn Pro Glu Ala Ser
            35                  40                  45 aaa ttg aac aag agg tgc cct aac act ggt gaa tta tgt gat gtg gtt       192
Lys Leu Asn Lys Arg Cys Pro Asn Thr Gly Glu Leu Cys Asp Val Val
             50                  55                  60 gaa caa aac tgc tgc tat acc tat tgc ttt att gta gtc tgc cta           237
Glu Gln Asn Cys Cys Tyr Thr Tyr Cys Phe Ile Val Val Cys Leu
            65                  70                  75 taaaactacc gtgatgtctt ctactcccat ctgtgctacc cctcgag                   284
```

<210> SEQ ID NO 330
<211> LENGTH: 77
<212> TYPE: PRT
<213> ORGANISM: Conus lividus

<400> SEQUENCE: 330

```
Met Lys Leu Thr Cys Val Val Ile Val Ala Val Leu Phe Leu Thr Ala
1               5                   10                  15

Trp Thr Phe Ala Thr Ala Asp Asp Pro Arg Asn Gly Leu Glu Asn Leu
            20                  25                  30

Phe Ser Lys Ala His His Glu Met Lys Asn Pro

```
Xaa Thr Xaa Cys Phe Ile Val Val Cys Leu
        20                  25

<210> SEQ ID NO 332
<211> LENGTH: 281
<212> TYPE: DNA
<213> ORGANISM: Conus pulicarius
<220> FEATURE:
<221> NAME/KEY: CDS
<222> LOCATION: (7)..(234)

<400> SEQUENCE: 332 ggatcc atg aaa ctg acg tgc atg gtg atc gtt gct gtg ctg ttc ttg       48
       Met Lys Leu Thr Cys Met Val Ile Val Ala Val Leu Phe Leu
       1               5                   10 acc gcc tgg aca ttc gtc aag gct gat gac tcc aga aat gga ttg gag      96
Thr Ala Trp Thr Phe Val Lys Ala Asp Asp Ser Arg Asn Gly Leu Glu
15              20                  25                  30 aat ctt ttt ccg aag gca cgt cac gaa atg aag aac tcc aaa gcc tct     144
Asn Leu Phe Pro Lys Ala Arg His Glu Met Lys Asn Ser Lys Ala Ser
                35                  40                  45 aaa tta aac aag agg tgc gtt gaa gat ggt gat ttt tgt ggt ccg gga     192
Lys Leu Asn Lys Arg Cys Val Glu Asp Gly Asp Phe Cys Gly Pro Gly
        50                  55                  60 tat gaa gag tgc tgc agt ggc ttc tgc ctt tac gtc tgc atc             234
Tyr Glu Glu Cys Cys Ser Gly Phe Cys Leu Tyr Val Cys Ile
        65                  70                  75 taaaactgcc gtgatgtctt ctactcccat ctgtgctacc cctcgag                 281

<210> SEQ ID NO 333
<211> LENGTH: 76
<212> TYPE: PRT
<213> ORGANISM: Conus pulicarius

<400> SEQUENCE: 333

Met Lys Leu Thr Cys Met Val Ile Val Ala Val Leu Phe Leu Thr Ala
1               5                   10                  15

Trp Thr Phe Val Lys Ala Asp Asp Ser Arg Asn Gly Leu Glu Asn Leu
            20                  25                  30

Phe Pro Lys Ala Arg His Glu Met Lys Asn Ser Lys Ala Ser Lys Leu
        35                  40                  45

Asn Lys Arg Cys Val Glu Asp Gly Asp Phe Cys Gly Pro Gly Tyr Glu
    50                  55                  60

Glu Cys Cys Ser Gly Phe Cys Leu Tyr Val Cys Ile
65                  70                  75

<210> SEQ ID NO 334
<211> LENGTH: 25
<212> TYPE: PRT
<213> ORGANISM: Conus pulicarius
<220> FEATURE:
<221> NAME/KEY: SITE
<222> LOCATION: (1)..(25)
<223> OTHER INFORMATION: Xaa at residues 3, 13 and 14 may be Glu or
      gamma-carboxy-Glu; Xaa at residue 10 may be Pro or hydroxy-Pro;
      Xaa at residues 12 and 22 may be Tyr, 125-I-Tyr, mono-iodo-Tyr,
      di-iodo-Tyr, O-sulpho-Tyr or O-phospho-Tyr

<400> SEQUENCE: 334

Cys Val Xaa Asp Gly Asp Phe Cys Gly Xaa Gly Xaa Xaa Xaa Cys Cys
1               5                   10                  15

Ser Gly Phe Cys Leu Xaa Val Cys Ile
            20                  25
```

<210> SEQ ID NO 335
<211> LENGTH: 293
<212> TYPE: DNA
<213> ORGANISM: Conus generalis
<220> FEATURE:
<221> NAME/KEY: CDS
<222> LOCATION: (7)..(249)

<400> SEQUENCE: 335

```
ggatcc atg aaa ctg acg tgt gtg gtg atc gtt gct gtg cta ttc ttg      48
       Met Lys Leu Thr Cys Val Val Ile Val Ala Val Leu Phe Leu
       1               5                  10 acc gcc tgg aca ttc gtc acg gct gat gac aca aga tat aaa ctg gag     96
Thr Ala Trp Thr Phe Val Thr Ala Asp Asp Thr Arg Tyr Lys Leu Glu
15              20                  25                  30 aat cct ttt ctg aag gca cgc aac gaa ctg cag aaa cac gaa gcc tct    144
Asn Pro Phe Leu Lys Ala Arg Asn Glu Leu Gln Lys His Glu Ala Ser
                35                  40                  45 caa ctg aac gag aga ggc tgc ctt gac cca ggt tac ttc tgt ggg acg    192
Gln Leu Asn Glu Arg Gly Cys Leu Asp Pro Gly Tyr Phe Cys Gly Thr
            50                  55                  60 ccg ttt ctt gga gca tac tgc tgc ggt ggc att tgc ctt att gtc tgc    240
Pro Phe Leu Gly Ala Tyr Cys Cys Gly Gly Ile Cys Leu Ile Val Cys
        65                  70                  75 ata gaa acg taaaggcttg atgtcttcta ctcccatctg tgctaccct cgag         293
Ile Glu Thr
    80
```

<210> SEQ ID NO 336
<211> LENGTH: 81
<212> TYPE: PRT
<213> ORGANISM: Conus generalis

<400> SEQUENCE: 336

```
Met Lys Leu Thr Cys Val Val Ile Val Ala Val Leu Phe Leu Thr Ala
1               5                  10                  15

Trp Thr Phe Val Thr Ala Asp Asp Thr Arg Tyr Lys Leu Glu Asn Pro
            20                  25                  30

Phe Leu Lys Ala Arg Asn Glu Leu Gln Lys His Glu Ala Ser Gln Leu
        35                  40                  45

Asn Glu Arg Gly Cys Leu Asp Pro Gly Tyr Phe Cys Gly Thr Pro Phe
    50                  55                  60

Leu Gly Ala Tyr Cys Cys Gly Gly Ile Cys Leu Ile Val Cys Ile Glu
65                  70                  75                  80

Thr
```

<210> SEQ ID NO 337
<211> LENGTH: 30
<212> TYPE: PRT
<213> ORGANISM: Conus generalis
<220> FEATURE:
<221> NAME/KEY: SITE
<222> LOCATION: (1)..(30)
<223> OTHER INFORMATION: Xaa at residues 5 and 12 may be Pro or
      hydroxy-Pro; Xaa at residues 7 and 17 may be Tyr, 125-I-Tyr,
      mono-iodo-Tyr, di-iodo-Tyr, O-sulpho-Tyr or O-phospho-Tyr

<400> SEQUENCE: 337

```
Gly Cys Leu Asp Xaa Gly Xaa Phe Cys Gly Thr Xaa Phe Leu Gly Ala
1               5                  10                  15

Xaa Cys Cys Gly Gly Ile Cys Leu Ile Val Cys Ile Xaa Thr
```

-continued

```
                    20                  25                  30
```

<210> SEQ ID NO 338
<211> LENGTH: 400
<212> TYPE: DNA
<213> ORGANISM: Conus episcopatus
<220> FEATURE:
<221> NAME/KEY: CDS
<222> LOCATION: (7)..(234)

<400> SEQUENCE: 338

| ggatcc atg aaa ctg acg tgc gtg gtg atc gtt gct gtg ctg ttc ttg | 48 |
|---|---|
|        Met Lys Leu Thr Cys Val Val Ile Val Ala Val Leu Phe Leu | |
|        1               5                10 | |
| acc gcc tgg aca ttt gcc acg gct gat gac ccc aga aat gga ttg ggg | 96 |
| Thr Ala Trp Thr Phe Ala Thr Ala Asp Asp Pro Arg Asn Gly Leu Gly | |
| 15               20              25              30 | |
| aat ctt ttt tcg aat gta cat cac gaa atg aag aac ctc gaa gac tct | 144 |
| Asn Leu Phe Ser Asn Val His His Glu Met Lys Asn Leu Glu Asp Ser | |
|               35              40              45 | |
| aaa ttg gac aag aag tgc ctt ggg ttt ggt gaa gct tgt ctt atg ctt | 192 |
| Lys Leu Asp Lys Lys Cys Leu Gly Phe Gly Glu Ala Cys Leu Met Leu | |
|      50               55              60 | |
| tat tca gac tgc tgc agc tat tgc gtt gct ctt gtc tgc cta | 234 |
| Tyr Ser Asp Cys Cys Ser Tyr Cys Val Ala Leu Val Cys Leu | |
| 65               70              75 | |
| taaaactacc gtgacgtctt ctactcccct ctgtgctacc tggcttgatc tttgattggc | 294 |
| gtgtgcgctt cactggttat gaacccctct gatcctactc tctgaagacc tctggggtcc | 354 |
| aacatccaaa taaagcgaca tcacaaaaaa aaaaaaaaa aaaaaa | 400 |

<210> SEQ ID NO 339
<211> LENGTH: 76
<212> TYPE: PRT
<213> ORGANISM: Conus episcopatus

<400> SEQUENCE: 339

Met Lys Leu Thr Cys Val Val Ile Val Ala Val Leu Phe Leu Thr Ala
1               5                   10                  15

Trp Thr Phe Ala Thr Ala Asp Asp Pro Arg Asn Gly Leu Gly Asn Leu
            20                  25                  30

Phe Ser Asn Val His His Glu Met Lys Asn Leu Glu Asp Ser Lys Leu
        35                  40                  45

Asp Lys Lys Cys Leu Gly Phe Gly Glu Ala Cys Leu Met Leu Tyr Ser
    50                  55                  60

Asp Cys Cys Ser Tyr Cys Val Ala Leu Val Cys Leu
65                  70                  75

<210> SEQ ID NO 340
<211> LENGTH: 25
<212> TYPE: PRT
<213> ORGANISM: Conus episcopatus
<220> FEATURE:
<221> NAME/KEY: SITE
<222> LOCATION: (1)..(25)
<223> OTHER INFORMATION: Xaa at residue 6 may be Glu or
      gamma-carboxy-Glu; Xaa at residues 12 and 18 may be Tyr,
      125-I-Tyr, mono-iodo-Tyr, di-iodo-Tyr, O-s
      ulpho-Tyr or O-phospho-Tyr

<400> SEQUENCE: 340

Cys Leu Gly Phe Gly Xaa Ala Cys Leu Met Leu Xaa Ser Asp Cys Cys
1               5                   10                  15
```

```
Ser Xaa Cys Val Ala Leu Val Cys Leu
        20                  25

<210> SEQ ID NO 341
<211> LENGTH: 404
<212> TYPE: DNA
<213> ORGANISM: Conus episcopatus
<220> FEATURE:
<221> NAME/KEY: CDS
<222> LOCATION: (7)..(240)

<400> SEQUENCE: 341 ggatcc atg aaa ctg acg tgc gtg gtg atc att gct gtg ctg ttc ttg        48
       Met Lys Leu Thr Cys Val Val Ile Ile Ala Val Leu Phe Leu
       1               5                   10 acc gcc tgg aca ttc gtc atg gct gat gac ccc aga gat gaa ccg gag       96
Thr Ala Trp Thr Phe Val Met Ala Asp Asp Pro Arg Asp Glu Pro Glu
15              20                  25                  30 gca cgt gac gaa atg aac ccc gca gcc tct aaa ttg aac gag aga ggc       144
Ala Arg Asp Glu Met Asn Pro Ala Ala Ser Lys Leu Asn Glu Arg Gly
                35                  40                  45 tgc ctt gca gtt gat tat ttt tgc ggc ata ccg ttt gtg agc aac ggg       192
Cys Leu Ala Val Asp Tyr Phe Cys Gly Ile Pro Phe Val Ser Asn Gly
            50                  55                  60 cta tgc tgc agt ggc aat tgt gtt ttt gtc tgc aca ccc caa ggg aag       240
Leu Cys Cys Ser Gly Asn Cys Val Phe Val Cys Thr Pro Gln Gly Lys
        65                  70                  75 taaaactgcc gtgacgtctt ctactcccct ctgtgctacc tggcttgatc tttgattggc     300
gtgtgcactt cactggttat gaacccctct gatcctactc tctgaagacc tctggggtcc    360
aacatccaaa taaagcgaca tcccaaaaaa aaaaaaaaaa aaaa                      404

<210> SEQ ID NO 342
<211> LENGTH: 78
<212> TYPE: PRT
<213> ORGANISM: Conus episcopatus

<400> SEQUENCE: 342

Met Lys Leu Thr Cys Val Val Ile Ile Ala Val Leu Phe Leu Thr Ala
1               5                   10                  15

Trp Thr Phe Val Met Ala Asp Asp Pro Arg Asp Glu Pro Glu Ala Arg
            20                  25                  30

Asp Glu Met Asn Pro Ala Ala Ser Lys Leu Asn Glu Arg Gly Cys Leu
        35                  40                  45

Ala Val Asp Tyr Phe Cys Gly Ile Pro Phe Val Ser Asn Gly Leu Cys
    50                  55                  60

Cys Ser Gly Asn Cys Val Phe Val Cys Thr Pro Gln Gly Lys
65                  70                  75

<210> SEQ ID NO 343
<211> LENGTH: 31
<212> TYPE: PRT
<213> ORGANISM: Conus episcopatus
<220> FEATURE:
<221> NAME/KEY: SITE
<222> LOCATION: (1)..(31)
<223> OTHER INFORMATION: Xaa at residue 7 may be Tyr, 125-I-Tyr,
      mono-iodo-Tyr, di-iodo-Tyr, O-sulpho-Tyr or O-phospho-Tyr; Xaa at
      residues 12 and 30 may be Pro or hydroxy-Pro

<400> SEQUENCE: 343

Gly Cys Leu Ala Val Asp Xaa Phe Cys Gly Ile Xaa Phe Val Ser Asn
```

-continued

```
                1               5                  10                  15
Gly Leu Cys Cys Ser Gly Asn Cys Val Phe Val Cys Thr Xaa Gln
            20                  25                  30
```

<210> SEQ ID NO 344
<211> LENGTH: 202
<212> TYPE: DNA
<213> ORGANISM: Conus achatinus
<220> FEATURE:
<221> NAME/KEY: CDS
<222> LOCATION: (85)..(171)

<400> SEQUENCE: 344

```
cgatcctctg tcctccatct attattattc gctgccaaac tgtgttaaat attcaagtct      60
ctctttctgt tgtgtctaa cagg ttg aga tgg tgc att cct aga ggt gat         111
                         Leu Arg Trp Cys Ile Pro Arg Gly Asp
                          1               5 ctt tgt ttc ccc tcg gat cgc ata caa tgc tgc agt ggc aag tgc aca      159
Leu Cys Phe Pro Ser Asp Arg Ile Gln Cys Cys Ser Gly Lys Cys Thr
 10                  15                  20                  25 ttc gtc tgc atg taaaactgcc gtgatgtctt ctcctcccct c                   202
Phe Val Cys Met
```

<210> SEQ ID NO 345
<211> LENGTH: 29
<212> TYPE: PRT
<213> ORGANISM: Conus achatinus

<400> SEQUENCE: 345

```
Leu Arg Trp Cys Ile Pro Arg Gly Asp Leu Cys Phe Pro Ser Asp Arg
 1               5                  10                  15

Ile Gln Cys Cys Ser Gly Lys Cys Thr Phe Val Cys Met
            20                  25
```

<210> SEQ ID NO 346
<211> LENGTH: 27
<212> TYPE: PRT
<213> ORGANISM: Conus achatinus
<220> FEATURE:
<221> NAME/KEY: SITE
<222> LOCATION: (1)..(27)
<223> OTHER INFORMATION: Xaa at residue 1 may be Trp or bromo-Trp; Xaa
      at residues 4 and 11 may be Pro or hydroxy-Pro

<400> SEQUENCE: 346

```
Xaa Cys Ile Xaa Arg Gly Asp Leu Cys Phe Xaa Ser Asp Arg Ile Gln
 1               5                  10                  15

Cys Cys Ser Gly Lys Cys Thr Phe Val Cys Met
            20                  25
```

<210> SEQ ID NO 347
<211> LENGTH: 202
<212> TYPE: DNA
<213> ORGANISM: Conus achatinus
<220> FEATURE:
<221> NAME/KEY: CDS
<222> LOCATION: (85)..(171)

<400> SEQUENCE: 347

```
cgatcctctg tcctcctcct tcattcattc gctgccaaac tgtattaaat attcgaatct      60
ctctttctgt tgtgtctga caga ttg aga ggg tgc gtt cct agt ggt gaa        111
                         Leu Arg Gly Cys Val Pro Ser Gly Glu
                          1               5
```

```
att tgt tac ttc atg gat cac ata gga tgc tgc agt ggc aag tgc aca    159
Ile Cys Tyr Phe Met Asp His Ile Gly Cys Cys Ser Gly Lys Cys Thr
 10              15              20              25 ttc gtc tgc atg taaaactgcc gtgatgtctt ctcctcccat c                 202
Phe Val Cys Met
```

<210> SEQ ID NO 348
<211> LENGTH: 29
<212> TYPE: PRT
<213> ORGANISM: Conus achatinus

<400> SEQUENCE: 348

```
Leu Arg Gly Cys Val Pro Ser Gly Glu Ile Cys Tyr Phe Met Asp His
 1               5                  10                  15

Ile Gly Cys Cys Ser Gly Lys Cys Thr Phe Val Cys Met
                 20                  25
```

<210> SEQ ID NO 349
<211> LENGTH: 27
<212> TYPE: PRT
<213> ORGANISM: Conus achatinus
<220> FEATURE:
<221> NAME/KEY: SITE
<222> LOCATION: (1)..(27)
<223> OTHER INFORMATION: Xaa at residue 4 may be Pro or hydroxy-Pro; Xaa
      at residue 7 may be Glu or gamma-carboxy-Glu; Xaa at residue 10
      may be Tyr, 125-I- Tyr, mono-iodo-Tyr, di-iodo-Tyr, O-sulpho-Tyr
      or O-phospho-Tyr

<400> SEQUENCE: 349

```
Gly Cys Val Xaa Ser Gly Xaa Ile Cys Xaa Phe Met Asp His Ile Gly
 1               5                  10                  15

Cys Cys Ser Gly Lys Cys Thr Phe Val Cys Met
                 20                  25
```

<210> SEQ ID NO 350
<211> LENGTH: 264
<212> TYPE: DNA
<213> ORGANISM: Conus bullatus
<220> FEATURE:
<221> NAME/KEY: CDS
<222> LOCATION: (1)..(234)

<400> SEQUENCE: 350

```
atg aaa ctg acg tgc gtg atc gtt act gtg ctg ttc ttg acc gcc        48
Met Lys Leu Thr Cys Val Met Ile Val Thr Val Leu Phe Leu Thr Ala
 1               5                  10                  15 tgg aca ttc gtc acg gct gat gac tcc aca tat gga ttg aag aat ctt   96
Trp Thr Phe Val Thr Ala Asp Asp Ser Thr Tyr Gly Leu Lys Asn Leu
                 20                  25                  30 ttg ccg aac gga cgt cat gaa atg atg aac ccc gaa gcc cct aaa ttg   144
Leu Pro Asn Gly Arg His Glu Met Met Asn Pro Glu Ala Pro Lys Leu
             35                  40                  45 aac aag aaa gat gaa tgc tct gct cct ggt gca ttt tgt ctc atc agg   192
Asn Lys Lys Asp Glu Cys Ser Ala Pro Gly Ala Phe Cys Leu Ile Arg
         50                  55                  60 cca gga ctc tgc tgc agc gag ttc tgc ttc ttt gcg tgt ttt           234
Pro Gly Leu Cys Cys Ser Glu Phe Cys Phe Phe Ala Cys Phe
 65                  70                  75 tagtgacggt tgatgtcttc tactcccctc                                   264
```

<210> SEQ ID NO 351
<211> LENGTH: 78
<212> TYPE: PRT

<213> ORGANISM: Conus bullatus

<400> SEQUENCE: 351

Met Lys Leu Thr Cys Val Met Ile Val Thr Val Leu Phe Leu Thr Ala
1               5                   10                  15

Trp Thr Phe Val Thr Ala Asp Asp Ser Thr Tyr Gly Leu Lys Asn Leu
                20                  25                  30

Leu Pro Asn Gly Arg His Glu Met Met Asn Pro Glu Ala Pro Lys Leu
            35                  40                  45

Asn Lys Lys Asp Glu Cys Ser Ala Pro Gly Ala Phe Cys Leu Ile Arg
        50                  55                  60

Pro Gly Leu Cys Cys Ser Glu Phe Cys Phe Phe Ala Cys Phe
65                  70                  75

<210> SEQ ID NO 352
<211> LENGTH: 27
<212> TYPE: PRT
<213> ORGANISM: Conus bullatus
<220> FEATURE:
<221> NAME/KEY: SITE
<222> LOCATION: (1)..(27)
<223> OTHER INFORMATION: Xaa at residues 2 and 20 may be Glu or
      gamma-carboxy-Glu; Xaa at residues 6 and 14 may be Pro or
      hydroxy-Pro

<400> SEQUENCE: 352

Asp Xaa Cys Ser Ala Xaa Gly Ala Phe Cys Leu Ile Arg Xaa Gly Leu
1               5                   10                  15

Cys Cys Ser Xaa Phe Cys Phe Phe Ala Cys Phe
                20                  25

<210> SEQ ID NO 353
<211> LENGTH: 276
<212> TYPE: DNA
<213> ORGANISM: Conus bullatus
<220> FEATURE:
<221> NAME/KEY: CDS
<222> LOCATION: (1)..(246)

<400> SEQUENCE: 353 atg aaa ctg acg tgc gtg atg atc gtt act gtg ctg ttc ttg acc gcc        48
Met Lys Leu Thr Cys Val Met Ile Val Thr Val Leu Phe Leu Thr Ala
1               5                   10                  15 tgg aca ttc gtc acg gct gat gac tcc aga gac gct ccg gat agt gca        96
Trp Thr Phe Val Thr Ala Asp Asp Ser Arg Asp Ala Pro Asp Ser Ala
                20                  25                  30 gaa gga tgg gag aaa ctt ttc tcg gag gca cgt gac gaa atg aag aac       144
Glu Gly Trp Glu Lys Leu Phe Ser Glu Ala Arg Asp Glu Met Lys Asn
            35                  40                  45 cgc aaa gac ttt gaa ttg aga ggg tgc ctt cct agg tgg gaa ttt tgt       192
Arg Lys Asp Phe Glu Leu Arg Gly Cys Leu Pro Arg Trp Glu Phe Cys
        50                  55                  60 ccc atc ttt aaa aaa aac gat tgc tgc agt ggc ata tgc ata agc atc       240
Pro Ile Phe Lys Lys Asn Asp Cys Cys Ser Gly Ile Cys Ile Ser Ile
65              70                  75                  80 tgc ttg taaaactccg tgatgtcttc tcttcccatc                              276
Cys Leu <210> SEQ ID NO 354
<211> LENGTH: 82
<212> TYPE: PRT
<213> ORGANISM: Conus bullatus

```
<400> SEQUENCE: 354

Met Lys Leu Thr Cys Val Met Ile Val Thr Val Leu Phe Leu Thr Ala
1               5                   10                  15

Trp Thr Phe Val Thr Ala Asp Asp Ser Arg Asp Ala Pro Asp Ser Ala
            20                  25                  30

Glu Gly Trp Glu Lys Leu Phe Ser Glu Ala Arg Asp Glu Met Lys Asn
        35                  40                  45

Arg Lys Asp Phe Glu Leu Arg Gly Cys Leu Pro Arg Trp Glu Phe Cys
    50                  55                  60

Pro Ile Phe Lys Lys Asn Asp Cys Cys Ser Gly Ile Cys Ile Ser Ile
65                  70                  75                  80

Cys Leu

<210> SEQ ID NO 355
<211> LENGTH: 27
<212> TYPE: PRT
<213> ORGANISM: Conus bullatus
<220> FEATURE:
<221> NAME/KEY: SITE
<222> LOCATION: (1)..(27)
<223> OTHER INFORMATION: Xaa at residues 4 and 10 may be Pro or
      hydroxy-Pro; Xaa at residue 6 may be Trp or bromo-Trp; Xaa at
      residue 7 may be Glu or gamma-carboxy-Glu

<400> SEQUENCE: 355

Gly Cys Leu Xaa Arg Xaa Xaa Phe Cys Xaa Ile Phe Lys Lys Asn Asp
1               5                   10                  15

Cys Cys Ser Gly Ile Cys Ile Ser Ile Cys Leu
            20                  25

<210> SEQ ID NO 356
<211> LENGTH: 268
<212> TYPE: DNA
<213> ORGANISM: Conus striolatus
<220> FEATURE:
<221> NAME/KEY: CDS
<222> LOCATION: (1)..(237)

<400> SEQUENCE: 356 atg aaa ctg acg tgc atg atg att gtt gct gtg ctg ttc ttg acc gcc        48
Met Lys Leu Thr Cys Met Met Ile Val Ala Val Leu Phe Leu Thr Ala
1               5                   10                  15 tgg ata ttt gta atg gct gat gac tcc aga aat gga ttg gag aat ctt        96
Trp Ile Phe Val Met Ala Asp Asp Ser Arg Asn Gly Leu Glu Asn Leu
            20                  25                  30 cct cag act aca cgt cac gaa atg aag aac ccc gaa gcc tct aaa ttg       144
Pro Gln Thr Thr Arg His Glu Met Lys Asn Pro Glu Ala Ser Lys Leu
        35                  40                  45 aac cag aca gac tgc ctt gct aaa gac gct ttc tgt gcc tgg ccg ata       192
Asn Gln Thr Asp Cys Leu Ala Lys Asp Ala Phe Cys Ala Trp Pro Ile
    50                  55                  60 ctt gga cca ctg tgc tgc agt cgc ttg tgc tta tac gtc tgc atg           237
Leu Gly Pro Leu Cys Cys Ser Arg Leu Cys Leu Tyr Val Cys Met
65                  70                  75 taaaactgcc gtgatgtctt ctactcccct c                                    268

<210> SEQ ID NO 357
<211> LENGTH: 79
<212> TYPE: PRT
<213> ORGANISM: Conus striolatus

<400> SEQUENCE: 357
```

```
Met Lys Leu Thr Cys Met Met Ile Val Ala Val Leu Phe Leu Thr Ala
1               5                   10                  15

Trp Ile Phe Val Met Ala Asp Asp Ser Arg Asn Gly Leu Glu Asn Leu
                20                  25                  30

Pro Gln Thr Thr Arg His Glu Met Lys Asn Pro Glu Ala Ser Lys Leu
                35                  40                  45

Asn Gln Thr Asp Cys Leu Ala Lys Asp Ala Phe Cys Ala Trp Pro Ile
                50                  55                  60

Leu Gly Pro Leu Cys Cys Ser Arg Leu Cys Leu Tyr Val Cys Met
65              70                  75
```

<210> SEQ ID NO 358
<211> LENGTH: 28
<212> TYPE: PRT
<213> ORGANISM: Conus striolatus
<220> FEATURE:
<221> NAME/KEY: SITE
<222> LOCATION: (1)..(28)
<223> OTHER INFORMATION: Xaa at residue 11 may be Trp or bromo-Trp; Xaa
at residues 12 and 16 may be Pro or hydroxy-Pro; Xaa at residue 25
may be Tyr, 125-I-Tyr, mono-iodo-Tyr, di-iodo-Tyr, O-sulpho-Tyr or
O-phospho-Tyr.

<400> SEQUENCE: 358

```
Asp Cys Leu Ala Lys Asp Ala Phe Cys Ala Xaa Xaa Ile Leu Gly Xaa
1               5                   10                  15

Leu Cys Cys Ser Arg Leu Cys Leu Xaa Val Cys Met
                20                  25
```

<210> SEQ ID NO 359
<211> LENGTH: 266
<212> TYPE: DNA
<213> ORGANISM: Conus consors
<220> FEATURE:
<221> NAME/KEY: CDS
<222> LOCATION: (1)..(246)

<400> SEQUENCE: 359

```
atg aaa ctg acg tgc atg atg atc gtt gct gtg ctg ttc ttg acc gcc      48
Met Lys Leu Thr Cys Met Met Ile Val Ala Val Leu Phe Leu Thr Ala
1               5                   10                  15 tgg aca ttc gtc acg gct gat gac tcc aga aat gga ttg gag aat ctt      96
Trp Thr Phe Val Thr Ala Asp Asp Ser Arg Asn Gly Leu Glu Asn Leu
                20                  25                  30 tct ccg aag gca cgt cac gaa atg aag aac ccc gaa gcc tct aaa tcg     144
Ser Pro Lys Ala Arg His Glu Met Lys Asn Pro Glu Ala Ser Lys Ser
                35                  40                  45 aac aag aga tat gag tgc tat tct act ggt aca ttt tgt ggc atc aac     192
Asn Lys Arg Tyr Glu Cys Tyr Ser Thr Gly Thr Phe Cys Gly Ile Asn
                50                  55                  60 gga gga ctc tgc tgc agc aac ctt tgc tta ttt ttc gtg tgc tta aca     240
Gly Gly Leu Cys Cys Ser Asn Leu Cys Leu Phe Phe Val Cys Leu Thr
65              70                  75                  80 ttt tcg tgatgtcttc tcctcccctc                                       266
Phe Ser
```

<210> SEQ ID NO 360
<211> LENGTH: 82
<212> TYPE: PRT
<213> ORGANISM: Conus consors

<400> SEQUENCE: 360

-continued

```
Met Lys Leu Thr Cys Met Met Ile Val Ala Val Leu Phe Leu Thr Ala
1               5                   10                  15

Trp Thr Phe Val Thr Ala Asp Asp Ser Arg Asn Gly Leu Glu Asn Leu
                20                  25                  30

Ser Pro Lys Ala Arg His Glu Met Lys Asn Pro Glu Ala Ser Lys Ser
            35                  40                  45

Asn Lys Arg Tyr Glu Cys Tyr Ser Thr Gly Thr Phe Cys Gly Ile Asn
        50                  55                  60

Gly Gly Leu Cys Cys Ser Asn Leu Cys Leu Phe Val Cys Leu Thr
65                  70                  75                  80

Phe Ser
```

<210> SEQ ID NO 361
<211> LENGTH: 31
<212> TYPE: PRT
<213> ORGANISM: Conus consors
<220> FEATURE:
<221> NAME/KEY: SITE
<222> LOCATION: (1)..(31)
<223> OTHER INFORMATION: Xaa at residues 1 and 4 may be Tyr, 125-I-Tyr, mono-iodo-Tyr, di-iodo-Tyr, O-sulpho-Tyr or O-phospho-Tyr; Xaa at residue 2 may be Glu or gamma-carboxy-Glu

<400> SEQUENCE: 361

```
Xaa Xaa Cys Xaa Ser Thr Gly Thr Phe Cys Gly Ile Asn Gly Gly Leu
1               5                   10                  15

Cys Cys Ser Asn Leu Cys Leu Phe Val Cys Leu Thr Phe Ser
                20                  25                  30
```

<210> SEQ ID NO 362
<211> LENGTH: 289
<212> TYPE: DNA
<213> ORGANISM: Conus consors
<220> FEATURE:
<221> NAME/KEY: CDS
<222> LOCATION: (1)..(252)

<400> SEQUENCE: 362

```
atg aaa ctg acg tgc ctg atg atc gtt gct gtg ctg ttc ttg acc acc        48
Met Lys Leu Thr Cys Leu Met Ile Val Ala Val Leu Phe Leu Thr Thr
1               5                   10                  15 tgg aca ttc gtc acg gct gat gac tcc aga tat gga ttg aag aat ctt        96
Trp Thr Phe Val Thr Ala Asp Asp Ser Arg Tyr Gly Leu Lys Asn Leu
                20                  25                  30 ttt ccg aag gca cgt cat gaa atg aag aac cct gaa gcc tct aaa ttg       144
Phe Pro Lys Ala Arg His Glu Met Lys Asn Pro Glu Ala Ser Lys Leu
            35                  40                  45 aac aag aga gat ggg tgc tat aat gct ggt aca ttt tgt ggc atc cgt       192
Asn Lys Arg Asp Gly Cys Tyr Asn Ala Gly Thr Phe Cys Gly Ile Arg
        50                  55                  60 cca gga ctc tgc tgc agc gag ttt tgc ttt tta tgg tgc ata aca ttt       240
Pro Gly Leu Cys Cys Ser Glu Phe Cys Phe Leu Trp Cys Ile Thr Phe
65                  70                  75                  80 gtt gat tct ggc taacagtgtg cgttggttga tgtcttctac tccctc               289
Val Asp Ser Gly
```

<210> SEQ ID NO 363
<211> LENGTH: 84
<212> TYPE: PRT
<213> ORGANISM: Conus consors

<400> SEQUENCE: 363

```
Met Lys Leu Thr Cys Leu Met Ile Val Ala Val Leu Phe Leu Thr Thr
1               5                   10                  15

Trp Thr Phe Val Thr Ala Asp Asp Ser Arg Tyr Gly Leu Lys Asn Leu
            20                  25                  30

Phe Pro Lys Ala Arg His Glu Met Lys Asn Pro Glu Ala Ser Lys Leu
            35                  40                  45

Asn Lys Arg Asp Gly Cys Tyr Asn Ala Gly Thr Phe Cys Gly Ile Arg
    50                  55                  60

Pro Gly Leu Cys Cys Ser Glu Phe Cys Phe Leu Trp Cys Ile Thr Phe
65              70                  75                  80

Val Asp Ser Gly
```

<210> SEQ ID NO 364
<211> LENGTH: 32
<212> TYPE: PRT
<213> ORGANISM: Conus consors
<220> FEATURE:
<221> NAME/KEY: SITE
<222> LOCATION: (1)..(32)
<223> OTHER INFORMATION: Xaa at residue 4 may be Tyr, 125-I-Tyr,
      mono-iodo-Tyr, di-iodo-Tyr, O-sulpho-Tyr or O-phospho-Tyr; Xaa at
      residue 14 may be Pro or hydroxy-Pro; Xaa at residue 20 may be Glu
      or gamma-carboxy-Glu; Xaa at residue 25 may be Trp or bromo-Trp

<400> SEQUENCE: 364

```
Asp Gly Cys Xaa Asn Ala Gly Thr Phe Cys Gly Ile Arg Xaa Gly Leu
1               5                   10                  15

Cys Cys Ser Xaa Phe Cys Phe Leu Xaa Cys Ile Thr Phe Val Asp Ser
            20                  25                  30
```

<210> SEQ ID NO 365
<211> LENGTH: 205
<212> TYPE: DNA
<213> ORGANISM: Conus circumcisus
<220> FEATURE:
<221> NAME/KEY: CDS
<222> LOCATION: (83)..(175)

<400> SEQUENCE: 365

```
cgatccatct gtccatccat ctattcattc attcgctgcc aaactgtatt aaatattcaa      60
gtctctcttt ctgtttgtgt ct aac aga ttg agt agg tgc att cct agt ggt     112
               Asn Arg Leu Ser Arg Cys Ile Pro Ser Gly
                 1               5                  10 gat ctt tgt ttc ccc tcg gat cac ata caa tgc tgc aat gcc aag tgc      160
Asp Leu Cys Phe Pro Ser Asp His Ile Gln Cys Cys Asn Ala Lys Cys
            15                  20                  25 gca ttc gtc tgc ttg taaaactgcc gtgatgtctt ctcttccctc                  205
Ala Phe Val Cys Leu
            30
```

<210> SEQ ID NO 366
<211> LENGTH: 31
<212> TYPE: PRT
<213> ORGANISM: Conus circumcisus

<400> SEQUENCE: 366

```
Asn Arg Leu Ser Arg Cys Ile Pro Ser Gly Asp Leu Cys Phe Pro Ser
1               5                   10                  15

Asp His Ile Gln Cys Cys Asn Ala Lys Cys Ala Phe Val Cys Leu
            20                  25                  30
```

<210> SEQ ID NO 367

```
<211> LENGTH: 26
<212> TYPE: PRT
<213> ORGANISM: Conus circumcisus
<220> FEATURE:
<221> NAME/KEY: SITE
<222> LOCATION: (1)..(26)
<223> OTHER INFORMATION: Xaa at residues 3 and 10 may be Pro or
      hydroxy-Pro.

<400> SEQUENCE: 367

Cys Ile Xaa Ser Gly Asp Leu Cys Phe Xaa Ser Asp His Ile Gln Cys
1               5                  10                  15

Cys Asn Ala Lys Cys Ala Phe Val Cys Leu
                20                  25

<210> SEQ ID NO 368
<211> LENGTH: 206
<212> TYPE: DNA
<213> ORGANISM: Conus circumcisus
<220> FEATURE:
<221> NAME/KEY: CDS
<222> LOCATION: (83)..(175)

<400> SEQUENCE: 368
cgatccatct gtccatccat ctattcattc attcgctgtc aaactgtatt aaatattcaa      60
gtctctcttt ctgtttgtgt ct aac aga ttg agt tgg tgc att cct agt ggt     112
              Asn Arg Leu Ser Trp Cys Ile Pro Ser Gly
                1               5                  10 gat ctt tgt ttc ccc tcg gat cac ata caa tgc tgc agt gcc aag tgc     160
Asp Leu Cys Phe Pro Ser Asp His Ile Gln Cys Cys Ser Ala Lys Cys
                15                  20                  25 gca ttc gtc tgc ttg taaaactgcc gtgatgtctt ctactcccct c              206
Ala Phe Val Cys Leu
                30

<210> SEQ ID NO 369
<211> LENGTH: 31
<212> TYPE: PRT
<213> ORGANISM: Conus circumcisus

<400> SEQUENCE: 369

Asn Arg Leu Ser Trp Cys Ile Pro Ser Gly Asp Leu Cys Phe Pro Ser
1               5                  10                  15

Asp His Ile Gln Cys Cys Ser Ala Lys Cys Ala Phe Val Cys Leu
                20                  25                  30

<210> SEQ ID NO 370
<211> LENGTH: 27
<212> TYPE: PRT
<213> ORGANISM: Conus circumcisus
<220> FEATURE:
<221> NAME/KEY: SITE
<222> LOCATION: (1)..(27)
<223> OTHER INFORMATION: Xaa at residue 1 may be Trp or bromo-Trp; Xaa
      at residues 4 and 11 may be Pro or hydroxy-Pro

<400> SEQUENCE: 370

Xaa Cys Ile Xaa Ser Gly Asp Leu Cys Phe Xaa Ser Asp His Ile Gln
1               5                  10                  15

Cys Cys Ser Ala Lys Cys Ala Phe Val Cys Leu
                20                  25

<210> SEQ ID NO 371
<211> LENGTH: 206
<212> TYPE: DNA
```

```
<213> ORGANISM: Conus circumcisus
<220> FEATURE:
<221> NAME/KEY: CDS
<222> LOCATION: (83)..(175)

<400> SEQUENCE: 371
cgatccatct gtccatccat ctattcattc attcgctgtc aaactgtatt aaatattcaa      60
gtctctcttt ctgtttgtgt ct aac aga ttg agt agg tgc att cct agt ggt     112
                         Asn Arg Leu Ser Arg Cys Ile Pro Ser Gly
                          1               5                  10 gat ctt tgt ttc ccc tcg gat cac ata caa tgc tgc agt gcc aag tgc     160
Asp Leu Cys Phe Pro Ser Asp His Ile Gln Cys Cys Ser Ala Lys Cys
            15                  20                  25 gca ttc gtc tgc ttg taaaactgcc gtgatgtctt ctcctcccct c               206
Ala Phe Val Cys Leu
            30

<210> SEQ ID NO 372
<211> LENGTH: 31
<212> TYPE: PRT
<213> ORGANISM: Conus circumcisus

<400> SEQUENCE: 372

Asn Arg Leu Ser Arg Cys Ile Pro Ser Gly Asp Leu Cys Phe Pro Ser
 1               5                  10                  15

Asp His Ile Gln Cys Cys Ser Ala Lys Cys Ala Phe Val Cys Leu
             20                  25                  30

<210> SEQ ID NO 373
<211> LENGTH: 26
<212> TYPE: PRT
<213> ORGANISM: Conus circumcisus
<220> FEATURE:
<221> NAME/KEY: SITE
<222> LOCATION: (1)..(26)
<223> OTHER INFORMATION: Xaa at residues 3 and 10 may be Pro or
      hydroxy-Pro.

<400> SEQUENCE: 373

Cys Ile Xaa Ser Gly Asp Leu Cys Phe Xaa Ser Asp His Ile Gln Cys
 1               5                  10                  15

Cys Ser Ala Lys Cys Ala Phe Val Cys Leu
             20                  25

<210> SEQ ID NO 374
<211> LENGTH: 206
<212> TYPE: DNA
<213> ORGANISM: Conus circumcisus
<220> FEATURE:
<221> NAME/KEY: CDS
<222> LOCATION: (83)..(175)

<400> SEQUENCE: 374
cgatccatct gtccatccat ctattcattc attcgctgcc aaactgtatt aaatattcaa      60
gtctctcttt ctgtttgtgt ct aac aga ttg agt agg tgc att cct agt ggt     112
                         Asn Arg Leu Ser Arg Cys Ile Pro Ser Gly
                          1               5                  10 gat ctt tgt ttc ccc tcg gat cac ata caa tgc tgc aat gcc gag tgc     160
Asp Leu Cys Phe Pro Ser Asp His Ile Gln Cys Cys Asn Ala Glu Cys
            15                  20                  25 gca ttc gtc tgc ttg taaaactgcc gtgatgtctt ctcctcccct c               206
Ala Phe Val Cys Leu
            30
```

```
<210> SEQ ID NO 375
<211> LENGTH: 31
<212> TYPE: PRT
<213> ORGANISM: Conus circumcisus

<400> SEQUENCE: 375

Asn Arg Leu Ser Arg Cys Ile Pro Ser Gly Asp Leu Cys Phe Pro Ser
1               5                   10                  15

Asp His Ile Gln Cys Cys Asn Ala Glu Cys Ala Phe Val Cys Leu
            20                  25                  30

<210> SEQ ID NO 376
<211> LENGTH: 26
<212> TYPE: PRT
<213> ORGANISM: Conus circumcisus
<220> FEATURE:
<221> NAME/KEY: SITE
<222> LOCATION: (1)..(26)
<223> OTHER INFORMATION: Xaa at residues 3 and 10 may be Pro or
      hydroxy-Pro; Xaa at residue 20 may be Glu or gamma-carboxy-Glu

<400> SEQUENCE: 376

Cys Ile Xaa Ser Gly Asp Leu Cys Phe Xaa Ser Asp His Ile Gln Cys
1               5                   10                  15

Cys Asn Ala Xaa Cys Ala Phe Val Cys Leu
            20                  25

<210> SEQ ID NO 377
<211> LENGTH: 206
<212> TYPE: DNA
<213> ORGANISM: Conus circumcisus
<220> FEATURE:
<221> NAME/KEY: CDS
<222> LOCATION: (83)..(175)

<400> SEQUENCE: 377
cgatccatct gtccatccat ctattcattc attcgctgtc aaactgtatt aaatattcaa      60
gtctctcttt ctgtttgtgt ct aac aga ttg agt tgg tgc att cct agt ggt     112
              Asn Arg Leu Ser Trp Cys Ile Pro Ser Gly
              1               5                   10 gat ctt tgt ttc ccc tcg gat cac ata cga tgc tgc agt gcc aag tgc     160
Asp Leu Cys Phe Pro Ser Asp His Ile Arg Cys Cys Ser Ala Lys Cys
            15                  20                  25 gca ttc gtc tgc ttg taaaactgcc gtgatgtctt ctcttcccat c               206
Ala Phe Val Cys Leu
            30

<210> SEQ ID NO 378
<211> LENGTH: 31
<212> TYPE: PRT
<213> ORGANISM: Conus circumcisus

<400> SEQUENCE: 378

Asn Arg Leu Ser Trp Cys Ile Pro Ser Gly Asp Leu Cys Phe Pro Ser
1               5                   10                  15

Asp His Ile Arg Cys Cys Ser Ala Lys Cys Ala Phe Val Cys Leu
            20                  25                  30

<210> SEQ ID NO 379
<211> LENGTH: 27
<212> TYPE: PRT
<213> ORGANISM: Conus circumcisus
<220> FEATURE:
<221> NAME/KEY: SITE
```

```
<222> LOCATION: (1)..(27)
<223> OTHER INFORMATION: Xaa at residue 1 may be Trp or bromo-Trp; Xaa
      at residues 4 and 11 may be Pro or hydroxy-Pro

<400> SEQUENCE: 379

Xaa Cys Ile Xaa Ser Gly Asp Leu Cys Phe Xaa Ser Asp His Ile Arg
1               5                   10                  15

Cys Cys Ser Ala Lys Cys Ala Phe Val Cys Leu
            20                  25

<210> SEQ ID NO 380
<211> LENGTH: 206
<212> TYPE: DNA
<213> ORGANISM: Conus circumcisus
<220> FEATURE:
<221> NAME/KEY: CDS
<222> LOCATION: (83)..(175)

<400> SEQUENCE: 380
cgatccatct gtccatccat ctattcattc attcgctgcc aaactgtatt aaatattcaa      60
gtctctcttt ctgtttgtgt ct aac aga ttg agt agg tgc att cct agt ggt     112
               Asn Arg Leu Ser Arg Cys Ile Pro Ser Gly
                1               5                   10 gat ctt tgt ttc ccc tcg gat cac ata caa tgc tgc aat gcc aag tgc      160
Asp Leu Cys Phe Pro Ser Asp His Ile Gln Cys Cys Asn Ala Lys Cys
            15                  20                  25 gca ttc gcc tgc ttg taaaactgcc gtgatgtctt ctcttcccct c                206
Ala Phe Ala Cys Leu
            30

<210> SEQ ID NO 381
<211> LENGTH: 31
<212> TYPE: PRT
<213> ORGANISM: Conus circumcisus

<400> SEQUENCE: 381

Asn Arg Leu Ser Arg Cys Ile Pro Ser Gly Asp Leu Cys Phe Pro Ser
1               5                   10                  15

Asp His Ile Gln Cys Cys Asn Ala Lys Cys Ala Phe Ala Cys Leu
            20                  25                  30

<210> SEQ ID NO 382
<211> LENGTH: 26
<212> TYPE: PRT
<213> ORGANISM: Conus circumcisus
<220> FEATURE:
<221> NAME/KEY: SITE
<222> LOCATION: (1)..(26)
<223> OTHER INFORMATION: Xaa at residues 3 and 10 may be Pro or
      hydroxy-Pro.

<400> SEQUENCE: 382

Cys Ile Xaa Ser Gly Asp Leu Cys Phe Xaa Ser Asp His Ile Gln Cys
1               5                   10                  15

Cys Asn Ala Lys Cys Ala Phe Ala Cys Leu
            20                  25

<210> SEQ ID NO 383
<211> LENGTH: 206
<212> TYPE: DNA
<213> ORGANISM: Conus circumcisus
<220> FEATURE:
<221> NAME/KEY: CDS
<222> LOCATION: (83)..(175)
```

<400> SEQUENCE: 383

```
cgatccatct gtccatccat ctattcattc attcgctgcc aaactgtatt aaatattcaa      60
gtctctcttt ctgtttgtgt ct aac aga ttg agt tgg tgc att cct agt ggt     112
                         Asn Arg Leu Ser Trp Cys Ile Pro Ser Gly
                          1               5                  10 gat ctt tgt ttc ccc tcg gat cac ata caa tgc tgc aat gcc aag tgc      160
Asp Leu Cys Phe Pro Ser Asp His Ile Gln Cys Cys Asn Ala Lys Cys
             15                  20                  25 gca ttc gtc tgc ttg taaaactgcc gtgatgtctt ctactcccct c                206
Ala Phe Val Cys Leu
             30
```

<210> SEQ ID NO 384
<211> LENGTH: 31
<212> TYPE: PRT
<213> ORGANISM: Conus circumcisus

<400> SEQUENCE: 384

```
Asn Arg Leu Ser Trp Cys Ile Pro Ser Gly Asp Leu Cys Phe Pro Ser
 1               5                  10                  15

Asp His Ile Gln Cys Cys Asn Ala Lys Cys Ala Phe Val Cys Leu
             20                  25                  30
```

<210> SEQ ID NO 385
<211> LENGTH: 27
<212> TYPE: PRT
<213> ORGANISM: Conus circumcisus
<220> FEATURE:
<221> NAME/KEY: SITE
<222> LOCATION: (1)..(27)
<223> OTHER INFORMATION: Xaa at residue 1 may be Trp or bromo-Trp; Xaa
      at residues 4 and 11 may be Pro or hydroxy-Pro

<400> SEQUENCE: 385

```
Xaa Cys Ile Xaa Ser Gly Asp Leu Cys Phe Xaa Ser Asp His Ile Gln
 1               5                  10                  15

Cys Cys Asn Ala Lys Cys Ala Phe Val Cys Leu
             20                  25
```

<210> SEQ ID NO 386
<211> LENGTH: 200
<212> TYPE: DNA
<213> ORGANISM: Conus circumcisus
<220> FEATURE:
<221> NAME/KEY: CDS
<222> LOCATION: (77)..(169)

<400> SEQUENCE: 386

```
cgatcctctg tcctcctcta ttattattcg ctgccaactg tattaaatat tcaagtctct      60
ctttctgttt gtgtct aac aga ttg agt tgg tgc att cct act ggt gat ctt    112
               Asn Arg Leu Ser Trp Cys Ile Pro Thr Gly Asp Leu
                1               5                  10 tgt ttc ccc tcg gat cac ata caa tgc tgc agt ggc aag tgc aca ttc      160
Cys Phe Pro Ser Asp His Ile Gln Cys Cys Ser Gly Lys Cys Thr Phe
             15                  20                  25 gtc tgc atg taaaactgcc gtgatgtctt ctcctcccct c                        200
Val Cys Met
        30
```

<210> SEQ ID NO 387
<211> LENGTH: 31
<212> TYPE: PRT
<213> ORGANISM: Conus circumcisus

```
<400> SEQUENCE: 387

Asn Arg Leu Ser Trp Cys Ile Pro Thr Gly Asp Leu Cys Phe Pro Ser
1               5                  10                  15
Asp His Ile Gln Cys Cys Ser Gly Lys Cys Thr Phe Val Cys Met
            20                  25                  30

<210> SEQ ID NO 388
<211> LENGTH: 27
<212> TYPE: PRT
<213> ORGANISM: Conus circumcisus
<220> FEATURE:
<221> NAME/KEY: SITE
<222> LOCATION: (1)..(27)
<223> OTHER INFORMATION: Xaa at residue1 may be Trp or bromo-Trp; Xaa
      at residues 4 and 11 may be Pro or hydroxy-Pro

<400> SEQUENCE: 388

Xaa Cys Ile Xaa Thr Gly Asp Leu Cys Phe Xaa Ser Asp His Ile Gln
1               5                  10                  15
Cys Cys Ser Gly Lys Cys Thr Phe Val Cys Met
            20                  25

<210> SEQ ID NO 389
<211> LENGTH: 266
<212> TYPE: DNA
<213> ORGANISM: Conus monachus
<220> FEATURE:
<221> NAME/KEY: CDS
<222> LOCATION: (1)..(246)

<400> SEQUENCE: 389 atg aaa ctg acg tgc atg atg atc gtt gct gtg ctg ttc ttg acc gcc     48
Met Lys Leu Thr Cys Met Met Ile Val Ala Val Leu Phe Leu Thr Ala
1               5                  10                  15 tgg aca ttc gtc acg gct gat gac tcc aga aat gga ttg gag aat ctt     96
Trp Thr Phe Val Thr Ala Asp Asp Ser Arg Asn Gly Leu Glu Asn Leu
            20                  25                  30 tct ccg aag gca cgt cac gaa atg aag aac ccc gaa gcc tct aaa tcg    144
Ser Pro Lys Ala Arg His Glu Met Lys Asn Pro Glu Ala Ser Lys Ser
        35                  40                  45 aac aag aga tat gag tgc tat tct act ggt aca ttt tgt ggc atc aac    192
Asn Lys Arg Tyr Glu Cys Tyr Ser Thr Gly Thr Phe Cys Gly Ile Asn
    50                  55                  60 gga gga ctc tgc tgc agc aac ctt tgc tta ttt ttc gtg tgc tta aca    240
Gly Gly Leu Cys Cys Ser Asn Leu Cys Leu Phe Phe Val Cys Leu Thr
65                  70                  75                  80 ttt tcg tgatgtcttc tcctccctc                                        266
Phe Ser

<210> SEQ ID NO 390
<211> LENGTH: 82
<212> TYPE: PRT
<213> ORGANISM: Conus monachus

<400> SEQUENCE: 390

Met Lys Leu Thr Cys Met Met Ile Val Ala Val Leu Phe Leu Thr Ala
1               5                  10                  15

Trp Thr Phe Val Thr Ala Asp Asp Ser Arg Asn Gly Leu Glu Asn Leu
            20                  25                  30

Ser Pro Lys Ala Arg His Glu Met Lys Asn Pro Glu Ala Ser Lys Ser
        35                  40                  45
```

```
Asn Lys Arg Tyr Glu Cys Tyr Ser Thr Gly Thr Phe Cys Gly Ile Asn
 50                  55                  60

Gly Gly Leu Cys Cys Ser Asn Leu Cys Leu Phe Phe Val Cys Leu Thr
 65                  70                  75                  80

Phe Ser

<210> SEQ ID NO 391
<211> LENGTH: 31
<212> TYPE: PRT
<213> ORGANISM: Conus monachus
<220> FEATURE:
<221> NAME/KEY: SITE
<222> LOCATION: (1)..(31)
<223> OTHER INFORMATION: Xaa at residues 1 and 4 may be Tyr, 125-I-Tyr,
      mono-iodo-Tyr, di-iodo-Tyr, O-sulpho-Tyr or O-phospho-Tyr; Xaa at
      residue 2 may be Glu or gamma-carboxy-Glu

<400> SEQUENCE: 391

Xaa Xaa Cys Xaa Ser Thr Gly Thr Phe Cys Gly Ile Asn Gly Gly Leu
 1               5                  10                  15

Cys Cys Ser Asn Leu Cys Leu Phe Phe Val Cys Leu Thr Phe Ser
             20                  25                  30

<210> SEQ ID NO 392
<211> LENGTH: 277
<212> TYPE: DNA
<213> ORGANISM: Conus stercusmuscarum
<220> FEATURE:
<221> NAME/KEY: CDS
<222> LOCATION: (1)..(246)

<400> SEQUENCE: 392 atg aaa ctg acg tgc atg atg atc gtt gct gtg ctg ttc ttg acc gcc      48
Met Lys Leu Thr Cys Met Met Ile Val Ala Val Leu Phe Leu Thr Ala
 1               5                  10                  15 tgg aca ttc gtc aca gct gat gac tcc ata aat gga ccg gag aat aga      96
Trp Thr Phe Val Thr Ala Asp Asp Ser Ile Asn Gly Pro Glu Asn Arg
             20                  25                  30 cga ata tgg gag aaa ctt ttg ttg aag gca cgt gac gaa atg aag aac     144
Arg Ile Trp Glu Lys Leu Leu Leu Lys Ala Arg Asp Glu Met Lys Asn
         35                  40                  45 ccc gaa gcc tct caa ttg aga tgg tgc att cct agt ggt gaa ctt tgt     192
Pro Glu Ala Ser Gln Leu Arg Trp Cys Ile Pro Ser Gly Glu Leu Cys
     50                  55                  60 ttc cgc tcg gat cac ata caa tgc tgc agt gcc aag tgc gca ttc gtc     240
Phe Arg Ser Asp His Ile Gln Cys Cys Ser Ala Lys Cys Ala Phe Val
 65                  70                  75                  80 tgc ttg taaaactacc gtgatgtctt ctcctcccat c                          277
Cys Leu

<210> SEQ ID NO 393
<211> LENGTH: 82
<212> TYPE: PRT
<213> ORGANISM: Conus stercusmuscarum

<400> SEQUENCE: 393

Met Lys Leu Thr Cys Met Met Ile Val Ala Val Leu Phe Leu Thr Ala
 1               5                  10                  15

Trp Thr Phe Val Thr Ala Asp Asp Ser Ile Asn Gly Pro Glu Asn Arg
             20                  25                  30

Arg Ile Trp Glu Lys Leu Leu Leu Lys Ala Arg Asp Glu Met Lys Asn
         35                  40                  45
```

```
Pro Glu Ala Ser Gln Leu Arg Trp Cys Ile Pro Ser Gly Glu Leu Cys
 50                  55                  60

Phe Arg Ser Asp His Ile Gln Cys Cys Ser Ala Lys Cys Ala Phe Val
 65                  70                  75                  80

Cys Leu

<210> SEQ ID NO 394
<211> LENGTH: 27
<212> TYPE: PRT
<213> ORGANISM: Conus stercusmuscarum
<220> FEATURE:
<221> NAME/KEY: SITE
<222> LOCATION: (1)..(27)
<223> OTHER INFORMATION: Xaa at residue 1 may be Trp or bromo-Trp; Xaa
      at residue 4 may be Pro or hydroxy-Pro; Xaa at residue 7 may be
      Glu or gamma-carboxy-Glu

<400> SEQUENCE: 394

Xaa Cys Ile Xaa Ser Gly Xaa Leu Cys Pro Arg Ser Asp His Ile Gln
1               5                  10                  15

Cys Cys Ser Ala Lys Cys Ala Phe Val Cys Leu
            20                  25

<210> SEQ ID NO 395
<211> LENGTH: 266
<212> TYPE: DNA
<213> ORGANISM: Conus stercusmuscarum
<220> FEATURE:
<221> NAME/KEY: CDS
<222> LOCATION: (1)..(246)

<400> SEQUENCE: 395 atg aaa ctg acg tgt gtg atg atc gtt gct gtg ctg ttc ttg atc gcc      48
Met Lys Leu Thr Cys Val Met Ile Val Ala Val Leu Phe Leu Ile Ala
1               5                  10                  15 tgg aca ttc gtc acg gct gat gac tcc aga aat gga ttg aag aat ctt      96
Trp Thr Phe Val Thr Ala Asp Asp Ser Arg Asn Gly Leu Lys Asn Leu
            20                  25                  30 ttt ccg aag gca cgt cat gaa atg aag aac ccc gaa gcc tct aaa ttg     144
Phe Pro Lys Ala Arg His Glu Met Lys Asn Pro Glu Ala Ser Lys Leu
        35                  40                  45 aac aag aga gat ggg tgc tct agt ggt ggt aca ttt tgt ggc atc cgt     192
Asn Lys Arg Asp Gly Cys Ser Ser Gly Gly Thr Phe Cys Gly Ile Arg
    50                  55                  60 cca gga ctc tgc tgc agc gag ttt tgc ttt ctt tgg tgc ata aca ttt     240
Pro Gly Leu Cys Cys Ser Glu Phe Cys Phe Leu Trp Cys Ile Thr Phe
65                  70                  75                  80 att gat tgatgtcttc tattccctc                                         266
Ile Asp <210> SEQ ID NO 396
<211> LENGTH: 82
<212> TYPE: PRT
<213> ORGANISM: Conus stercusmuscarum

<400> SEQUENCE: 396

Met Lys Leu Thr Cys Val Met Ile Val Ala Val Leu Phe Leu Ile Ala
1               5                  10                  15

Trp Thr Phe Val Thr Ala Asp Asp Ser Arg Asn Gly Leu Lys Asn Leu
            20                  25                  30

Phe Pro Lys Ala Arg His Glu Met Lys Asn Pro Glu Ala Ser Lys Leu
        35                  40                  45
```

```
Asn Lys Arg Asp Gly Cys Ser Ser Gly Gly Thr Phe Cys Gly Ile Arg
    50                  55                  60

Pro Gly Leu Cys Cys Ser Glu Phe Cys Phe Leu Trp Cys Ile Thr Phe
65              70                  75                  80

Ile Asp

<210> SEQ ID NO 397
<211> LENGTH: 31
<212> TYPE: PRT
<213> ORGANISM: Conus stercusmuscarum
<220> FEATURE:
<221> NAME/KEY: SITE
<222> LOCATION: (1)..(31)
<223> OTHER INFORMATION: Xaa at residue 14 may be Pro or hydroxy-Pro;
      Xaa at residue 20 may be Glu or gamma-carboxy-Glu; Xaa at
      residue 25 may be Trp or bromo-Trp

<400> SEQUENCE: 397

Asp Gly Cys Ser Ser Gly Gly Thr Phe Cys Gly Ile Arg Xaa Gly Leu
1               5                   10                  15

Cys Cys Ser Xaa Phe Cys Phe Leu Xaa Cys Ile Thr Phe Ile Asp
            20                  25                  30

<210> SEQ ID NO 398
<211> LENGTH: 265
<212> TYPE: DNA
<213> ORGANISM: Conus striolatus
<220> FEATURE:
<221> NAME/KEY: CDS
<222> LOCATION: (1)..(234)

<400> SEQUENCE: 398 atg aaa ctg acg tgc ata atg acc gtt gct gtg ctg ttc ttg acc gct      48
Met Lys Leu Thr Cys Ile Met Thr Val Ala Val Leu Phe Leu Thr Ala
1               5                   10                  15 tgg aca ttc gtc acg gct gat gac tcc aga aat gga ttg gag aat ctt      96
Trp Thr Phe Val Thr Ala Asp Asp Ser Arg Asn Gly Leu Glu Asn Leu
                20                  25                  30 ctt ctg aag aca cgt cac gaa gtg gaa aac ccc aaa gcc tct agg tcg     144
Leu Leu Lys Thr Arg His Glu Val Glu Asn Pro Lys Ala Ser Arg Ser
            35                  40                  45 ggc ggt agg tgc cgt cct ggt ggt acg gtt tgt ggc ttt ccg aaa cct     192
Gly Gly Arg Cys Arg Pro Gly Gly Thr Val Cys Gly Phe Pro Lys Pro
        50                  55                  60 gga cca tac tgc tgc agt ggc tgg tgc ttt ttt gtc tgc gcc                234
Gly Pro Tyr Cys Cys Ser Gly Trp Cys Phe Phe Val Cys Ala
65                  70                  75 taaacctgcc gtgatgtctt ctcctcccat c                                    265

<210> SEQ ID NO 399
<211> LENGTH: 78
<212> TYPE: PRT
<213> ORGANISM: Conus striolatus

<400> SEQUENCE: 399

Met Lys Leu Thr Cys Ile Met Thr Val Ala Val Leu Phe Leu Thr Ala
1               5                   10                  15

Trp Thr Phe Val Thr Ala Asp Asp Ser Arg Asn Gly Leu Glu Asn Leu
                20                  25                  30

Leu Leu Lys Thr Arg His Glu Val Glu Asn Pro Lys Ala Ser Arg Ser
            35                  40                  45
```

```
Gly Gly Arg Cys Arg Pro Gly Gly Thr Val Cys Gly Phe Pro Lys Pro
         50                  55                  60

Gly Pro Tyr Cys Cys Ser Gly Trp Cys Phe Phe Val Cys Ala
 65                  70                  75

<210> SEQ ID NO 400
<211> LENGTH: 27
<212> TYPE: PRT
<213> ORGANISM: Conus striolatus
<220> FEATURE:
<221> NAME/KEY: SITE
<222> LOCATION: (1)..(27)
<223> OTHER INFORMATION: Xaa at residues 3, 11, 13 and 15 may be Pro or
      hydroxy-Pro; Xaa at residue 16 may be Tyr, 125-I-Tyr,
      mono-iodo-Tyr, di-iodo-Tyr, O-sulpho-Tyr or O-phospho-Tyr; Xaa at
      residue 21 may be Trp or bromo-Trp

<400> SEQUENCE: 400

Cys Arg Xaa Gly Gly Thr Val Cys Gly Phe Xaa Lys Xaa Gly Xaa Xaa
 1               5                  10                  15

Cys Cys Ser Gly Xaa Cys Phe Phe Val Cys Ala
             20                  25

<210> SEQ ID NO 401
<211> LENGTH: 272
<212> TYPE: DNA
<213> ORGANISM: Conus striolatus
<220> FEATURE:
<221> NAME/KEY: CDS
<222> LOCATION: (1)..(243)

<400> SEQUENCE: 401 atg aaa ctg acg tgc gtg atg atc gtt gct gtg ctg ttc ttg act gcc      48
Met Lys Leu Thr Cys Val Met Ile Val Ala Val Leu Phe Leu Thr Ala
 1               5                  10                  15 tgg aca ttc gtc acg gct gat gac tcc aaa aat gga ctg gag aat cat      96
Trp Thr Phe Val Thr Ala Asp Asp Ser Lys Asn Gly Leu Glu Asn His
             20                  25                  30 ttt tgg aag gca cgt gac gaa atg aag aac cgc gaa gcc tct aaa ttg     144
Phe Trp Lys Ala Arg Asp Glu Met Lys Asn Arg Glu Ala Ser Lys Leu
         35                  40                  45 gac aaa aag gaa gcc tgc tat ccg cct ggt act ttt tgt ggc ata aag     192
Asp Lys Lys Glu Ala Cys Tyr Pro Pro Gly Thr Phe Cys Gly Ile Lys
 50                  55                  60 ccc ggg cta tgc tgc agt gag ttg tgt tta ccg gcc gtc tgc gtc ggt     240
Pro Gly Leu Cys Cys Ser Glu Leu Cys Leu Pro Ala Val Cys Val Gly
 65                  70                  75                  80 ggt taactgccgt gatgtcttct attcccctc                                 272
Gly

<210> SEQ ID NO 402
<211> LENGTH: 81
<212> TYPE: PRT
<213> ORGANISM: Conus striolatus

<400> SEQUENCE: 402

Met Lys Leu Thr Cys Val Met Ile Val Ala Val Leu Phe Leu Thr Ala
 1               5                  10                  15

Trp Thr Phe Val Thr Ala Asp Asp Ser Lys Asn Gly Leu Glu Asn His
             20                  25                  30

Phe Trp Lys Ala Arg Asp Glu Met Lys Asn Arg Glu Ala Ser Lys Leu
         35                  40                  45

Asp Lys Lys Glu Ala Cys Tyr Pro Pro Gly Thr Phe Cys Gly Ile Lys
```

-continued

```
                    50                   55                  60
Pro Gly Leu Cys Cys Ser Glu Leu Cys Leu Pro Ala Val Cys Val Gly
 65                  70                  75                  80

Gly

<210> SEQ ID NO 403
<211> LENGTH: 29
<212> TYPE: PRT
<213> ORGANISM: Conus striolatus
<220> FEATURE:
<221> NAME/KEY: SITE
<222> LOCATION: (1)..(29)
<223> OTHER INFORMATION: Xaa at residues 1 and 20  may be Glu or
      gamma-carboxy-Glu; Xaa at residue 4 may be Tyr, 125-I-Tyr,
      mono-iodo-Tyr, di-iodo-Tyr, O-sulpho-Tyr or O-phospho-Tyr; Xaa at
      residues 5, 6, 14 and 24 may be Pro or hydroxy-Pro

<400> SEQUENCE: 403

Xaa Ala Cys Xaa Xaa Xaa Gly Thr Phe Cys Gly Ile Lys Xaa Gly Leu
  1               5                  10                  15

Cys Cys Ser Xaa Leu Cys Leu Xaa Ala Val Cys Val Gly
                 20                  25

<210> SEQ ID NO 404
<211> LENGTH: 265
<212> TYPE: DNA
<213> ORGANISM: Conus striolatus
<220> FEATURE:
<221> NAME/KEY: CDS
<222> LOCATION: (1)..(246)

<400> SEQUENCE: 404 atg aaa ctg acg tgt ctg atg gct gtt gct gtg ctg ttc ttg acc gcc        48
Met Lys Leu Thr Cys Leu Met Ala Val Ala Val Leu Phe Leu Thr Ala
  1               5                  10                  15 cgg aca ttc gtc acg gct gat gac tcc aga aat gga ttg gag aat ctt        96
Arg Thr Phe Val Thr Ala Asp Asp Ser Arg Asn Gly Leu Glu Asn Leu
                 20                  25                  30 tct ccg aag gca cgt cac gaa atg aag aac ccc gaa gcc tct aaa tcg       144
Ser Pro Lys Ala Arg His Glu Met Lys Asn Pro Glu Ala Ser Lys Ser
             35                  40                  45 aac aag aga tat gag tgc tat tct act ggt aca ttt tgt ggc atc aac       192
Asn Lys Arg Tyr Glu Cys Tyr Ser Thr Gly Thr Phe Cys Gly Ile Asn
         50                  55                  60 gga gga ctc tgc tgc agc aac ctt tgc tta ttt ttc gtg tgc tta aca       240
Gly Gly Leu Cys Cys Ser Asn Leu Cys Leu Phe Phe Val Cys Leu Thr
 65                  70                  75                  80 ttt tcg tgatgtcttc tatcccctc                                           265
Phe Ser <210> SEQ ID NO 405
<211> LENGTH: 82
<212> TYPE: PRT
<213> ORGANISM: Conus striolatus

<400> SEQUENCE: 405

Met Lys Leu Thr Cys Leu Met Ala Val Ala Val Leu Phe Leu Thr Ala
  1               5                  10                  15

Arg Thr Phe Val Thr Ala Asp Asp Ser Arg Asn Gly Leu Glu Asn Leu
                 20                  25                  30

Ser Pro Lys Ala Arg His Glu Met Lys Asn Pro Glu Ala Ser Lys Ser
             35                  40                  45
```

```
Asn Lys Arg Tyr Glu Cys Tyr Ser Thr Gly Thr Phe Cys Gly Ile Asn
         50                  55                  60

Gly Gly Leu Cys Cys Ser Asn Leu Cys Leu Phe Val Cys Leu Thr
 65              70                  75                  80

Phe Ser
```

<210> SEQ ID NO 406
<211> LENGTH: 31
<212> TYPE: PRT
<213> ORGANISM: Conus striolatus
<220> FEATURE:
<221> NAME/KEY: SITE
<222> LOCATION: (1)..(31)
<223> OTHER INFORMATION: Xaa at residues 1 and 4 may be Tyr, 125-I-Tyr, mono-iodo-Tyr, di-iodo-Tyr, O-sulpho-Tyr or O-phospho-Tyr; Xaa at residue 2 may be Glu or gamma-carboxy-Glu

<400> SEQUENCE: 406

```
Xaa Xaa Cys Xaa Ser Thr Gly Thr Phe Cys Gly Ile Asn Gly Gly Leu
 1               5                  10                  15

Cys Cys Ser Asn Leu Cys Leu Phe Phe Val Cys Leu Thr Phe Ser
         20                  25                  30
```

<210> SEQ ID NO 407
<211> LENGTH: 287
<212> TYPE: DNA
<213> ORGANISM: Conus striolatus
<220> FEATURE:
<221> NAME/KEY: CDS
<222> LOCATION: (1)..(231)

<400> SEQUENCE: 407

```
atg aaa ctg acg tgt atg gtg atc gtc gcc gtg ctg ctc ctg acg acc      48
Met Lys Leu Thr Cys Met Val Ile Val Ala Val Leu Leu Leu Thr Thr
 1               5                  10                  15 tgt cat ctc atc aca gct gat gac tcc aga ggt acg cag aag cat cgt      96
Cys His Leu Ile Thr Ala Asp Asp Ser Arg Gly Thr Gln Lys His Arg
             20                  25                  30 tcc ctg agg tcg act acc aaa gtc tcc aag tcg act agc tgc atg aaa     144
Ser Leu Arg Ser Thr Thr Lys Val Ser Lys Ser Thr Ser Cys Met Lys
         35                  40                  45 gcc ggg tct tat tgc gtc gct act acg aga atc tgc tgc ggt tat tgc     192
Ala Gly Ser Tyr Cys Val Ala Thr Thr Arg Ile Cys Cys Gly Tyr Cys
     50                  55                  60 gct tat ttc ggc aaa ata tgt att ggc tat ccc aaa aac tgatcctccc      241
Ala Tyr Phe Gly Lys Ile Cys Ile Gly Tyr Pro Lys Asn
 65                  70                  75 cctactgtgc tctatccttt tctgcctgat gtcttctcct cccctc                   287
```

<210> SEQ ID NO 408
<211> LENGTH: 77
<212> TYPE: PRT
<213> ORGANISM: Conus striolatus

<400> SEQUENCE: 408

```
Met Lys Leu Thr Cys Met Val Ile Val Ala Val Leu Leu Leu Thr Thr
 1               5                  10                  15

Cys His Leu Ile Thr Ala Asp Asp Ser Arg Gly Thr Gln Lys His Arg
             20                  25                  30

Ser Leu Arg Ser Thr Thr Lys Val Ser Lys Ser Thr Ser Cys Met Lys
         35                  40                  45

Ala Gly Ser Tyr Cys Val Ala Thr Thr Arg Ile Cys Cys Gly Tyr Cys
```

```
                50                  55                  60
Ala Tyr Phe Gly Lys Ile Cys Ile Gly Tyr Pro Lys Asn
65                  70                  75

<210> SEQ ID NO 409
<211> LENGTH: 35
<212> TYPE: PRT
<213> ORGANISM: Conus striolatus
<220> FEATURE:
<221> NAME/KEY: SITE
<222> LOCATION: (1)..(35)
<223> OTHER INFORMATION: Xaa at residues 10, 21, 24 and 32 may be Tyr,
      125-I-Tyr, mono-iodo-Tyr, di-iodo-Tyr, O-sulpho-Tyr or
      O-phospho-Tyr; Xaa at residue 33 may be Pro or hydroxy-Pro

<400> SEQUENCE: 409

Ser Thr Ser Cys Met Lys Ala Gly Ser Xaa Cys Val Ala Thr Thr Arg
1               5                   10                  15

Ile Cys Cys Gly Xaa Cys Ala Xaa Phe Gly Lys Ile Cys Ile Gly Xaa
            20                  25                  30

Xaa Lys Asn
        35
```